US010724103B2

(12) United States Patent
Tureci et al.

(10) Patent No.: US 10,724,103 B2
(45) Date of Patent: *Jul. 28, 2020

(54) IDENTIFICATION OF SURFACE ASSOCIATED ANTIGEN FLJ31461 FOR TUMOR DIAGNOSIS AND THERAPY

(71) Applicant: BioNTech AG, Mainz (DE)

(72) Inventors: Ozlem Tureci, Mainz (DE); Ugur Sahin, Mainz (DE); Sandra Schneider, Stutensee (DE); Gerd Helftenbein, Germunden (DE); Volker Schluter, Neuried (DE); Dirk Usener, Wiesbaden (DE); Philippe Thiel, Planegg (DE); Michael Koslowski, Mainz (DE)

( * ) Notice: Subject to any disclaimer, the term of this patent is extended or adjusted under 35 U.S.C. 154(b) by 41 days.

This patent is subject to a terminal disclaimer.

(21) Appl. No.: 15/675,148

(22) Filed: Aug. 11, 2017

(65) Prior Publication Data

US 2018/0169236 A1 Jun. 21, 2018

Related U.S. Application Data

(60) Division of application No. 15/009,061, filed on Jan. 28, 2016, now abandoned, which is a continuation of application No. 12/851,980, filed on Aug. 6, 2010, now Pat. No. 9,255,131, which is a division of application No. 11/596,106, filed as application No. PCT/EP2005/005104 on May 11, 2005, now Pat. No. 7,785,801.

(30) Foreign Application Priority Data

May 11, 2004 (DE) ........................ 10 2004 023 187

(51) Int. Cl.

| | |
|---|---|
| ***C12Q 1/686*** | (2018.01) |
| ***C12Q 1/6886*** | (2018.01) |
| ***C07K 14/47*** | (2006.01) |
| ***A61K 39/395*** | (2006.01) |
| ***A61K 45/06*** | (2006.01) |
| ***C07K 16/28*** | (2006.01) |
| ***C07K 16/30*** | (2006.01) |
| *G01N 33/53* | (2006.01) |

(52) U.S. Cl.

CPC ...... *C12Q 1/6886* (2013.01); *A61K 39/39558* (2013.01); *A61K 45/06* (2013.01); *C07K 14/4748* (2013.01); *C07K 16/28* (2013.01); *C07K 16/30* (2013.01); *C12Q 1/686* (2013.01); *A61K 39/395* (2013.01); *C12Q 2600/106* (2013.01); *C12Q 2600/156* (2013.01); *G01N 33/53* (2013.01)

(58) Field of Classification Search

None

See application file for complete search history.

(56) References Cited

U.S. PATENT DOCUMENTS

| | | | | |
|---|---|---|---|---|
| 4,732,847 A * | 3/1988 | Stuart | C12Q 1/6804 | 435/188 |
| 6,979,557 B2 | 12/2005 | Isogai et al. | | |
| 7,034,146 B2 * | 4/2006 | Park | C12Q 1/6886 | 536/23.1 |
| 9,255,131 B2 | 2/2016 | Tureci et al. | | |
| 2005/0037445 A1 | 2/2005 | Poulsen et al. | | |
| 2006/0013817 A1 | 1/2006 | Sahin et al. | | |
| 2006/0035852 A1 | 2/2006 | Sahin et al. | | |
| 2008/0020990 A1 * | 1/2008 | Yano | A61K 31/7105 | 514/44 A |
| 2014/0120085 A1 * | 5/2014 | Tureci | C12Q 1/6886 | 424/133.1 |

FOREIGN PATENT DOCUMENTS

| | | |
|---|---|---|
| CA | 2478413 A1 | 9/2003 |
| DE | 10211088 A1 | 9/2003 |
| JP | 2003-530816 A | 10/2003 |
| WO | 9310813 A1 | 6/1993 |
| WO | WO 00/18916 A3 | 11/2000 |
| WO | 0194629 A2 | 12/2001 |
| WO | 02086443 A2 | 10/2002 |
| WO | 03003906 A2 | 1/2003 |

OTHER PUBLICATIONS

Ludwig et Al. (Nature Reviews: Cancer, vol. 5, p. 845-856, 2005) (Year: 2005).*
Pepe et Al. (Journal of the National Cancer Institute, vol. 93, No. 14, p. 1054-1061, 2001) (Year: 2001).*
Mettlin et Al. (Cancer, vol. 74, No. 5, p. 1615-1620, 1994) (Year: 1994).*
Brawer et Al. (Urology, vol. 52, No. 3, p. 372-378, 1998) (Year: 1998).*
Budman et Al. (CUAJ, vol. 2, Issue 3, p. 212-221, 2008) (Year: 2008).*
Mantovani (European Journal of Cancer, vol. 30A, No. 3, p. 363-369, 1994) (Year: 1994).*
"Agenourt_7926639 mRNA Sequence," EBI Accession No. BQ427878 (last updated May 24, 2002).
"Sequence 695 from Patent EP 1293569," EBI Accession No. AX714011 (Apr. 15, 2003).
"*Homo sapiens* cDNA FLJ31461 fis, Clone NT2NE2001247," EBI Accession No. AK056023 (submitted Oct. 24, 2001).
"Hypothetical Protein FLJ31461," EBI Accession No. 096N35 (Last updated Dec. 1, 2001).

(Continued)

*Primary Examiner* — Michael Allen
(74) *Attorney, Agent, or Firm* — Olson & Cepuritis, Ltd.

(57) ABSTRACT

The invention relates to the identification of gene products that are the result of tumor-associated expression and the nucleic acids encoding the same. The invention also relates to the therapy and diagnosis of diseases wherein these gene products are the result of an aberrant tumor-associated expression. The invention also relates to the proteins, polypeptides and peptides that are the result of tumor-associated expression and to the nucleic acids encoding the same.

3 Claims, 56 Drawing Sheets

Specification includes a Sequence Listing.

(56) References Cited

OTHER PUBLICATIONS

Scheurle et al., "Cancer Gene Discovery Using Digital Differential Display," Cancer Research vol. 60, No. 15, pp. 4037-4043 (2000).
Zhau et al., "Biomarkers Associated With Prostate Cancer Progression," Journal of Cellular Biochem., Supplement vol. 19, pp. 208-216 (1994).
Russo et al., Int. J. Cancer vol. 64, pp. 216-221 (1995).
Kibel et al., J. Urology vol. 164(1): 192-196 (2000).
Gingrich et al., Cancer Research vol. 56(18): 4096-4102 (1996).
Goldberg et al., "Models of Neoplasia and Their Diagnostic Implications: A Historical Perspective," Clin. Chem. vol. 39/11(B), pp. 2360-2374 (1993).
Tockman et al., "Considerations in Bringing a Cancer Biomarker to Clinical Application," Cancer Research, Supplement vol. 52, pp. 2711s-2718s (1992).
Glinsky et al., "Gene Expression Profiling Predicts Clinical Outcome of Prostate Cancer," Journal of Clinical Investigation vol. 113, No. 6, pp. 913-923 (2004).
Stanton et al., "Epidermal Growth Factor Receptor Expression by Human Squamous Cell . . . ," Br. J. Cancer vol. 70, pp. 427-433 (1994).
Bodey et al., "Failure of Cancer Vaccines: The Significant Limitations of this Approach to Immunotherapy," Anti-Cancer Research, vol. 20, pp. 2665-2676 (2000).
Dong et al., "Deletion at 13q21 is Associated with Aggressive Prostate Cancers," Cancer Research vol. 60. pp. 3880-3883 (2000).
Kljuic et al., "Desmoglein 4 in Hair Follicle Differentiation and Epidermal Adhesion: Evidence from Inherited Hypotrichosis . . . ," Cell vol. 113, pp. 249-260 (2003).
Whittock et al., "Genetic Evidence for a Novel Human Desmosomal Cadherin, Desmoglein 4," Journal of Investigative Dermatology vol. 120, pp. 523-530 (2003).
Teh et al., J. Oral Pathol. Med., 40(1): 67-76, epub date Oct. 4, 2010; Abstract Only.
Maumi et al., Dermatol. Pract. Conc., 3(4):14, see pp. 55-57, 2013.
Database Geneseq, Human Bladder Cancer Associated Protein SEQ ID No. 199, GSP:ABR48239, Jun. 12, 2003.
Database EMBL AX334325, Cancer Gene Determination and Therapeutic Screening Using Signature Gene Sets, XP-002606031, Jan. 9, 2002.
GenBank Database BC030524, *Homo sapiens* claudin 19, mRNA, (cDNA clone MGC:40523 Image:5207628), complete cds, Oct. 7, 2003.
GenBank Database NCBI Accession No. AY207008, *Homo sapiens* ATP-Binding Cassette Transporter C4(ABCC4)mRNA, complete cds, Jun. 1, 2003.
GenBank Database, NCBI Accession No. 007127, *Homo sapiens* villin 1 (VIL 1), mRNA, Dec. 20, 2003.
GenBank Database. NCBI Accession No. BC028743, *Homo sapiens* solute carrier family 44, member 5, mRNA (cDNA clone MGC:34032 Image:4828797). complete cds, Oct. 7, 2003.
GenBank Database, NCBI Accession No. U58130, Human bumetanide-sensitive Na—K—2Cl cotransporter (NKCC2) mRNA, complete cds, Sep. 1, 1996.
GenBank Database, NCBI Accession No. X81892, *H. sapiens* mRNA for HE6 Tm7 receptor, May 21, 1997.
IEDB Analysis Resource, Prediction Results, Input Sequences, Aug. 5, 2009.
Gruber, A.D. et al., "Molecular Cloning and Transmembrane Structure of hCLCA2 from Human Lung, Trachea, and Mammary Gland," American Journal of Physiology, Cell Physiology vol. 276(6), C1261-1270 (1999).
Grotzinger, C. et al., "LI-Cadherin: A Marker of Gastric Metaplasia and Neoplasia," Gut vol. 49(1): 73-81 (2001).
Haupt, K. et al., "The Potential of DNA Vaccination Against Tumor-Associated Antigens for Antitumor Therapy," Society for Experimental Biology and Medicine vol. 227(4): 227-237 (2002).
Hildebrandt, M.O. et al., "Detection of Tumor Cells in Peripheral Blood Samples from Patients with Germ Cell Tumors Using Immunocytochemical and Reverse Transcriptase-Polymerase Chain Reaction Techniques," Bone Marrow Transplantation vol. 22(8): 771-775 (1998).
Imamura, T. et al., "Expression of Enteropeptidase in Differentiated Enterocytes, Goblet Cells, and the Tumor Cells in Human Duodenum," American Journal of Physiology vol. 285(6) Part 1, G1235-G1241 (2003).
Lemmer, K. et al., "Expression of Dopamine Receptors and Transporter in Neuroendocrine Gastrointestinal Tumor Cells," Life Sciences 71, 667-678 (2002).
Roguska, M. et al., "Overview on the Use of Therapeutic Antibodies in Drug Discovery," Current Protocols in Pharmacology, Unit 9.7 (Abstract) (2004).
Scallon, B.J. et al., "A Review of Antibody Therapeutics and Anti-Body Related Technologies for Oncology," Journal Immunother. vol. 29(4):351-364 (2006).
Stockwin, L.H. et al., "The Role of Therapeutic Antibodies in Drug Discovery," Biochemical Society Trans. vol. 31, 433-436 (2003).
Weiner, L.M. et al., "Monoclonal Antibodies for Cancer Immunotherapy," Lancet vol. 373 (9668): 1033-1040 (2009).
Wice, B.M. et al., "A Tetraspan Membrane Glycoprotein Produced in the Human Intestinal Epithelium and Liver That Can Regulate Cell Density-Dependent Proliferation," The Journal of Biological Chemistry vol. 270(37): 21907-21918 (1995).
Wong, B.W. et al., "Identification of Liver-Intestine Cadherin in Hepatocellular Carcinoma—A Potential Disease Marker," Biochemical and Biophysical Research Communications vol. 311(3): 618-624 (2003).
Wu, S. et al. "Group III Human Metabotropic Glutamate Receptors 4, 7, and 8: Molecular Cloning, Functional Expression, and Comparison of Pharmacological Properties in RGT Cells," Molecular Brain Research 53(1-2): 88-97 (1998).
GenBank NCBI Accession No. NM_152454.1 *Homo sapiens* transmembrane protein 83 (TMEM83), mRNA, Jan. 26, 2004.
GenBank BAB71075.1, unnamed protein product [*Homo sapiens*], submitted Oct. 24, 2001.
Pelacho, B. et al., "Pemphigus Vulgaris Autoantibodies Induce Apoptosis in HaCaT Keratinocytes," FEBS Letters vol. 566, (1-3), 6-10 (2004).
Gordon, L.A. et al., "Breast Cell Invasive Potential Relates to the Myoepithelial Phenotype," International Journal of Cancer vol. 106(1), 8-16 (2003).
Tsunoda, K. et al., "Induction of Pemphigus Phenotype by a Mouse Monoclonal Antibody Against the Amino-Terminal Adhesive Interface of Desmoglein 3," Journal of Immunology vol. 170(4): 2170-2178 (2003).
Krunic, A.L. et al., British Journal of Cancer, 77(8): 1275-1279 (1998).
Wucherpfennig, K.W. et al., Proc. Natl. Acad. Sci. USA, 92: 11935-11939 (1995).
Hiraki, A. et al., British Journal of Cancer, 73: 1491-1497 (1996).

* cited by examiner

Fig. 1D

| Tissues | Normal tissues | Tumor tissues (positive/total) |
|---|---|---|
| Breast | Neg. | 10/12 |
| Lung | Neg. | 8/16 |
| Esophagus | Neg. | 3/10 |
| Ovary | Neg. | 3/8 |
| Stomach | Neg. | 3/10 |
| ENT | not tested | 4/5 |
| Cervix | Neg. | 2/4 |
| Skin | Neg. | 2/5 |
| Prostate | Neg. | 2/10 |
| Kidney | Neg. | 3/12 |
| Colon | Neg. | 1/12 |
| Uterus | Neg. | 1/5 |
| Skin | Neg. | 2/5 |

Cervix carcinoma

Bronchial carcinoma

Lymph node metastasis of a breast tumor

Fig. 3C

| Tissues | Tumor tissues (positive/total) |
|---|---|
| Breast | 3 / 5 |
| Lymph node metastasis of breast tumors | 5 / 7 |
| Skin | 1 / 1 |
| ENT | 6 / 6 |
| Lung | 7 / 8 |

Fig. 4B

| Tissues | Tumor tissues (positive/total) |
|---|---|
| Esophagus | 6 / 10 |
| Stomach | 1 / 10 |
| Cervix | 2 / 4 |
| ENT | 4 / 5 |
| Lung | 2 / 16 |

Cells transfected by DSG4

Cells transfected by control

Fig. 7C

| Tissues | Tumor tissues (positive/total) |
|---|---|
| Esophagus | 6 / 10 |
| Stomach | 1 / 10 |
| Cervix | 2 / 4 |
| ENT | 4 / 5 |
| Lung | 2 / 16 |

Fig. 14D

| Tissues | Tumor tissues (positive/total) |
|---|---|
| Colon | 3 / 12 |
| Esophagus | 8 / 10 |
| Lung | 7 / 16 |
| Ovary | 3 / 8 |
| Kidney | 3 / 12 |
| ENT | 3 / 12 |

Fig. 18C

| Tissues | Tumor tissues (positive/total) |
|---|---|
| Esophagus | 8 / 10 |
| Lung | 5 / 16 |
| Breast | 2 / 12 |
| ENT | 3 / 5 |
| Pancreas | 1 / 6 |
| Cervix | 2 / 2 |

IDENTIFICATION OF SURFACE ASSOCIATED ANTIGEN FLJ31461 FOR TUMOR DIAGNOSIS AND THERAPY

CROSS-REFERENCE TO RELATED APPLICATIONS

This application is a division of U.S. Ser. No. 15/009,061, filed on Jan. 28, 2016, which is a continuation of U.S. Ser. No. 12/851,980, filed on Aug. 6, 2010, now U.S. Pat. No. 9,255,131, which is a division of U.S. application Ser. No. 11/596,106, filed on Jun. 26, 2007, now U.S. Pat. No. 7,785,801, which is the National Stage of PCT/EP05/005104, filed on May 11, 2005; each of which is incorporated herein by reference in its entirety.

INCORPORATION OF SEQUENCE LISTING

Biological sequence information for this application is included in an ASCII text file having the file name "342-20-PCTUST4.txt" created on Sep. 23, 2019, and having a file size of 396,507 bytes, which is incorporated herein by reference.

BACKGROUND OF THE INVENTION

Despite interdisciplinary approaches and exhaustive use of classical therapeutic procedures, cancers are still among the leading causes of death. More recent therapeutic concepts aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced. Tumor cells biologically differ substantially from their nonmalignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens.

The specific recognition of tumor-associated antigens involves cellular and humoral mechanisms which are two functionally interconnected units: $CD4^+$ and $CD8^+$ T lymphocytes recognize the processed antigens presented on the molecules of the MHC (major histocompatibility complex) classes II and I, respectively, while B lymphocytes produce circulating antibody molecules which bind directly to unprocessed antigens.

The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, *Nat. Med.* 4:525-31, 1998). Accordingly, a central aim of tumor immunology is to molecularly define these structures. The molecular nature of these antigens has been enigmatic for a long time. Only after development of appropriate cloning techniques has it been possible to screen cDNA expression libraries of tumors systematically for tumor-associated antigens by analyzing the target structures of cytotoxic T lymphocytes (CTL) (van der Bruggen et al., *Science* 254:1643-7, 1991) or by using circulating autoantibodies (Sahin et al., *Curr. Opin. Immunol.* 9:709-16, 1997) as probes. To this end, cDNA expression libraries were prepared from fresh tumor tissue and recombinantly expressed as proteins in suitable systems. Immunoeffectors isolated from patients, namely CTL clones with tumor-specific lysis patterns, or circulating autoantibodies were utilized for cloning the respective antigens.

In recent years a multiplicity of antigens have been defined in various neoplasias by these approaches. The class of cancer/testis antigens (CTA) is of great interest here. CTA and genes encoding them (cancer/testis genes or CTG) are defined by their characteristic expression pattern [Tureci et al, *Mol Med Today.* 3:342-9, 1997]. They are not found in normal tissues, except testis and germ cells, but are expressed in a number of human malignomas, not tumor type-specifically but with different frequency in tumor entities of very different origins (Chen & Old, *Cancer J. Sci. Am.* 5:16-7, 1999). Antibodies against CTA are not found in healthy individuals but in tumor patients. This class of antigens, in particular owing to its tissue distribution, is particularly valuable for immunotherapeutic projects and is tested in current clinical patient studies (Marchand et al., *Int. J. Cancer* 80:219-30, 1999; Knuth et al., *Cancer Chemother. Pharmacol.* 46:p46-51, 2000).

However, the probes utilized for antigen identification in the classical methods illustrated above are immunoeffectors (circulating autoantibodies or CTL clones) from patients usually having already advanced cancer. A number of data indicate that tumors can lead, for example, to tolerization and anergization of T cells and that, during the course of the disease, especially those specificities which could cause effective immune recognition are lost from the immunoeffector repertoire. Current patient studies have not yet produced any solid evidence of a real action of the previously found and utilized tumor-associated antigens. Accordingly, it cannot be ruled out that proteins evoking spontaneous immune responses are the wrong target structures.

SUMMARY OF THE INVENTION

It was the object of the present invention to provide target structures for a diagnosis and therapy of cancers.

According to the invention, this object is achieved by the subject matter of the claims.

According to the invention, a strategy for identifying and providing antigens expressed in association with a tumor and the nucleic acids coding therefor was pursued. This strategy is based on the evaluation of human protein and nucleic acid data bases with respect to potential cancer-specific antigens which are accessible on the cell surface. The definition of the filter criteria which are necessary for this together with a high throughput methodology for analysing all proteins, if possible, form the central part of the invention. Data mining first produces a list which is as complete as possible of all known genes which according to the basic principle "gene to mRNA to protein" are examined for the presence of one or more transmembrane domains. This is followed by a homology search, a classification of the hits in tissue specific groups (among others tumor tissue) and an inspection of the real existence of the mRNA. Finally, the proteins which are identified in this manner are evaluated for their aberrant activation in tumors, e.g. by expression analyses and protein chemical procedures.

Data mining is a known method of identifying tumor-associated genes. In the conventional strategies, however, transcriptoms of normal tissue libraries are usually subtracted electronically from tumor tissue libraries, with the assumption that the remaining genes are tumor-specific (Schmitt et al., *Nucleic Acids Res.* 27:4251-60, 1999; Vasmatzis et al., *Proc. Natl. Acad. Sci. USA.* 95:300-4, 1998; Scheurle et al., *Cancer Res.* 60:4037-43, 2000).

The concept of the invention, however, is based on utilizing data mining for electronically extracting all genes coding for cancer specific antigens which are accessible on the cell surfaces and then evaluating said genes for ectopic expression in tumors.

The invention thus relates in one aspect to a strategy for identifying genes differentially expressed in tumors. Said strategy combines data mining of public sequence libraries ("in silico") with subsequent laboratory-experimental ("wet bench") studies.

According to the invention, a combined strategy based on different bioinformatic scripts enabled new genes coding for cancer specific antigens which are accessible on the cell surfaces to be identified. According to the invention, these tumor-associated genes and the genetic products encoded thereby were identified and provided independently of an immunogenic action.

The tumor-associated antigens identified according to the invention have an amino acid sequence encoded by a nucleic acid which is selected from the group consisting of (a) a nucleic acid which comprises a nucleic acid sequence selected from the group consisting of SEQ ID NOs: 1, 3, 5, 7, 9, 11, 13, 15, 17, 19, 21, 23, 25, 27, 29, 69, 71, 73, 75, 79, 80, 85, 87, 102, 104, 106, 108, 110, 112, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, a tumor-associated antigen identified according to the invention has an amino acid sequence encoded by a nucleic acid which is selected from the group consisting of SEQ ID NOs: 1, 3, 5, 7, 9, 11, 13, 15, 17, 19, 21, 23, 25, 27, 29, 69, 71, 73, 75, 79, 80, 85, 87, 102, 104, 106, 108, 110, 112. In a further preferred embodiment, a tumor-associated antigen identified according to the invention comprises an amino acid sequence selected from the group consisting of SEQ ID NOs: 2, 4, 6, 8, 10, 12, 14, 16, 18, 20, 22, 24, 26, 28, 30, 61 to 68, 70, 72, 74, 76, 81, 82, 86, 88, 96 to 101, 103, 105, 107, 109, 111, 113, a part or derivative thereof.

The present invention generally relates to the use of tumor-associated antigens identified according to the invention or of parts thereof, of nucleic acids coding therefor or of nucleic acids directed against said coding nucleic acids or of antibodies directed against the tumor-associated antigens identified according to the invention or parts thereof for therapy and diagnosis. This utilization may relate to individual but also to combinations of two or more of these antigens, functional fragments, nucleic acids, antibodies, etc., in one embodiment also in combination with other tumor-associated genes and antigens for diagnosis, therapy and progress control.

The property of the tumor-associated antigens identified according to the invention that they are localized on or at the cell surface qualifies them as suitable targets or means for therapy and diagnosis. Especially suitable for this is a part of the tumor-associated antigens identified according to the invention which corresponds to the non-transmembrane portion, in particular the extracellular portion of the antigens, or is comprised thereof. Therefore, according to the invention, a part of the tumor-associated antigens identified according to the invention which corresponds to the non-transmembrane portion of the antigens or is comprised thereof, or a corresponding part of the nucleic acids coding for the antigens identified according to the invention is preferred for therapy or diagnosis. Similarly, the use of antibodies is preferred which are directed against a part of the tumor-associated antigens identified according to the invention which corresponds to the non-transmembrane portion of the antigens or is comprised thereof.

Preferred diseases for a therapy and/or diagnosis are those in which one or more of the tumor-associated antigens identified according to the invention are selectively expressed or abnormally expressed.

The invention also relates to nucleic acids and genetic products which are expressed in association with a tumor cell and which are produced by altered splicing (splice variants) of nucleic acids of the tumor-associated antigens identified according to the invention or by altered translation with utilization of alternative open reading frames. The splice variants of the invention can be used according to the invention as targets for diagnosis and therapy of tumor diseases.

Very different mechanisms may cause splice variants to be produced, for example

- utilization of variable transcription initiation sites
- utilization of additional exons
- complete or incomplete splicing out of single or two or more exons,
- splice regulator sequences altered via mutation (deletion or generation of new donor/acceptor sequences),
- incomplete elimination of intron sequences.

Altered splicing of a gene results in an altered transcript sequence (splice variant). Translation of a splice variant in the region of its altered sequence results in an altered protein which may be distinctly different in the structure and function from the original protein. Tumor-associated splice variants may produce tumor-associated transcripts and tumor-associated proteins/antigens. These may be utilized as molecular markers both for detecting tumor cells and for therapeutic targeting of tumors. Detection of tumor cells, for example in blood, serum, bone marrow, sputum, bronchial lavage, bodily secretions and tissue biopsies, may be carried out according to the invention, for example, after extraction of nucleic acids by PCR amplification with splice variant-specific oligonucleotides. According to the invention, all sequence-dependent detection systems are suitable for detection. These are, apart from PCR, for example gene chip/microarray systems, Northern blot, RNAse protection assays (RDA) and others. All detection systems have in common that detection is based on a specific hybridization with at least one splice variant-specific nucleic acid sequence. However, tumor cells may also be detected according to the invention by antibodies which recognize a specific epitope encoded by the splice variant. Said antibodies may be prepared by using for immunization peptides which are specific for said splice variant. Suitable for immunization are particularly the amino acids whose epitopes are distinctly different from the variant(s) of the genetic product, which is (are) preferably produced in healthy cells. Detection of the tumor cells with antibodies may be carried out here on a sample isolated from the patient or as imaging with intravenously administered antibodies.

In addition to diagnostic usability, splice variants having new or altered epitopes are attractive targets for immunotherapy. The epitopes of the invention may be utilized for targeting therapeutically active monoclonal antibodies or T lymphocytes. In passive immunotherapy, antibodies or T lymphocytes which recognize splice variant-specific epitopes are adoptively transferred here. As in the case of other antigens, antibodies may be generated also by using standard technologies (immunization of animals, panning strategies for isolation of recombinant antibodies) with utilization of polypeptides which include these epitopes. Alternatively, it is possible to utilize for immunization nucleic acids coding for oligo- or polypeptides which contain said epitopes. Various techniques for in vitro or in vivo generation of epitope-specific T lymphocytes are known and have been described in detail (for example Kessler J H, et al. 2001, Sahin et al., 1997) and are likewise based on utilizing oligo- or polypeptides which contain the splice variant-specific epitopes or nucleic acids coding for said oligo- or polypeptides. Oligo- or polypeptides which contain the splice variant-specific epitopes or nucleic acids coding for said polypeptides may also be used for utilization as pharmaceutically active substances in active immunotherapy (vaccination, vaccine therapy).

In a further aspect, the invention also relates to posttranslationally modified protein domains such as glycosylations or myristoylations. This kind of modifications can result in a differential recognition pattern of an antigen, e.g. by an antibody, and recognize different conditions possibly associated with a disease. In particular by using antibodies, this differentiation of an antigen can be utilized diagnostically as well as therapeutically. It has been published for tumor cells that the tumor-associated cellular degeneration can result in altered posttranslational modifications (Durand & Seta. 2000. *Clin Chem* 46: 795-805; Granovsky et al. 2000. *Nat Med* 6: 306-312). In particular, glycosylation patterns are strongly altered on tumor cells. These special epitopes according to the invention can discriminate tumor cells from non-carcinogenic cells diagnostically. If an epitope which can be modified posttranslationally is glycosylated in normal non-degenerated cells and is deglycosylated in tumor cells, this situation makes the development of a tumor specific therapeutic antibody within the scope of the invention possible.

In one aspect, the invention relates to a pharmaceutical composition comprising an agent which recognizes the tumor-associated antigen identified according to the invention and which is preferably selective for cells which have expression or abnormal expression of a tumor-associated antigen identified according to the invention. In particular embodiments, said agent may cause induction of cell death, reduction in cell growth, damage to the cell membrane or secretion of cytokines and preferably have a tumor-inhibiting activity. In one embodiment, the agent is an antisense nucleic acid which hybridizes selectively with the nucleic acid coding for the tumor-associated antigen. In a further embodiment, the agent is an antibody which binds selectively to the tumor-associated antigen, in particular a complement-activated antibody which binds selectively to the tumor-associated antigen. In a further embodiment, the agent comprises two or more agents which each selectively recognize different tumor-associated antigens, at least one of which is a tumor-associated antigen identified according to the invention. Recognition needs not be accompanied directly with inhibition of activity or expression of the antigen. In this aspect of the invention, the antigen selectively limited to tumors preferably serves as a label for recruiting effector mechanisms to this specific location. In a preferred embodiment, the agent is a cytotoxic T lymphocyte which recognizes the antigen on an HLA molecule and lyses the cell labeled in this way. In a further embodiment, the agent is an antibody which binds selectively to the tumor-associated antigen and thus recruits natural or artificial effector mechanisms to said cell. In a further embodiment, the agent is a T helper lymphocyte which enhances effector functions of other cells specifically recognizing said antigen.

In one aspect, the invention relates to a pharmaceutical composition comprising an agent which inhibits expression or activity of a tumor-associated antigen identified according to the invention. In a preferred embodiment, the agent is an antisense nucleic acid which hybridizes selectively with the nucleic acid coding for the tumor-associated antigen. In a further embodiment, the agent is an antibody which binds selectively to the tumor-associated antigen. In a further embodiment, the agent comprises two or more agents which each selectively inhibit expression or activity of different tumor-associated antigens, at least one of which is a tumor-associated antigen identified according to the invention.

The activity of a tumor-associated antigen identified according to the invention can be any activity of a protein or a peptide. Thus, the therapeutic and diagnostic methods according to the invention can also aim at inhibiting or reducing this activity or testing this activity.

The invention furthermore relates to a pharmaceutical composition which comprises an agent which, when administered, selectively increases the amount of complexes between an HLA molecule and a peptide epitope from the tumor-associated antigen identified according to the invention. In one embodiment, the agent comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule. In one embodiment, the agent comprises two or more agents which each selectively increase the amount of complexes between MHC molecules and peptide epitopes of different tumor-associated antigens, at least one of which is a tumor-associated antigen identified according to the invention.

The invention furthermore relates to a pharmaceutical composition which comprises one or more components selected from the group consisting of (i) a tumor-associated antigen identified according to the invention or a part thereof, (ii) a nucleic acid which codes for a tumor-associated antigen identified according to the invention or for a part thereof, (iii) an antibody which binds to a tumor-associated antigen identified according to the invention or to a part thereof, (iv) an antisense nucleic acid which hybridizes specifically with a nucleic acid coding for a tumor-associated antigen identified according to the invention, (v) a host cell which expresses a tumor-associated antigen identified according to the invention or a part thereof, and (vi) isolated complexes between a tumor-associated antigen identified according to the invention or a part thereof and an HLA molecule.

A nucleic acid coding for a tumor-associated antigen identified according to the invention or for a part thereof may be present in the pharmaceutical composition in an expression vector and functionally linked to a promoter.

A host cell present in a pharmaceutical composition of the invention may secrete the tumor-associated antigen or the part thereof, express it on the surface or may additionally express an HLA molecule which binds to said tumor-associated antigen or said part thereof. In one embodiment, the host cell expresses the HLA molecule endogenously. In a further embodiment, the host cell expresses the HLA molecule and/or the tumor-associated antigen or the part thereof in a recombinant manner. The host cell is preferably nonproliferative. In a preferred embodiment, the host cell is an antigen-presenting cell, in particular a dendritic cell, a monocyte or a macrophage.

An antibody present in a pharmaceutical composition of the invention may be a monoclonal antibody. In further embodiments, the antibody is a chimeric or humanized antibody, a fragment of a natural antibody or a synthetic antibody, all of which may be produced by combinatory techniques. The antibody may be coupled to a therapeutically or diagnostically useful agent.

An antisense nucleic acid present in a pharmaceutical composition of the invention may comprise a sequence of 6-50, in particular 10-30, 15-30 and 20-30, contiguous nucleotides of the nucleic acid coding for the tumor-associated antigen identified according to the invention.

In further embodiments, a tumor-associated antigen, provided by a pharmaceutical composition of the invention either directly or via expression of a nucleic acid, or a part thereof binds to MHC molecules on the surface of cells, said binding preferably causing a cytolytic response and/or inducing cytokine release.

A pharmaceutical composition of the invention may comprise a pharmaceutically compatible carrier and/or an adjuvant. The adjuvant may be selected from saponin, GM-CSF, CpG oligonucleotides, RNA, a cytokine or a chemokine. A pharmaceutical composition of the invention is preferably used for the treatment of a disease characterized by selective expression or abnormal expression of a tumor-associated antigen. In a preferred embodiment, the disease is cancer.

The invention furthermore relates to methods of treating or diagnosing a disease characterized by expression or abnormal expression of one of more tumor-associated antigens. In one embodiment, the treatment comprises administering a pharmaceutical composition of the invention.

In one aspect, the invention relates to a method of diagnosing a disease characterized by expression or abnormal expression of a tumor-associated antigen identified according to the invention. The method comprises (i) detection of a nucleic acid which codes for the tumor-associated antigen or of a part thereof and/or (ii) detection of the tumor-associated antigen or of a part thereof, and/or (iii) detection of an antibody to the tumor-associated antigen or to a part thereof and/or (iv) detection of cytotoxic or T helper lymphocytes which are specific for the tumor-associated antigen or for a part thereof in a biological sample isolated from a patient. In particular embodiments, detection comprises (i) contacting the biological sample with an agent which binds specifically to the nucleic acid coding for the tumor-associated antigen or to the part thereof, to said tumor-associated antigen or said part thereof, to the antibody or to cytotoxic or T helper lymphocytes specific for the tumor-associated antigen or parts thereof, and (ii) detecting the formation of a complex between the agent and the nucleic acid or the part thereof, the tumor-associated antigen or the part thereof, the antibody or the cytotoxic or T helper lymphocytes. In one embodiment, the disease is characterized by expression or abnormal expression of two or more different tumor-associated antigens and detection comprises detection of two or more nucleic acids coding for said two or more different tumor-associated antigens or of parts thereof, detection of two or more different tumor-associated antigens or of parts thereof, detection of two or more antibodies binding to said two or more different tumor-associated antigens or to parts thereof or detection of two or more cytotoxic or T helper lymphocytes specific for said two or more different tumor-associated antigens. In a further embodiment, the biological sample isolated from the patient is compared to a comparable normal biological sample.

The methods of diagnosing according to the invention can concern also the use of the tumor-associated antigens identified according to the invention as prognostic markers, in order to predict metastasis, e.g. through testing the migration behavior of cells, and therefore a worsened course of the disease, whereby among other things planning of a more aggressive therapy is made possible.

In a further aspect, the invention relates to a method for determining regression, course or onset of a disease characterized by expression or abnormal expression of a tumor-associated antigen identified according to the invention, which method comprises monitoring a sample from a patient who has said disease or is suspected of falling ill with said disease, with respect to one or more parameters selected from the group consisting of (i) the amount of nucleic acid which codes for the tumor-associated antigen or of a part thereof, (ii) the amount of the tumor-associated antigen or a part thereof, (iii) the amount of antibodies which bind to the tumor-associated antigen or to a part thereof, and (iv) the amount of cytolytic T cells or T helper cells which are specific for a complex between the tumor-associated antigen or a part thereof and an MHC molecule. The method preferably comprises determining the parameter(s) in a first sample at a first point in time and in a further sample at a second point in time and in which the course of the disease is determined by comparing the two samples. In particular embodiments, the disease is characterized by expression or abnormal expression of two or more different tumor-associated antigens and monitoring comprises monitoring (i) the amount of two or more nucleic acids which code for said two or more different tumor-associated antigens or of parts thereof, and/or (ii) the amount of said two or more different tumor-associated antigens or of parts thereof, and/or (iii) the amount of two or more antibodies which bind to said two or more different tumor-associated antigens or to parts thereof, and/or (iv) the amount of two or more cytolytic T cells or of T helper cells which are specific for complexes between said two or more different tumor-associated antigens or of parts thereof and MHC molecules.

According to the invention, detection of a nucleic acid or of a part thereof or monitoring the amount of a nucleic acid or of a part thereof may be carried out using a polynucleotide probe which hybridizes specifically to said nucleic acid or said part thereof or may be carried out by selective amplification of said nucleic acid or said part thereof. In one embodiment, the polynucleotide probe comprises a sequence of 6-50, in particular 10-30, 15-30 and 20-30, contiguous nucleotides of said nucleic acid.

According to the invention, detection of a tumor-associated antigen or of a part thereof or monitoring the amount of a tumor-associated antigen or of a part thereof may be carried out using an antibody binding specifically to said tumor-associated antigen or said part thereof.

In certain embodiments, the tumor-associated antigen to be detected or the part thereof is present in a complex with an MHC molecule, in particular an HLA molecule.

According to the invention, detection of an antibody or monitoring the amount of antibodies may be carried out using a protein or peptide binding specifically to said antibody.

According to the invention, detection of cytolytic T cells or of T helper cells or monitoring the amount of cytolytic T cells or of T helper cells which are specific for complexes between an antigen or a part thereof and MHC molecules may be carried out using a cell presenting the complex between said antigen or said part thereof and an MHC molecule.

The polynucleotide probe, the antibody, the protein or peptide or the cell, which is used for detection or monitoring, is preferably labeled in a detectable manner. In particular embodiments, the detectable marker is a radioactive marker or an enzymic marker. T lymphocytes may additionally be detected by detecting their proliferation, their cytokine production, and their cytotoxic activity triggered by specific stimulation with the complex of MHC and tumor-associated antigen or parts thereof. T lymphocytes may also be detected via a recombinant MHC molecule or else a complex of two or more MHC molecules which are loaded with the particular immunogenic fragment of one or more of the tumor-associated antigens and by contacting the specific T cell receptor which can identify the specific T lymphocytes.

In a further aspect, the invention relates to a method of treating, diagnosing or monitoring a disease characterized by expression or abnormal expression of a tumor-associated antigen identified according to the invention, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of a natural antibody.

The invention also relates to a method of treating a patient having a disease characterized by expression or abnormal expression of a tumor-associated antigen identified according to the invention, which method comprises (i) removing a sample containing immunoreactive cells from said patient, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. The invention likewise relates to cloning the T cell receptor of cytolytic T cells against the tumor-associated antigen. Said receptor may be transferred to other T cells which thus receive the desired specificity and, as under (iii), may be introduced into the patient.

In one embodiment, the host cell endogenously expresses an HLA molecule. In a further embodiment, the host cell recombinantly expresses an HLA molecule and/or the tumor-associated antigen or the part thereof. The host cell is preferably nonproliferative. In a preferred embodiment, the host cell is an antigen-presenting cell, in particular a dendritic cell, a monocyte or a macrophage.

In a further aspect, the invention relates to a method of treating a patient having a disease characterized by expression or abnormal expression of a tumor-associated antigen, which method comprises (i) identifying a nucleic acid which codes for a tumor-associated antigen identified according to the invention and which is expressed by cells associated with said disease, (ii) transfecting a host cell with said nucleic acid or a part thereof, (iii) culturing the transfected host cell for expression of said nucleic acid (this is not obligatory when a high rate of transfection is obtained), and (iv) introducing the host cells or an extract thereof into the patient in an amount suitable for increasing the immune response to the patient's cells associated with the disease. The method may further comprise identifying an MHC molecule presenting the tumor-associated antigen or a part thereof, with the host cell expressing the identified MHC molecule and presenting said tumor-associated antigen or a part thereof. The immune response may comprise a B cell response or a T cell response. Furthermore, a T cell response may comprise production of cytolytic T cells and/or T helper cells which are specific for the host cells presenting the tumor-associated antigen or a part thereof or specific for cells of the patient which express said tumor-associated antigen or a part thereof.

The invention also relates to a method of treating a disease characterized by expression or abnormal expression of a tumor-associated antigen identified according to the invention, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

Preferably, the host cells used according to the invention are nonproliferative or are rendered nonproliferative. A disease characterized by expression or abnormal expression of a tumor-associated antigen is in particular cancer.

The present invention furthermore relates to a nucleic acid selected from the group consisting of (a) a nucleic acid which comprises a nucleic acid sequence selected from the group consisting of SEQ ID NOs: 69, 71, 73, 79, 80, 85, 87, 102, 104, 106, 108, 110, 112, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The invention furthermore relates to a nucleic acid, which codes for a protein or polypeptide comprising an amino acid sequence selected from the group consisting of SEQ ID NOs: 61-68, 70, 72, 74, 81, 82, 86, 88, 96-101, 103, 105, 107, 109, 111, 113, a part or derivative thereof.

In a further aspect, the invention relates to a recombinant nucleic acid molecule, in particular DNA or RNA molecule, which comprises a nucleic acid of the invention.

The invention also relates to host cells which contain a nucleic acid of the invention or a recombinant nucleic acid molecule comprising a nucleic acid of the invention.

The host cell may also comprise a nucleic acid coding for a HLA molecule. In one embodiment, the host cell endogenously expresses the HLA molecule. In a further embodiment, the host cell recombinantly expresses the HLA molecule and/or the nucleic acid of the invention or a part thereof. Preferably, the host cell is nonproliferative. In a preferred embodiment, the host cell is an antigen-presenting cell, in particular a dendritic cell, a monocyte or a macrophage.

In a further embodiment, the invention relates to oligonucleotides which hybridize with a nucleic acid identified according to the invention and which may be used as genetic probes or as "antisense" molecules. Nucleic acid molecules in the form of oligonucleotide primers or competent samples, which hybridize with a nucleic acid identified according to the invention or parts thereof, may be used for finding nucleic acids which are homologous to said nucleic acid identified according to the invention. PCR amplification, Southern and Northern hybridization may be employed for finding homologous nucleic acids. Hybridization may be carried out under low stringency, more preferably under medium stringency and most preferably under high stringency conditions. The term "stringent conditions" according to the invention refers to conditions which allow specific hybridization between polynucleotides.

In a further aspect, the invention relates to a protein or polypeptide which is encoded by a nucleic acid selected from the group consisting of (a) a nucleic acid which comprises a nucleic acid sequence selected from the group consisting of SEQ ID NOs: 69, 71, 73, 79, 80, 85, 87, 102, 104, 106, 108, 110, 112, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the invention relates to a protein or polypeptide which comprises an amino acid sequence selected from the group consisting of SEQ ID NOs: 61-68, 70, 72, 74, 81, 82, 86, 88, 96-101, 103, 105, 107, 109, 111, 113, a part or derivative thereof.

In a further aspect, the invention relates to an immunogenic fragment of a tumor-associated antigen identified according to the invention. Said fragment preferably binds to a human HLA receptor or to a human antibody. A fragment of the invention preferably comprises a sequence of at least 6, in particular at least 8, at least 10, at least 12, at least 15, at least 20, at least 30 or at least 50, amino acids. In particular an immunogenic fragment according to the invention comprises an amino acid sequence selected from the group consisting of SEQ ID NOs: 61-68, 81, 82, and 96-101, a part or derivative thereof.

In a further aspect, the invention relates to an agent which binds to a tumor-associated antigen identified according to the invention or to a part thereof. In a preferred embodiment, the agent is an antibody. In further embodiments, the antibody is a chimeric, a humanized antibody or an antibody produced by combinatory techniques or is a fragment of an antibody. Furthermore, the invention relates to an antibody which binds selectively to a complex of (i) a tumor-associated antigen identified according to the invention or a part thereof and (ii) an MHC molecule to which said tumor-associated antigen identified according to the invention or said part thereof binds, with said antibody not binding to (i) or (ii) alone. An antibody of the invention may be a monoclonal antibody. In further embodiments, the antibody is a chimeric or humanized antibody or a fragment of a natural antibody.

The invention furthermore relates to a conjugate between an agent of the invention which binds to a tumor-associated antigen identified according to the invention or to a part thereof or an antibody of the invention and a therapeutic or diagnostic agent. In one embodiment, the therapeutic or diagnostic agent is a toxin.

In a further aspect, the invention relates to a kit for detecting expression or abnormal expression of a tumor-associated antigen identified according to the invention, which kit comprises agents for detection (i) of the nucleic acid which codes for the tumor-associated antigen or of a part thereof, (ii) of the tumor-associated antigen or of a part thereof, (iii) of antibodies which bind to the tumor-associated antigen or to a part thereof, and/or (iv) of T cells which are specific for a complex between the tumor-associated antigen or a part thereof and an MHC molecule. In one embodiment, the agents for detection of the nucleic acid or the part thereof are nucleic acid molecules for selective amplification of said nucleic acid, which comprise, in particular a sequence of 6-50, in particular 10-30, 15-30 and 20-30, contiguous nucleotides of said nucleic acid.

BRIEF DESCRIPTION OF THE DRAWINGS

FIG. 1D: Summary of the FLJ31461-specific expression in various analysed tumors. Shown is the number of positively tested tumor samples relative to the total number of analysed tumor samples. While all investigated normal somatic tissues (3-10 tissues each, depending on tissue type) exhibit no expression of FLJ31461, the gene is expressed in many tumors with variable frequency.

FIG. 2 shows the endogenous protein expression of the breast tumor cell-line MCF7.

FIG. 3C: Summary of the immunohistochemical analyses of the FLJ31461-protein. Shown is the number of positively tested tumor samples in relation to the total number of analysed tumor samples. While all investigated normal somatic tissues did not exhibit any expression of FLJ31461, the protein is detected in many of the tumors with varying frequency at the cell surface.

FIG. 4B: Summary of the specific expression of the DSG4-exons 10-12 in various analysed tumors. Shown is the number of positively tested tumor samples relative to the total number. While almost all investigated normal somatic tissues did not exhibit any expression of DSG4, this gene-section is detectable in many of the tumors with varying frequency.

FIG. 7C: Summary of the DSG3-specific expression in various analysed tumors. Shown is the number of positively tested tumor samples relative to the total number of analysed tumor samples. While all investigated normal somatic tissues (3-10 tissues each, depending on tissue type) do not show any expression of DSG3, the gene is expressed in many tumors with varying frequency.

FIG. 14D: Summary of the MGC34032-specific expression in various analysed tumors. Shown is the number of positively tested tumor samples relative to the total number of the analysed tumor samples. While all investigated somatic normal tissues (3-10 tissues each, depending on tissue type) exhibit a significantly lower expression of MGC34032, the gene is overexpressed in many tumors with varying frequency.

FIG. 18C: Summary of the CLCA2-specific expression in various analysed tumors. Shown is the number of positively tested tumor samples relative to the number of total samples of analysed tumors. While all investigated normal somatic tissues exhibit a significantly lower expression of CLCA2, the gene is overexpressed in many tumors with varying frequency.

DETAILED DESCRIPTION OF THE INVENTION

Figure 1A:
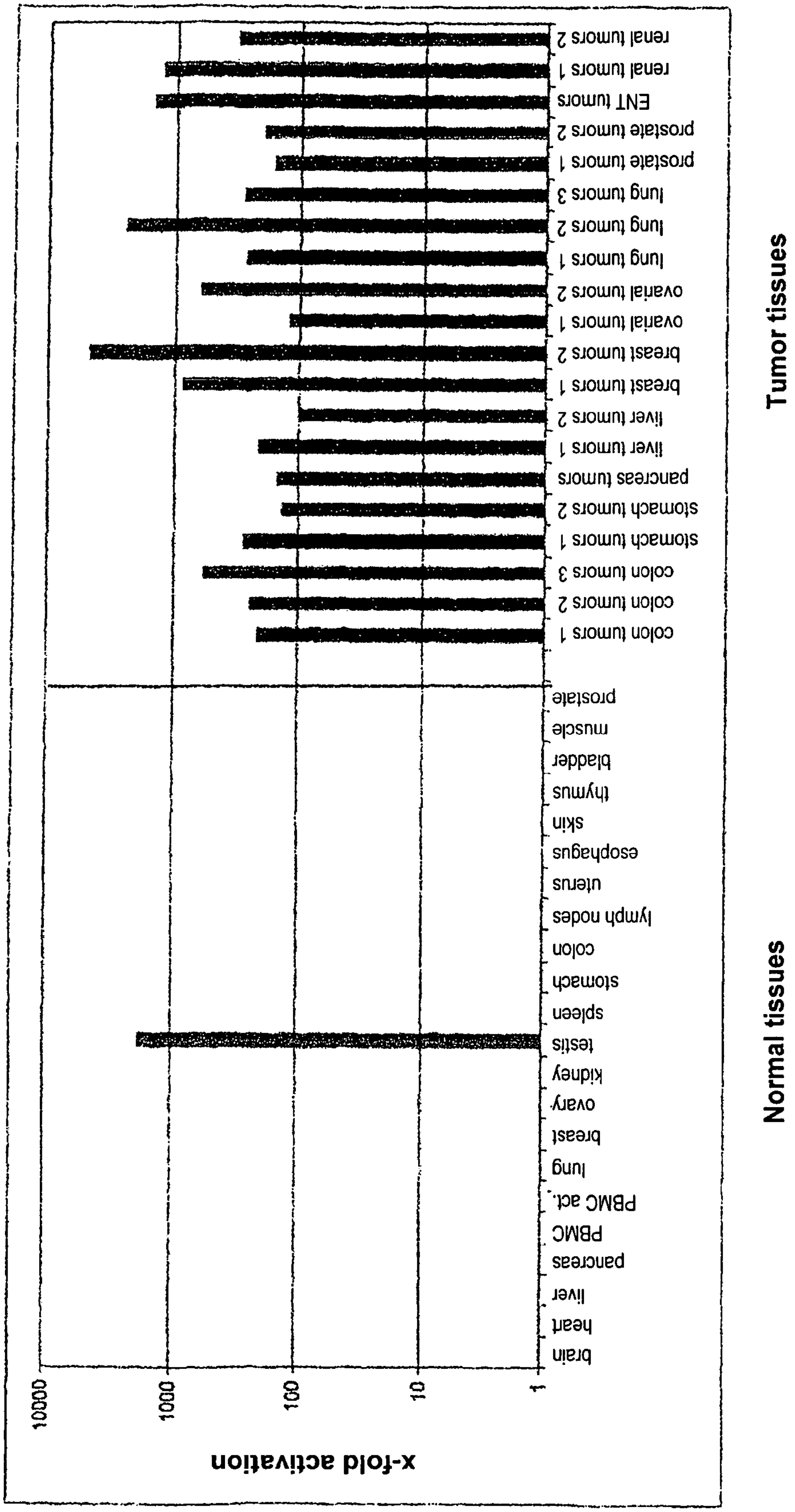
FIG. 1A: Quantitative expression analysis of FLJ31461 in normal tissues (left) and in various tumors (pools consisting of 3-4 individual samples each, right) in a logarithmic representation of the relative expression (x-fold activation). In most tumors and at least 100-fold overexpression of FLJ31461 is observed in comparison to the level of expression in healthy tissues.

According to the invention, genes are described which are expressed in tumor cells selectively or aberrantly and which are tumor-associated antigens.

According to the invention, these genes or their derivatives are preferred target structures for therapeutic approaches. Conceptionally, said therapeutic approaches may aim at inhibiting the activity of the selectively expressed tumor-associated genetic product. This is useful, if said aberrant respective selective expression is functionally important in tumor pathogenecity and if its ligation is accompanied by selective damage of the corresponding cells. Other therapeutic concepts contemplate tumor-associated antigens as labels which recruit effector mechanisms having cell-damaging potential selectively to tumor cells. Here, the function of the target molecule itself and its role in tumor development are totally irrelevant.

"Derivative" of a nucleic acid means according to the invention that single or multiple nucleotide substitutions, deletions and/or additions are present in said nucleic acid. Furthermore, the term "derivative" also comprises chemical derivatization of a nucleic acid on a base, on a sugar or on a phosphate of a nucleotide. The term "derivative" also comprises nucleic acids which contain nucleotides and nucleotide analogs not occurring naturally.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1× SDS at temperatures of up to 68° C.

According to the invention, complementary nucleic acids have at least 40%, in particular at least 50%, at least 60%, at least 70%, at least 80%, at least 90% and preferably at least 95%, at least 98% or at least 99%, identical nucleotides.

Nucleic acids coding for tumor-associated antigens may, according to the invention, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

Thus, on the one hand, the tumor-associated antigens illustrated herein may be combined with any expression control sequences and promoters. On the other hand, however, the promoters of the tumor-associated genetic products illustrated herein may, according to the invention, be combined with any other genes. This allows the selective activity of these promoters to be utilized.

According to the invention, a nucleic acid may furthermore be present in combination with another nucleic acid which codes for a polypeptide controlling secretion of the protein or polypeptide encoded by said nucleic acid from a host cell. According to the invention, a nucleic acid may also be present in combination with another nucleic acid which codes for a polypeptide causing the encoded protein or polypeptide to be anchored on the cell membrane of the host cell or compartmentalized into particular organelles of said cell.

In a preferred embodiment, a recombinant DNA molecule is according to the invention a vector, where appropriate with a promoter, which controls expression of a nucleic acid, for example a nucleic acid coding for a tumor-associated antigen of the invention. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids coding for a tumor-associated antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application. According to the invention, the term "host cell" relates to any cell which can be transformed or transfected with an exogenous nucleic acid. The term "host cells" comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the invention, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selective marker such as a gene imparting resistance to G418 (and thus enabling stably transfected cell lines to be selected) and the enhancer-promoter sequences of cytomegalovirus (CMV).

In those cases of the invention in which an HLA molecule presents a tumor-associated antigen or a part thereof, an expression vector may also comprise a nucleic acid sequence coding for said HLA molecule. The nucleic acid sequence coding for the HLA molecule may be present on the same expression vector as the nucleic acid coding for the tumor-associated antigen or the part thereof, or both nucleic acids may be present on different expression vectors. In the latter case, the two expression vectors may be cotransfected into a cell. If a host cell expresses neither the tumor-associated antigen or the part thereof nor the HLA molecule, both nucleic acids coding therefor are transfected into the cell either on the same expression vector or on different expression vectors. If the cell already expresses the HLA molecule, only the nucleic acid sequence coding for the tumor-associated antigen or the part thereof can be transfected into the cell.

The invention also comprises kits for amplification of a nucleic acid coding for a tumor-associated antigen. Such kits comprise, for example, a pair of amplification primers which hybridize to the nucleic acid coding for the tumor-associated antigen. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid coding for the tumor-associated antigen, and the other primer will hybridize to the complementary strand in an arrangement which allows amplification of the nucleic acid coding for the tumor-associated antigen.

"Antisense" molecules or "antisense" nucleic acids may be used for regulating, in particular reducing, expression of a nucleic acid. The term "antisense molecule" or "antisense nucleic acid" refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, the "antisense molecule" also comprises a construct which contains a nucleic acid or a part thereof in reverse orientation with respect to its natural promoter. An antisense transcript of a nucleic acid or of a part thereof may form a duplex with the naturally occurring mRNA specifying the enzyme and thus prevent accumulation of or translation of the mRNA into the active enzyme. Another possibility is the use of ribozymes for inactivating a nucleic acid. Antisense oligonucleotides preferred according to the invention have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a "modified" oligonucleotide. Here, the oligonucleotide may be modified in very different ways, without impairing its ability to bind its target, in order to increase, for example, its stability or therapeutic efficacy. According to the invention, the term "modified oligonucleotide" means an oligonucleotide in which (i) at least two of its nucleotides are linked to one another by a synthetic intemucleoside bond (i.e. an intemucleoside bond which is not a phosphodiester bond) and/or (ii) a chemical group which is usually not found in nucleic acids is covalently linked to the oligonucleotide. Preferred synthetic intemucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

Preferably, the proteins and polypeptides described according to the invention have been isolated. The terms "isolated protein" or "isolated polypeptide" mean that the protein or polypeptide has been separated from its natural environment. An isolated protein or polypeptide may be in an essentially purified state. The term "essentially purified" means that the protein or polypeptide is essentially free of other substances with which it is associated in nature or in vivo.

Such proteins and polypeptides may be used, for example, in producing antibodies and in an immunological or diagnostic assay or as therapeutics. Proteins and polypeptides described according to the invention may be isolated from biological samples such as tissue or cell homogenates and may also be expressed recombinantly in a multiplicity of pro- or eukaryotic expression systems.

For the purposes of the present invention, "derivatives" of a protein or polypeptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid deletion variants are characterized by the removal of one or more amino acids from the sequence. Amino acid substitution variants are characterized by at least one residue in the sequence being removed and another residue being inserted in its place. Preference is given to the modifications being in positions in the amino acid sequence which are not conserved between homologous proteins or polypeptides. Preference is given to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:

1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

The amino acid variants described above may be readily prepared with the aid of known peptide synthesis techniques such as, for example, by solid phase synthesis (Merrifield, 1964) and similar methods or by recombinant DNA manipulation. Techniques for introducing substitution mutations at predetermined sites into DNA which has a known or partially known sequence are well known and comprise M13 mutagenesis, for example. The manipulation of DNA sequences for preparing proteins having substitutions, insertions or deletions, is described in detail in Sambrook et al. (1989), for example.

According to the invention, "derivatives" of proteins or polypeptides also comprise single or multiple substitutions, deletions and/or additions of any molecules associated with the enzyme, such as carbohydrates, lipids and/or proteins or polypeptides. The term "derivative" also extends to all functional chemical equivalents of said proteins or polypeptides.

According to the invention, a part or fragment of a tumor-associated antigen has a functional property of the polypeptide from which it has been derived. Such functional properties comprise the interaction with antibodies, the interaction with other polypeptides or proteins, the selective binding of nucleic acids and an enzymatic activity. A particular property is the ability to form a complex with HLA and, where appropriate, generate an immune response. This immune response may be based on stimulating cytotoxic or T helper cells. A part or fragment of a tumor-associated antigen of the invention preferably comprises a sequence of at least 6, in particular at least 8, at least 10, at least 12, at least 15, at least 20, at least 30 or at least 50, consecutive amino acids of the tumor-associated antigen. A part or fragment of a tumor-associated antigen is preferably a part of the tumor-associated antigen which corresponds to the non-transmembrane portion, in particular the extracellular portion of the antigen or is comprised thereof.

A part or a fragment of a nucleic acid coding for a tumor-associated antigen relates according to the invention to the part of the nucleic acid, which codes at least for the tumor-associated antigen and/or for a part or a fragment of said tumor-associated antigen, as defined above. Preferably, a part or fragment of a nucleic acid coding for a tumor-associated antigen is that part which corresponds to the open reading frame, in particular as indicated in the sequence listing.

The isolation and identification of genes coding for tumor-associated antigens also make possible the diagnosis of a disease characterized by expression of one or more tumor-associated antigens. These methods comprise determining one or more nucleic acids which code for a tumor-associated antigen and/or determining the encoded tumor-associated antigens and/or peptides derived therefrom. The nucleic acids may be determined in the conventional manner, including by polymerase chain reaction or hybridization with a labeled probe. Tumor-associated antigens or peptides derived therefrom may be determined by screening patient antisera with respect to recognizing the antigen and/or the peptides. They may also be determined by screening T cells of the patient for specificities for the corresponding tumor-associated antigen.

The present invention also enables proteins binding to tumor-associated antigens described herein to be isolated, including antibodies and cellular binding partners of said tumor-associated antigens.

According to the invention, particular embodiments ought to involve providing "dominant negative" polypeptides derived from tumor-associated antigens. A dominant negative polypeptide is an inactive protein variant which, by way of interacting with the cellular machinery, displaces an active protein from its interaction with the cellular machinery or which competes with the active protein, thereby reducing the effect of said active protein. For example, a dominant negative receptor which binds to a ligand but does not generate any signal as response to binding to the ligand can reduce the biological effect of said ligand. Similarly, a dominant negative catalytically inactive kinase which usually interacts with target proteins but does not phosphorylate said target proteins may reduce phosphorylation of said target proteins as response to a cellular signal. Similarly, a dominant negative transcription factor which binds to a promoter site in the control region of a gene but does not increase transcription of said gene may reduce the effect of a normal transcription factor by occupying promoter binding sites, without increasing transcription.

The result of expression of a dominant negative polypeptide in a cell is a reduction in the function of active proteins. The skilled worker may prepare dominant negative variants of a protein, for example, by conventional mutagenesis methods and by evaluating the dominant negative effect of the variant polypeptide.

The invention also comprises substances such as polypeptides which bind to tumor-associated antigens. Such binding substances may be used, for example, in screening assays for detecting tumor-associated antigens and complexes of tumor-associated antigens with their binding partners and in a purification of said tumor-associated antigens and of complexes thereof with their binding partners. Such substances may also be used for inhibiting the activity of tumor-associated antigens, for example by binding to such antigens.

The invention therefore comprises binding substances such as, for example, antibodies or antibody fragments, which are capable of selectively binding to tumor-associated antigens. Antibodies comprise polyclonal and monoclonal antibodies which are produced in the conventional manner.

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology,* 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as $F(ab')_2$ fragment, carries both antigen binding sites of a complete antibody. Similarly, an antibody from which the Fc region has been enzymatically removed or which has been produced without said Fc region, referred to Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

WO 92/04381 for example, describes production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

The invention also provides $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The invention also comprises "single-chain" antibodies.

Preferably, an antibody used according to the invention is directed against one of the sequences according to SEQ ID NOs: 2, 4, 6, 8, 10, 12, 14, 16, 18, 20, 22, 24, 26, 28, 30, 61-68, 70, 72, 74, 76, 81, 82, 86, 88, 96-101, 103, 105, 107, 109, 111, 113, or a part or derivative thereof and/or may be obtained by immunization using these peptides.

The invention also comprises polypeptides which bind specifically to tumor-associated antigens. Polypeptide binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Phage display may be particularly effective in identifying binding peptides of the invention. In this connection, for example, a phage library is prepared (using, for example, the M13, fd or lambda phages) which presents inserts of from 4 to about 80 amino acid residues in length. Phages are then selected which carry inserts which bind to the tumor-associated antigen. This process may be repeated via two or more cycles of a reselection of phages binding to the tumor-associated antigen. Repeated rounds result in a concentration of phages carrying particular sequences. An analysis of DNA sequences may be carried out in order to identify the sequences of the expressed polypeptides. The smallest linear portion of the sequence binding to the tumor-associated antigen may be determined. The "two-hybrid system" of yeast may also be used for identifying polypeptides which bind to a tumor-associated antigen. Tumor-associated antigens described according to the invention or fragments thereof may be used for screening peptide libraries, including phage-display libraries, in order to identify and select peptide binding partners of the tumor-associated antigens. Such molecules may be used, for example, for screening assays, purification protocols, for interference with the function of the tumor-associated antigen and for other purposes known to the skilled worker.

The antibodies described above and other binding molecules may be used, for example, for identifying tissue which expresses a tumor-associated antigen. Antibodies may also be coupled to specific diagnostic substances for displaying cells and tissues expressing tumor-associated antigens. They may also be coupled to therapeutically useful substances. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium. According to the invention, the term "therapeutically useful substance" means any therapeutic molecule which, as desired, is selectively guided to a cell which expresses one or more tumor-associated antigens, including anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-C, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

According to the invention, the term "disease" refers to any pathological state in which tumor-associated antigens are expressed or abnormally expressed. "Abnormal expression" means according to the invention that expression is altered, preferably increased, compared to the state in a healthy individual. An increase in expression refers to an increase by at least 10%, in particular at least 20%, at least 50% or at least 100%. In one embodiment, the tumor-associated antigen is expressed only in tissue of a diseased individual, while expression in a healthy individual is repressed. One example of such a disease is cancer, in particular seminomas, melanomas, teratomas, gliomas, colon cancer, rectal cancer, kidney cancer, breast cancer, prostate cancer, cancer of the uterus, ovarian cancer, endometrial cancer, cancer of the esophagus, blood cancer, liver cancer, pancreatic cancer, skin cancer, brain cancer and lung cancer, lymphomas, and neuroblastomas. Examples for this are lung tumor, breast tumor, prostate tumor, colon tumor, renal cell carcinoma, cervical carcinoma, colon carcinoma and mamma carcinoma or metastases of the above cancer types or tumors.

According to the invention, a biological sample may be a tissue sample and/or a cellular sample and may be obtained in the conventional manner such as by tissue biopsy, including punch biopsy, and by taking blood, bronchial aspirate, urine, feces or other body fluids, for use in the various methods described herein.

According to the invention, the term "immunoreactive cell" means a cell which can mature into an immune cell (such as B cell, T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

Some therapeutic methods are based on a reaction of the immune system of a patient, which results in a lysis of antigen-presenting cells such as cancer cells which present one or more tumor-associated antigens. In this connection, for example autologous cytotoxic T lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-96/33265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for detecting specific clones of cytotoxic T lymphocytes (Altman et al., *Science* 274:94-96, 1996; Dunbar et al., *Curr. Biol.* 8:413-416, 1998). Soluble MHC class I molecules are folded in vitro in the presence of $\beta_2$ microglobulin and a peptide antigen binding to said class I molecule. The MHC/peptide complexes are purified and then labeled with biotin. Tetramers are formed by mixing the biotinylated peptide-MHC complexes with labeled avidin (e.g. phycoerythrin) in a molar ratio of 4:1. Tetramers are then contacted with cytotoxic T lymphocytes such as peripheral blood or lymph nodes. The tetramers bind to cytotoxic T lymphocytes which recognize the peptide antigen/MHC class I complex. Cells which are bound to the tetramers may be sorted by fluorescence-controlled cell sorting to isolate reactive cytotoxic T lymphocytes. The isolated cytotoxic T lymphocytes may then be propagated in vitro.

In a therapeutic method referred to as adoptive transfer (Greenberg, *J. Immunol.* 136(5):1917, 1986; Riddel et al., *Science* 257:238, 1992; Lynch et al., *Eur. J. Immunol.* 21:1403-1410, 1991; Kast et al., *Cell* 59:603-614, 1989), cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Often, of the T cell repertoire of a patient, only T cells with low affinity for a specific complex of this kind can be propagated, since those with high affinity have been extinguished due to development of tolerance. An alternative here may be a transfer of the T cell receptor itself. For this too, cells presenting the desired complex (e.g. dendritic cells) are combined with cytotoxic T lymphocytes of healthy individuals. This results in propagation of specific cytotoxic T lymphocytes with high affinity if the donor had no previous contact with the specific complex. The high affinity T cell receptor of these propagated specific T lymphocytes is cloned and can be transduced via gene transfer, for example using retroviral vectors, into T cells of other patients, as desired. Adoptive transfer is then carried out using these genetically altered T lymphocytes (Stanislawski et al., *Nat Immunol.* 2:962-70, 2001; Kessels et al., *Nat Immunol.* 2:957-61, 2001).

The therapeutic aspects above start out from the fact that at least some of the abnormal cells of the patient present a complex of a tumor-associated antigen and an HLA molecule. Such cells may be identified in a manner known per se. As soon as cells presenting the complex have been identified, they may be combined with a sample from the patient, which contains cytotoxic T lymphocytes. If the cytotoxic T lymphocytes lyse the cells presenting the complex, it can be assumed that a tumor-associated antigen is presented.

Adoptive transfer is not the only form of therapy which can be applied according to the invention. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting HLA molecule). Various cell types may be used. Furthermore, it is possible to use vectors which carry one or both of the genes of interest. Particular preference is given to viral or bacterial vectors. For example, nucleic acids coding for a tumor-associated antigen or for a part thereof may be functionally linked to promoter and enhancer sequences which control expression of said tumor-associated antigen or a fragment thereof in particular tissues or cell types. The nucleic acid may be incorporated into an expression vector. Expression vectors may be nonmodified extrachromosomal nucleic acids, plasmids or viral genomes into which exogenous nucleic acids may be inserted. Nucleic acids coding for a tumor-associated antigen may also be inserted into a retroviral genome, thereby enabling the nucleic acid to be integrated into the genome of the target tissue or target cell. In these systems, a microorganism such as vaccinia virus, pox virus, Herpes simplex virus, retrovirus or adenovirus carries the gene of interest and de facto "infects" host cells. Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen-presenting cells in vivo possible. The tumor-associated antigen or a fragment thereof may be represented as protein, as DNA (e.g. within a vector) or as RNA. The tumor-associated antigen is processed to produce a peptide partner for the HLA molecule, while a fragment thereof may be presented without the need for further processing. The latter is the case in particular, if these can bind to HLA molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor-associated antigen to a patient by intradermal injection, for example. However, injection may also be carried out intranodally into a lymph node (Maloy et al., *Proc Natl Acad Sci USA* 98:3299-303, 2001). It may also be carried out in combination with reagents which facilitate uptake into dendritic cells. Preferred tumor-associated antigens comprise those which react with allogenic cancer antisera or with T cells of many cancer patients. Of particular interest, however, are those against which no spontaneous immune responses pre-exist. Evidently, it is possible to induce against these immune responses which can lyse tumors (Keogh et al., *J. Immunol.* 167:787-96, 2001; Appella et al., *Biomed Pept Proteins Nucleic Acids* 1:177-84, 1995; Wentworth et al., *Mol Immunol.* 32:603-12, 1995).

The pharmaceutical compositions described according to the invention may also be used as vaccines for immunization. According to the invention, the terms "immunization" or "vaccination" mean an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization, one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and stimulating particular lymphocytes. Adjuvants are known and comprise in a nonlimiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., *Mol. Cells* 7:178-186, 1997), incomplete Freund's adjuvant, complete Freund's adjuvant, vitamin E, montanide, alum, CpG oligonucleotides (cf. Krieg et al., *Nature* 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 µg to about 100 µg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids. Examples of such costimulating molecules are B7-1 and B7-2 (CD80 and CD86, respectively) which are expressed on dendritic cells (DC) and interact with the CD28 molecule expressed on the T cells. This interaction provides a costimulation (signal 2) for an antigen/MHC/TCR-stimulated (signal 1) T cell, thereby enhancing propagation of said T cell and the effector function. B7 also interacts with CTLA4 (CD152) on T cells, and studies involving CTLA4 and B7 ligands demonstrate that B7-CTLA4 interaction can enhance antitumor immunity and CTL propagation (Zheng, P. et al., *Proc. Natl. Acad. Sci. USA* 95(11):6284-6289 (1998)).

B7 is typically not expressed on tumor cells so that these are no effective antigen-presenting cells (APCs) for T cells. Induction of B7 expression would enable tumor cells to stimulate more effectively propagation of cytotoxic T lymphocytes and an effector function. Costimulation by a combination of B7/IL-6/IL-12 revealed induction of IFN-gamma and Th1-cytokine profile in a T cell population, resulting in further enhanced T cell activity (Gajewski et al., *J. Immunol.* 154:5637-5648 (1995)).

A complete activation of cytotoxic T lymphocytes and a complete effector function require an involvement of T helper cells via interaction between the CD40 ligand on said T helper cells and the CD40 molecule expressed by dendritic cells (Ridge et al., *Nature* 393:474 (1998), Bennett et al., *Nature* 393:478 (1998), Schönberger et al., *Nature* 393:480 (1998)). The mechanism of this costimulating signal probably relates to the increase in B7 production and associated IL-6/IL-12 production by said dendritic cells (antigen-presenting cells). CD40-CD40L interaction thus complements the interaction of signal 1 (antigen/MHC-TCR) and signal 2 (B7-CD28).

The use of anti-CD40 antibodies for stimulating dendritic cells would be expected to directly enhance a response to tumor antigens which are usually outside the range of an inflammatory response or which are presented by nonprofessional antigen-presenting cells (tumor cells). In these situations, T helper and B7-costimulating signals are not provided. This mechanism could be used in connection with therapies based on antigen-pulsed dendritic cells or in situations in which T helper epitopes have not been defined in known TRA precursors.

The invention also provides for administration of nucleic acids, polypeptides or peptides. Polypeptides and peptides may be administered in a manner known per se. In one embodiment, nucleic acids are administered by ex vivo methods, i.e. by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The invention also provides for administering nucleic acids in vivo by using vectors such as viruses and target-controlled liposomes.

In a preferred embodiment, a viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Various methods may be used in order to introduce according to the invention nucleic acids into cells in vitro or in vivo. Methods of this kind comprise transfection of nucleic acid $CaPO_4$ precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants (e.g. CpG oligonucleotides) and cytokines and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of a particular condition characterized by expression of one or more tumor-associated antigens, the desired reaction relates to inhibition of the course of the disease. This comprises slowing down the progress of the disease and, in particular, interrupting the progress of the disease. The desired reaction in a treatment of a disease or of a condition may also be delay of the onset or a prevention of the onset of said disease or said condition.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 μg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, parabens and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixir or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

EXAMPLES

Materials and Methods

The terms "in silico" and "electronic" refer solely to the utilization of methods based on databases, which may also be used to simulate laboratory experimental processes.

Unless expressly defined otherwise, all other terms and expressions are used so as to be understood by the skilled worker. The techniques and methods mentioned are carried out in a manner known per se and are described, for example, in Sambrook et al., *Molecular Cloning: A Laboratory Manual,* 2nd edition (1989), Cold Spring Harbor Laboratory Press, Cold Spring Harbor, N.Y. All methods including the use of kits and reagents are carried out according to the manufacturers' information.

A. Data Mining-Based Strategy for Identifying Tumor-Associated Antigens

According to the invention, public human protein and nucleic acid databases were screened with regard to cancer-specific antigens accessible on the cell surface. The definition of the screening criteria required therefor, together with high throughput methods for analyzing, if possible, all proteins, formed the central component of this strategy.

The starting point consisted of the validated protein entries (NP) and, respectively, the corresponding mRNAs (NM) which have been deposited in the RefSeq database (Pruitt et al., *Trends Genet.* January; 16(1):44-47, 2000) of the National Center for Biotechnology Information (NCBI). Following the fundamental principle of gene→mRNA→protein, the proteins were first studied for the presence of one or more transmembrane domains. To this end, the protein analysis program TMHMM server v.2.0 (Krogh et al., *Journal of Molecular Biology* 305(3):567-580, 2001) was used and the results thereof then verified again using the program ALOM 2 (Nakai et al., *Genomics* 14:897-911, 1992). The prediction of further signal sequences which influenced the intracellular localisation of proteins was done using the programs PSORT II (Horton et al., *Intelligent Systems for Molecular Biology* 4:109-115, 1996) and iPSORT (Bannai et al., *Bioinformatics,* 18(2):298-305, 2002). The human NP fraction having a total of 19 110 entries provided 4634 filtered proteins.

The corresponding mRNA of each of these 4634 proteins, respectively, was then subjected to a homology search in the EST database (Boguski et al., *Nat. Genet.* 4(4):332-333, 1993) of the NCBI with the aid of the BLAST algorithm (Altschul et al., *Nucleic Acids Res.* 25:3389-3402, 1997). The screening criteria in this search were set to an e-value <10e-20 and a minimal sequence identity of 93% in such a way that the hits resulting therefrom with high probability could only be derived from the respective mRNA but not from the homologous transcripts. Almost all mRNAs provided at least one hit in the EST database wherein in some cases the number of hits exceeded 4000.

Subsequently, the tissue-specific origin of the underlying cDNA library as well as the name of the library were determined for each of these valid hits. The tissues resulting therefrom were divided into 4 different groups ranging from dispensable organs (group 3) to absolutely essential organs (group 0). Another group, group 4, consisted of any samples obtained from cancer tissue. The distribution of hits to the five groups was recorded in a table which was sorted according to the best ratio of the sum of groups 3 and 4 to the sum of groups 0-2. Those mRNAs whose EST hits originated exclusively from cancer tissue reached a top position, followed by those which can additionally be found also in tissues of dispensable organs of group 3. A further criterium for the significance of this distribution was the number of the independent cDNA libraries from which the ESTs were obtained and was recorded in a separate column of the table.

Since the transcripts determined in the first approach and the corresponding proteins are firstly hypothetic constructs, further screening criteria were used with the intention to prove the real existence of the mRNAs and consequently also of the proteins. For this purpose, each mRNA was compared to the predicted gene locus using the program "Spidey" (Wheelan et al., *Genome Res.* 11(11): 1952-1957, 2001). Only those transcripts which have at least one splicing process, i.e. which spread over at least 2 exons, were used for more detailed analyses.

Sequential application of all the filters mentioned led to the tumor-associated antigens of the invention which can be considered extracellularly accessible, owing to a predicted transmembrane domain and the topology related thereto. The expression profile derived from the EST data indicates, in all cases, cancer-specific expression which may at most extend only to dispensable organs.

B. Strategy of Validating the Tumor-Associated Antigens Identified by in Silico Analysis In order to utilize the targets for immunotherapeutic purposes (antibody therapy by means of monoclonal antibodies, vaccination, T-cell receptor-mediated therapeutic approaches; cf. EP-B-0 879 282), in cancer therapy as well as for diagnostic problems, the validation of the targets identified according to the invention is of central importance. In this connection, validation is carried out by expression analysis at both RNA and protein levels.

1. Examination of RNA Expression

The identified tumor antigens are first validated with the aid of RNA which is obtained from various tissues or from tissue-specific cell lines. Since the differential expression pattern of healthy tissue in comparison with tumor tissue is of decisive importance for the subsequent therapeutic application, the target genes are preferably characterized with the aid of these tissue samples.

Total RNA is isolated from native tissue samples or from tumor cell lines by standard methods of molecular biology. Said isolation may be carried out, for example, with the aid of the RNEASY Maxi RNA isolation kit (Qiagen, Cat. No. 75162) according to the manufacturer's instructions. This isolation method is based on the use of chaotropic reagent guanidinium isothiocyanate. Alternatively, acidic phenol can be used for isolation (Chomczynski & Sacchi, Anal. Biochem. 162: 156-159, 1987). After the tissue has been worked up by means of guanidinium isothiocyanate, RNA is extracted with acidic phenol, subsequently precipitated with isopropanol and taken up in DEPC-treated water.

2-4 μg of the RNA isolated in this way are subsequently transcribed into cDNA, for example by means of SUPERSCRIPT II reverse transcriptase kit (Invitrogen) according to the manufacturer's protocol. cDNA synthesis is primed with the aid of random hexamers (e.g. Roche Diagnostics) according to standard protocols of the relevant manufacturer. For quality control, the cDNAs are amplified over 30 cycles, using primers specific for the p53 gene which is expressed only lowly. Only p53-positive cDNA samples will be used for the subsequent reaction steps.

The antigens are analyzed in detail by carrying out an expression analysis by means of PCR or quantitative PCR (qPCR) on the basis of a cDNA archive which has been isolated from various normal and tumor tissues and from tumor cell lines. For this purpose, 0.5 μl of cDNA of the above reaction mixture is amplified by a DNA polymerase (e.g. 1 U of HOTSTARTAQ DNA polymerase kit, Qiagen) according to the protocols of the particular manufacturer (total volume of the reaction mixture: 25-50 μl). Aside from said polymerase, the amplification mixture comprises 0.3 mM dNTPs, reaction buffer (final concentration 1×, depending on the manufacturer of the DNA polymerase) and in each case 0.3 mM gene-specific forward and reverse primers.

The specific primers of the target gene are, as far as possible, selected in such a way that they are located in two different exons so that genomic contaminations do not lead to false-positive results. In a non-quantitative end point PCR, the cDNA is typically incubated at 95° C. for 15 minutes in order to denature the DNA and to activate the HOT-START enzyme. Subsequently the DNA is amplified over 35 cycles (1 min at 95° C., 1 min at the primer-specific hybridization temperature (approx. 55-65° C.), 1 min at 72° C. to elongate the amplicons). Subsequently, 10 μl of the PCR mixture are applied to agarose gels and fractionated in the electric field. The DNA is made visible in the gels by staining with ethidium bromide and the PCR result is documented by way of a photograph.

As an alternative to conventional PCR, expression of a target gene may also be analyzed by quantitative real time PCR. Meanwhile various analytical systems are available for this analysis, of which the best known ones are the ABI 7900 HT sequence detection system (Applied Biosystems), the ICYCLER PCR detection system (Biorad) and the LIGHT CYCLER PCR detection system (Roche Diagnostics). As described above, a specific PCR mixture is subjected to a run in the real time instruments. By adding a DNA-intercalating dye (e.g. ethidium bromide, CybrGreen), the newly synthesized DNA is made visible by specific light excitation (according to the dye manufacturers' information). A multiplicity of points measured during amplification enables the entire process to be monitored and the nucleic acid concentration of the target gene to be determined quantitatively. The PCR mixture is normalized by measuring a housekeeping gene (e.g. 18S RNA, β-actin, GAPDH). Alternative strategies via fluorescently labeled DNA probes likewise allow quantitative determination of the target gene of a specific tissue sample (see TAQMAN assay applications from Applied Biosystems).

2. Cloning

The complete target gene which is required for further characterization of the tumor antigen is cloned according to common molecular-biological methods (e.g. in "Current Protocols in Molecular Biology", John Wiley & Sons Ltd., Wiley InterScience). In order to clone the target gene or to analyze its sequence, said gene is first amplified by a DNA polymerase having a proof reading function (e.g. pfu, Roche Diagnostics). The amplicon is then ligated by standard methods into a cloning vector. Positive clones are identified by sequence analysis and subsequently characterized with the aid of prediction programs and known algorithms.

3. Production of Antibodies

The tumor-associated antigens identified according to the invention are characterized, for example, by using antibodies. The invention further comprises the diagnostic or therapeutic use of antibodies. Antibodies may recognize proteins in the native and/or denatured state (Anderson et al., *J. Immunol.* 143: 1899-1904, 1989; Gardsvoll, *J. Immunol. Methods* 234: 107-116, 2000; Kayyem et al., *Eur. J. Biochem.* 208: 1-8, 1992; Spiller et al., *J. Immunol. Methods* 224: 51-60, 1999).

Antisera comprising specific antibodies which specifically bind to the target protein may be prepared by various standard methods; cf., for example, "Monoclonal Antibodies: A Practical Approach" by Phillip Shepherd, Christopher Dean ISBN 0-19-963722-9, "Antibodies: A Laboratory Manual" by Ed Harlow, David Lane ISBN: 0879693142 and "Using Antibodies: A Laboratory Manual: Portable Protocol NO" by Edward Harlow, David Lane, Ed Harlow ISBN: 0879695447. It is also possible here to generate affine and specific antibodies which recognize complex membrane proteins in their native form (Azorsa et al., *J. Immunol. Methods* 229: 35-48, 1999; Anderson et al., *J. Immunol.* 143: 1899-1904, 1989; Gardsvoll, *J. Immunol. Methods.* 234: 107-116, 2000). This is especially important in the preparation of antibodies which are intended to be used therapeutically but also for many diagnostic applications. For this purpose, both the complete protein and extracellular partial sequences may be used for immunization.

Immunization and Production of Polyclonal Antibodies

Several immunization protocols have been published. A species (e.g. rabbits, mice) is immunized by a first injection of the desired target protein. The immune response of the animal to the immunogen can be enhanced by a second or third immunization within a defined period of time (approx. 2-4 weeks after the previous immunization). Blood is taken from said animals and immune sera obtained, again after various defined time intervals (1st bleeding after 4 weeks, then every 2-3 weeks, up to 5 takings). The immune sera taken in this way comprise polyclonal antibodies which may be used to detect and characterize the target protein in Western blotting, by flow cytometry, immunofluorescence or immunohistochemistry.

The animals are usually immunized by any of four well-established methods, with other methods also in existence. The immunization may be carried out using peptides specific for the target protein, using the complete protein, using extracellular partial sequences of a protein which can be identified experimentally or via prediction programs. Since the prediction programs do not always work perfectly, it is also possible to employ two domains separated from one another by a transmembrane domain. In this case, one of the two domains has to be extracellular, which may then be proved experimentally (see below). The immunization is provided by various commercial service providers.

(1) In the first case, peptides (length: 8-12 amino acids) are synthesized by in vitro methods (possibly carried out by a commercial service), and said peptides are used for immunization. Normally 3 immunizations are carried out (e.g. with a concentration of 5-100 μg/immunization).

(2) Alternatively, immunization may be carried out using recombinant proteins. For this purpose, the cloned DNA of the target gene is cloned into an expression vector and the target protein is synthesized, for example, cell-free in vitro, in bacteria (e.g. *E. coli*), in yeast (e.g. *S. pombe*), in insect cells or in mammalian cells, according to the conditions of the particular manufacturer (e.g. Roche Diagnostics, Invitrogen, Clontech, Qiagen). It is also possible to synthesize the target protein with the aid of viral expression systems (e.g. baculovirus, vacciniavirus, adenovirus). After it has been synthesized in one of said systems, the target protein is purified, normally by employing chromatographic methods. In this context, it is also possible to use for immunization proteins which have a molecular anchor as an aid for purification (e.g. His tag, Qiagen; FLAG epitope tag, Roche Diagnostics; GST fusion proteins). A multiplicity of protocols can be found, for example, in "Current Protocols in Molecular Biology", John Wiley & Sons Ltd., Wiley InterScience. After the target protein has been purified, an immunization is carried out as described above.

(3) If a cell line is available which synthesizes the desired protein endogenously, it is also possible to use this cell line directly for preparing the specific antiserum. In this case, immunization is carried out by 1-3 injections with in each case approx. 1-5×$10^7$ cells.

(4) The immunization may also be carried out by injecting DNA (DNA immunization). For this purpose, the target gene is first cloned into an expression vector so that the target sequence is under the control of a strong eukaryotic promoter (e.g. CMV promoter). Subsequently, DNA (e.g. 1-10 μg per injection) is transferred as immunogen using a gene gun into capillary regions with a strong blood flow in an organism (e.g. mouse, rabbit). The transferred DNA is taken up by the animal's cells, the target gene is expressed, and the animal finally develops an immune response to the target protein (Jung et al., *Mol. Cells* 12: 41-49, 2001; Kasinrerk et al., *Hybrid Hybridomics* 21: 287-293, 2002).

Production of Monoclonal Antibodies

Monoclonal antibodies are traditionally produced with the aid of the hybridoma technology (technical details: see "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142, "Using Antibodies: A Laboratory Manual: Portable Protocol NO" by Edward Harlow, David Lane, Ed Harlow ISBN: 0879695447). A new method which is also used is the "SLAM" technology. Here, B cells are isolated from whole blood and the cells are made monoclonal. Subsequently the supernatant of the isolated B cell is analyzed for its antibody specificity. In contrast to the hybridoma technology, the variable region of the antibody gene is then amplified by single-cell PCR and cloned into a suitable vector. In this manner production of monoclonal antibodies is accelerated (de Wildt et al., *J. Immunol. Methods* 207:61-67, 1997).

4. Validation of the Targets by Protein-Chemical Methods Using Antibodies

The antibodies which can be produced as described above can be used to make a number of important statements about the target protein. Specifically the following analyses of validating the target protein are useful:

Specificity of the Antibody

Assays based on cell culture with subsequent Western blotting are most suitable for demonstrating the fact that an antibody binds specifically only to the desired target protein (various variations are described, for example, in "Current Protocols in Proteinchemistry", John Wiley & Sons Ltd., Wiley InterScience). For the demonstration, cells are transfected with a cDNA for the target protein, which is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). As an alternative, it is also possible to use cell lines which express the target gene endogenously (detection via target gene-specific RT-PCR). As a control, in the ideal case, homologous genes are cotransfected in the experiment, in order to be able to demonstrate in the following Western blot the specificity of the analyzed antibody.

In the subsequent Western blotting, cells from cell culture or tissue samples which might contain the target protein are lysed in a 1% strength SDS solution, and the proteins are denatured in the process. The lysates are fractionated according to size by electrophoresis on 8-15% strength denaturing polyacrylamide gels (contain 1% SDS) (SDS polyacrylamide gel electrophoresis, SDS-PAGE). The proteins are then transferred by one of a plurality of blotting methods (e.g. semi-dry electroblot; Biorad) to a specific membrane (e.g. nitrocellulose, Schleicher & Schüll). The desired protein can be visualized on this membrane. For this purpose, the membrane is first incubated with the antibody which recognizes the target protein (dilution approx. 1:20-1:200, depending on the specificity of said antibody), for 60 minutes. After a washing step, the membrane is incubated with a second antibody which is coupled to a marker (e.g. enzymes such as peroxidase or alkaline phosphatase) and which recognizes the first antibody. It is then possible to make the target protein visible on the membrane in a color or chemiluminescent reaction (e.g. ECL, Amersham Bioscience). An antibody with a high specificity for the target protein should in the ideal case only recognise the desired protein itself.

Localization of the Target Protein

Various methods are used to confirm the membrane localization, identified in the in silico approach, of the target protein. An important and well-established method using the antibodies described above is immunofluorescence (IF). For this purpose, cells of established cell lines which either synthesize the target protein (detection of the RNA by RT-PCR or of the protein by Western blotting) or else have been transfected with plasmid DNA are utilized. A wide variety of methods (e.g. electroporation, liposome-based transfection, calcium phosphate precipitation) are well established for transfection of cell lines with DNA (e.g. Lemoine et al., *Methods Mol. Biol.* 75: 441-7, 1997). The plasmid transfected, in immunofluorescence, may encode the unmodified protein or else couple different amino acid markers to the target protein. The principle markers are, for example, the fluorescent green fluorescent protein (GFP) in various differentially fluorescent forms, short peptide sequences of 6-12 amino acids for which high-affinity and specific antibodies are available, or the short amino acid sequence Cys-Cys-X-X-Cys-Cys (SEQ ID NO: 114) which can bind via its cysteines specific fluorescent substances (Invitrogen). Cells which synthesize the target protein are fixed, for example, with paraformaldehyde or methanol. The cells may then, if required, be permeabilized by incubation with detergents (e.g. 0.2% TRITON X-100 solution). The cells are then incubated with a primary antibody which is directed against the target protein or against one of the coupled markers. After a washing step, the mixture is incubated with a second antibody coupled to a fluorescent marker (e.g. fluorescein, Texas Red, Dako), which binds to the first antibody. The cells labeled in this way are then overlaid with glycerol and analyzed with the aid of a fluorescence microscope according to the manufacturer's information. Specific fluorescence emissions are achieved in this case by specific excitation depending on the substances employed. The analysis usually permits reliable localization of the target protein, the antibody quality and the target protein being confirmed in double stainings with, in addition to the target protein, also the coupled amino acid markers or other marker proteins whose localization has already been described in the literature being stained. GFP and its derivatives represent a special case, being excitable directly and themselves fluorescing. The membrane permeability which may be controlled through the use of detergents, in immunofluorescence, allows demonstration of whether an immunogenic epitope is located inside or outside the cell. The prediction of the selected proteins can thus be supported experimentally. An alternative possibility is to detect extracellular domains by means of flow cytometry. For this purpose, cells are fixed under non-permeabilizing conditions (e.g. with PBS/Na azide/2% FCS/5 mM EDTA) and analyzed in a flow cytometer in accordance with the manufacturer's instructions. Only extracellular epitopes can be recognized by the antibody to be analyzed in this method. A difference from immunofluorescence is that it is possible to distinguish between dead and living cells by using, for example, propidium iodide or Trypan blue, and thus avoid false-positive results.

Another important detection is by immunohistochemistry (IHC) on specific tissue samples. The aim of this method is to identify the localization of a protein in a functionally intact tissue aggregate. IHC serves specifically for (1) being able to estimate the amount of target protein in tumor and normal tissues, (2) analyzing how many cells in tumor and healthy tissues express the target gene, and (3) defining the cell type in a tissue (tumor, healthy cells) in which the target protein is detectable. Alternatively, the amounts of protein of a target gene may be quantified by tissue immunofluorescence using a digital camera and suitable software (e.g. Tillvision, Till-photonics, Germany). The technology has frequently been published, and details of staining and microscopy can therefore be found, for example, in "Diagnostic Immunohistochemistry" by David J., MD Dabbs ISBN: 0443065667 or in "Microscopy, Immunohistochemistry, and Antigen Retrieval Methods: For Light and Electron Microscopy" ISBN: 0306467704. It should be noted that, owing to the properties of antibodies, different protocols have to be used (an example is described below) in order to obtain a meaningful result.

Normally, histologically defined tumor tissues and, as reference, comparable healthy tissues are employed in IHC. It is also possible to use as positive and negative controls cell lines in which the presence of the target gene is known through RT-PCR analyses. A background control must always be included.

Formalin-fixed (another fixation method, for example with methanol, is also possible) and paraffin-embedded tissue pieces with a thickness of 4 μm are applied to a glass support and deparaffinated with xylene, for example. The samples are washed with TBS-T and blocked in serum. This is followed by incubation with the first antibody (dilution: 1:2 to 1:2000) for 1-18 hours, with affinity-purified antibodies normally being used. A washing step is followed by incubation with a second antibody which is coupled to an alkaline phosphatase (alternative: for example peroxidase) and directed against the first antibody, for approx. 30-60 minutes. This is followed by a color reaction using said alkaline phosphatase (cf., for example, Shi et al., *J. Histochem. Cytochem.* 39: 741-748, 1991; Shin et al., *Lab. Invest.* 64: 693-702, 1991). To demonstrate antibody specificity, the reaction can be blocked by previous addition of the immunogen.

Analysis of Protein Modifications

Secondary protein modifications such as, for example, N- and O-glycosylations or myristilations may impair or even completely prevent the accessibility of immunogenic epitopes and thus call into question the efficacy of antibody therapies. Moreover, it has frequently been demonstrated that the type and amount of secondary modifications differ in normal and tumor tissues (e.g. Durand & Seta, 2000*; Clin. Chem.* 46: 795-805; Hakomori, 1996*; Cancer Res.* 56: 5309-18). The analysis of these modifications is therefore essential to the therapeutic success of an antibody. Potential binding sites can be predicted by specific algorithms.

Analysis of protein modifications usually takes place by Western blotting (see above). Glycosylations which usually have a size of several kDa, especially lead to a larger total mass of the target protein, which can be fractionated in SDS-PAGE. To detect specific O- and N-glycosidic bonds, protein lysates are incubated prior to denaturation by SDS with O- or N-glycosylases (in accordance with their respective manufacturer's instructions, e.g. PNgase, endoglycosidase F, endoglycosidase H, Roche Diagnostics). This is followed by Western blotting as described above. Thus, if there is a reduction in the size of a target protein after incubation with a glycosidase, it is possible to detect a specific glycosylation and, in this way, also analyze the tumor specificity of a modification.

Functional Analysis of the Target Gene

The function of the target molecule may be crucial for its therapeutic usefulness, so that functional analyses are an important component in the characterization of therapeutically utilizable molecules. The functional analysis may take place either in cells, in cell culture experiments or else in vivo with the aid of animal models. This involves either switching off the gene of the target molecule by mutation (knockout) or inserting the target sequence into the cell or the organism (knockin). Thus it is possible to analyze functional modifications in a cellular context firstly by way of the loss of function of the gene to be analyzed (loss of function). In the second case, modifications caused by addition of the analyzed gene can be analyzed (gain of function).

A. Functional Analysis in Cells

Transfection. In order to analyze the gain of function, the gene of the target molecule must be transferred into the cell. For this purpose, cells are transfected with a DNA which allows synthesis of the target molecule. Normally, the gene of the target molecule here is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). The gene may be synthesized either transiently, without genomic integration, or else stably, with genomic integration after selection with neomycin, for example.

RNA interference (siRNA). An inhibition of expression of the target gene, which may induce a complete loss of function of the target molecule in cells, may be generated by the RNA interference (siRNA) technology in cells (Hannon, G J. 2002. RNA interference. *Nature* 418: 244-51; Czauderna et al. 2003. *Nucl. Acid Res.* 31: 670-82). For this purpose, cells are transfected with short, double-stranded RNA molecules of approx. 20-25 nucleotides in length, which are specific for the target molecule. An enzymic process then results in degradation of the specific RNA of the target gene and thus in an inhibition of the function of the target protein and consequently enables the target gene to be functionally analyzed.

Cell lines which have been modified by means of transfection or siRNA may subsequently be analyzed in different ways. The most common examples are listed below.

1. Proliferation

A multiplicity of methods for analyzing cell proliferation are established and are commercially supplied by various companies (e.g. Roche Diagnostics, Invitrogen; details of the assay methods are described in the numerous application protocols). The number of cells in cell culture experiments can be determined by simple counting or by colorimetric assays which measure the metabolic activity of the cells (e.g. wst-1, Roche Diagnostics). Metabolic assay methods measure the number of cells in an experiment indirectly via enzymic markers. Cell proliferation may be measured directly by analyzing the rate of DNA synthesis, for example by adding bromodeoxyuridine (BrdU), with the integrated BrdU being detected colorimetrically via specific antibodies.

2. Apoptosis and Cytotoxicity

A large number of assay systems for detecting cellular apoptosis and cytotoxicity are available. A decisive characteristic is the specific, enzyme-dependent fragmentation of genomic DNA, which is irreversible and results in any case in death of the cell. Methods for detecting these specific DNA fragments are commercially obtainable. An additional method available is the TUNEL assay which can detect DNA single-strand breaks also in tissue sections. Cytotoxicity is mainly detected via an altered cell permeability which serves as marker of the vitality state of cells. This involves on the one hand the analysis of markers which can typically be found intracellularly in the cell culture supernatant. On the other hand, it is also possible to analyze the absorbability of dye markers which are not absorbed by intact cells. The best-known examples of dye markers are Trypan blue and propidium iodide, a common intracellular marker is lactate dehydrogenase which can be detected enzymatically in the supernatant. Different assay systems of various commercial suppliers (e.g. Roche Diagnostics, Invitrogen) are available.

3. Migration Assay

The ability of cells to migrate is analyzed in a specific migration assay, preferably with the aid of a Boyden chamber (Corning Costar) (Cinamon G., Alon R. *J. Immunol. Methods.* 2003 February; 273(1-2):53-62; Stockton et al. 2001. *Mol. Biol. Cell.* 12: 1937-56). For this purpose, cells are cultured on a filter with a specific pore size. Cells which can migrate are capable of migrating through this filter into another culture vessel below. Subsequent microscopic analysis then permits determination of a possibly altered migration behavior induced by the gain of function or loss of function of the target molecule.

B. Functional Analysis in Animal Models

A possible alternative of cell culture experiments for the analysis of target gene function are complicated in vivo experiments in animal models. Compared to the cell-based methods, these models have the advantage of being able to detect faulty developments or diseases which are detectable only in the context of the whole organism. A multiplicity of models for human disorders are available by now (Abate-Shen & Shen. 2002. *Trends in Genetics* 51-5; Matsusue et al. 2003. *J. Clin. Invest.* 111:737-47). Various animal models such as, for example, yeast, nematodes or zebra fish have since been characterized intensively. However, models which are preferred over other species are animal models such as, for example, mice (*Mus musculus*) because they offer the best possibility of reproducing the biological processes in a human context. For mice, on the one hand transgenic methods which integrate new genes into the mouse genome have been established in recent years (gain of function; Jegstrup I. et al. 2003. *Lab Anim.* 2003 January; 37(1):1-9). On the other hand, other methodical approaches switch off genes in the mouse genome and thus induce a loss of function of a desired gene (knockout models, loss of function; Zambrowicz B P & Sands A T. 2003. *Nat. Rev. Drug Discov.* 2003 January; 2(1):38-51; Niwa H. 2001. *Cell Struct. Funct.* 2001 June; 26(3):137-48); technical details have been published in large numbers.

After the mouse models have been generated, alterations induced by the transgene or by the loss of function of a gene can be analyzed in the context of the whole organism (Balling R, 2001. *Ann. Rev. Genomics Hum. Genet.* 2:463-92). Thus it is possible to carry out, for example, behavior tests as well as to biochemically study established blood parameters. Histological analyses, immunohistochemistry or electron microscopy enable alterations to be characterized at the cellular level. The specific expression pattern of a gene can be detected by in-situ hybridization (Peters et al. 2003. *Hum. Mol. Genet* 12:2109-20).

Example 1: Identification of the Hypothetical Protein FLJ31461 as Diagnostic and Therapeutic Cancer Target Using gene prediction programs, F1131461 (SEQ ID NO: 1) filed under the gene bank accession number NM_152454 was determined as putative functionally not previously characterised gene on chromosome 15 (15q25.3). Two possible open reading frames result from the sequence deposited with the gene bank. The first reading frame encodes a protein with a length of 136 amino acids. The gene product (SEQ ID NO: 2) which was deposited in the RefSeq data bank of the NCBI under number NP_689667, accordingly has a calculated molecular weight of about 15 kDa. The second reading frame encodes a protein with a length of 100 amino acids (nucleotide sequence: SEQ ID NO: 69; amino acid sequence: SEQ ID NO: 70).

In sequence analyses of the gene FLJ31461 cloned by us, we were surprised to find the insertion of a nucleotide in the coding region in comparison to the sequences deposited in the databases. This results in a shifting of the reading frame. Two completely new open reading frames, which cannot be derived from the sequences already deposited in sequence databases, are the result. Hereby the new reading frame (SEQ ID NO: 71) encodes a new hypothetical protein with a length of 96 amino acids (SEQ ID NO: 72). SEQ ID NO: 73 encodes a hypothetical protein with the length of 133 amino acids (SEQ ID NO: 74). Because we have to assume, that the original depositions with the databases are incorrect, we have focussed further investigations on SEQ ID NO: 71, SEQ ID NO: 72, SEQ ID NO: 73 and SEQ ID NO: 74.

Figure 1B:
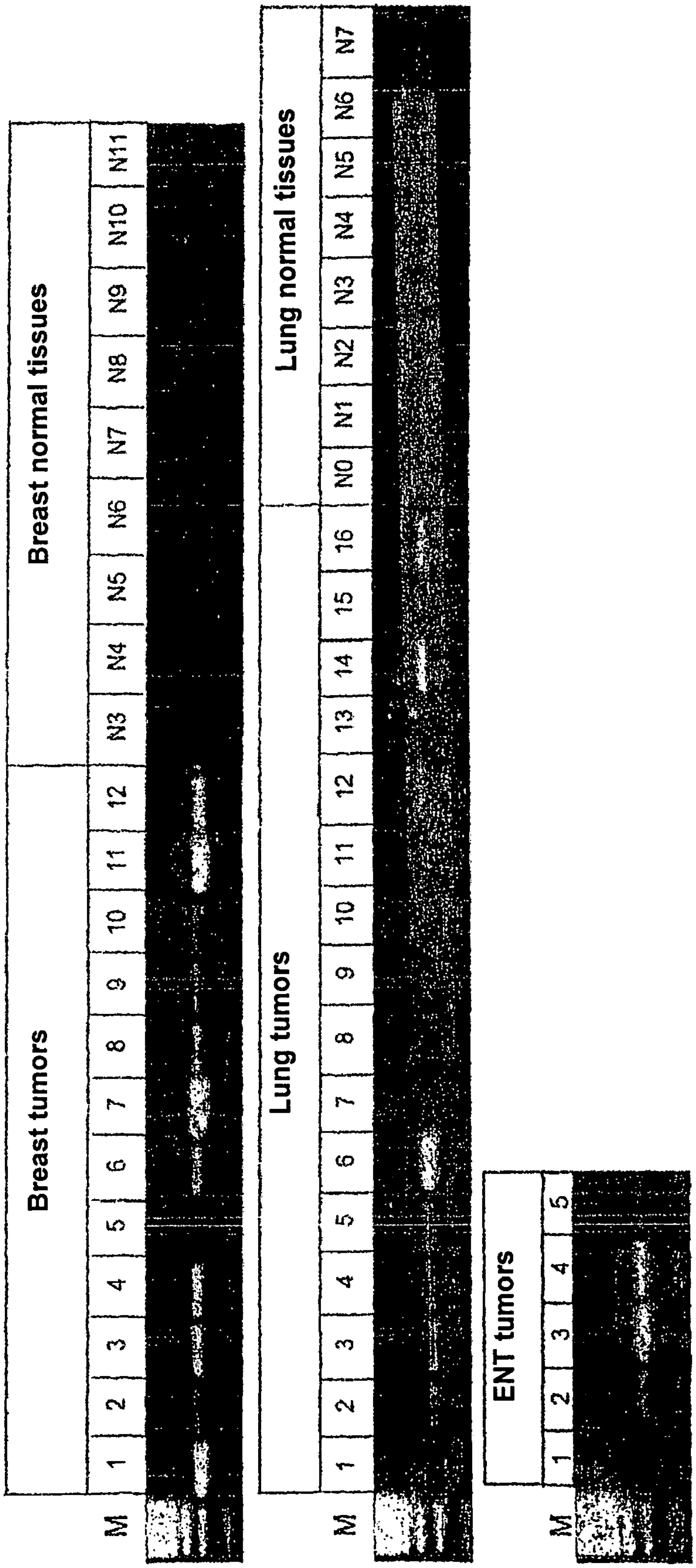
FIG. 1B: Gel image of a conventional RT-PCR-analysis of FLJ31461 in tumors of the breast, lungs and ear, nose and throat with the appropriate normal tissues $N_x$; M: DNA-length marker.
Figure 1C:
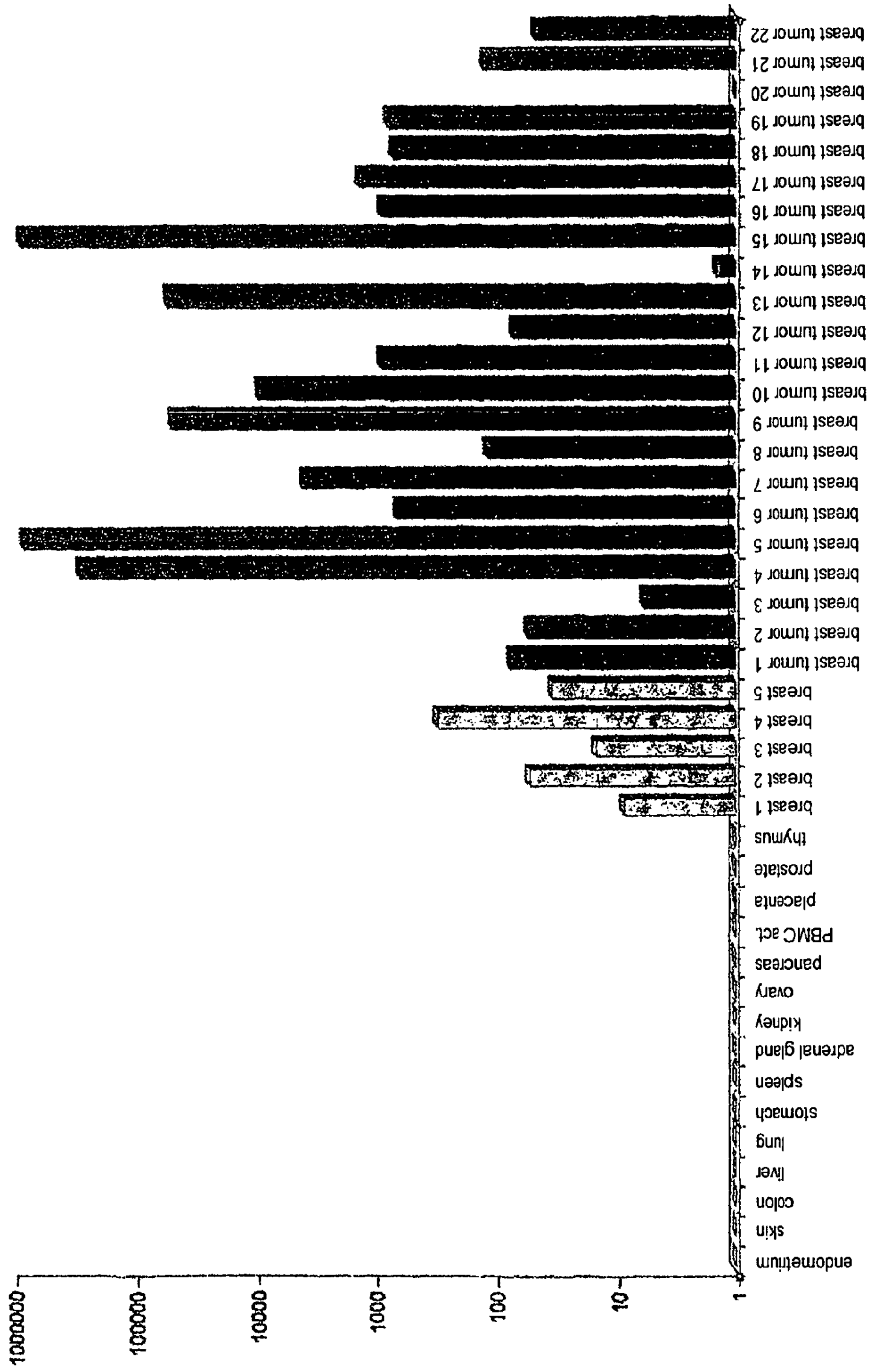
FIG. 1C: Quantitative expression analysis in various normal tissues (left) and in breast tumors in a logarithmic representation of the relative expression (x-fold activation). In almost all breast tumors and at least 100-fold overexpression of FLJ31461 is observed in comparison to the level of expression in healthy tissues.

In accordance with the invention, after the establishment of F1131461-specific quantitative RT-PCR (primer with the SEQ ID NO: 31, 32, 91, 92, 93, 94) the quantity of gene-specific transcripts was investigated in healthy tissue and in carcinoma samples (FIG. 1). With the exception of the testis, FLJ31461 cannot be detected in any of the normal tissues investigated by us (FIG. 1A). FLJ31461 is therefore with great probability a strongly gamete-specific gene-product. Surprisingly, we found during the analysis of tumors that FLJ31461 is switched on in many tumor types, while it is below the detection limit in the corresponding normal tissues (FIG. 1A-D). This does not only apply to virtually all breast tumors investigated by us (FIG. 1C) and also a series of lung tumors and nose-throat carcinomas, but also other neoplasias with varying frequency (FIG. 1D).

FLJ31461 is therefore a highly specific molecular marker for tumor tissues, which may be used diagnostically as well as therapeutically. As a typical representative of the class of so-called cancer/testis-antigens, which due to their selective tissue distribution serve as markers, this gene product can for example guarantee the precise targeting of tumor cells without damage to the normal tissues. Cancer/testis-genes are regarded as attractive target structures for targeted therapies and are already tested for specific immunotherapeutic approaches in cancerous diseases in phase I/II studies (i.e. Scanlan M J, Gure A O, Jungbluth A A, Old L J, Chen Y T. 2002. *Immunol. Rev.* 2002 October; 188: 22-32).

In order to confirm these data on protein level, specific antibodies or immune sera have been generated by immunisation of animals. The protein topology was predicted by analysis of the transmembrane domains of SEQ ID NO: 72 and SEQ ID NO: 74 with bioinformatics tools (TMHMM, TMPRED). In this way for SEQ ID NO: 72 for example two transmembrane domains were predicted; the N-terminus and C-terminus of the protein are extracellular.

In accordance with the invention, peptide epitopes were chosen for immunisation, particularly extracellular peptide epitopes, which are specific for both protein variants.

Amongst others, the following peptides were selected for immunization in order to produce antibodies: SEQ ID NO: 61, 62, 96, 97.

Figure 2:
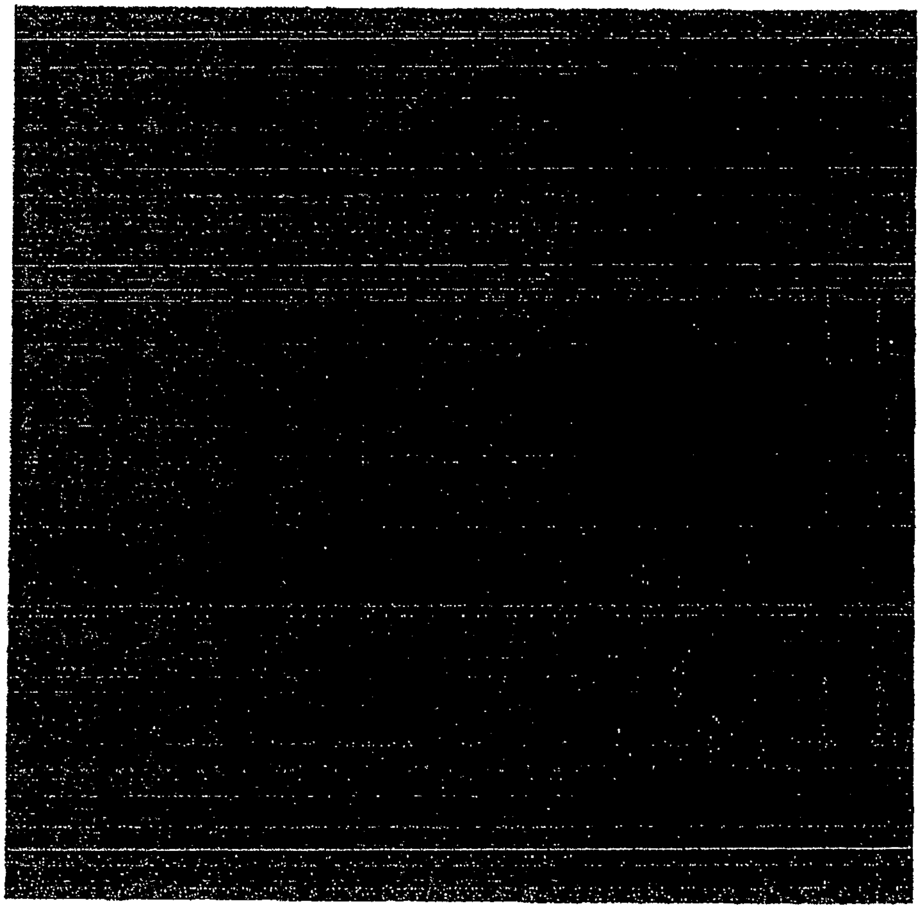
FIG. 2: Representation of the cellular localisation of the FLJ31461-protein.

By way of example the data for the antibody produced by immunisation using SEQ ID NO: 96, are shown. The specific antibody may be used under various fixation conditions for immunofluorescence investigations. In comparative staining of RT-PCR-positive as well as negative cell-lines, the respective protein is in well detectable quantity specific amongst others in those breast carcinoma cell-lines that were typed positive using quantitative RT-PCR (FIG. 2). The endogenous protein in this case presents membrane-localised.

Figure 3A:
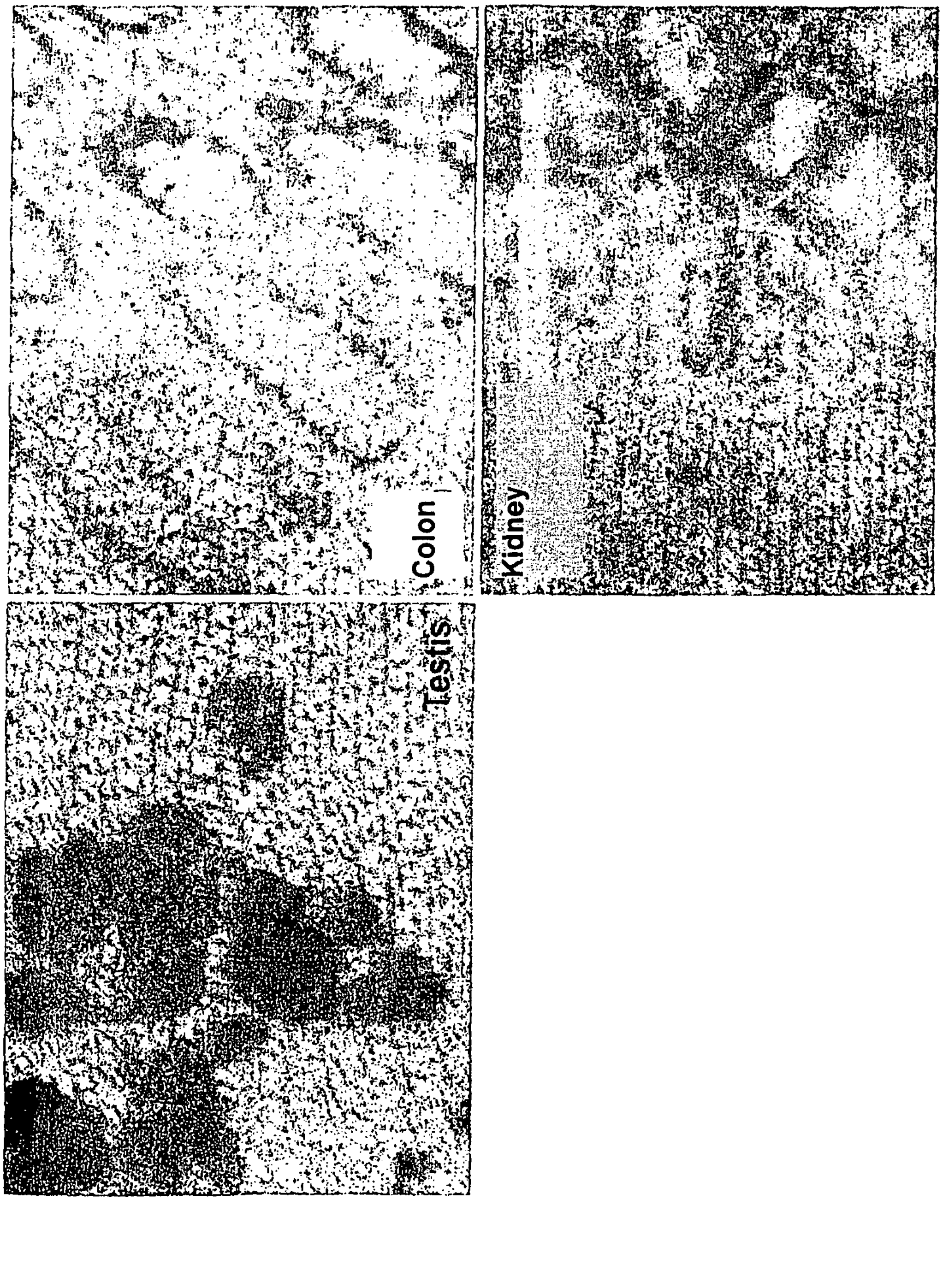
FIG. 3A: Normal tissue of testis (positive membrane localisation), colon and kidney (negative membrane localisation).
Figure 3B:
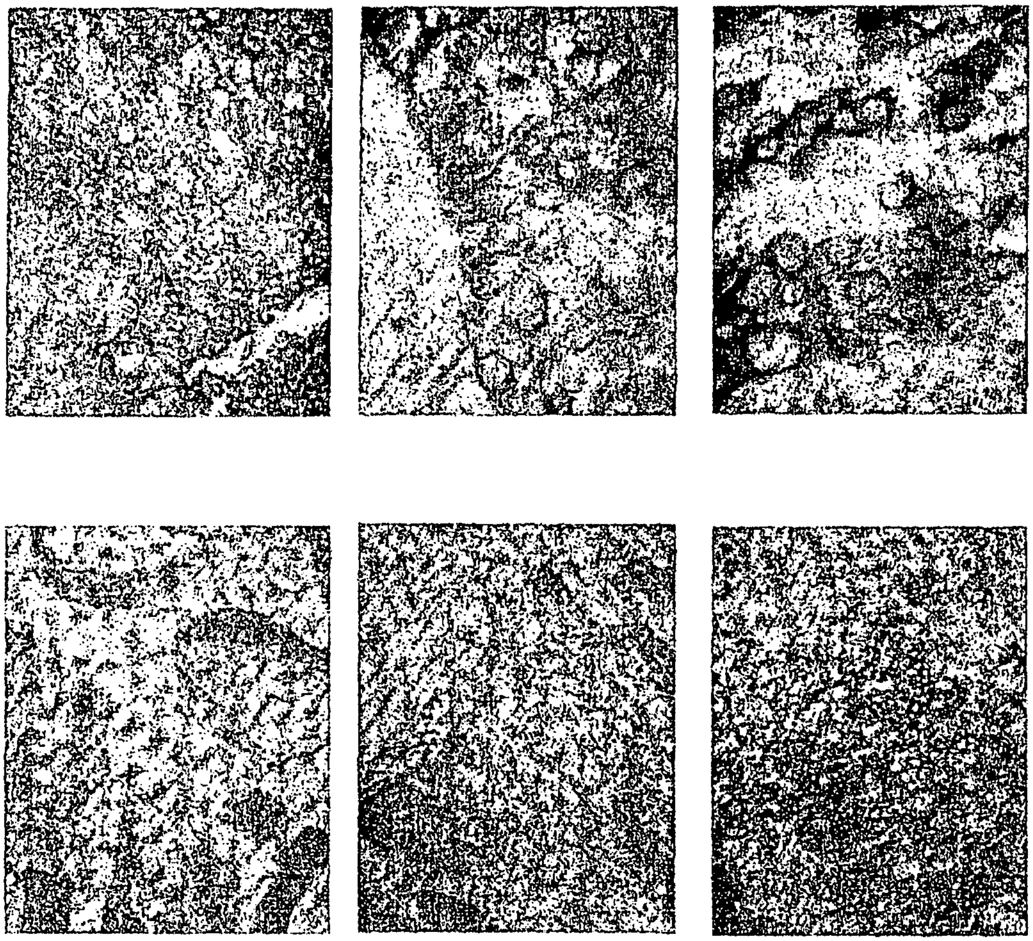
FIG. 3B: Detection of the FLJ31461-protein in a bronchial carcinoma, a cervical carcinoma as well as a lymphatic node metastasis of a breast tumor in an overview (left column) and in detail (right column).

Such antibodies are suitable for immunohistochemical staining of human tissue sections. To a large extent we were able to confirm the tissue distribution found on transcript level. While we observed hardly any reactivity of the antibody in normal tissue with the exception of testis tissue (FIG. 3A), antibodies against FLJ31461 stain various human tumor preparations, amongst these the tumors of breast and lung (FIG. 3B). The staining of the cells occurs accentuated at the membranes, which indicates a localisation of the protein at the cell surface. Surprisingly, we found that particularly metastases of tumors (FIG. 3B) express this protein particularly frequently and in a high proportion of cells.

These data indicate on one hand, that this gene found by us indeed does form a protein, that this protein is highly specific for human tumors and that it is present on the surface membrane of such tumor cells. Therefore this protein is accessible particularly for therapeutic antibodies. Likewise, our data prove, that specific antibodies against this protein may be produced. These antibodies bind selectively via the marker FLJ31461 to tumor cells.

In accordance with the invention such antibodies may be used for diagnostic purposes for example immunohistology. In particular, such antibodies may be used therapeutically. The produced antibodies can also be used directly for the production of chimeric or humanised recombinant antibodies. This can also be done directly with antibodies obtained from rabbits (cf. *J. Biol Chem.* 2000 May 5; 275(18):13668-76 by Rader C, Ritter G, Nathan S, Elia M, Gout I, Jungbluth A A, Cohen L S, Welt S, Old L J, Barbas C F 3rd "The rabbit antibody repertoire as a novel source for the generation of therapeutic human antibodies"). In order to achieve this, lymphocytes were taken from immunised animals. FLJ31461 is also a highly attractive target for immunotherapeutic procedures, such as vaccines or the adoptive transfer of antigen-specific T-lymphocytes.

Example 2: Identification of DSG4 (Desmoglein 4) as Diagnostic and Therapeutic Cancer Target Gene DSG4 (desmoglein 4; SEQ ID NO: 75) with its translation product (SEQ ID NO: 76) is a member of the desmosomal cadherin-family. The gene consists of 16 exons and is located on chromosome 18 (18q12). The derived amino acid sequence encodes a precursor protein with a length of 1040 amino acids. The processed protein (N-terminally truncated by 49 amino acids) has a length of 991 amino acids and without modifications a molecular weight of about 108 kDa. It must be assumed that DSG4 is a glycosylised type 1 cell surface protein, just like other desmogleins. DSG4 was able to be detected as constituent of desmosomes (Kljuic et al. 2003. *Cell* 113: 249-260). Desmosomes are complex intercellular connections, which provide epithelial tissues (such as the epidermis) with mechanical stability. Auto-antibodies against other members of the desmoglein-family appear to contribute to the loss of cell-cell-contacts in the epidermis by binding to desmosomes and appear to contribute to the skin disease Pemphigus vulgaris. It has been described that DSG4 is not expressed in most healthy tissues. Significant expression has to date only been reported for salivary gland, testis, prostate and skin (Whittock, Bower 2003. *J Invest Derm* 120: 523-530). A connection with tumor diseases has not been discussed previously.

In accordance with the invention, the expression was investigated on healthy tissues and tumors using DSG4-specific oligonucleotides. Several DSG4-specific primer pairs were used for RT-PCR-investigations in accordance with the invention. These are: DSG4 primer pair SEQ ID NO: 77, 78 (exon 10 and exon 12), DSG4-primer pair SEQ ID NO: 83, 84 (exon 1 and exon 5), DSG4-primer pair SEQ ID NO: 89, 90 (exon 5 and exon 8) and DSG4-primer pair SEQ ID NO: 95, 78 (exon 8 and exon 12).

Figure 4A:
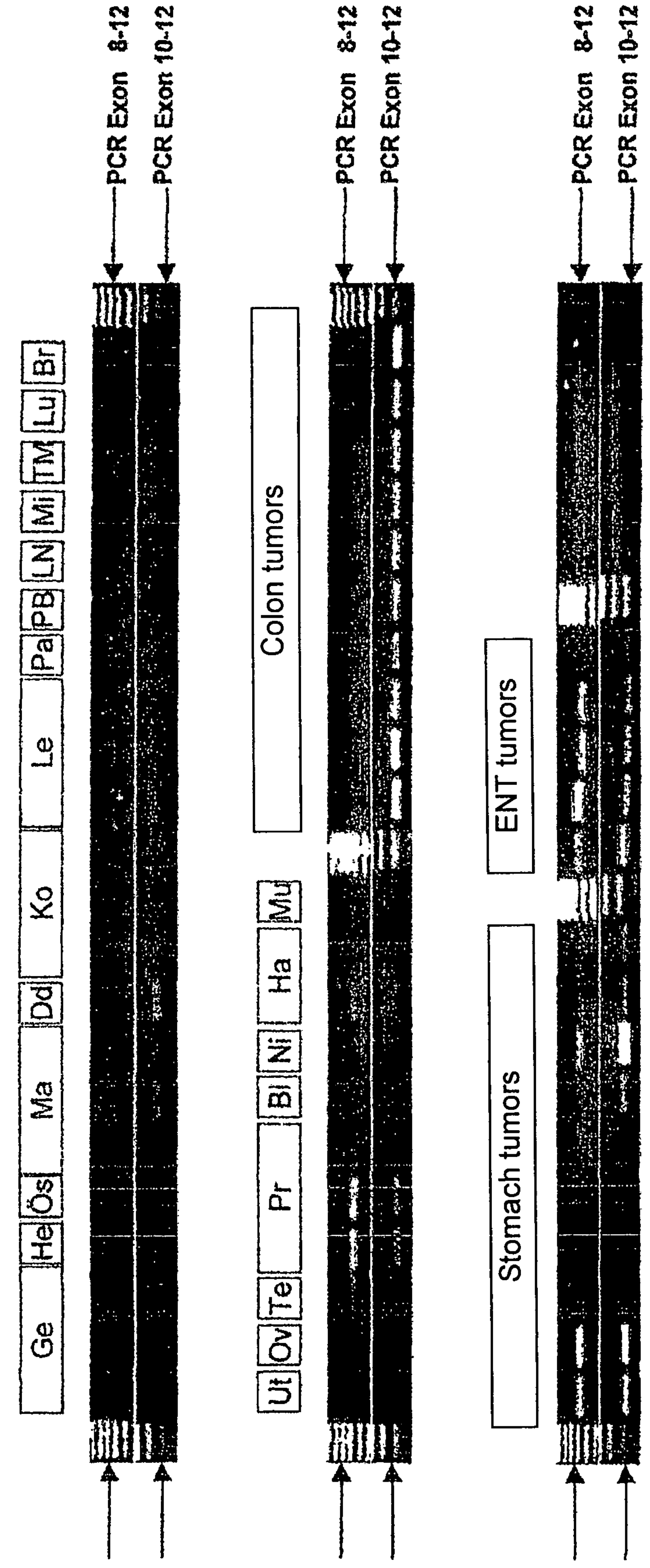
FIG. 4A: The PCR on normal tissues and various tumors was carried out using DSG4-specific oligonucleotides in exons 8-12 and exons 10-12. The dominant expression of the transcript of exons 10-12 is recognisable in colon tumors, while the transcript of exons 8-12 is also clearly expressed in normal tissues. Ge: brain, Dd: duodenum, Pa: pancreas, Mi: spleen, Te: testis, He: heart, Ko: colon, LN: lymphatic node, TM: thymus, Pr: prostate, Ös: esophagus, Le: liver, PB: active PBMC, Lu: lung, Bl: bladder, Ma: stomach, Br: breast, Ut: uterus, Ov: ovary, Ni: kidney, Ha: skin, Mu: muscle.
Figure 4C:
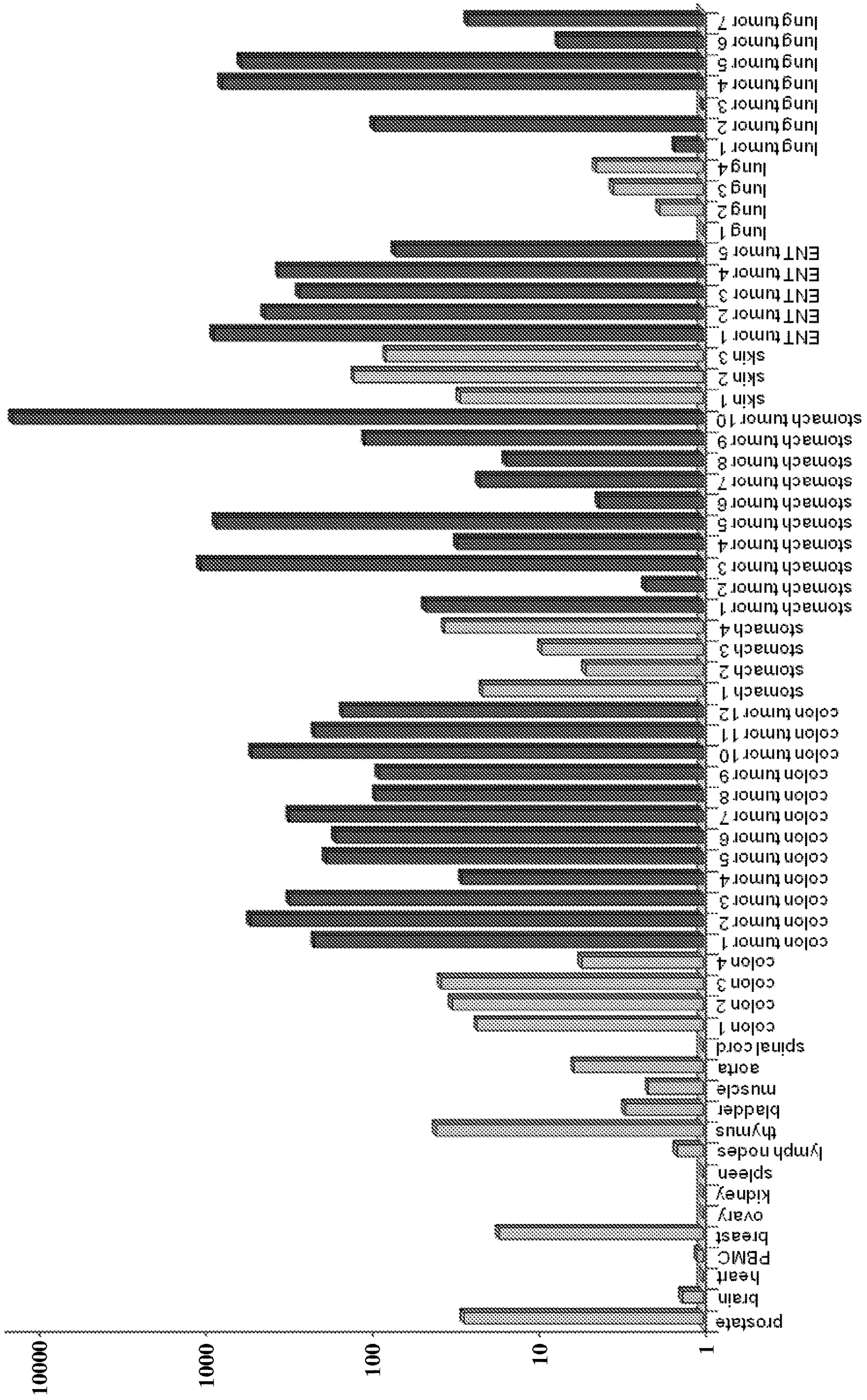
FIG. 4C: Quantitative expression analysis of the transcript section of the DSG4-exons 10-12 in normal tissues (left) and in tumors of the colon, stomach and the ear-nose-throat area in logarithmic representation of relative expression (x-fold activation). Most tumors exhibited an at least 50-fold overexpression of the DSG4-exons 10-12 in comparison to the expression levels in healthy tissues.

The investigation using all primer pairs confirmed that DSG4 is not expressed in most normal tissues. Depending on the primer pair however different expression patters were observed (FIG. 4B). With primer pairs SEQ ID NO: 95, 78 (exons 8-12) no expression was detected in normal tissue, with the exception of a very slight expression in prostate and skin. Surprisingly, DSG4 can be detected using this primer pair in a series of tumors. These are in particular tumors of the stomach, as well as carcinomas of the mouth, nose and throat area (FIG. 4A).

With primer pairs SEQ ID NO: 77, 78 (exons 10-12) even the expression in the above mentioned normal tissues of prostate and skin was less pronounced. Surprisingly, with this primer pair a more pronounced expression was observed in tumors (FIG. 4A). On one hand these tumors are those, which were conspicuous in investigations using the first primer pair, such as tumors of the stomach and carcinomas of the mouth, nose and throat area, but also other types of cancer (FIG. 4B, C). In particular in all intestinal tumors we detected a significant and high expression, which we were not able to detect using the first primer pair. The expression in the various tumors was manifold above that in the highest expressing toxicity-relevant normal tissue (FIG. 4B).

Figure 5:
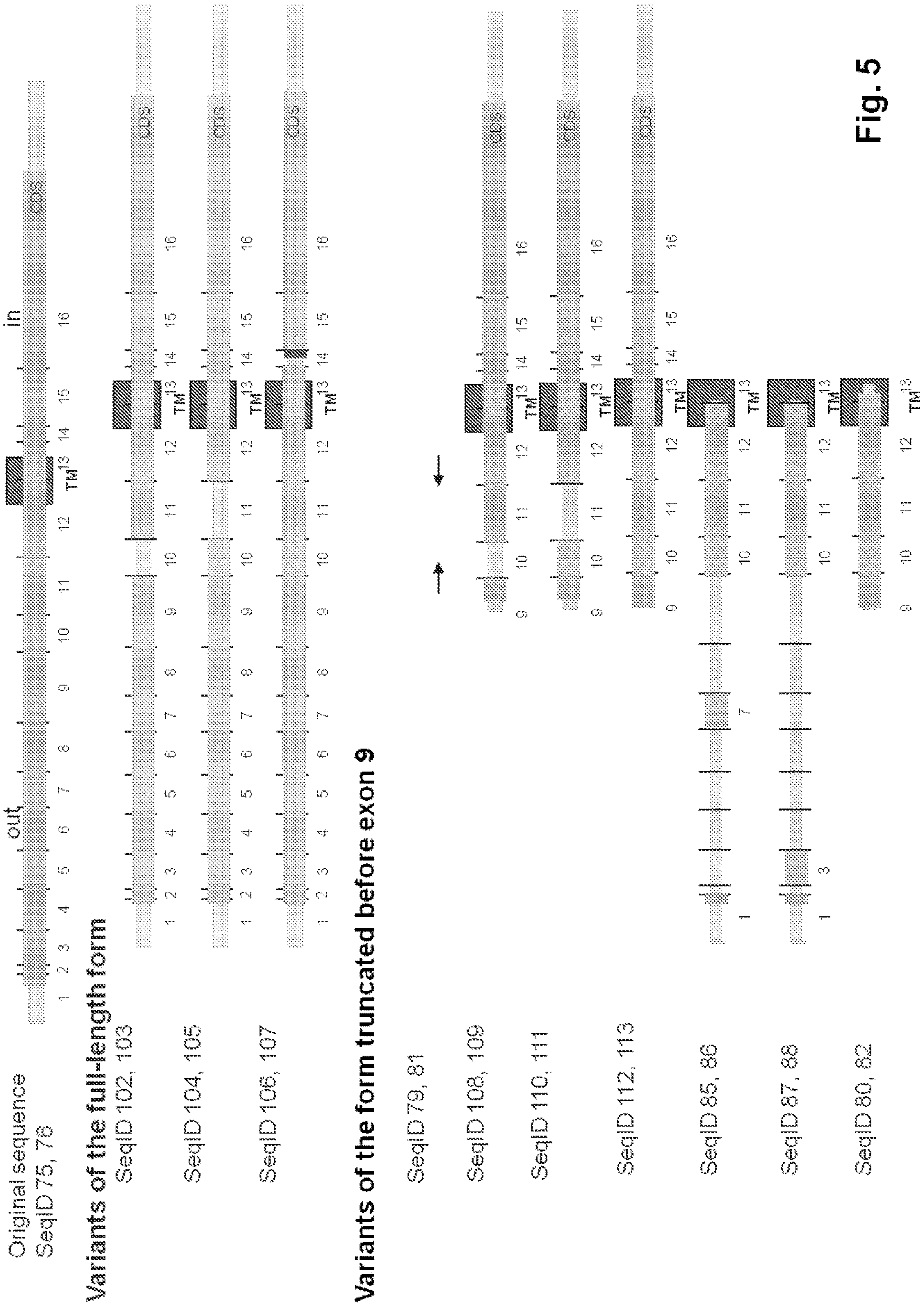
FIG. 5: Overview of the putative transcript variants of the DSG4-gene.

On the basis of these investigations, it appears that apart from the full-length transcript SEQ ID NO: 75 and the protein derived therefrom (SEQ ID NO: 76) also truncated variants of DSG4 exist, which lack regions before exon 9 (FIG. 5).

An extended analysis of the gene locus of DSG4 showed, that various variants of the molecule must be expected having a deletion before exon 9 (FIG. 5). These are the transcripts SEQ ID NO: 85, 87, 108, 110 and 112 and their altered protein products SEQ ID NO: 86, 88, 109, 111 and 113. The full-length transcript may also be modified in the regions beyond exon 10 and lead to variant transcripts SEQ ID NO: 102, 104, 106 and proteins SEQ ID NO: 103, 105, 107.

The variants truncated before exon 9 are even more tumor-selective than the full-length variant and can be found in additional tumor types, such as the colon carcinoma, in which the full-length variant is not expressed. Because the transmembrane domain is located in exon 12, the region amplified by primers SEQ ID NO: 77, 78 is extracellular and therefore should be accessible to antibodies. This truncated extracellular region contains the DSG4-gene sections exons 10, 11 and 12. Therefore transcripts containing exons 10, 11 and 12 (SEQ ID NO: 79) of DSG4, are particularly suitable as diagnostic and therapeutic cancer targets. These regions of DSG4 code for a domain (SEQ ID NO: 81), which is extracellular. Therefore DSG4-polynucleotides, which comprise exons 10, 11, 12 (SEQ ID NO: 75, 79, 80, 85, 87, 106, 112) and the polypeptides they encode (SEQ ID NO: 76, 81, 82, 86, 88, 107, 113) are particularly useful as target structure of monoclonal antibodies in accordance with the invention.

Accordingly, we have immunised animals with epitopes from the region of the full-length molecule (SEQ ID NO: 75) and from the extracellular area of the truncated molecule (SEQ ID NO: 81), respectively.

Figure 6A:
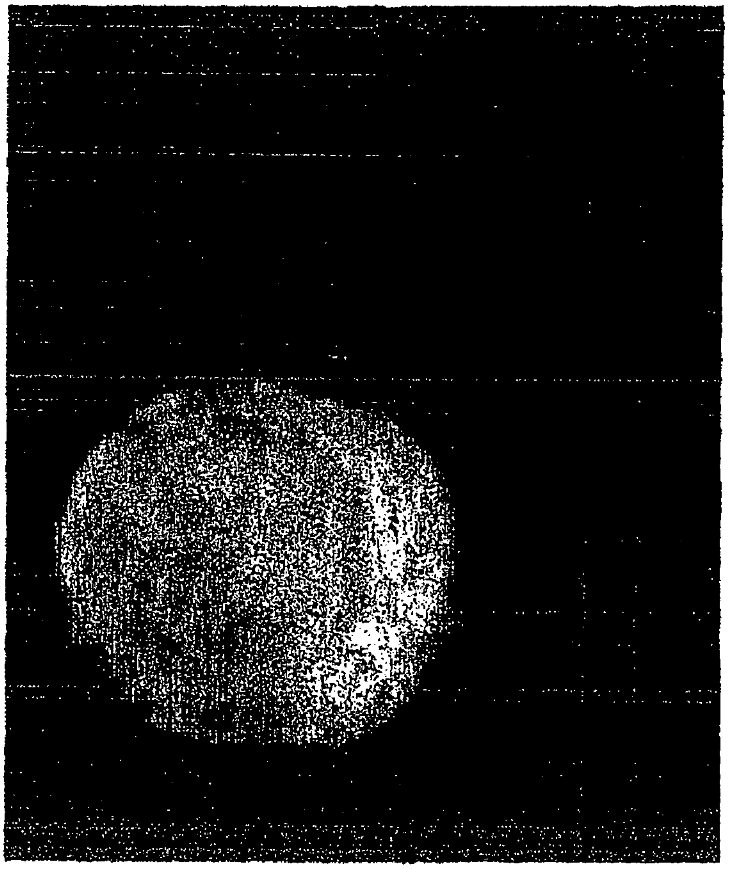
FIG. 6A: Representation of the cellular localisation of the DSG4-protein using immunofluorescence on a DSG4-transfected cell.
Figure 6B:
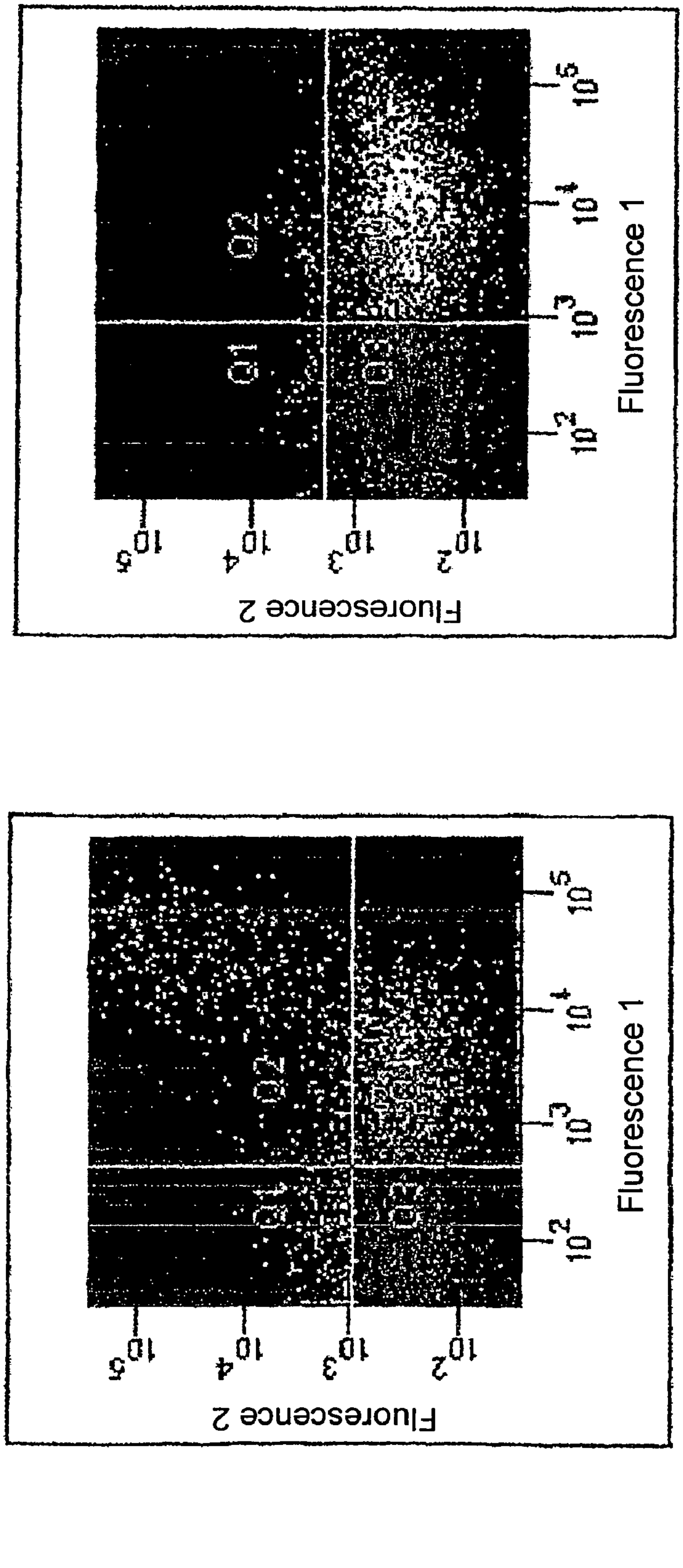
FIG. 6B: FACS-analysis of DSG4-transfected cells with DSG4-specific antibodies (left figure) and of Mock-transfected cells with DSG4-specific antibodies (negative control, right figure). The specific, surface-specific staining is clearly visible.

We were able to generate antibodies, which stain the DSG4 on the surface of cells transfected with DSG4. Specific antibodies are then able to specifically detect this protein using immunofluorescence (FIG. 6A) and flow cytometry (FIG. 6B) at the surface.

The pronounced expression and high incidence of this molecule for the presented tumor indications make this protein, and particularly its truncated variant, a highly interesting diagnostic and therapeutic marker in accordance with the invention. This also includes the detection of disseminated tumor cells in the serum, bone marrow and urine, as well as the detection of metastases in other organs using RT-PCR in accordance to the invention.

The extracellular domain of DSG4, particularly the part close to the cell membrane, may be utilised as target structure of monoclonal antibodies for therapy as well as immune diagnosis in accordance with the invention.

Furthermore, DSG4 can be used in accordance with the invention as vaccine (RNA, DNA, protein, peptides) for the induction of tumor-specific immune responses (T-cell and B-cell mediated immune reactions). In accordance with the invention, this comprises also the development of so-called "small compounds", which modulate the biological activity of DSG4 and can be used for the therapy of tumors.

Example 3: Identification of DSG3 (Desmoglein3) as Diagnostic and Therapeutic Cancer Target The gene DSG3 (desmoglein3; SEQ ID NO: 3) and its translation product (SEQ ID NO: 4) is a member of the desmosomal cadherin-family, which is published at the NCBI under accession number NM_001944 (nucleotide sequence) or NP_001935 (protein sequence). The gene consists of 15 exons and is located on chromosome 18 (18q12.1-q12.2). The derived amino acid sequence encodes a protein with 999 amino acids and a hypothetical size of about 130 kDa. DSG3 is a glycosylated type 1 cell surface protein and is able to be detected in desmosomes (Silos et al. *J. Biol. Chem.* 271: 17504-17511, 1996). Desmosomes are complex intracellular connections connecting the keratin filaments of adjacent cells in order to provide epithelial tissues (such as for example the epidermis) with mechanical stability. The desmosomal cadherines desmoglein and desmocollin are calcium-dependent adhesion molecules. Autoantibodies against desmoglein3 and the resulting loss of cell-cell-contacts in the epidermis are involved in the skin disease Pemphigus vulgaris (Amagai et al., 1991. *Cell* 67: 869-877). This was also proven in animal models (Koch et al, 1997. *J Cell Biol* 5: 1091-1102).

Figure 7A:
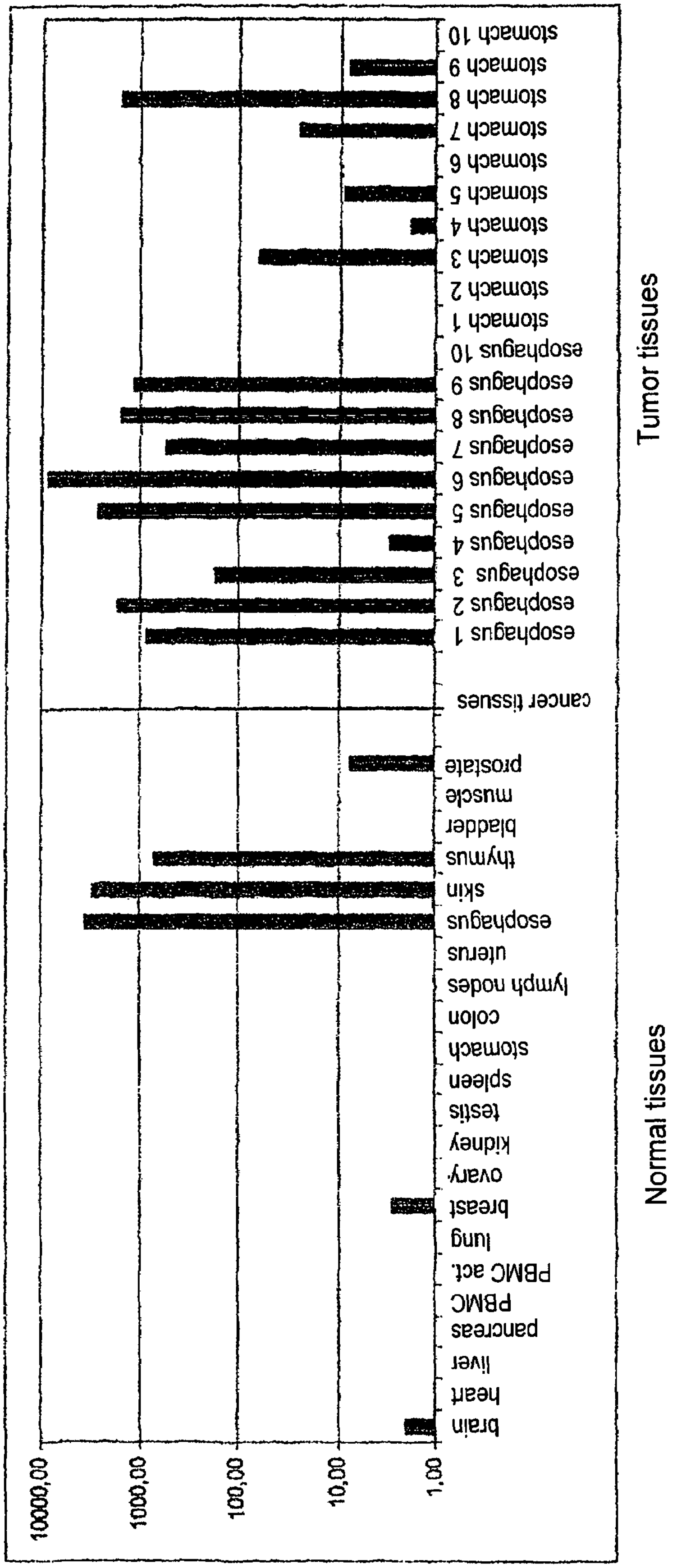
FIG. 7A: Quantitative expression analysis of DSG3 in normal tissues (left side) and in various tumors (pools consisting of 3-4 individual samples each, right side) in logarithmic representation of the relative expression (x-fold activation). The distinct overexpression in esophageal tumors in comparison to most normal tissues is recognisable.

In accordance with the invention, after establishment of a DSG3-specific quantitative RT-PCR (primer pair SEQ ID NO: 33, 34) the quantity of gene-specific transcripts was investigated in healthy tissues and carcinoma samples (FIG. 7; methods: compare Materials and Methods, Section B.1.). Our investigations demonstrated a differential distribution of the expression in normal tissues. DSG3 transcripts are hardly found in normal tissues. The only normal tissues expressing significant transcript quantities are the esophagus, skin and thymus (FIG. 7*a*). In all other analysed tissues, particularly brain, heart, liver, pancreas, PBMC, lung, mamma, ovary, kidney, spleen, colon, lymphatic node, uterus, bladder and prostate, transcription is low or not detectable (FIG. 7A). Surprisingly, we have been able to prove a significant, to date not described expression of DSG3 in some tumor types.

Figure 7B:
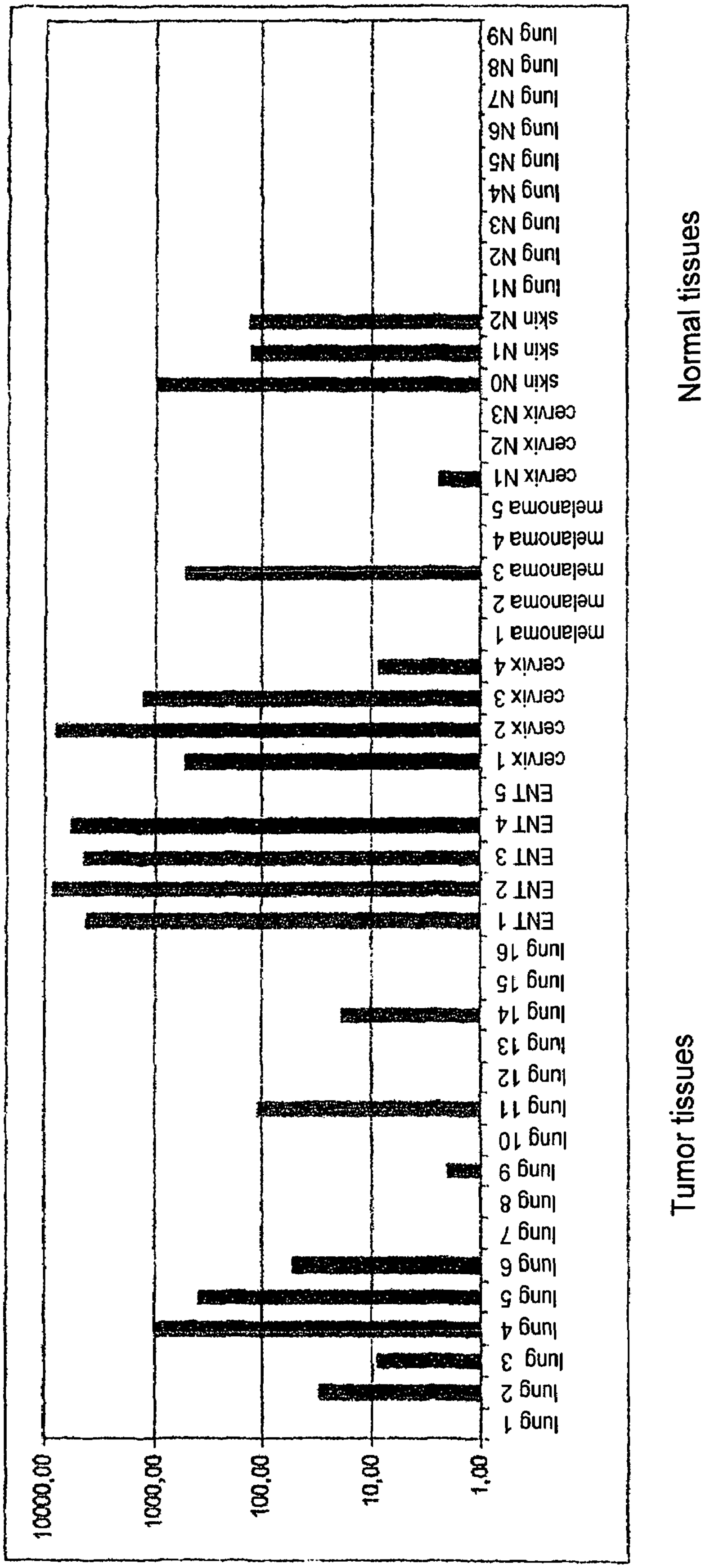
FIG. 7B: Quantitative expression analysis of DSG3 in various tumors of the cervix and lungs as well as in ear, nose, throat tumors in comparison to the expression in the respective normal tissues (n=3 (cervix); n=9 (lung)). Logarithmic representation.

In quantitative RT-PCR-analyses of tumors DSG3-specific transcripts were proven amongst others in tumors of the nose-throat area ("head neck cancer") in a quantity, which exceeded that of the highest expressing toxicity-relevant tissue (FIG. 7B). But also other tumors, such as carcinomas of the esophagus (FIG. 7C), express this protein.

Figure 8:
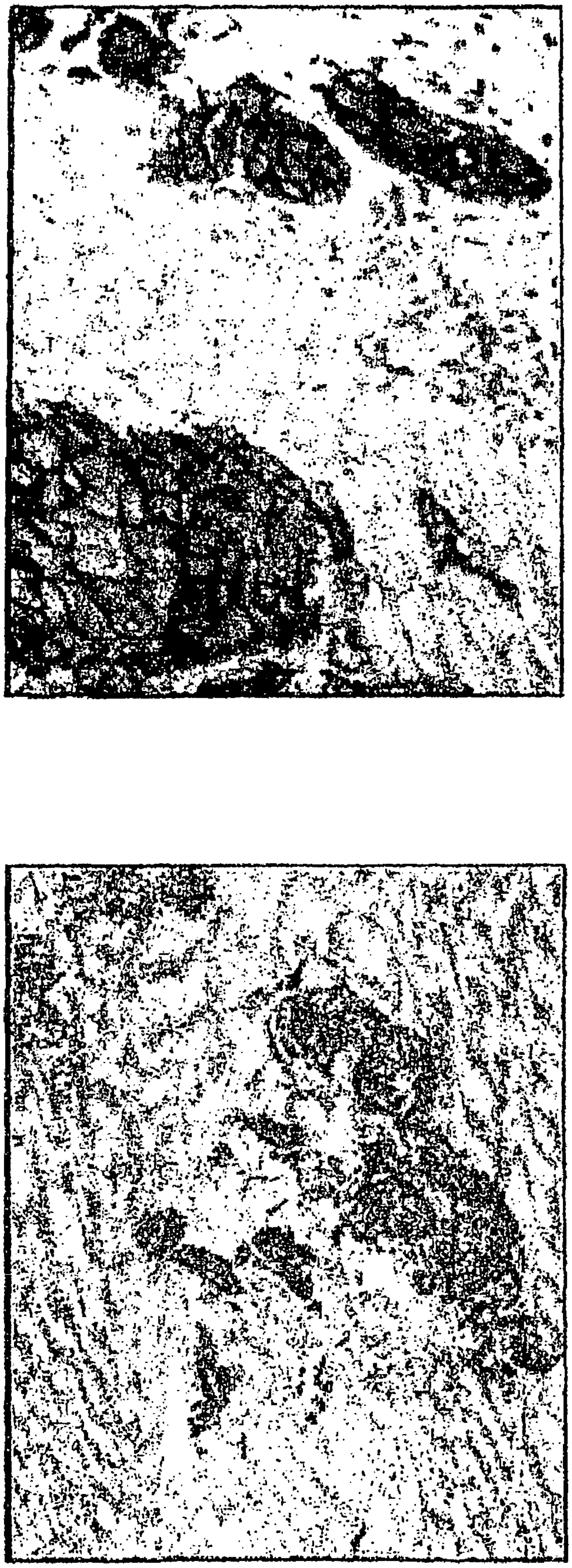
FIG. 8: Shows in an overview (left) and in detail (right) the homogenous DSG3-localisation in an ear, nose, throat tumor.
Figure 9A:
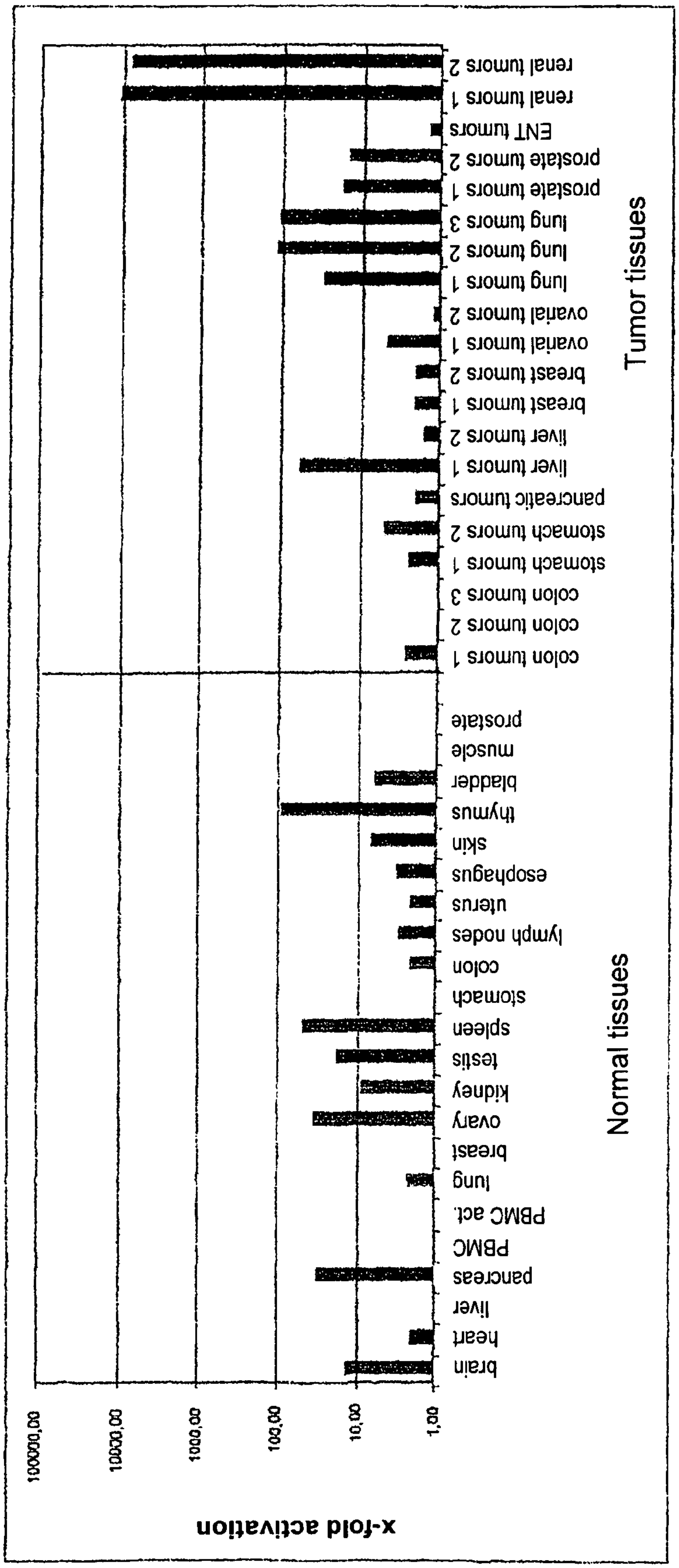
FIG. 9A: Quantitative expression analysis of SLC6A3 in normal tissues (left) and in tumor samples (pools consisting of 3-4 individual samples each, right) in logarithmic representation of the relative expression (x-fold activation).
Figure 9B:
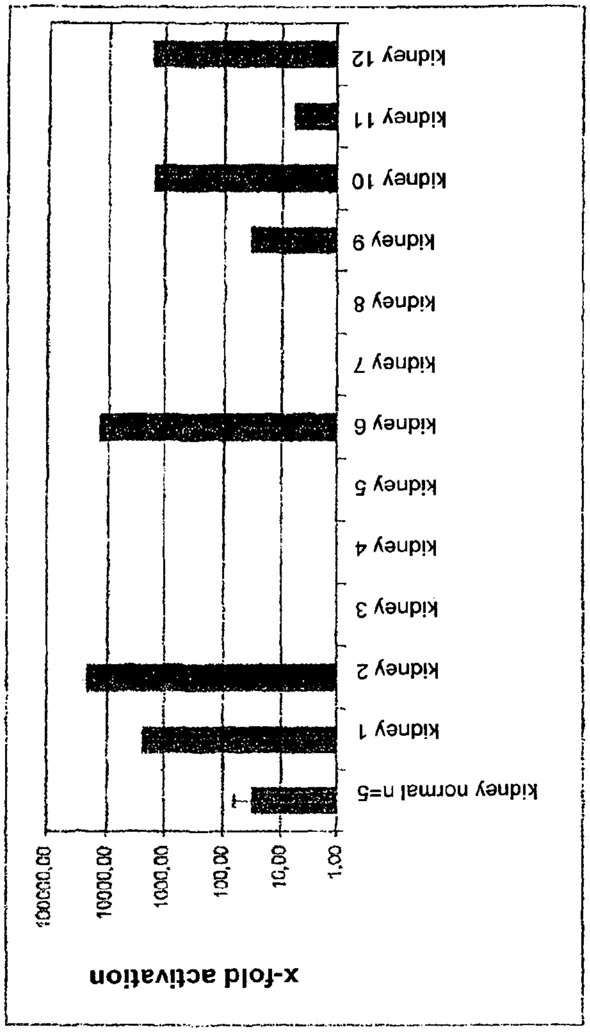
FIG. 9B: Quantitative expression analysis of SLC6A3 in various kidney tumors in comparison to the expression in normal kidney (n=5). Logarithmic representation of the relative expression.
Figure 9C:
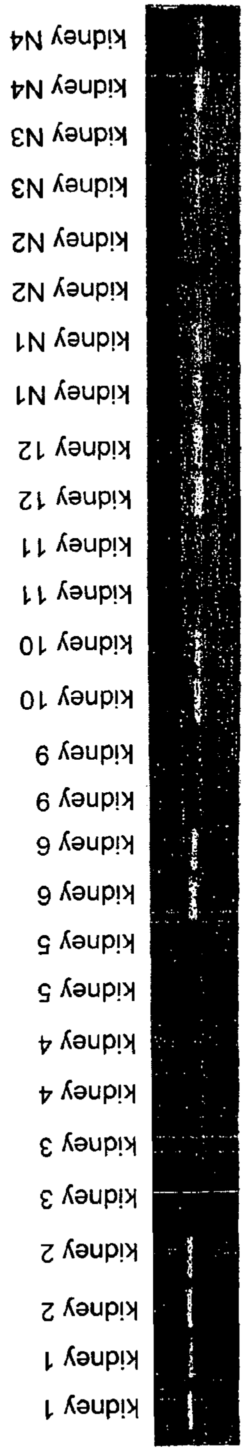
FIG. 9C: Conventional endpoint-RT-PCR-analysis of SLC6A3-specific transcripts (double determination) in kidney tumors and various normal kidney tissues. Image after gel-electrophoretic resolution of the SLC6A3-specific fragments.
Figure 9D:
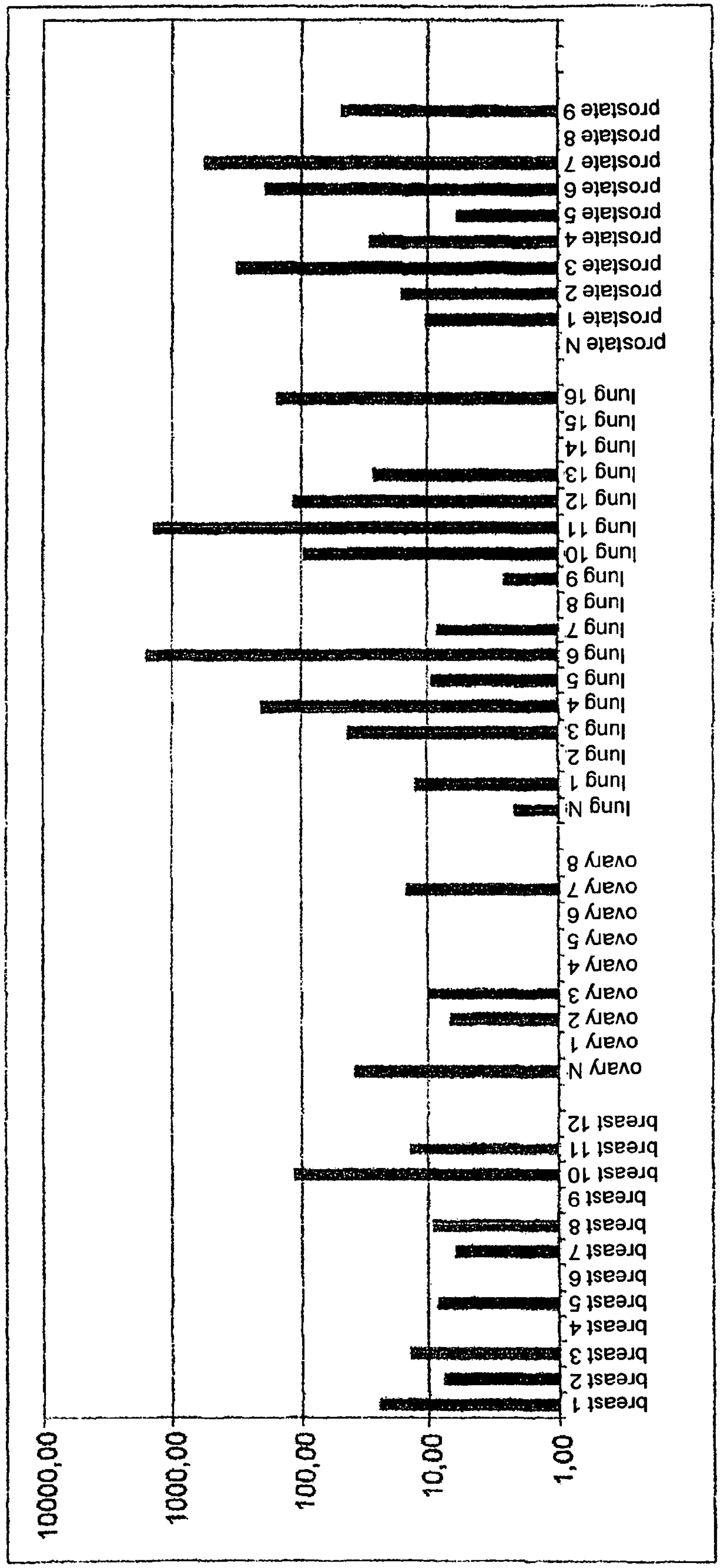
FIG. 9D: Quantitative expression analysis of SLC6A3 in carcinomas of the breast, ovary, lung and prostate; Logarithmic representation of the relative expression (x-fold activation). “Tissue” N: normal tissue; “Tissue”: tumor tissue.
Figure 9E:
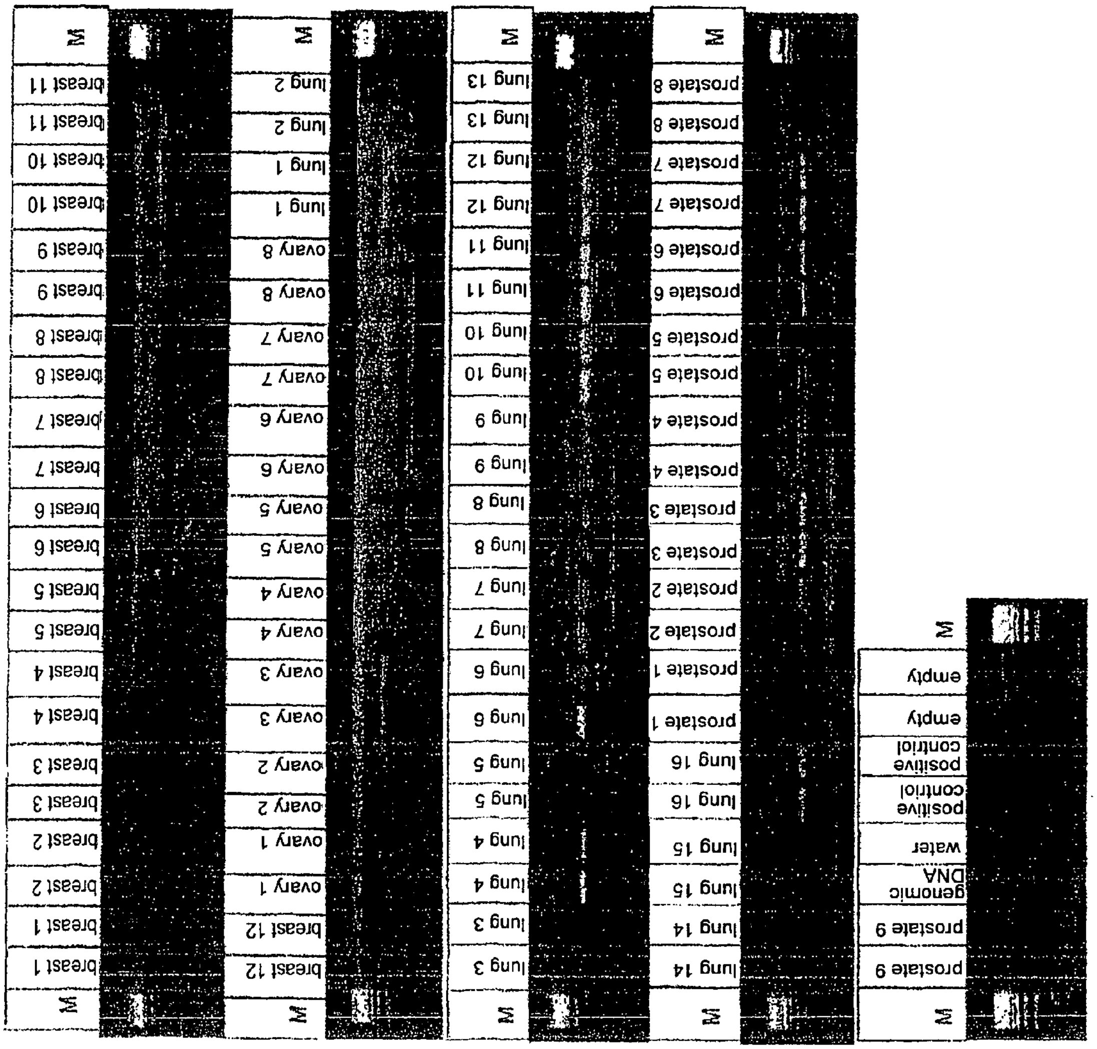
FIG. 9E: Conventional RT-PCR-analysis of SLC6A3 in tumors of the breast, ovary, lung and prostate after gel-electrophoretic separation in a double determination. M: DNA-length marker.

We have stained sections of human tissues with DSG3-specific antibodies and were able to confirm the tumor-selectivity observed in the PCR (FIG. 8).

The pronounced expression and high incidence of this molecule in the described tumor-indications make this protein a highly interesting diagnostic and therapeutic marker in accordance with the invention. This includes in accordance with the invention the detection of disseminated tumor cells in the serum, bone marrow and urine, as well as the detection of metastases in other organs using RT-PCR.

The extracellular domain of the type I membrane protein desmoglein3 (SEQ ID NO: 4, amino acids 1-611) located on the N-terminus can be used in accordance with the invention as target structure of monoclonal antibodies for therapy as well as immune diagnosis. Furthermore, in accordance with the invention, DSG3 can be used as vaccine (RNA, DNA, protein, peptides) for the induction of tumor-specific immune responses (T-cell and B-cell mediated immune reactions). In accordance with the invention this comprises also the development of so-called "small compounds", which modulate the biological activity of DSG3 and can be used for the therapy of tumors.

Example 4: Identification of the Transporter SLC6A3 (Solute Carrier Family 6) as Diagnostic and Therapeutic Cancer Target The gene SLC6A3 (SEQ ID NO: 5) and its translation product (SEQ ID NO: 6) is a member of the sodium-neurotransmitter symporter family (SNF-family) and is deposited under accession number NM_001044 (nucleotide sequence) or NP_001035 (protein sequence). The gene consists of 16 exons and is located on chromosome 5 (5p15.3). The SLC6A3-gene encodes a glycoprotein with a length of 620 amino acids. SLC6A3 is an integral membrane protein with a total of 12 transmembrane domains, which as homo-oligomer represents part of an ion-transporter complex (Hastrup et al., 2003. *J Biol Chem* 278: 45045-48).

In accordance with the invention, after the establishment of a SLC6A3-specific quantitative RT-PCR (primer pair SEQ ID NO: 35, 36) the distribution of SLC6A3-specific transcripts was investigated in healthy tissue and carcinoma samples (FIG. 9; methods: compare Materials and Methods, Section B.1.). In most normal tissues SLC6A3 is only little or not at all expressed, a moderate expression of SLC6A3 was found only in thymus, spleen, ovary, pancreas as well as kidney. A significant, about 100-fold increased overexpression of SLC6A3 was detected in kidney carcinomas (FIG. 9A). A detailed analysis of the various kidney tissues using quantitative (FIG. 9B) and conventional RT-PCR (FIG. 9C) demonstrated, that SLC6A3 was expressed in 7/12 kidney cell carcinomas and overexpressed in 5/12 samples in comparison to non-tumorigenic samples. A significantly lower but detectable SLC6A3-specific expression was also demonstrated in some tumor tissues of other carcinomas. Particularly in some mamma carcinomas, ovarian carcinomas, bronchial carcinomas and prostate carcinomas SLC6A3-specific transcripts were detected (FIGS. 9D and 9E).

In accordance with the invention, the various extracellular domains of SLC6A3 can be used as target structures of monoclonal therapeutic antibodies. The following sequence regions with respect to SEQ ID NO: 6 are predicted as extracellular for SLC6A3 (based on an analysis using the software TMHMM2): amino acids 89-97, 164-237, 288-310, 369-397, 470-478, 545-558. The peptides listed under SEQ ID NO: 63 and 64 were used for the production of SLC6A3-specific antibodies.

Example 5: Identification of GRM8 as Diagnostic and Therapeutic Cancer Target

The gene GRM8/GluR8 or "metabotrophic glutamate receptor 8" (SEQ ID NO: 7) and its translation product (SEQ ID NO: 8) belongs to the family of glutamate receptors. The gene consists of 10 exons and is located on chromosome 7 (7q31.3-q32.1). The protein encoded by the GRM8 gene has a length of 908 amino acids, its calculated molecular weight is 102 kDa. Prediction programs predict 7 transmembrane domains. The protein exhibits a high homology (67% to 70% similarity) with GluR4 and GluR7 (Scherrer et al., 1996. *Genomics* 31: 230-233).

L-glutamate is an important neurotransmitter in the central nervous system and activates ionotrophic as well as metabotrophic glutamate receptors. GRM8-specific transcripts were to date only detected in the brain or glia-cells. However, to date no investigations comparing transcript or protein on a quantitative level of a larger number of tissues have been reported (Wu et al., 1998. *Brain Res.* 53: 88-97).

Figure 10A:
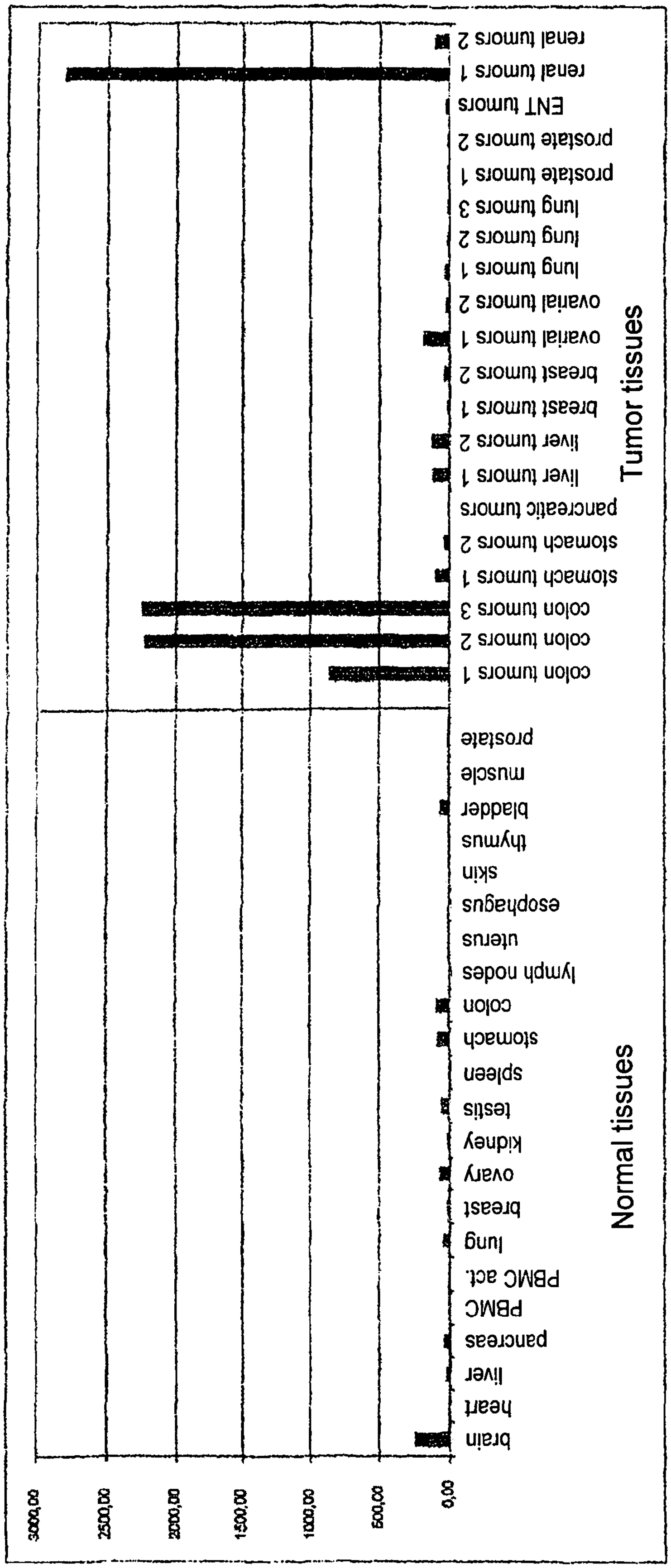
FIG. 10A: Quantitative expression analysis of GRM8 in normal tissues (left) and tumor tissues (pools consisting of 3-4 individual samples each, right) in linear representation of the relative expression (x-fold activation).
Figure 10B:
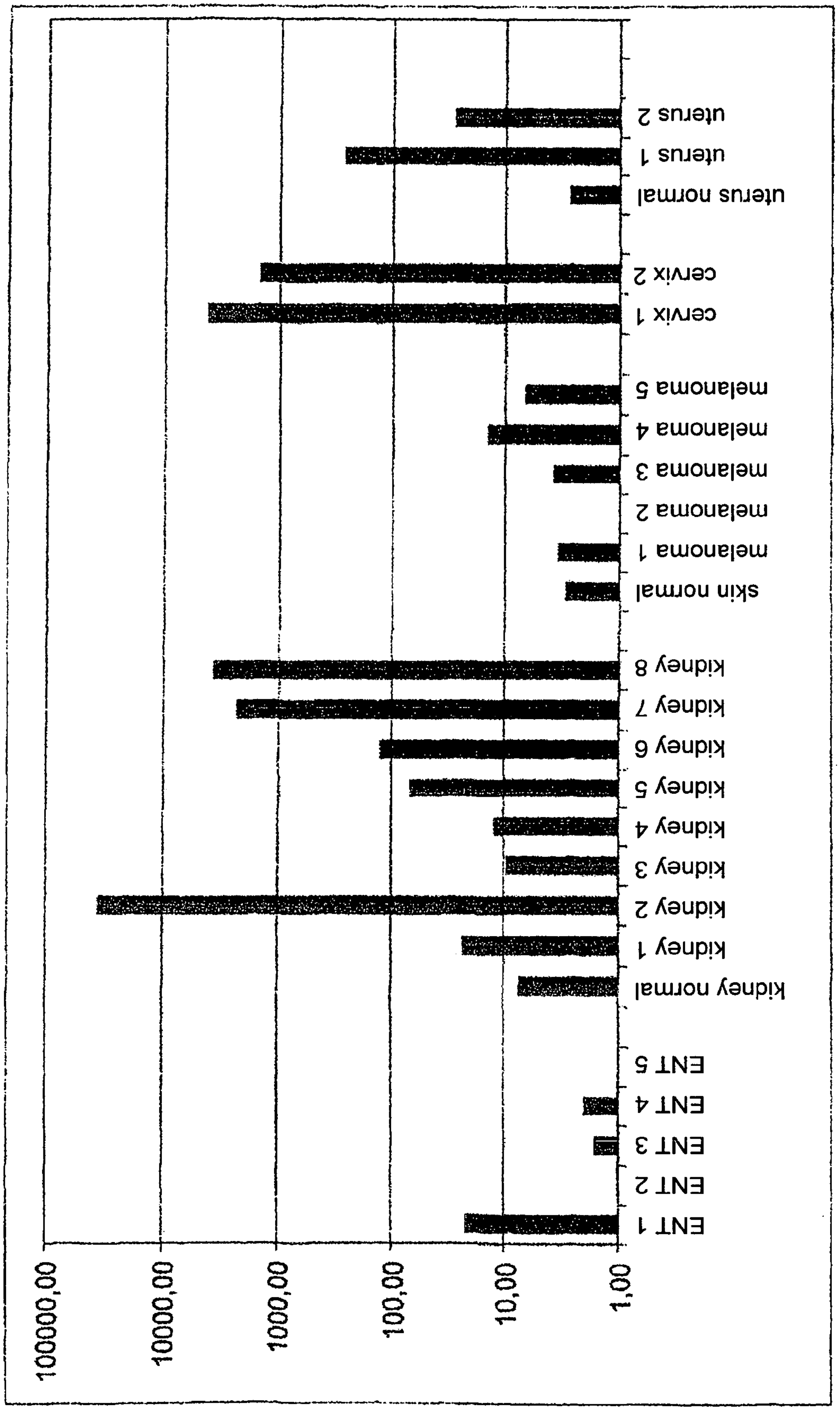
FIG. 10B: Quantitative expression analysis of GRM8 in various tumors of the kidney and uterus in comparison to the expression in the normal kidney and uterus, as well as relative expression in ear, nose, throat tumors, cervical tumors and melanomas. Logarithmic representation of the relative expression.

In accordance with the invention, after establishment of a GRM8-specific quantitative RT-PCR (primer pair SEQ ID NO: 37, 38) the distribution of GRM8-specific transcripts was investigated in healthy tissue and carcinoma samples (FIG. 10; methods: compare Materials and Methods, Section B.1.). Our investigations demonstrated a differential distribution of the expression in various normal tissues. We also found GRM8-transcripts selectively not only in the brain, but also in lesser quantities in the tissues of the stomach, intestinum, bladder, ovary, lung and pancreas. In most other normal tissues GRM8 is significantly less expressed or not at all detectable. In some tumors we were able to detect a significant, not previously described expression of GRM8. Particularly carcinomas of the colon, cervix and kidney cells exhibited a more than 10-fold overexpression in comparison to all other normal tissues and are also distinctly above the expression level of brain tissue (FIGS. 10A and 10B).

In accordance with the invention, the extracellular domains of GRM8 can be used as target structures of therapeutic monoclonal antibodies. With respect to SEQ ID NO: 8, the amino acids 1-582, 644-652, 717-743 and 806-819 are extracellularly localised.

Example 6: Identification of Cadherin 17 (CDH17) as Diagnostic and Therapeutic Cancer Target The gene CDH17 (SEQ ID NO: 9) and its translation product (SEQ ID NO: 10) is a member of the cadherin-family. The gene consists of 18 exons and is located on chromosome 8 (8q22.1). It encodes a type 1 transmembrane protein with a length of 832 amino acids, which without secondary modifications has a calculated molecular weight of 92.1 kDa and which has one transmembrane domain. Cadherin 17 was cloned as proton-dependent peptide transporter by Dantzig et al. (*Science* 264: 430-433, 1994). The calcium-dependent glycoprotein cadherin 17 contains 7 cadherin-domains in the extracellular region (Gessner et al., *Ann N Y Acad Sci.;* 915:136-43, 2000). The intracellular domain does not exhibit any homology with other cadherins. Expression investigations were available only sporadically and not in the form of quantitatively comparative transcript or protein investigations of a larger number of different tissues.

Figure 11A:
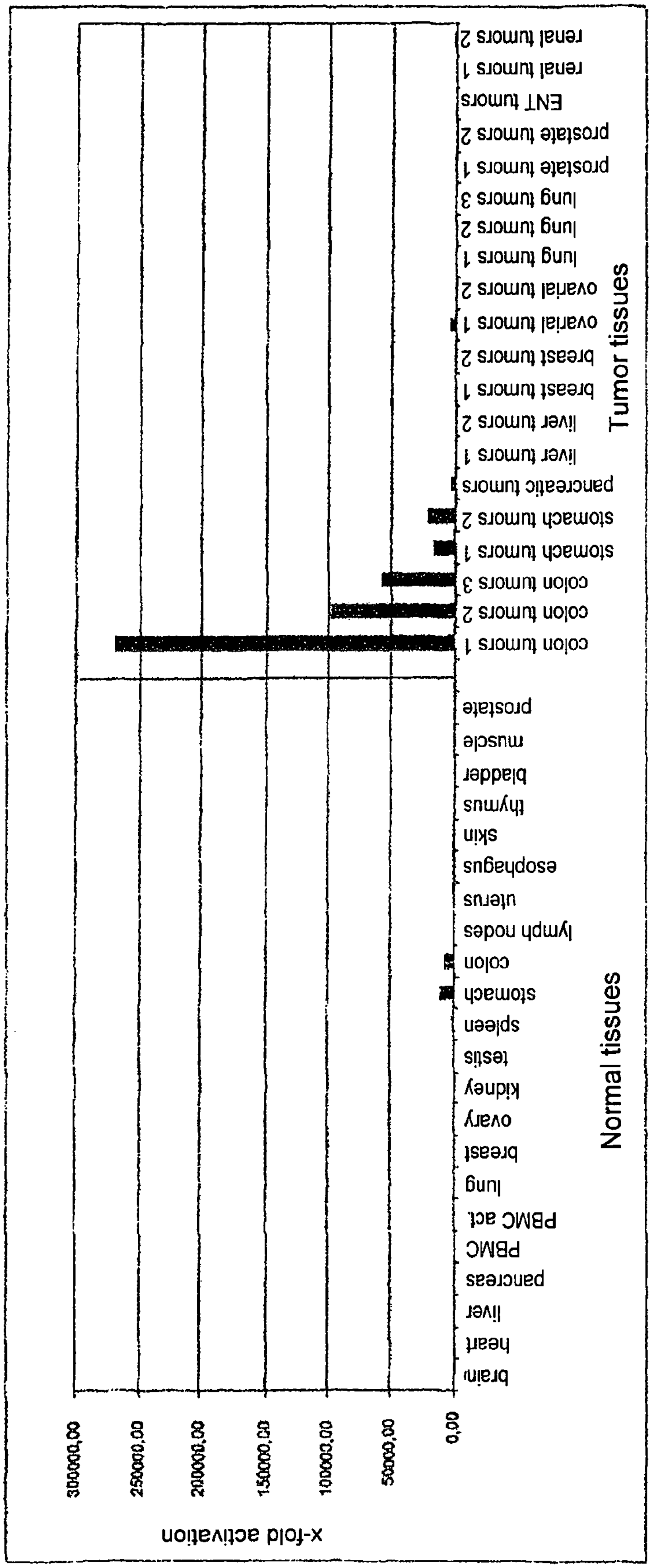
FIG. 11A: Quantitative expression analysis of CDH17 in normal tissues (left) and in tumor tissues (pools consisting of 3-4 individual samples each, right) in linear representation of the relative expression (x-fold activation).
Figure 11B:
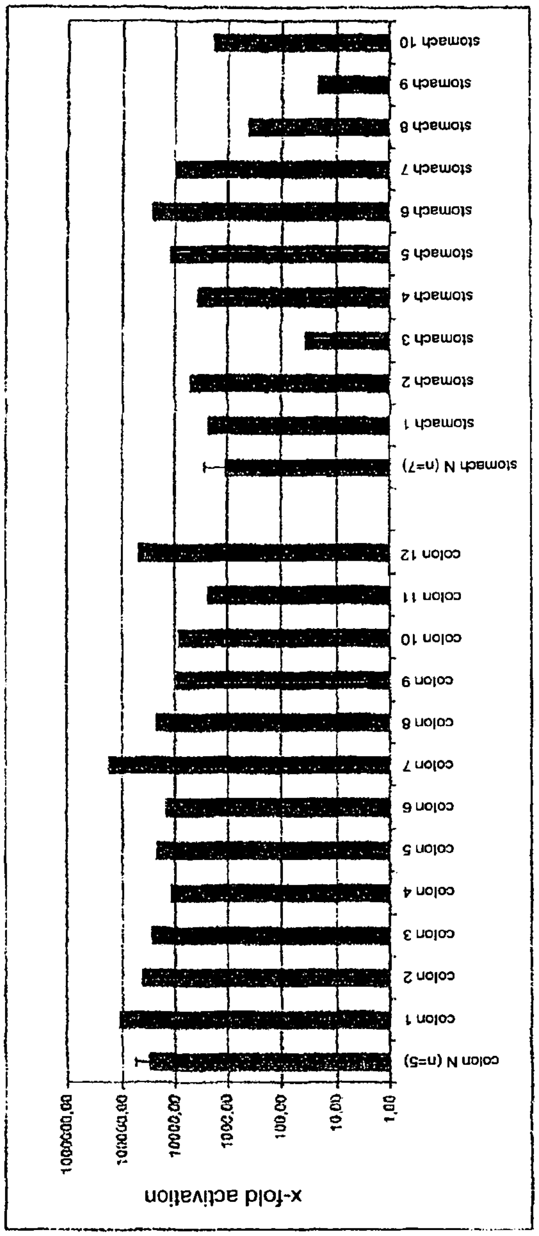
FIG. 11B: Quantitative expression analysis of CDH17 in various tumors of the colon and stomach in comparison to the expression in the respective normal tissues. Logarithmic representation.
Figure 11C:
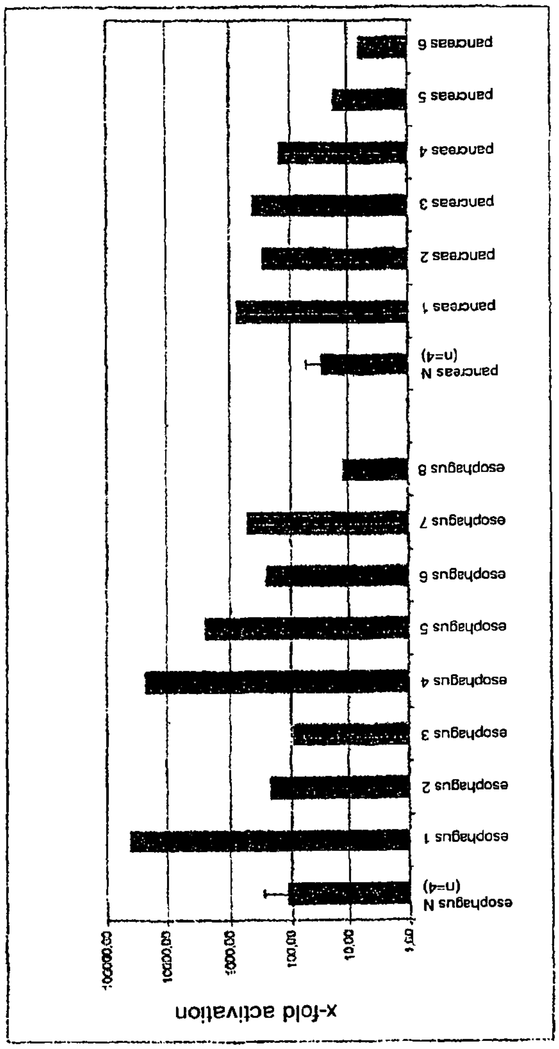
FIG. 11C: Quantitative expression analysis of CDH17 in various tumors of the esophagus and pancreas in comparison to the expression in the respective normal tissues. Logarithmic representation.

In accordance with the invention, after the establishment of a CDH17-specific quantitative RT-PCR (primer pair SEQ ID NO: 39, 40) the distribution of CDH17-specific transcripts was investigated in healthy tissue as well as carcinoma samples (FIG. 11; methods: compare Materials and Methods, Section B.1.). In most normal tissues CDH17 is not at all detectable (FIG. 11A). We found significant transcript quantities selectively in stomach and intestinal tissues, far less expression in bladder, spleen, lymph nodes, thymus, prostate and esophagus. Surprisingly, we detected a distinct, not previously described CDH17-specific expression in tumors. For CDH17 in intestinal tumors and at least 2-10-fold overexpression was measured in comparison to normal tissues. CDH17 is also strongly expressed in stomach and esophagus tumors (FIGS. 11B and 11C).

The pronounced expression and high incidence of this molecule for the described tumor indications make this protein a highly interesting diagnostic and therapeutic marker in accordance with the invention. This includes in accordance with the invention the detection of disseminated tumor cells in serum, bone marrow and urine, as well as the detection of metastases in other organs using RT-PCR.

In accordance with the invention, the extracellular domain of CDH17 can be used as target structure of monoclonal antibodies for therapy as well as immune diagnosis. With respect to SEQ ID NO: 10, the amino acids 1-785 are localised extracellularly (prediction occurred using the software TMHMM2).

Furthermore, CDH17 can be used as vaccine (RNA, DNA, protein, peptides) for the induction of tumor-specific immune responses (T-cell and B-cell mediated immune reactions) in accordance with the invention. This includes in accordance with the invention also the development of so-called "small compounds", which modulate the biological activity of CDH17 and can be used for the therapy of tumors.

Example 7: Identification of ABCC4 as Diagnostic and Therapeutic Cancer Target

The gene ABCC4 (SEQ ID NO: 11) and its translation product (SEQ ID NO: 12) encode an ABC transporter (ATP-binding-cassette). The gene consists of 31 exons and is located on chromosome 13 (13q31). It encodes a protein with a length of 1325 amino acids, which without modifications has a calculated molecular weight of about 149 kDa. ABCC4 is an integral membrane protein. The topology of ABCC4 is not yet clarified, prediction programs predict 12-14 transmembrane domains. ABC-transporters transport various molecules through extra- and intracellular membranes. ABCC4 is a member of the so-called MRP-family, of multi-drug-resistance proteins. The specific function of ABCC4 is not yet clarified, however it appears that the transporter plays a role in the cellular detoxification, which is made responsible for the chemotherapeutic resistance of many tumors.

Figure 12:
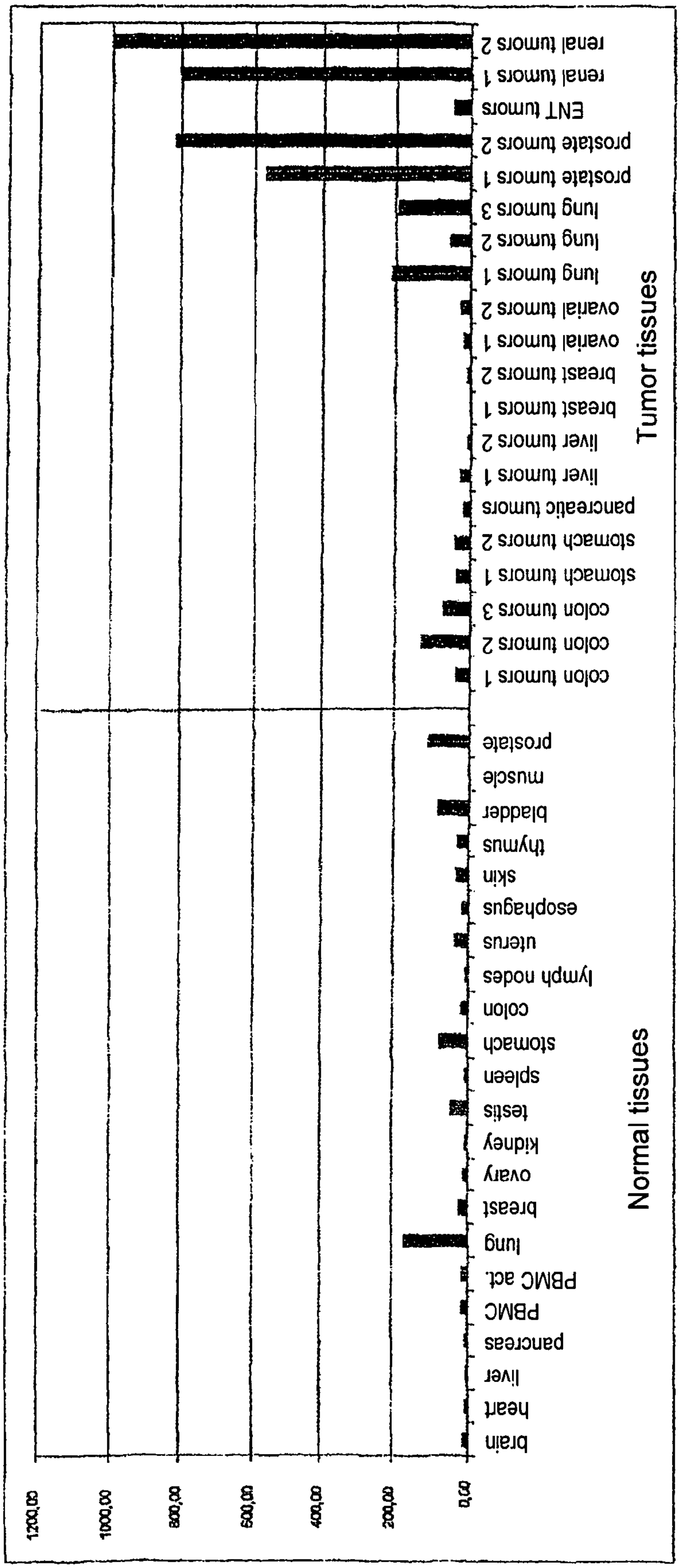
FIG. 12: Shows quantitative expression analysis of ABCC4 in normal tissues (left) and tumors (pools consisting of 3-4 individual samples each, right) in linear representation of the relative expression (x-fold activation).

The tissue distribution of this gene product over the various organs of the human body has not yet been investigated. In accordance with the invention, after establishment of an ABCC4-specific quantitative RT-PCR (primer pair SEQ ID NO: 41, 42) specific transcripts were investigated in healthy tissue and in carcinoma samples (FIG. 12; methods: compare Materials and Methods, Section B.1.). Our comparative investigations on all normal tissues confirm the published ubiquitous expression of ABCC4. ABCC4 was detected in all tested normal tissues. Surprisingly, we found, however, that in a number of tumors an overexpression of the transcript exceeding the expression for normal tissues was observed. In this respect, ABCC4 is found in 2-15-fold increased quantity in comparison to all analysed normal tissues for example in tumors of the kidney and prostate as well as bronchial tumors (FIG. 12).

The pronounced expression and high incidence of this molecule for the described tumor indications make this protein a highly interesting diagnostic and therapeutic marker in accordance with the invention. This includes in accordance with the invention the detection of disseminated tumor cells in serum, bone marrow and urine, as well as the detection of metastases in other organs with the aid of RT-PCR.

In accordance with the invention, the extracellular domains of ABCC4 can be used as target structures of monoclonal antibodies for therapy as well as immune diagnosis. The exact localisation of the extracellular domains is still unknown. With respect to SEQ ID NO: 12, the software TMHMM2 predicts the amino acids 114-132, 230-232, 347-350, 730-768, 879-946 and 999-1325 as extracellular.

Furthermore, ABCC4 may be used as vaccine (RNA, DNA, protein, peptides) in accordance with the invention for the induction of tumor-specific immune responses (T-cell and B-cell mediated immune reactions). This includes in accordance with the invention also the development of so-called "small compounds", which modulate the biological activity of ABCC4 and can be used for the therapy of tumors.

Example 8: Identification of VIL1 as Diagnostic and Therapeutic Cancer Target

The gene VIL1 or "Villin1" (SEQ ID NO: 13) and its translation product (SEQ ID NO: 14) are encoded by a gene consisting of 19 exons on chromosome 2 (2q35-q36). The gene encodes a protein with 826 amino acids, which without modifications has a calculated molecular weight of about 92 kDa. Villin is the structural main component of microvilli in cells of the gastro-intestinal and urogenital epithelia. It represents a calcium-regulated, actin-binding protein.

Pringault et al. (EMBO J. 5: 3119-3124, 1986) cloned villin1 and were able to prove the existence of two transcripts (2.7 kb and 3.5 kb). These variants arise due to the use of alternative polyadenylation signals in the last exon. VIL1-specific transcripts were previously described in a multitude of tissues such as brain, heart, lung, intestine, kidney and the liver. However, previously no comprehensive quantitatively comparative transcript or protein investigations on a larger number of tissues were carried out, which might have given information regarding the usefulness of VIL1 for therapeutic purposes.

Figure 13A:
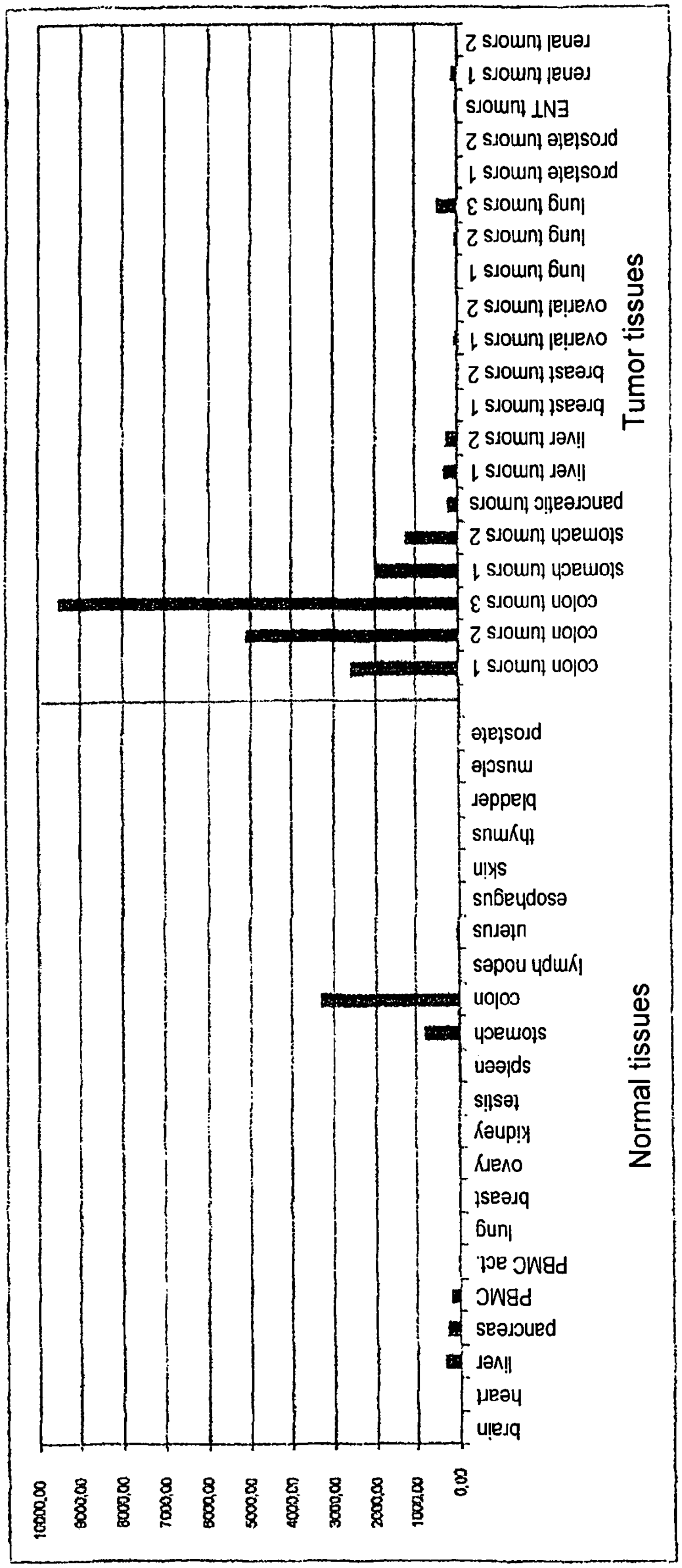
FIG. 13A: Quantitative expression analysis of VIL1 in normal tissues (left) and tumor tissues (pools consisting of 3-4 individual samples each, right) in linear representation of the relative expression (x-fold activation).

In accordance with the invention, after establishment of a VIL1-specific quantitative RT-PCR (primer pair SEQ ID NO: 43, 44) the distribution of the specific transcripts in healthy tissue and carcinoma samples were investigated (FIG. 13; methods: compare Materials and Methods, Section B.1.). Our comparative investigations regarding all normal tissues demonstrate a differential distribution of the VIL1-specific expression. In almost all normal tissues VIL1-specific transcripts are not detectable (FIG. 13A). In particular our findings disprove the previously described expression in brain, heart, breast, ovary, lymph nodes, esophagus, skin, thymus, bladder and muscle. We only found VIL1-transcripts in stomach and intestine and a lower expression in pancreas, liver and PBMCs.

Figure 13B:
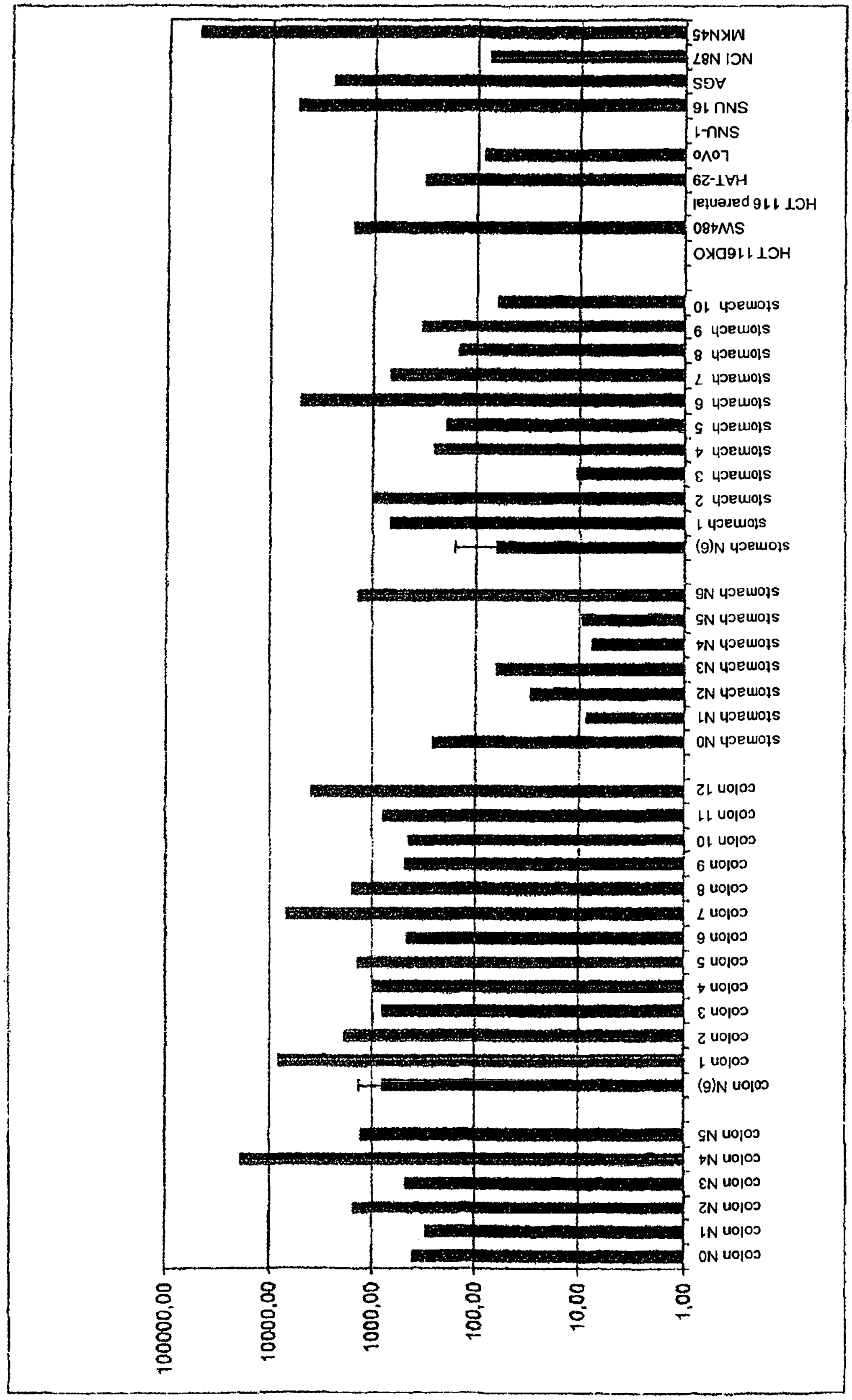
FIG. 13B: Quantitative expression analysis of VIL1 in various tumors of the colon and stomach in comparison to the expression in the respective normal tissues. Logarithmic representation.

Surprisingly, however, we detected a significant, but previously not described VIL1-specific overexpression in tumors. For example in carcinomas of the colon and stomach a 5- to 10-fold overexpression was observed in comparison to all analysed normal tissues (FIGS. 13A and 13B). A significant VIL1-specific expression is also detectable in tumors of the pancreas, stomach and liver as well as bronchial tumors.

The pronounced expression and high incidence of this molecule for the described tumor indications make this protein in accordance with the invention a highly interesting diagnostic and therapeutic marker. This includes in accordance with the invention the detection of disseminated tumor cells in serum, bone marrow and urine, as well as the detection of metastases in other organs with the aid of RT-PCR.

In accordance with the invention, it can be used as vaccine (RNA, DNA, protein, peptides) for the induction of tumors-specific immune responses (T-cell and B-cell mediated immune reactions). In accordance with the invention, this also includes the development of so-called "small compounds", which modulate the biological activity of VIL1 and can be used for the therapy of tumors.

Example 9: Identification of MGC34032 as Diagnostic and Therapeutic Cancer Target The translation product (SEQ ID NO: 16) of gene MGC34032 (SEQ ID NO: 15) is a hypothetical protein with currently unknown function. The gene consists of 28 exons and is located on chromosome 1 (1p31.1). The gene encodes a protein with a length of 719 amino acids which has a calculated molecular weight of about 79 kDa. Prediction programs consistently predict 8 transmembrane domains. Homologies are not known, publications regarding MGC34032 do not exist.

Figure 14A:
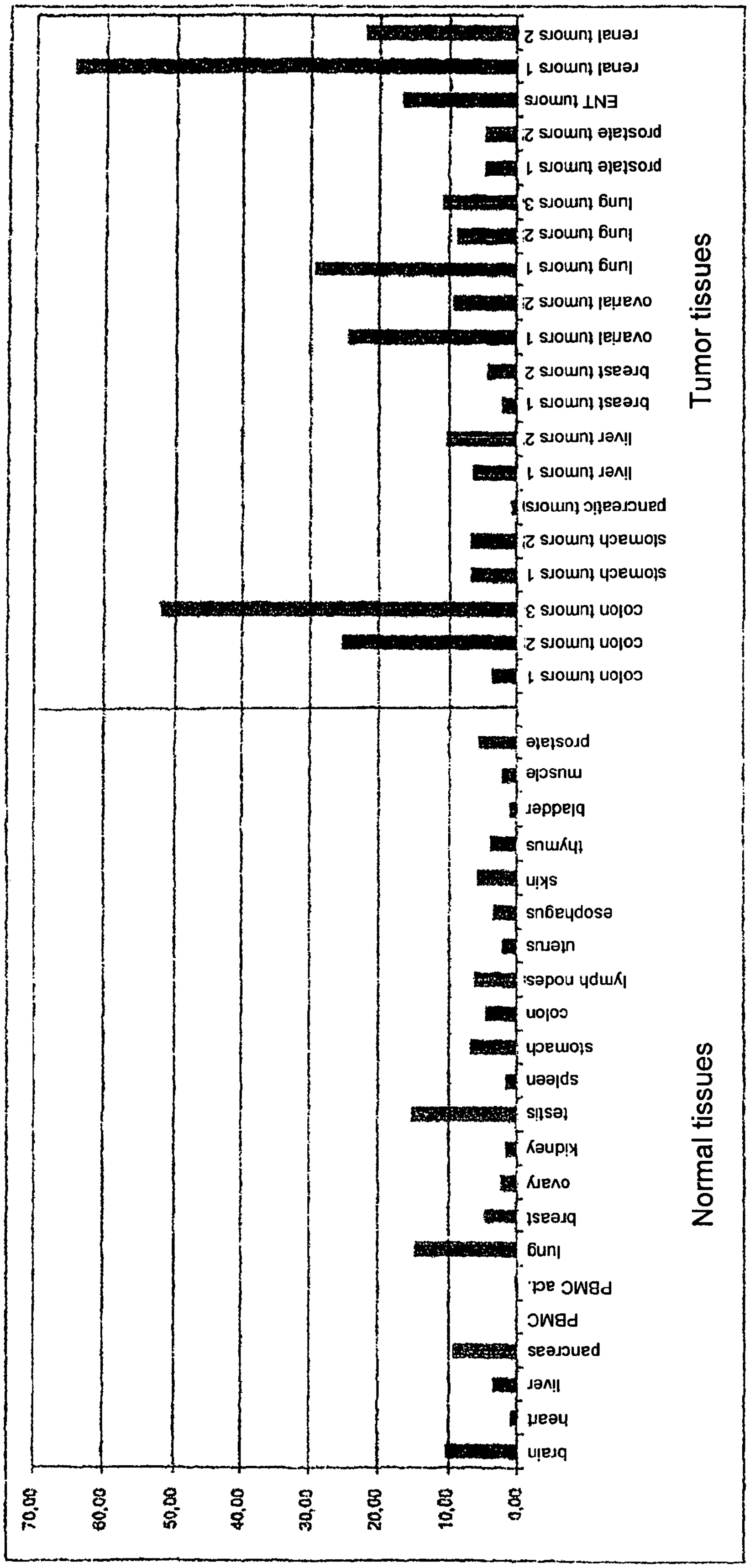
FIG. 14A: Quantitative expression analysis of MGC34032 in normal tissues (left) and various tumors (pools consisting of 3-4 individual samples each, right) in linear representation of the relative expression (x-fold activation).
Figure 14B:
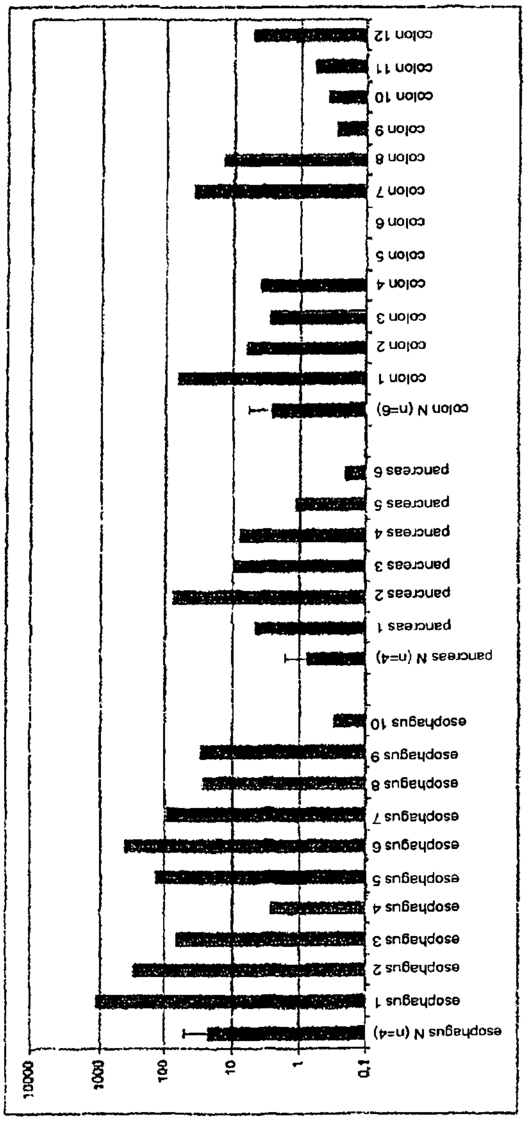
FIG. 14B: Quantitative expression analysis of MGC34032 in various tumors of the esophagus, pancreas and colon in comparison to the expression in the respective normal tissues. Logarithmic representation.
Figure 14C:
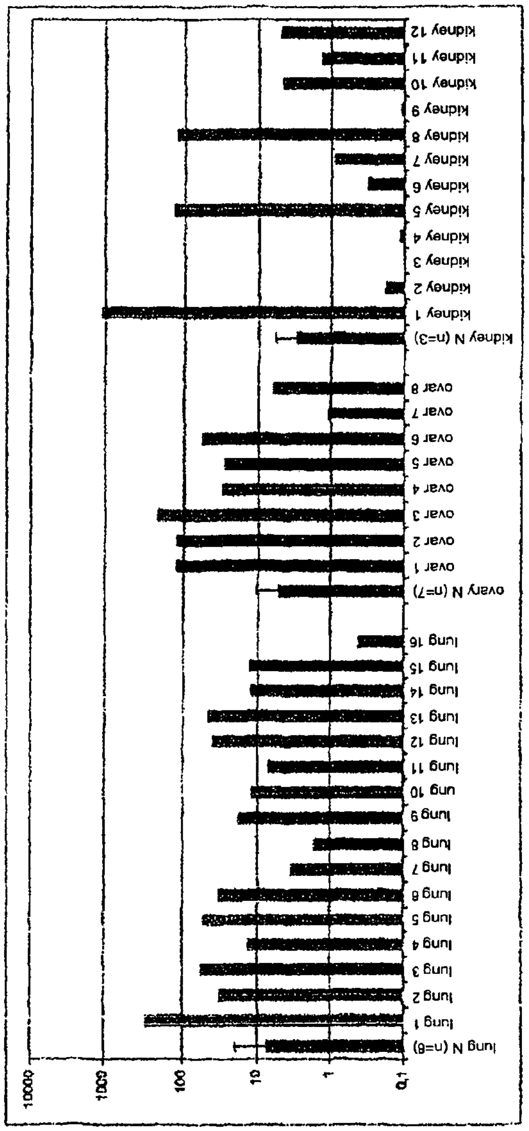
FIG. 14C: Quantitative expression analysis of MGC34032 in various tumors of the lung, ovary and kidney in comparison to the expression in the respective normal tissues. Logarithmic representation.

In accordance with the invention, after establishment of a MGC34032-specific quantitative RT-PCR (primer pair SEQ ID NO: 45, 46) the distribution of specific transcripts was investigated in healthy tissue and carcinoma samples (FIG. 14; methods: compare Materials and Methods, Section B.1.). We found MGC34032-transcripts in all tested normal tissues. The comparison of transcript quantities in normal tissues with those found in tumors, however, showed surprisingly, that various tumor-types exhibited a significant, not previously described 5- to 10-fold overexpression of this gene product. These are particularly carcinomas of the esophagus, colon, ovary, lung and kidney cells as well as ear-nose-throat carcinomas (FIG. 14A-D).

Figure 15:
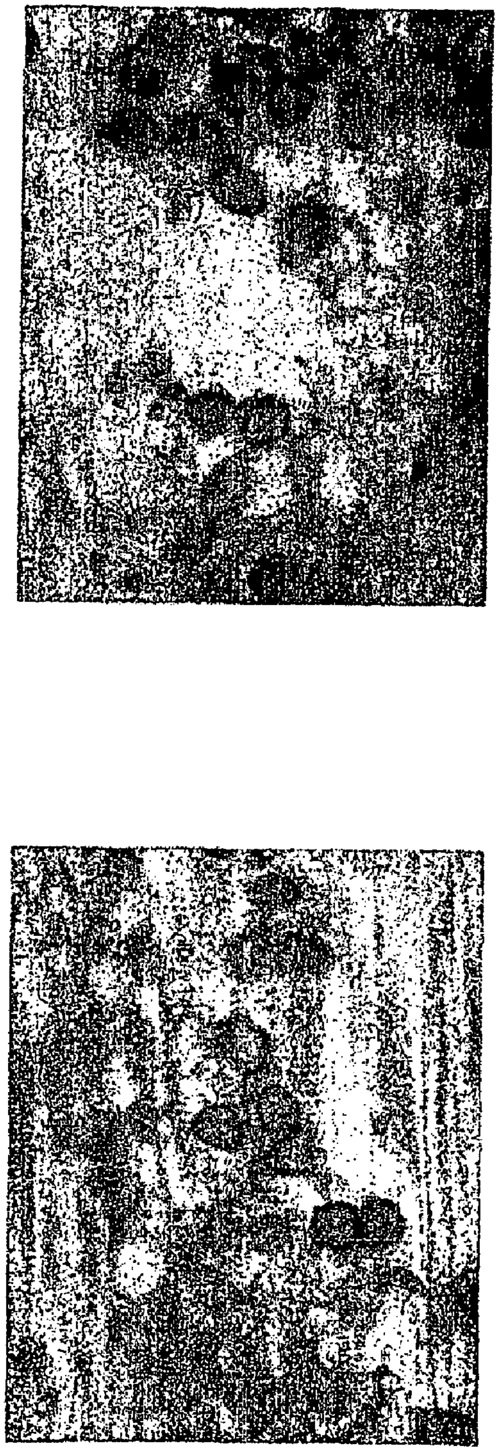
FIG. 15: Shows 2 detailed views of the cellular localisation of the MGC34032-protein in human testis tissue.

In order to produce MGC34032-specific antibodies the peptides listed under SEQ ID NO: 98 and 99 were used. These antibodies were able stain MGC34032 at the cell surface (FIG. 15A).

The pronounced expression and high incidence of this molecule for the described tumor indications make this protein in accordance with the invention a highly interesting diagnostic and therapeutic marker. This also includes in accordance with the invention the detection of disseminated tumor cells in serum, bone marrow and urine, as well as the detection of metastases in other organs with the aid of RT-PCR.

The extracellular domains of MGC34032 may be used in accordance with the invention as target structures of monoclonal antibodies for therapy as well as immune diagnosis. With respect to SEQ ID NO: 16, the amino acids 62-240, 288-323, 395-461 and 633-646 are extracellularly localised (prediction occurred with the aid of the TMHMM2-software).

Furthermore, MGC34032 may be used in accordance with the invention as vaccine (RNA, DNA, protein, peptides) for the induction of tumor-specific immune responses (T-cell and B-cell mediated immune reactions). This includes in accordance with the invention also the development of so-called "small compounds", which modulate the biological activity of MGC34032 and may be used for the therapy of tumors.

Example 10: Identification of the Serine Protease PRSS7 (Enterokinase) as Diagnostic and Therapeutic Cancer Target The gene PRSS7 (SEQ ID NO: 17) and its translation product (SEQ ID NO: 18) belong to the family of serine proteases. The gene consists of 25 exons and is located on chromosome 21 (21q21). The gene encodes a protein with a length of 1019 amino acids, which is further processed after translation. The active enzyme consists of 2 peptide chains, connected by a disulfide-bridge, which are derived from a common precursor molecule through proteolytic cleavage. The heavy chain consists of 784 amino acids. The light chain consisting of 235 amino acids exhibits a distinct homology to known serine proteases. Prediction programs predict one transmembrane domain for PRSS7. PRSS7 is particularly formed in the apical cells and enterocytes of the small intestine and therefore aids in the initial activation of the proteolytic enzymes of the pancreas (such as trypsin, chymotrypsin and carboxypeptidase) (Imamura and Kitamoto, *Am J Phsyiol Gastrointest Liver Physiol* 285: G1235-G1241, 2003). To date this protein had not been associated with human tumors.

Figure 16A:
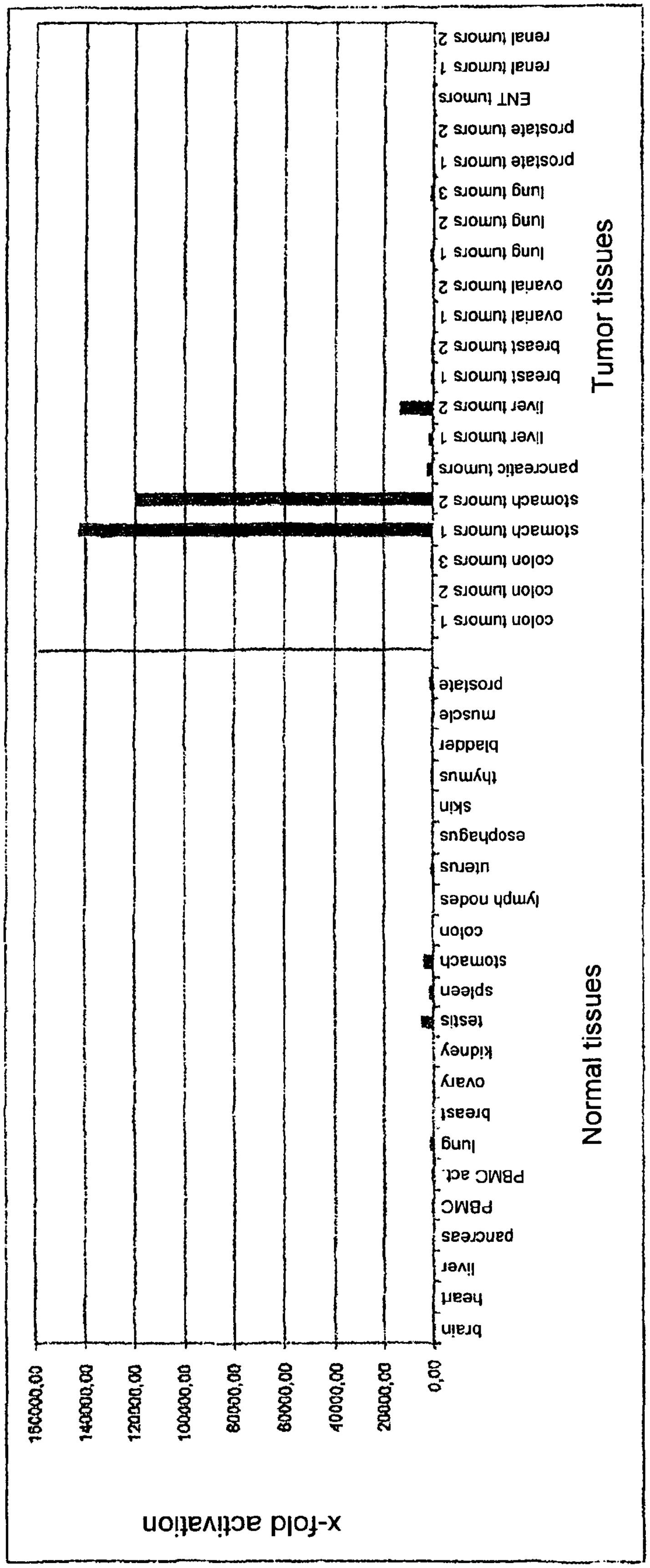
FIG. 16A: Quantitative expression analysis of PRSS7 in normal tissues (left) and various tumor tissues (pools consisting of 3-4 individual samples each, right) in linear representation of the relative expression (x-fold activation).
Figure 16B:
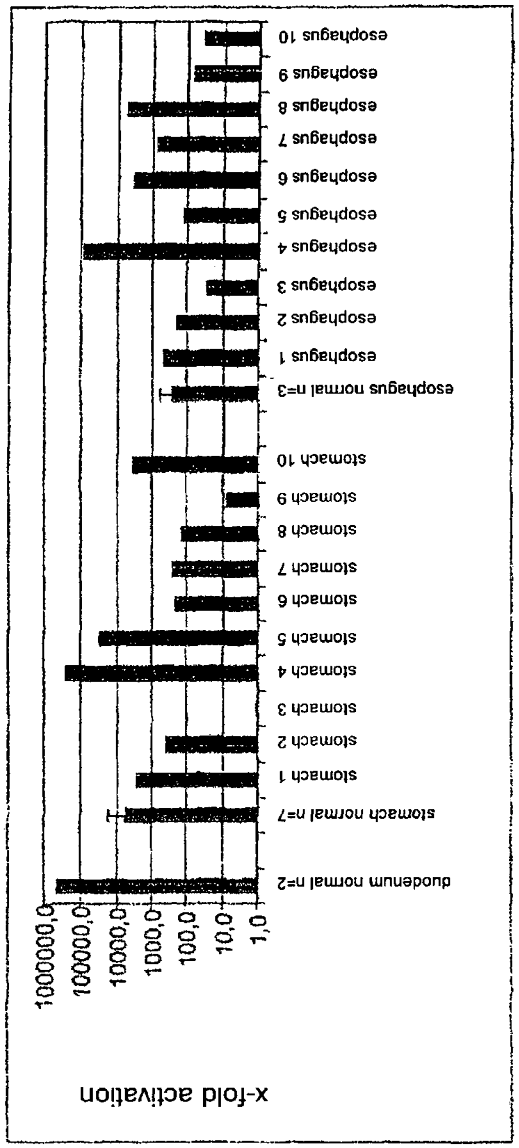
FIG. 16B: Quantitative expression analysis of PRSS7 in various tumors of the stomach and esophagus in comparison to the expression in the respective normal tissues (stomach: n=7; esophagus: n=3). For comparison the expression was measured in a normal duodenum (n=2). Logarithmic representation.

In accordance with the invention, after establishment of a PRSS7-specific quantitative RT-PCR (primer pair SEQ ID NO: 47, 48) the distribution of specific transcripts was investigated in healthy tissue and carcinoma samples (FIG. 16; methods: compare Materials and Methods, Section B.1.). In most analysed tissues we were not able to detect PRSS7-specific expression at all or only to a very small extent (FIG. 16A). Relevant expression was only found in the duodenum (FIG. 16B).

Figure 16C:
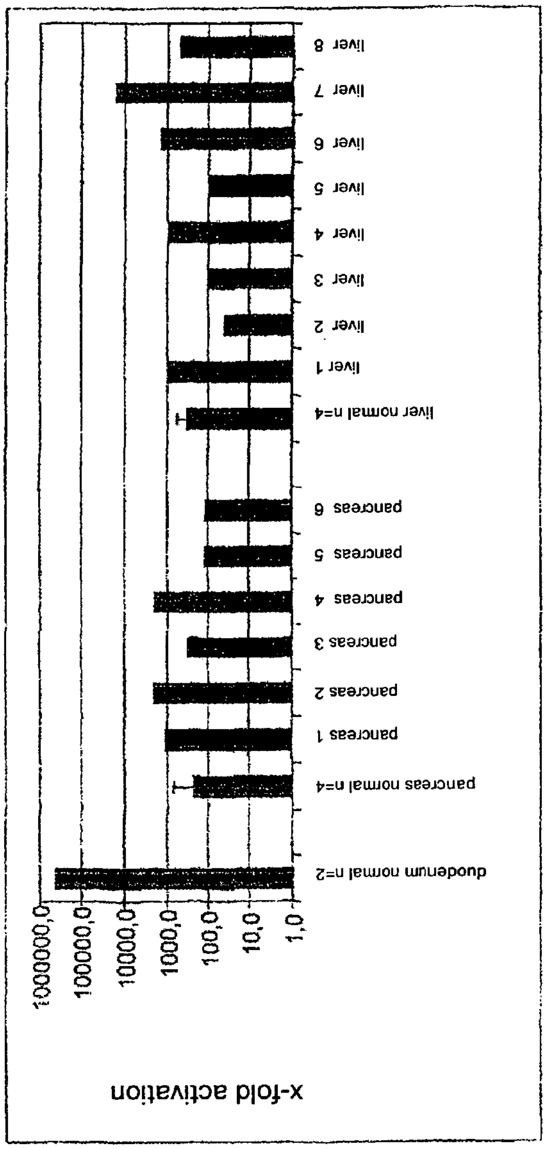
FIG. 16C: Quantitative expression analysis of PRSS7 in various pancreas and liver tumors in comparison to the expression in the respective normal tissues (n=4 for each). For comparison the expression in normal duodenum was measured (n=2). Logarithmic representation.

PRSS7 is expressed by various tumor types. In a part of the investigated stomach carcinomas a distinct overexpression was detected in comparison to normal stomach tissue (FIG. 16B). Furthermore, carcinomas of the esophagus, liver as well as pancreas expressed PRSS7, in part the gene was distinctly overexpressed in some tumor samples in comparison to the corresponding normal tissues (FIGS. 16B and 16C).

The pronounced expression and high incidence of this molecule for the described tumor indications make this protein in accordance with the invention a highly interesting diagnostic and therapeutic marker. This also includes in accordance with the invention the detection of disseminated tumor cells in serum, bone marrow and urine as well as the detection of metastases in other organs with the aid of RT-PCR.

Figure 17A:
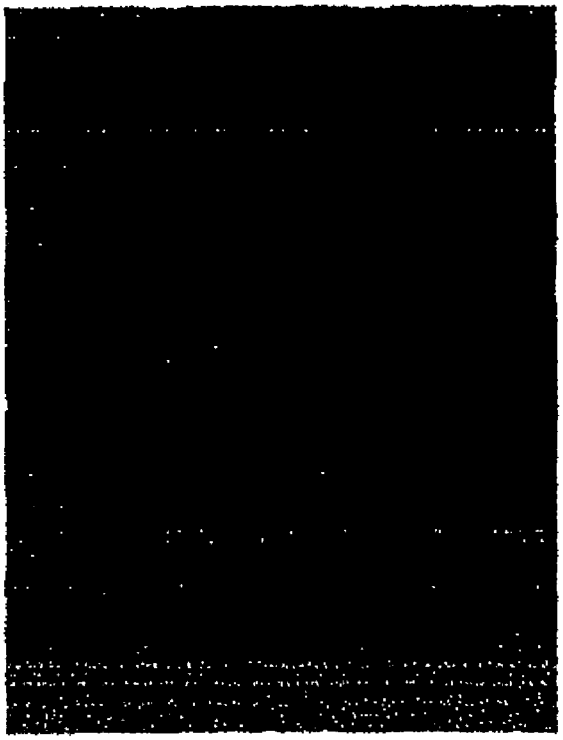
FIG. 17A: Representation of the cellular localisation of the PRSS7-protein on PRSS7-transfected cells.
Figure 17B:
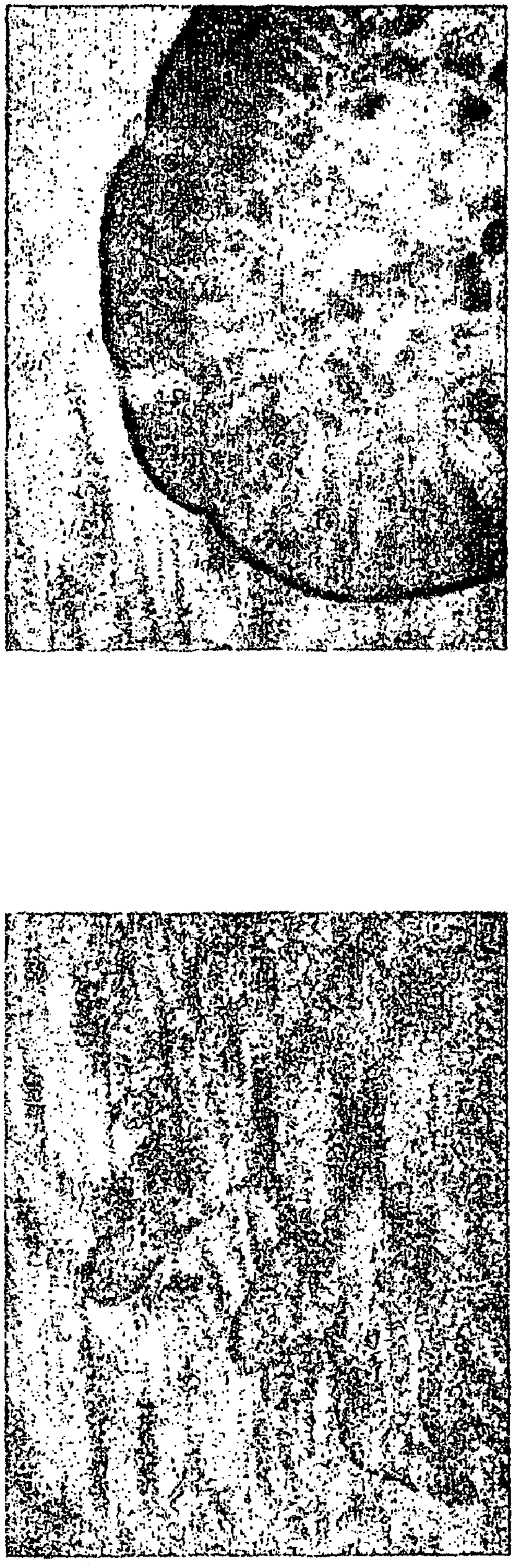
FIG. 17B: Detection of the PRSS7-protein in overview (left) and in detail (right).

We have stained cells transfected by PRSS7, as well as sections of human tissues with PRSS7-specific antibodies and were able to confirm the predicted protein topology on the membrane (FIGS. 17A and 17B).

The extracellular part of PRSS7 can be used in accordance with the invention as target structure of monoclonal antibodies for therapy as well as immune diagnosis. With respect to SEQ ID NO: 18, the amino acids starting from amino acid residue 50 are extracellularly localised. Furthermore, in accordance with the invention, PRSS7 can be used as vaccine (RNA, DNA, protein, peptides) for the induction of tumor-specific immune responses (T-cell and B-cell mediated immune reactions). This includes in accordance with the invention also the development of so-called "small compounds", which modulate the biological activity of PRSS7 and may be used in the therapy of tumors.

Example 11: Identification of CLCA2 as Diagnostic and Therapeutic Cancer Target The gene CLCA2 or "calcium activated chloride channel 2" (SEQ ID NO: 19) belongs to the family of chloride ion transporters. The gene consists of 14 exons and is located on chromosome 1 (1p31-p22). The gene encodes a protein with a length of 943 amino acids, which has a calculated molecular weight of about 120 kDa. Experimentally, 5 transmembrane domains as well as a large, N-terminally localised extracellular domain were detected. CLCA2 is an ion-transporter (Gruber, 1999. *Am J Physiol* 276, C1261-C1270).

CLCA2-transcripts were previously described in the lung, trachea and the mammary gland (Gruber, 1999. *Am J Physiol* 276, C1261-C1270), as well as in the tissues of testis, prostate and uterus (Agnel, 1999. *FEBS Letters* 435, 295-301). Comparative investigations in a comprehensive collection of tissues were not previously available.

Figure 18A:
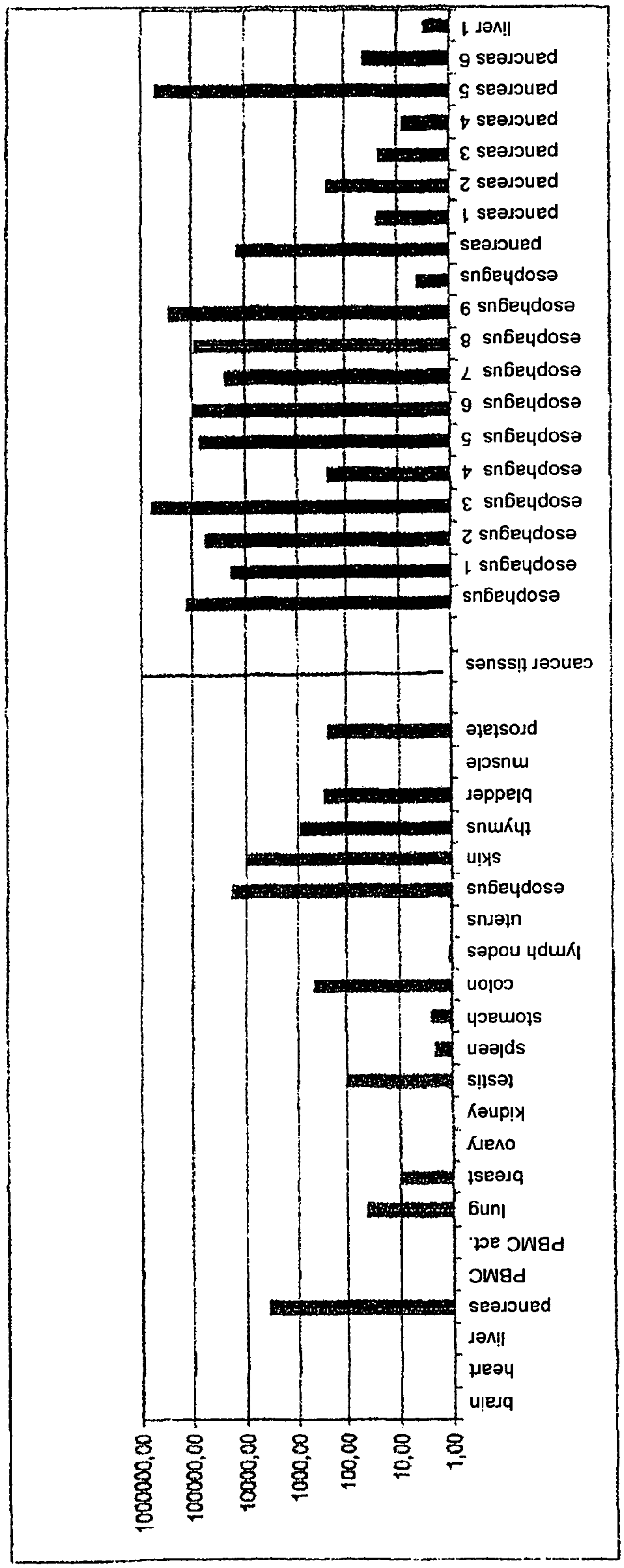
FIG. 18A: Quantitative expression analysis of CLCA2 in normal tissues (left) and various tumors (pools consisting of 3-4 individual samples each, right) in logarithmic representation of the relative expression (x-fold activation).
Figure 18B:
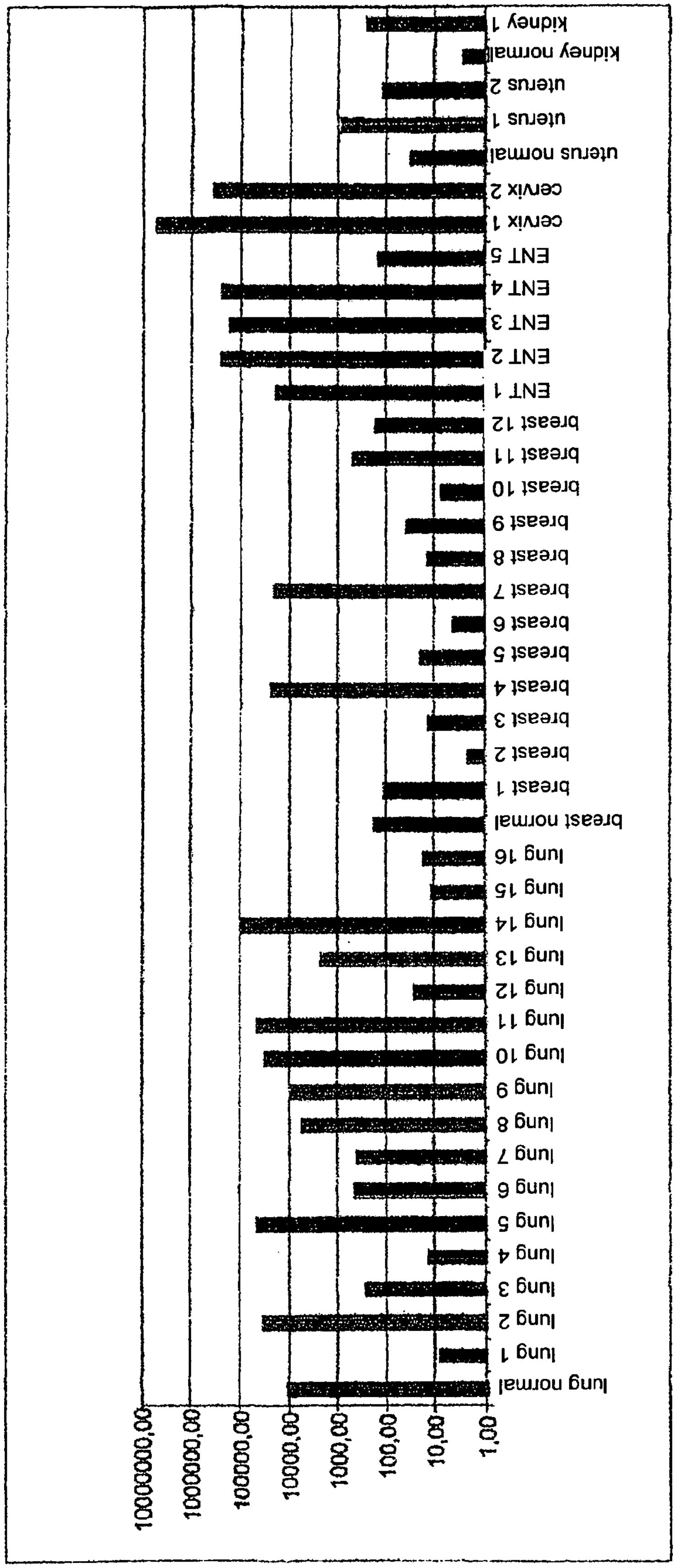
FIG. 18B: Quantitative expression analysis of CLCA2 in various tumors of the lung, breast, cervix and uterus and in ear, nose and throat tumors in comparison to the expression in the respective normal tissues. Logarithmic representation.

In accordance with the invention, after establishment of a CLCA2-specific quantitative RT-PCR (primer pair SEQ ID NO: 49, 50) the distribution of specific transcripts was investigated in almost all healthy tissues of the human body and in tumor samples (FIG. 18; methods: compare Materials and Methods, Section B.1.). We found a differential expression of CLCA2 in normal tissues. In most analysed tissues transcription is not detectable. Only in the esophagus, skin, pancreas, and significantly less in thymus, bladder, colon and prostate were we able to detect expression. Surprisingly, we found in some tumor types significant, not previously described expression of CLCA2. In particular tumors of the nose-throat area, as well as breast, esophagus, ovary and pancreas carcinomas as well as bronchial carcinomas exhibited a CLCA2-specific expression increased by a factor of 10 to 1000 in comparison to the corresponding normal tissues (FIG. 18).

The pronounced expression and high incidence of this molecule for the described tumor indications make this protein in accordance with the invention a highly interesting diagnostic and therapeutic marker. This includes in accordance with the invention also the detection of disseminated tumor cells in serum, bone marrow and urine as well as the detection of metastases in other organs with the aid of RT-PCR.

The two extracellular domains (with respect to SEQ ID NO: 20; amino acids 1-235, 448-552 and 925-943) may be used in accordance with the invention as target structures of monoclonal antibodies for therapy as well as in immune diagnosis.

Figure 19A:
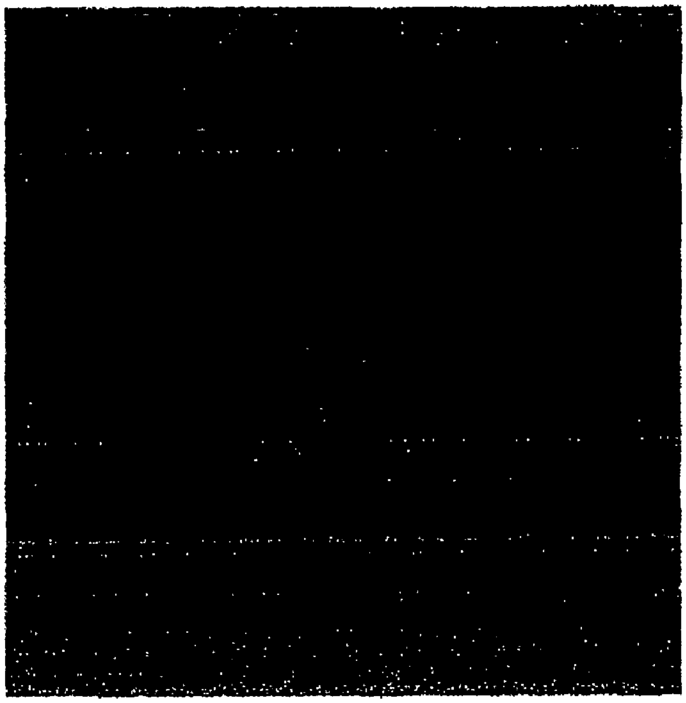
FIG. 19A: Representation of the localisation of the CLCA2-protein at the membrane of CLCA2-transfected cells.
Figure 19B:
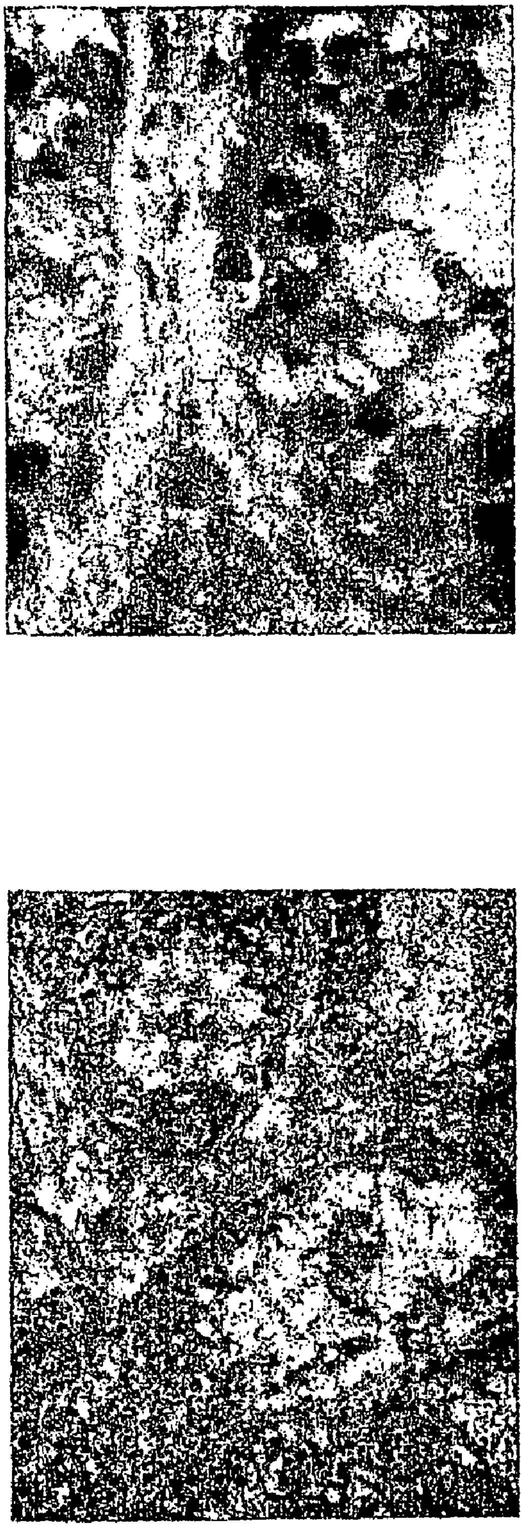
FIG. 19B: The figure shows the immunohistochemical analysis at the CLCA2-protein.

By immunization using CLCA2-specific peptides (SEQ ID NO: 100, SEQ ID NO: 101) antibodies could be produced staining CLCA2 on the cell surface. Cells transfected by CLCA2 express this protein on the cell membrane (FIG. 19A). The tumor selectivity could be confirmed in immunofluorescence using the specific antibody (FIG. 19B).

Furthermore, CLCA2 may be used in accordance with the invention as vaccine (RNA, DNA, protein, peptides) for the induction of tumor-specific immune responses (T-cell and B-cell mediated immune reactions). This includes in accordance with the invention also the development of so-called "small compounds", which modulate the biological activity of CLCA2 and may be used for the therapy of tumors.

Example 12: Identification of TM4SF4 ("Transmembrane 4 Superfamily Member 4") as Diagnostic and Therapeutic Cancer Target The gene TM4SF4 (SEQ ID NO: 21) and its translation product (SEQ ID NO: 22) is a member of the tetraspanin family (Hemler, 2001. *J Cell Biol* 155, 1103-07). The gene consists of 5 exons and is located on chromosome 3 (3q25).

The gene encodes a protein with a length of 202 amino acids and a calculated molecular weight of about 21.5 kDa. Prediction programs consistently predict 4 transmembrane domains for TM4SF4. The protein is N-glycosylated in the region of the second extracellular domain and is located in the cell membrane. It is described that the degree of N-glycosylation has an effect on the regulation of the cell proliferation and that it is inhibited with increasing glycosylation (Wice & Gordon, 1995. *J Biol Chem* 270, 21907-18). Tetraspanines form complexes with various members of the group of integrins. These high-molecular multi-complexes are ascribed a multitude of important functions in the cell. For example, they fulfil functions in the cell-cell-adhesion and in intercellular contacts, in the signal transduction and in cell motility (Bereditschevski, 2001. *J Cell Sci* 114, 4143-51).

Figure 20A:
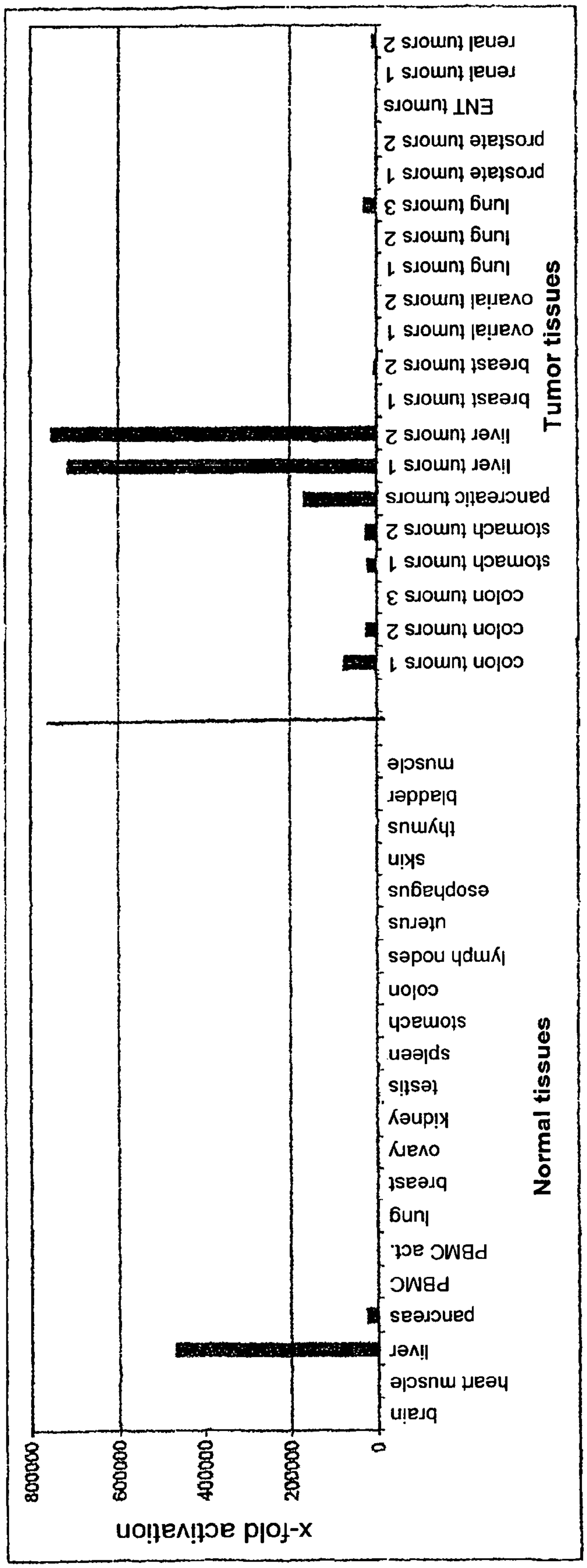
FIG. 20A: Quantitative expression analysis of TM4SF4 in normal tissues (left) and in various tumors (pools consisting of 3-4 individual samples each, right) in linear representation of the relative expression (x-fold activation).
Figure 20B:
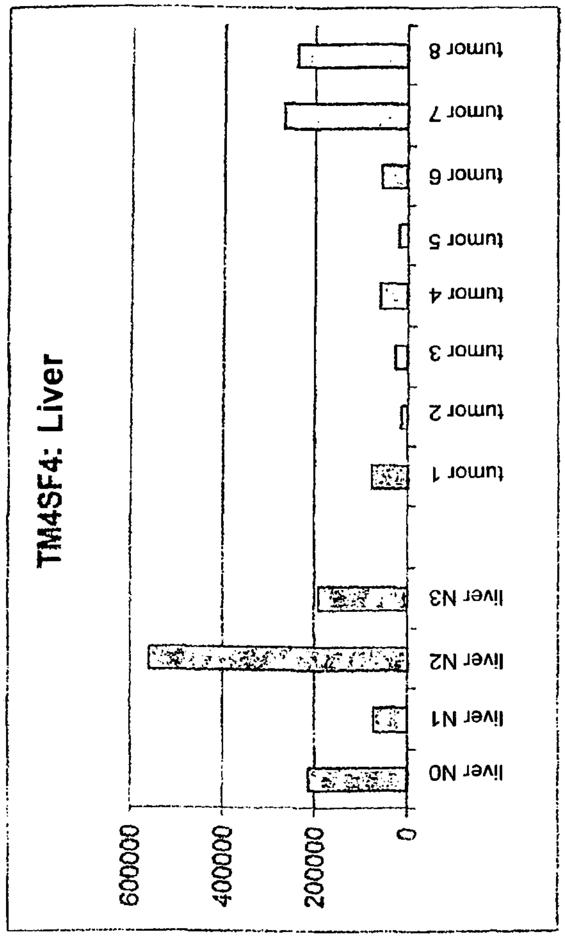
FIG. 20B: Quantitative expression analysis of TM4SF4 in various liver tumors in comparison to 4 different normal tissues of the liver (N0 to N3); linear representation.
Figure 20C:
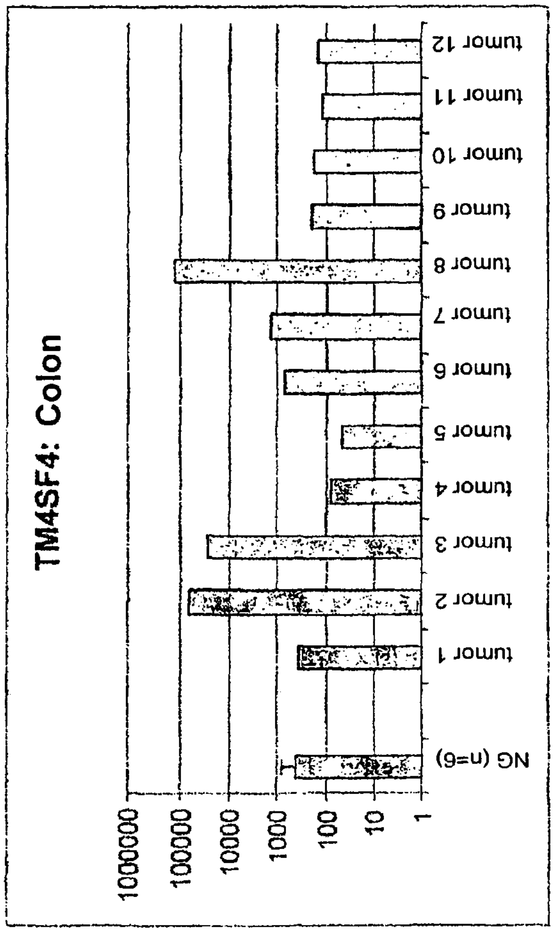
FIG. 20C: Logarithmic representation of the relative expression of TM4SF4 in 12 different colon tumors in comparison to normal colon samples (NG: normal tissue; 6 different normal tissues were investigated).

TM4SF4-transcripts are described in the periportal area of the liver as well as in specific sections of the intestine, but were not previously analysed in other tissues and in particular not in tumors (Wice & Gordon, 1995. *J Biol Chem* 270, 21907-18). In accordance with the invention, after establishment of a TM4SF4-specific quantitative RT-PCR (primer pair SEQ ID NO: 51, 52) the distribution of specific transcripts in healthy tissue and in carcinoma samples was investigated (FIG. 20; methods: compare Materials and Methods, Section B.1.). Our investigations showed a differential distribution of the expression in normal tissues. TM4SF4-specific transcripts were mainly found in samples of normal liver tissue. In several other normal tissues (amongst others pancreas) we found a distinctly lower expression (at least 10-fold). Expression was not detectable in the brain, heart muscle, skeletal muscles, skin, breast tissue, ovary, PBMC, spleen, lymph nodes and cervix. Contrary to the published prediction, that TM4SF4 is down-regulated in tumor tissue (Wice & Gordon, 1995. *J Biol Chem* 270, 21907-18), at least comparable TM4SF4-specific expression was shown in various tumors; in part TM4SF4 was overexpressed in tumors (FIG. 20A). In a detailed expression analysis we were also able to prove contrary to published data, that TM4SF4 is not suppressed in liver tumors (FIG. 20B). In addition, the gene was overexpressed in 4/12 colon tumor samples in comparison to normal colon tissue (FIG. 20C).

Figure 21A:
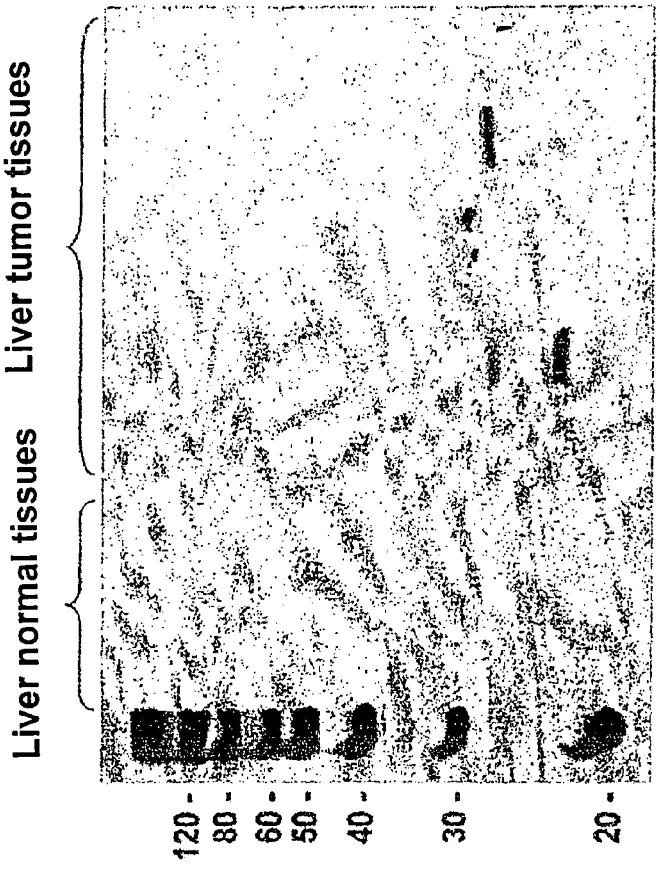
FIG. 21A: The image shows an immunoblot with TM4SF4-specific antibodies in normal liver tissue and liver tumor tissue. Two putative glycosylation parameters are recognisable.
Figure 21B:
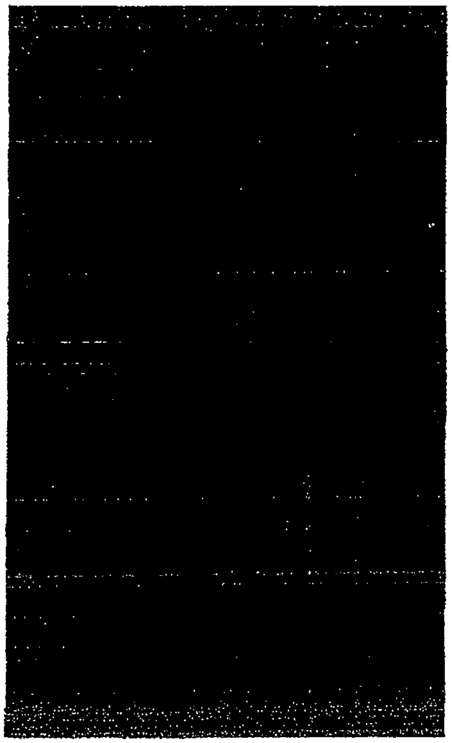
FIG. 21B: The figure shows the localisation of the TM4SF4-protein at the membrane of TM4SF4-transfected cells.
Figure 21C:
FIG. 21C: The immunohistochemical analysis was able to confirm the expression selectivity observed by PCR.
Figure 22A:
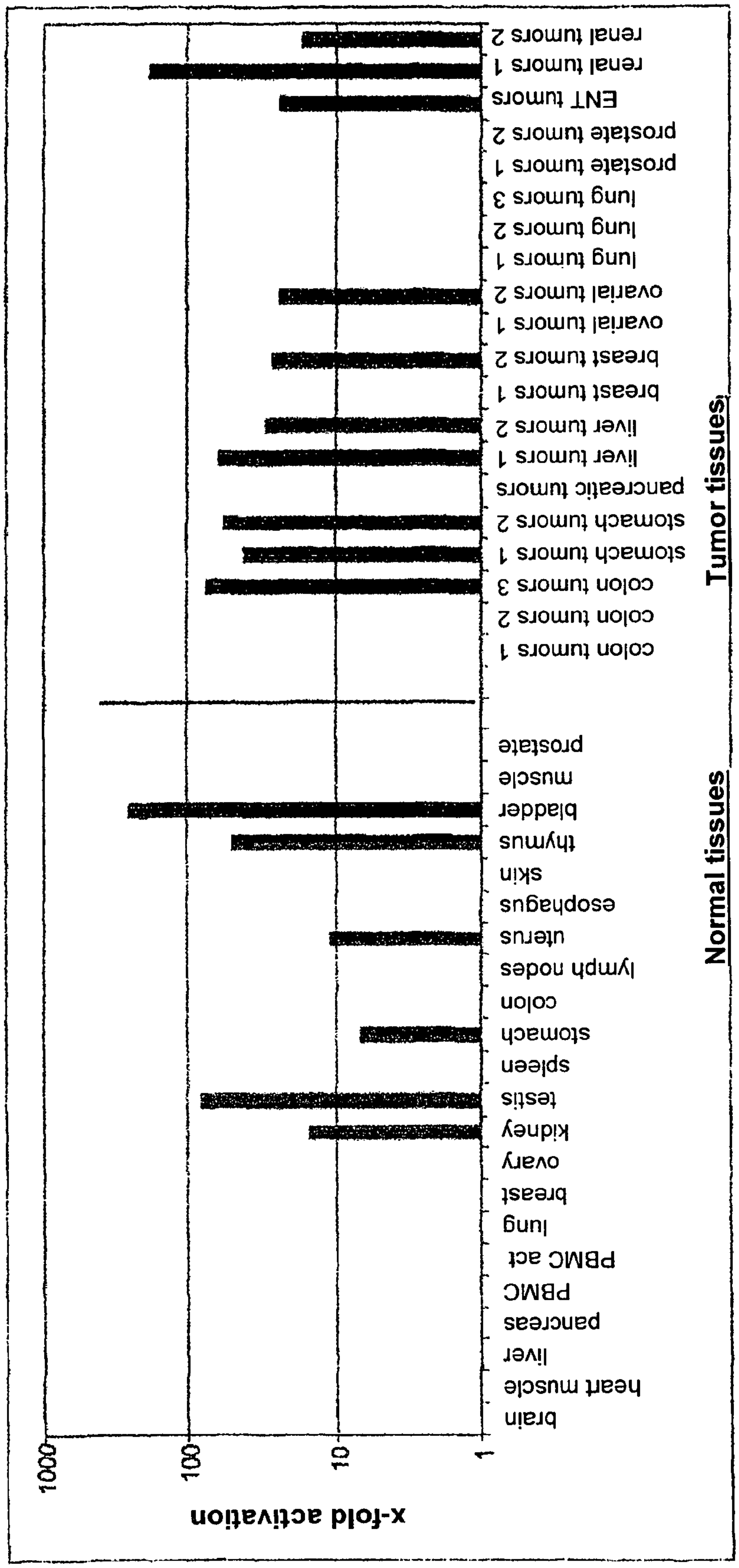
FIG. 22A: Quantitative expression analysis of claudin19 in normal tissues (left) and in various tumors (pools consisting of 3-4 individual samples each, right) in logarithmic representation of the relative expression (x-fold activation).
Figure 22B:
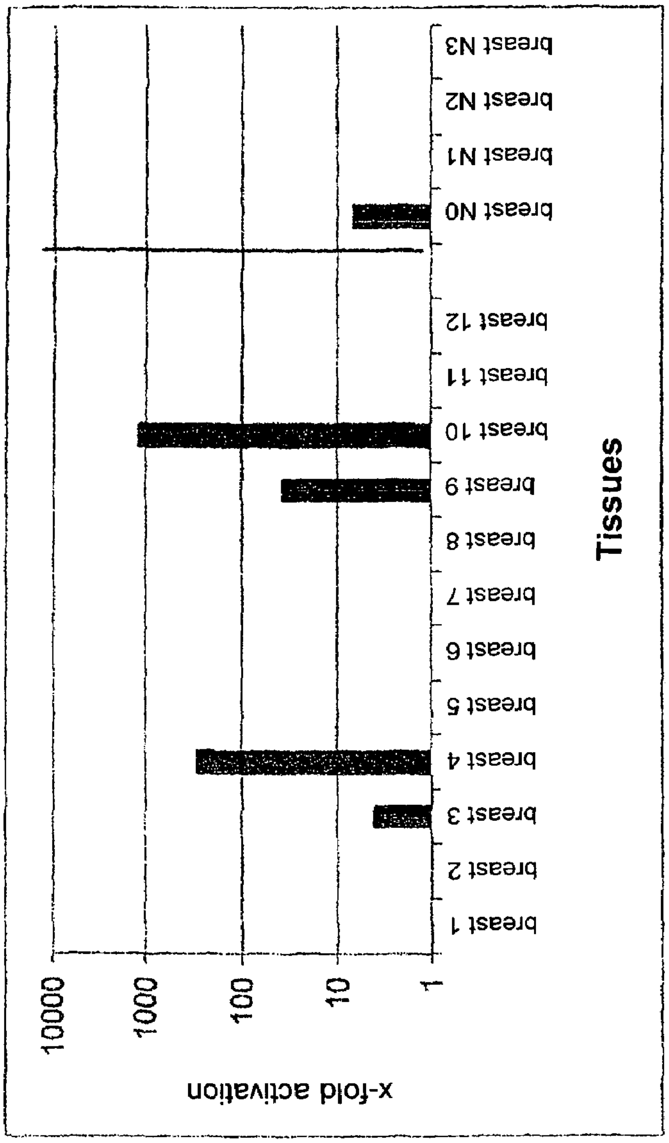
FIG. 22B: Quantitative expression analysis of claudin19 in various breast tumors and the respective normal breast tissues.
Figure 22C:
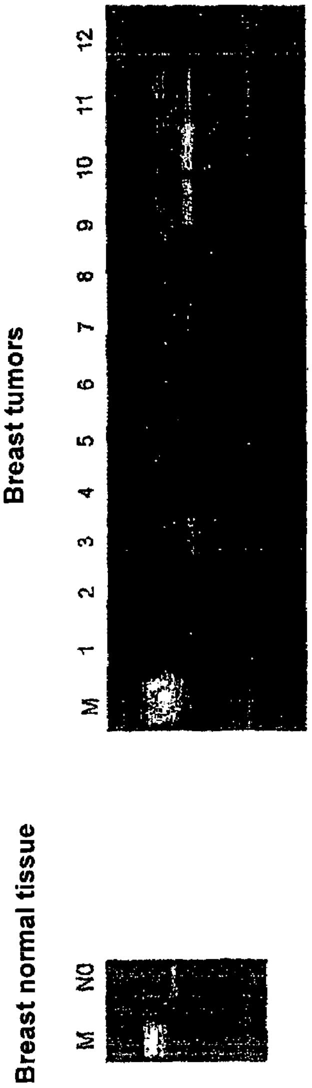
FIG. 22C: Conventional RT-PCR with analysis of claudin19 in various breast tumor samples as well as in a normal tissue; M: DNA-length marker.
Figure 22D:
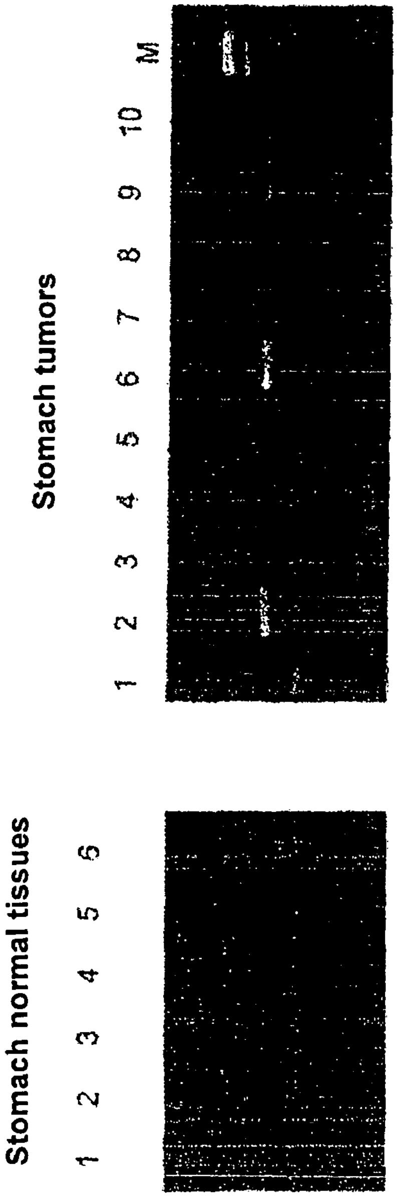
FIG. 22D: Conventional RT-PCR-analysis of claudin19 in various normal tissues of the stomach and stomach tumors.
Figure 22E:
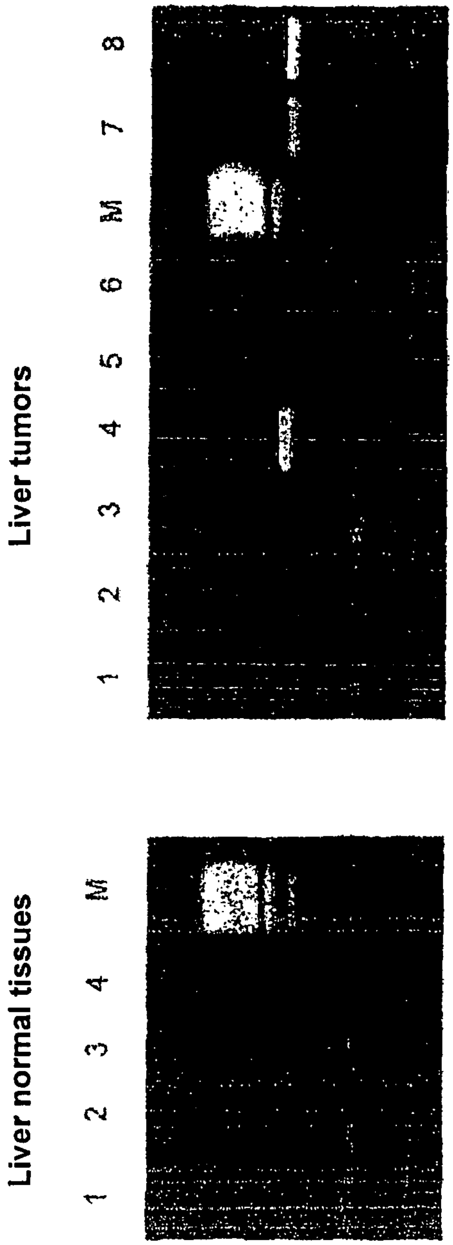
FIG. 22E: Conventional RT-PCR-analysis of claudin19 in various normal tissues of the liver and liver tumors; M: DNA-length marker.

In order to produce TM4SF4-specific antibodies, the peptides listed under SEQ ID NO: 65 and 66 were used. These antibodies were able to recognise the TM4SF4-protein in various sizes, which represent putative glycosylation patters (FIG. 21A). Furthermore, the surface localisation of TM4SF4 could be confirmed with the aid of immunofluorescence (FIG. 21B) and the tumor-selectivity observed in the PCR could be confirmed with the aid of immunhistological staining of human tissues (FIG. 21C).

In summary, TM4SF4 can be characterised as a membrane protein, whose expression is limited to cell-subpopulations of a few selected normal tissues. TM4SF4 is particularly detectable in the periportal hepatocytes in the liver and in the apical membrane of the epithelia of the gastro-intestinal tract. In the case of apical protein localisation, the protein is not accessible in normal cells to antibodies, because in the intestinal epithelium it faces the lumen and therefore is not connected to the vascular system. In intestinal tumors, however, these molecules, which are not accessible in healthy tissue, are no longer compartmented due to uncontrolled proliferation and the neovascularisation of the tumor, and are therefore accessible for therapeutic antibodies.

The two extracellular domains of TM4SF4 therefore may be used in accordance with the invention as target structures of monoclonal antibodies. With respect to SEQ ID NO: 22, the amino acids 23-45 and 110-156 are located extracellularly (prediction was performed using the software TMHMM2). For the peptides with the SEQ ID NO: 65 and 66 polyclonal antibodies were already successfully generated (Wice & Gordon, 1995. *J Biol Chem* 270:21907-18). For therapeutic approaches for the development of tumor-specific antibodies the peptides SEQ ID NO: 67 and SEQ ID NO: 68 are suitable, which each contain a conserved motive NXX' for posttranslational N-glycosylations, whereby "X" represents any amino acid except proline and X' represents S or T.

Example 13: Identification of CLDN19 as Diagnostic and Therapeutic Cancer Target The gene CLDN19 or claudin19 (SEQ ID NO: 23) with its translation product (SEQ ID NO: 24) is a member of the claudin family.

The gene encodes a protein with a length of 224 amino acids which has a calculated molecular weight of about 21.5 kDa. Prediction programs consistently predict for claudin19 the 4 transmembrane domains characteristic for the family of claudins. Claudin19 to date has not been functionally characterised in greater detail. Functions have been described for other members of the claudin-family. Accordingly, claudins play an important role in cell-cell-adhesion and in intercellular contacts. They are part of large molecule complexes and so form membrane pores ("tight junctions") for cell-cell-contacts.

In accordance with the invention, after establishment of a CLDN19-specific quantitative RT-PCR (primer pair SEQ ID NO: 53, 54) the distribution of specific transcripts was investigated in healthy tissue and carcinoma samples (FIG. 22; methods: compare Materials and Methods, Section B.1.). Surprisingly, we found a differential distribution of the expression in normal tissues. In the majority of normal tissues (in particular in the brain, heart muscle, skeletal muscle, liver, pancreas, PBMCs, lung, breast tissue, ovary, spleen, colon, stomach, lymph nodes, esophagus, skin and prostate) CLDN19 is not detectable. Only in normal tissue of the bladder, thymus and testis we were able to detect CLDN19-transcripts. The comparative investigation of tumor tissues showed surprisingly that CLDN19 is expressed by various tumors. These are particularly carcinomas of kidney, stomach, liver and breast, which in comparison to corresponding normal tissues exhibit an up to 10-fold overexpression. CLDN19 has not previously been described in the context of human tumors (FIG. 22A-22E).

The pronounced expression and high incidence of this molecule for the described tumor indications make this protein in accordance with the invention a highly interesting diagnostic and therapeutic marker. In accordance with the invention, this includes the detection of disseminated tumor cells in serum, bone mark and urine, as well as the detection of metastases in other organs with the aid of RT-PCR.

The two extracellular domains (amino acids 28-76 and 142-160 with respect to SEQ ID NO: 24) of CLDN19 may be used in accordance with the invention as target structures of monoclonal antibodies for the therapy and immune diagnosis.

Furthermore, CLDN19 may be used in accordance with the invention as vaccine (RNA, DNA, protein, peptides) for the induction of tumor-specific immune responses (T-cell and B-cell mediated immune reactions). In accordance with the invention, this includes the development of so-called "small compounds", which modulate the biological activity of CLDN19 and may be used for the therapy of tumors.

Example 14: Identification of ALPPL2 as Diagnostic and Therapeutic Cancer Target The gene ALPPL2 or "stem cell-specific alkaline phosphatase" or GCAP (SEQ ID NO: 25) encodes a protein (SEQ ID NO: 26) belonging to the family of alkaline phosphatases (AP). This consists of four very homologous members in total (homology: 90-98%). The gene codes for a transcript with a length of 2486 bp and consists of 11 exons. ALPPL2 is located on chromosome 2 (2q37.1) in the vicinity of its closely related family members ALPP and ALPI.

The derived protein has a length of 532 amino acids and a calculated molecular weight of about 57.3 kDa. ALPPL2 is glycosylated and located in the plasma membrane as homodimer via a GPI-anchor. The exact physiological function of the enzyme is not known. For osteosarcomas or Paget's disease the alkaline phosphatase enzyme activity is used as tumor marker (Millán, 1995. *Crit Rev Clin Lab Sci* 32, 1-39). However, this determination is non-specific and independent from the actual underlying molecule. It is not clear, which of the three above mentioned phosphatases or possibly even other currently not known phosphatases result in this activity.

ALPPL2 has been used previously only as diagnostic marker "in situ" for the diagnosis of gamete tumors (Roelofs et al., 1999. *J Pathol* 189, 236-244).

Figure 23A:
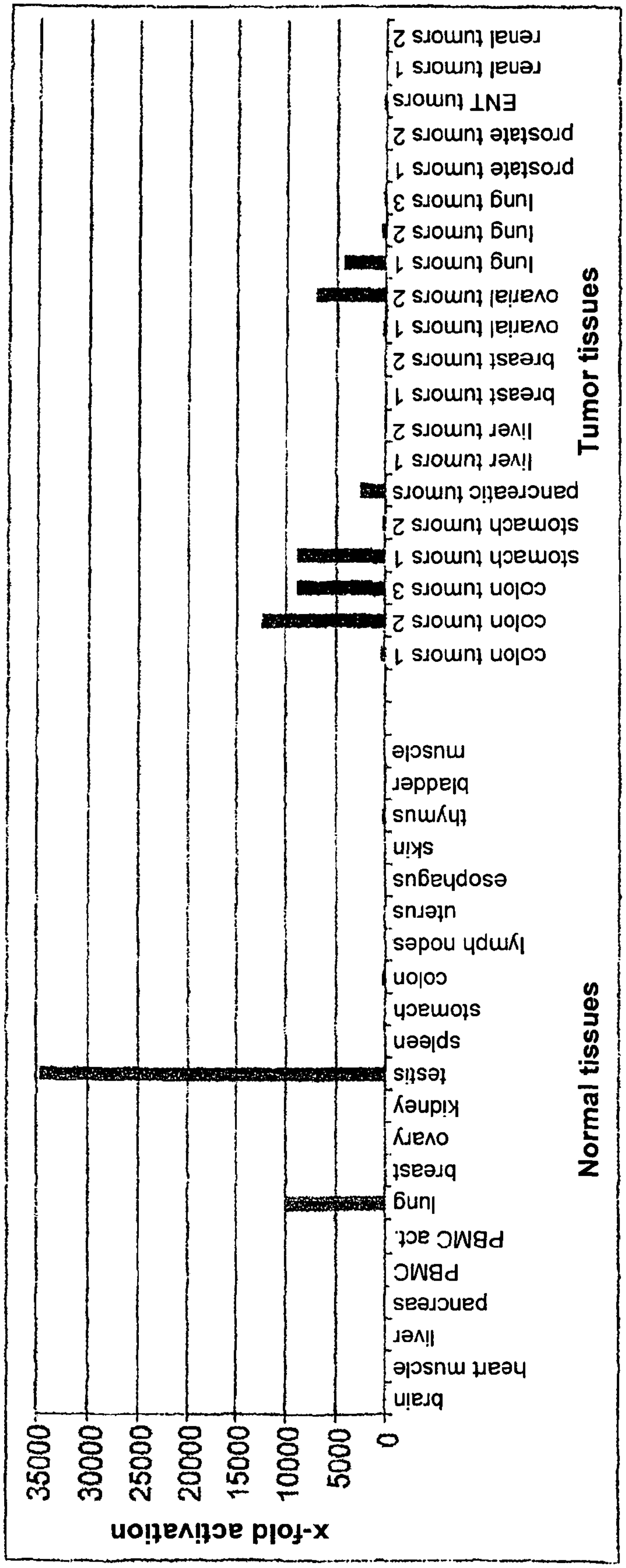
FIG. 23A: Quantitative expression analysis of ALPPL2 in normal tissues (left) and in tumors (pools consisting of 3-4 individual samples each, right) in linear determination of the relative expression (x-fold activation).
Figure 23B:
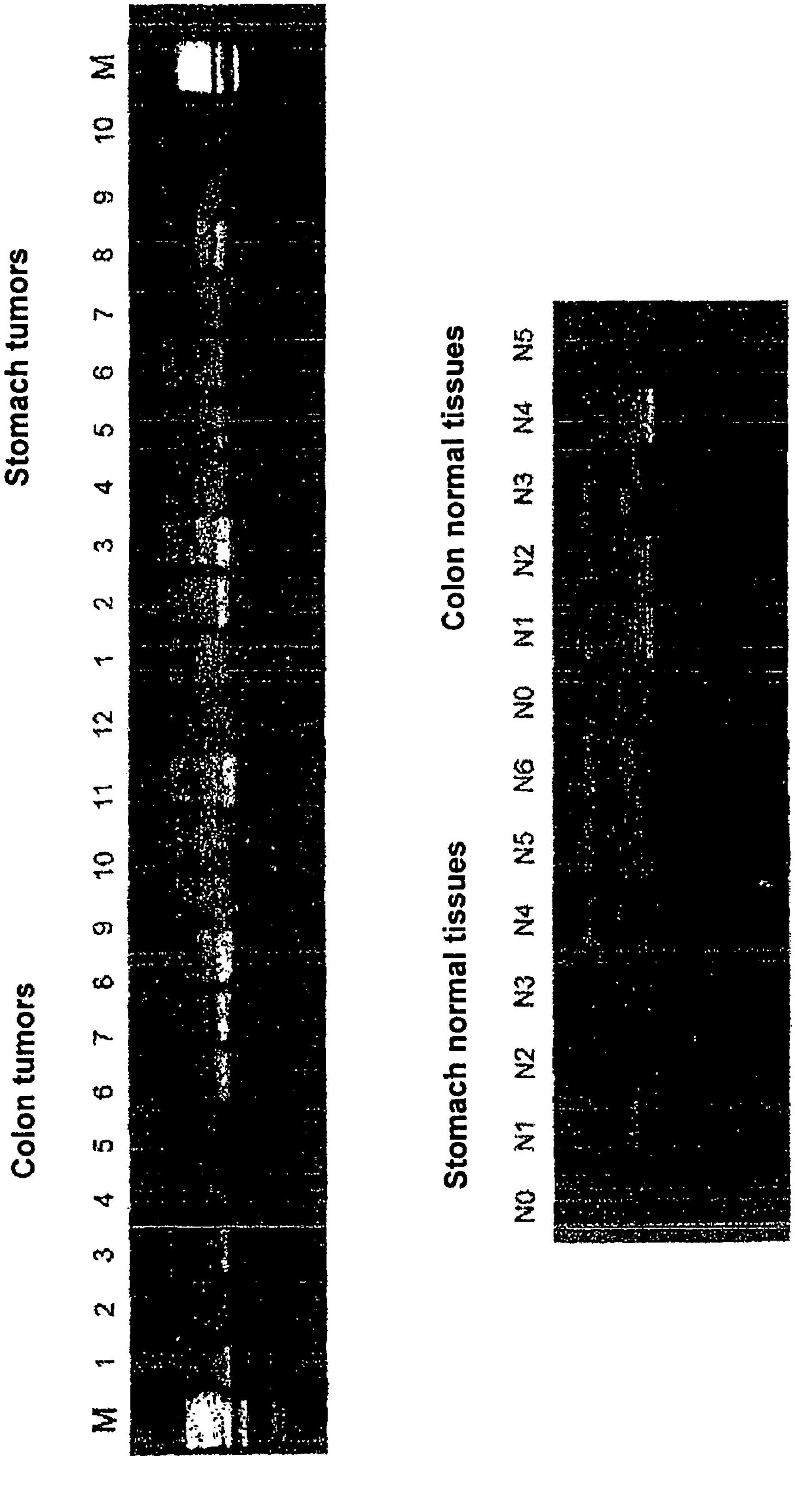
FIG. 23B: Gel image of a conventional RT-PCR-analysis of ALPPL2 in various tumors of the colon and stomach as well as in the respective normal tissues after gel-electrophoretic separation; M: DNA-length marker.

In accordance with the literature concerning a limited initial set of tissue types, ALPPL2 is expressed in testis and in the thymus as well as in some stem cell tumors (LeDu, 2002. *J Biol Chem* 277, 49808-49814). In accordance with the invention after establishment of an ALPPL2-specific quantitative RT-PCR (primer pair SEQ ID NO: 55, 56) the distribution of this gene product was investigated in healthy tissue and in carcinoma samples, whereby a comprehensive diversity of tissues was investigated, which amongst others also represented all body tissues (FIG. 23; methods: compare Materials and Methods B.1.). We detected no protein in most normal tissues (particularly in the brain, heart muscle, skeletal muscle, liver, pancreas, PBMCs, breast tissue, ovary, spleen, colon, stomach, lymph nodes, esophagus, skin and prostate). We demonstrated expression in normal tissues of testis and lung, and very low levels in the thymus and colon. The comparative investigation of tumors, however, surprisingly showed that ALPPL2 is expressed in significant quantities by various tumor types, particularly in carcinomas of the colon, stomach, pancreas, ovary and lung, but also in carcinomas of the nose-throat area (FIGS. 23A and 23B).

The pronounced expression and high incidence of this molecule for the described tumor indications make this protein in accordance with the invention a highly interesting diagnostic and therapeutic marker. This includes in accordance with the invention the detection of disseminated tumor cells in the serum, bone marrow and urine, as well as the detection of metastases in other organs with the aid of RT-PCR.

The entire ALPPL2-protein (SEQ ID NO: 26) is extracellularly located and therefore can be used in accordance with the invention as a target structure for developing monoclonal antibodies for therapy as well as immune diagnosis.

Furthermore, ALPPL2 in accordance with the invention can be used as vaccine (RNA, DNA, protein, peptides) for the induction of tumor-specific immune responses (T-cell and B-cell mediated immune reactions). This includes in accordance with the invention also the development of so-called "small compounds", which modulate the biological activity of ALPPL2 and can be used in the therapy of tumors.

Example 15: Identification of GPR64 as Diagnostic and Therapeutic Cancer Target

The gene GPR64 or "G-protein coupled receptor 64" (SEQ ID NO: 27) and its translation product (SEQ ID NO: 28) belongs to a large group of 7-transmembrane receptors. The gene encodes a transcript with a length of 3045 bp and consists of 27 exons. GPR64 is located on the chromosome (Xp22). The gene encodes a protein with a length of 987 amino acids which has a calculated molecular weight of about 108 kDa. The N-terminal region represents an extracellular domain, which is strongly glycosylated. The exact physiological function of this protein is not known.

Figure 24A:
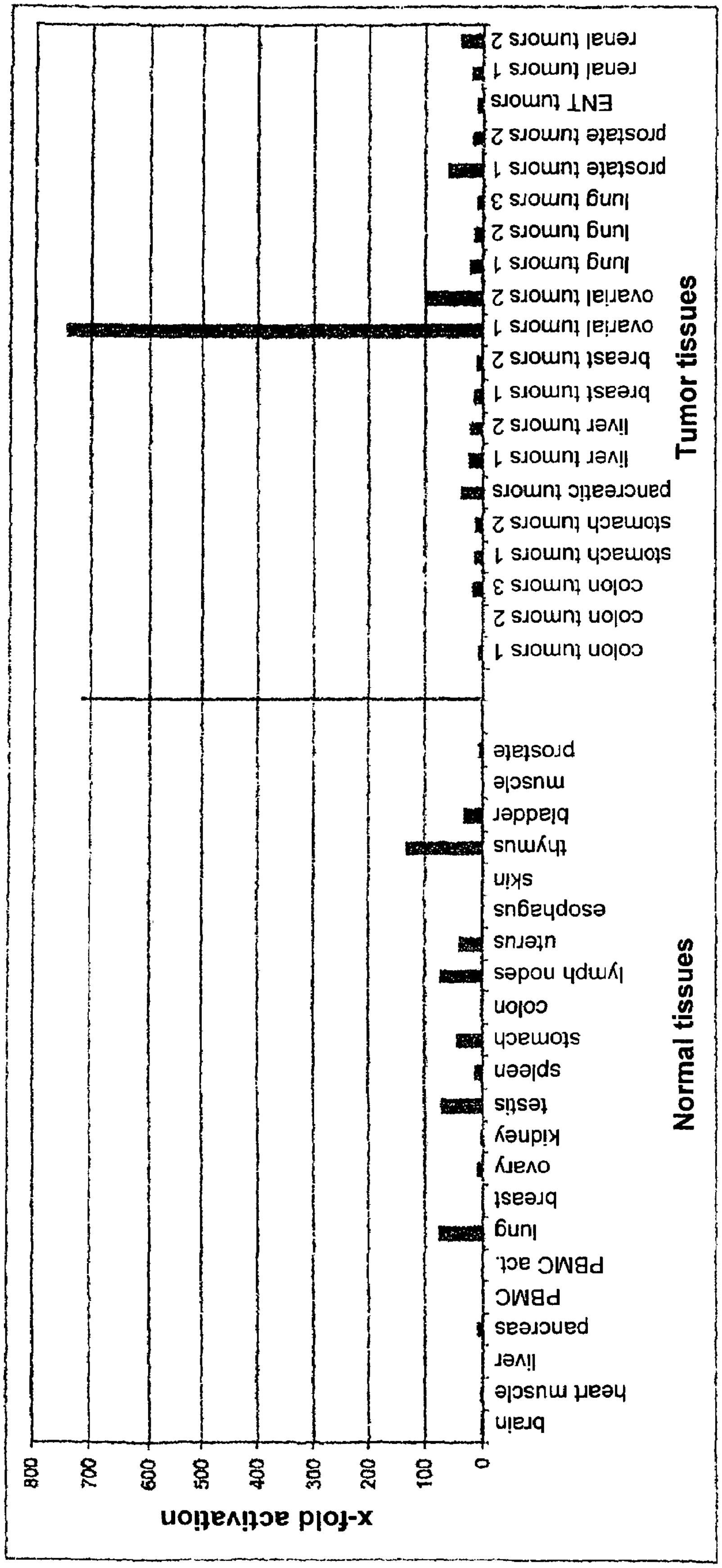
FIG. 24A: Quantitative expression analysis of GPR64 in normal tissues (left) and in tumors (pools consisting of 3-4 individual samples each, right) in linear representation of the relative expression (x-fold activation).
Figure 24B:
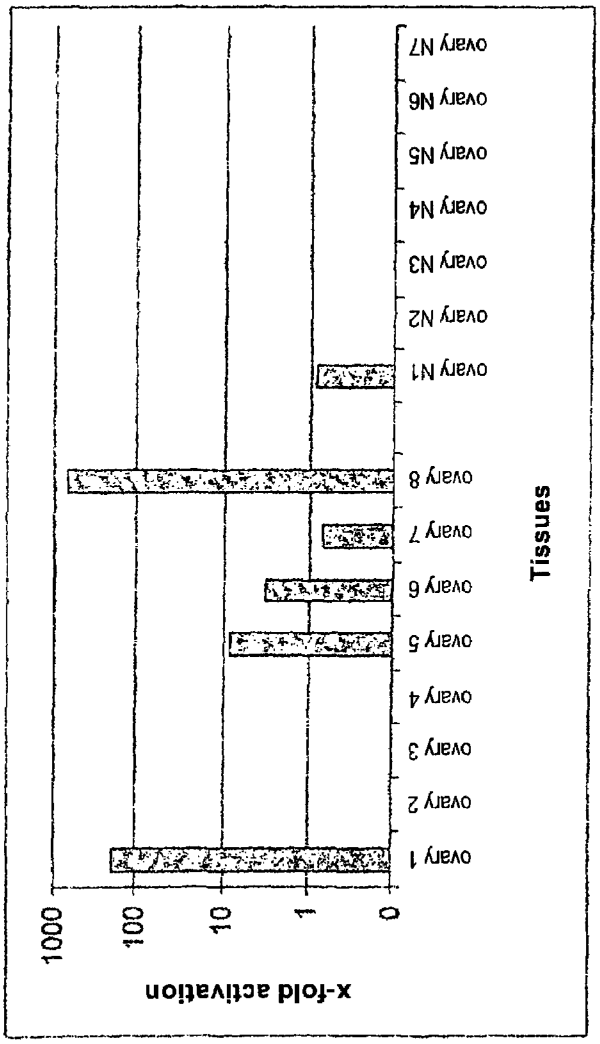
FIG. 24B: Quantitative expression analysis of GPR64 in various tumors of the ovary and the respective normal ovary tissues.
Figure 24C:
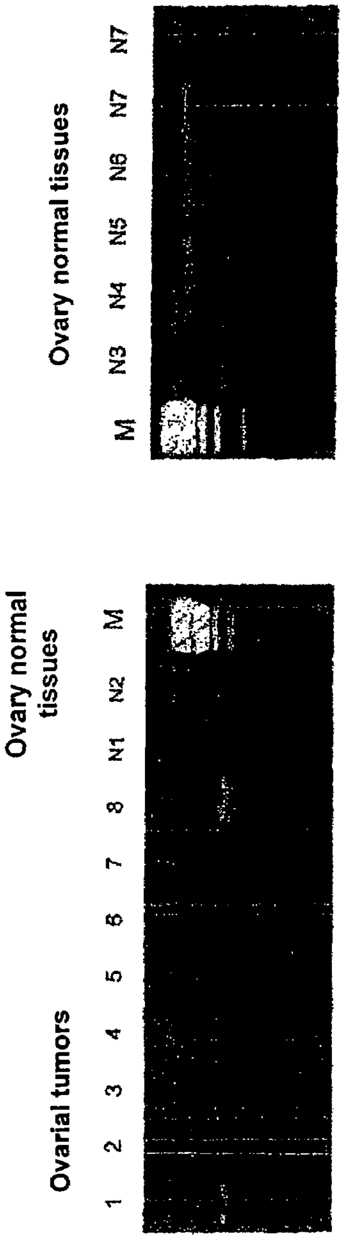
FIG. 24C: Gel-image of a RT-PCR-analysis of GPR64 in various tumors of the ovary and in normal tissues; M: DNA-length marker.
Figure 25A:
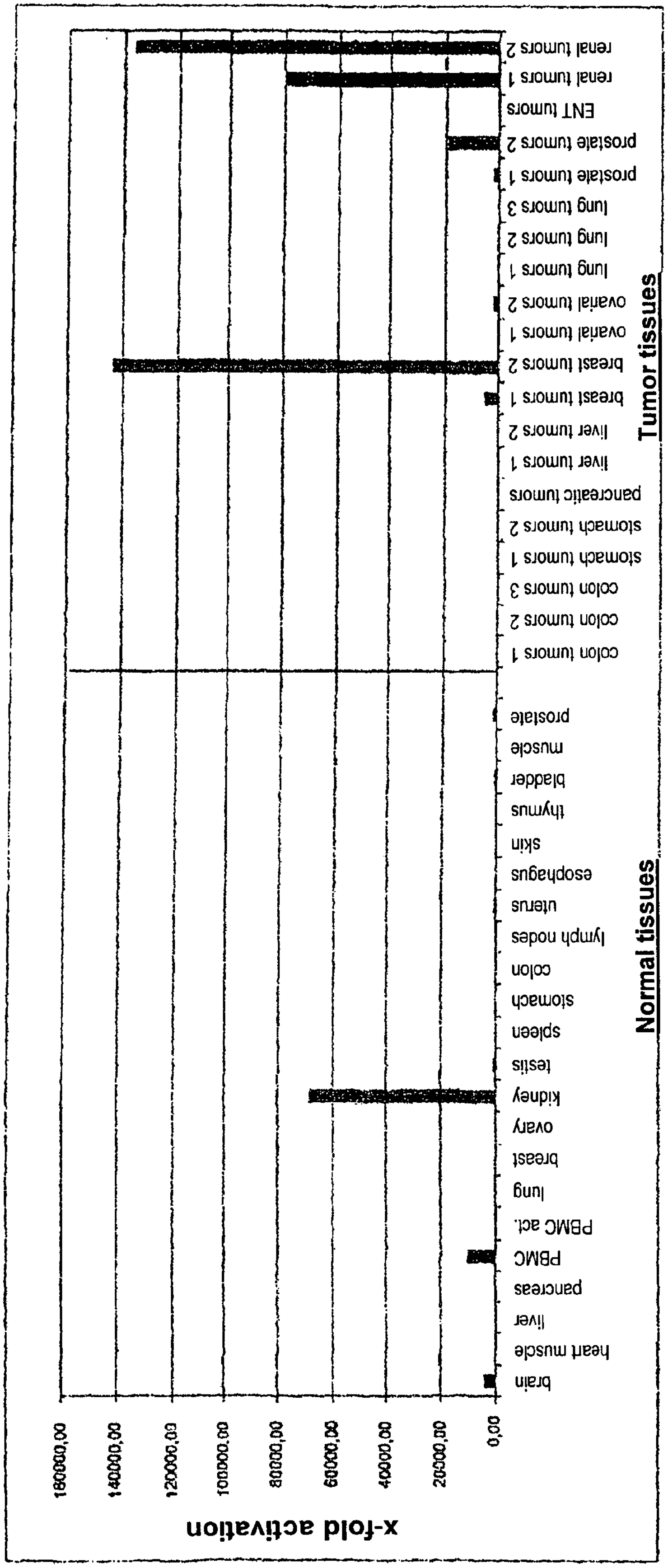
FIG. 25A: Quantitative expression analysis of SLC12A1 in normal tissues (left) and in tumors (pools consisting of 3-4 individual samples, right) in linear representation of the relative expression (x-fold activation).
Figure 25B:
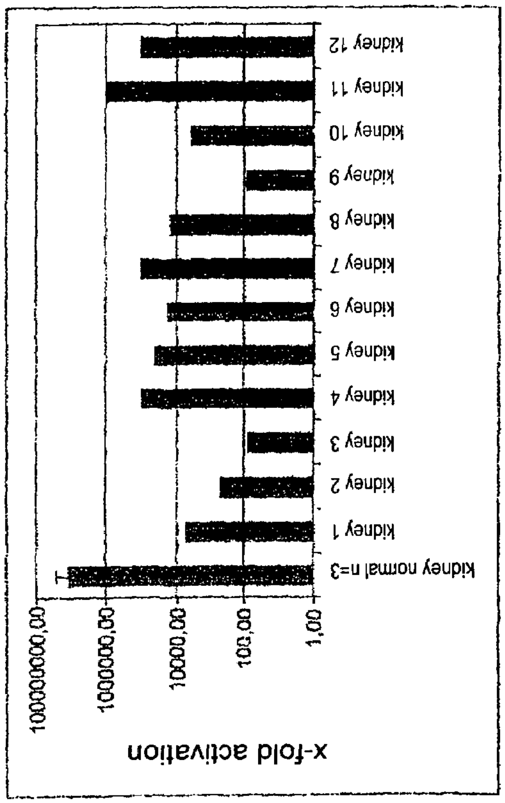
FIG. 25B: Quantitative expression analysis of SLC12A1 in 12 different kidney tumors in comparison to the expression in the normal kidney (n=3).
Figure 25C:
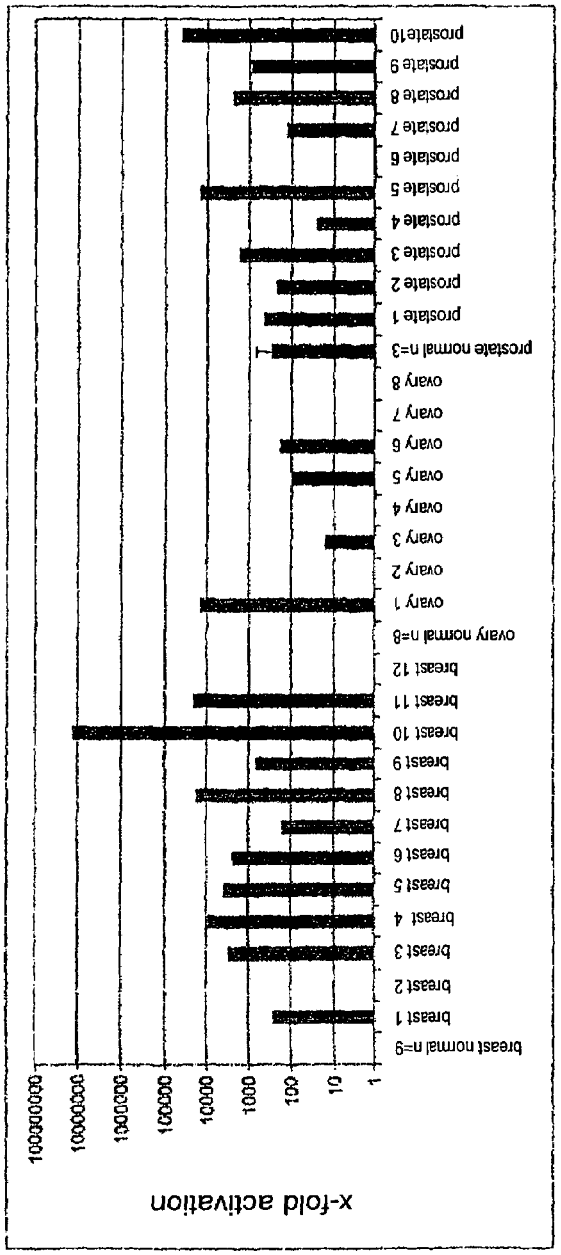
FIG. 25C: Quantitative expression analysis of SLC12A1 in tumors of the breast, ovary and prostate in comparison to the expression in the respective normal tissues (breast: n=9, ovary: n=8, prostate: n=3). Logarithmic representation.
Figure 25D:
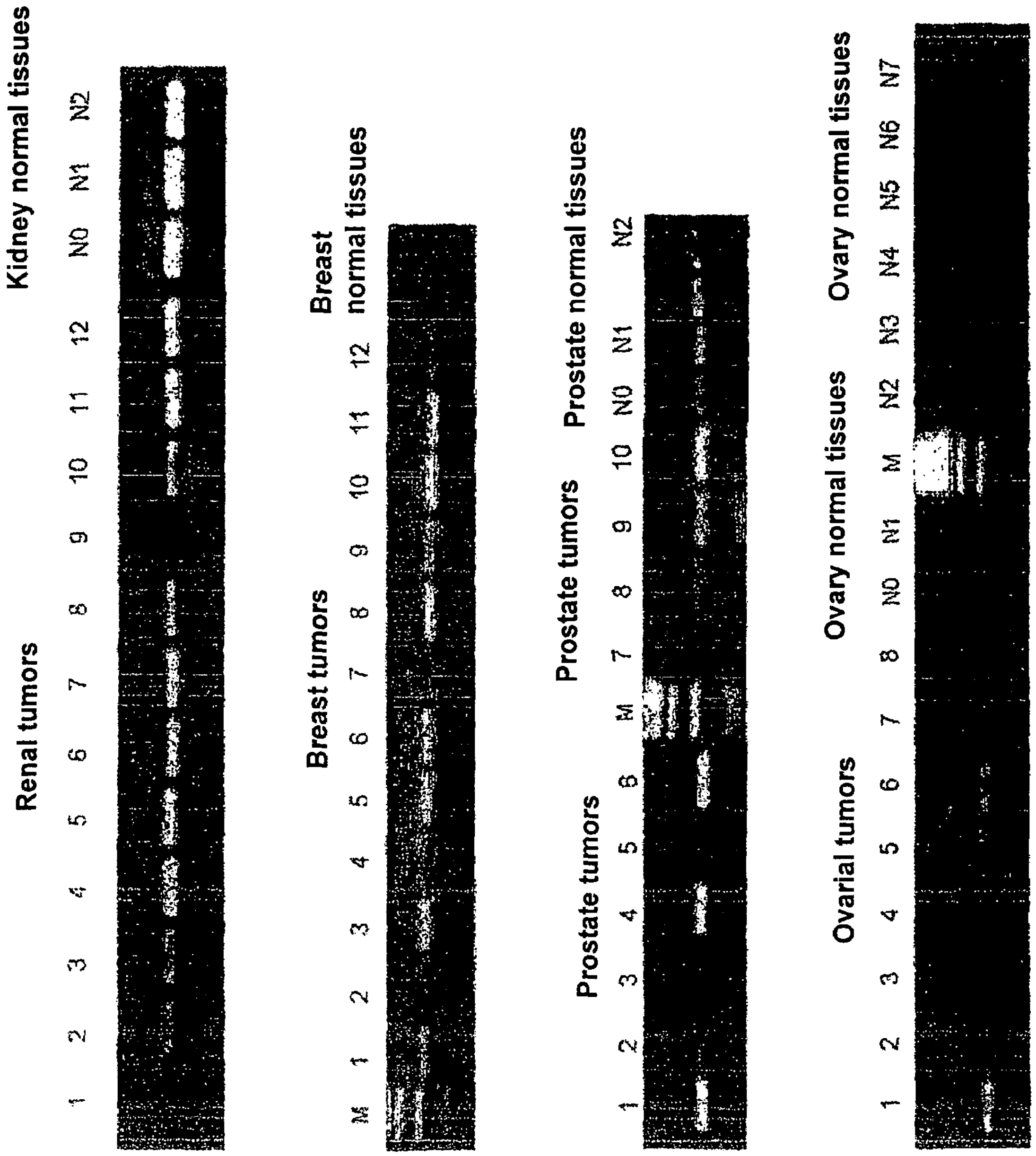
FIG. 25D: Conventional RT-PCR-analysis of SLC12A1 in kidney tumors, various normal kidneys and various tumor types (breast, prostate, ovary) with the respective normal tissues.

GPR64 has been investigated to date in only a small number of normal tissues, amongst which only the tissue of the epididymis was found to express this gene (Osterhoff, 1997. *DNA Cell Biol* 16, 379-389). In accordance with the invention we have established a GPR64-specific RT-PCR (primer pair SEQ ID NO: 57, 58) and have investigated the distribution of this gene product in a comprehensive collection of healthy tissues (FIG. 24; methods: compare Materials and Methods, Section B.1.). In many normal tissues GPR64 is not detectable at all, some exhibit a low expression. Surprisingly, the investigation of this protein in tumors exhibited an overexpression, which was many times higher than that of the relevant normal tissues. For example, we found significant overexpression in almost half of the ovary carcinomas (FIG. 24A to 24C).

The pronounced expression and high incidence of this molecule in the described tumor indications make this protein in accordance with the invention a highly interesting diagnostic and therapeutic marker. This includes in accordance with the invention the detection of disseminated tumor cells in serum, bone marrow and urine, as well as the detection of metastases in other organs with the aid of RT-PCR.

The four extracellular domains of GPR64 may be used in accordance with the invention as target structures of monoclonal antibodies for therapy as well as immune diagnosis. With respect to SEQ ID NO: 28, the amino acids 1-625, 684-695, 754-784 and 854-856 are located extracellularly.

Furthermore, GPR64 can be used in accordance with the invention as vaccine (RNA, DNA, protein, peptides) for the induction of tumor-specific immune responses (T-cell and B-cell mediated immune reactions). This also includes in accordance with the invention the development of so-called "small compounds", which modulate the biological activity of GPR64 and may be used for the therapy of tumors.

Example 16: Identification of the Sodium/Potassium/Chloride Transporter SLC12A1 (Solute Carrier Family 12) as Diagnostic and Therapeutic Cancer Target The gene SLC12A1 (SEQ ID NO: 29) encodes a translation product (SEQ ID NO: 30) and belongs to the family of sodium-potassium-chloride-co-transporters. The gene consists of 26 exons and is located on chromosome 15 (15q15-q21.1). It encodes a protein with a length of 1099 amino acids which has a calculated molecular weight without secondary modifications of about 120 kDa. SLC12A1 is an integral membrane protein with 10 transmembrane domains. SLC12A1 mediates the reabsorption of sodium chloride in the Henle-Schleife and is the target point of many clinically relevant diuretic agents (Quaggin et al., *Mammalian Genome* 6: 557-561, 1995). Correspondingly, this molecule is principally accessible as target structure for medicaments, in other words it is "drugable".

In accordance with the invention, after establishment of a SLC12A1-specific quantitative RT-PCR (primer pair SEQ ID NO: 59, 60) the distribution of specific transcripts in healthy tissue and in carcinoma samples was investigated (FIG. 25). We confirmed that in normal tissues the expression of SLC12A1 is first and foremost limited to normal kidney tissue, as has also been described in the literature. In all other normal tissues SLC12A1-specific transcripts are detectable in only very small quantities or not all (FIG. 25A). Surprisingly, in the comparative analysis of tumors we found an expression of SLC12A1. Especially in carcinomas of the kidney, breast, ovary and prostate (FIG. 25A to 25C) we found unexpectedly an up to 1,000,000-fold over-expression in comparison to the corresponding normal tissues (FIG. 25B to 25D). Previously, SLC12A1 has not been described in the context of tumor diseases.

The pronounced expression and high incidence of this molecule for the described tumor indications make this protein in accordance with the invention a highly interesting diagnostic and therapeutic marker. This includes in accordance with the invention the detection of disseminated tumor cells in serum, bone marrow and urine, as well as the detection of metastases in other organs with the aid of RT-PCR. The extracellular domains of SLC12A1 may be used in accordance with the invention as target structures of monoclonal antibodies for therapy and also immune diagnosis. With respect to SEQ ID NO: 30, the amino acids 1-181, 234-257, 319-327, 402-415, 562-564 and 630-1099 are located extracellularly.

Furthermore, SLC12A1 can be used in accordance with the invention as vaccine (RNA, DNA, protein, peptides) for the induction of tumor-specific immune responses (T-cell and B-cell mediated immune reactions). This includes in accordance with the invention also the development of so-called "small compounds", which modulate the biological activity of SLC12A1 and may be used for the therapy of tumors.

We claim:

1. A method of detecting a cancer cell characterized by expressing a tumor-associated antigen consisting of SEQ ID NO: 72, which method comprises detecting or quantifying in a tumor tissue sample isolated from a human patient a nucleic acid which encodes the tumor-associated antigen consisting of SEQ ID NO: 72;

wherein the detecting or quantifying comprises:

(i) extracting total RNA from the tumor tissue sample;

(ii) transcribing extracted RNA from step (i) into cDNA;

(iii) amplifying the cDNA from step (ii) utilizing PCR with a primer pair specific for a region of the nucleic acid that encodes the tumor-associated antigen consisting of SEQ ID NO: 72 to thereby detect the nucleic acid;

wherein the primer pair comprises SEQ ID NO: 93 and SEQ ID NO: 94; and the detection of the nucleic acid is indicative for the presence of a cancer cell.

2. The method of claim 1, wherein the cancer cell is from a cancer tissue which is selected from the group consisting of breast, lung, ear, nose, throat, esophagus, ovary, cervix, skin, prostate, kidney, colon, stomach, pancreas, liver, and uterus.

3. The method of claim 1, wherein the cancer cell is a breast cancer cell.

* * * * *

SEQUENCE LISTING

```
<160> NUMBER OF SEQ ID NOS: 114

<210> SEQ ID NO 1
<211> LENGTH: 1785
<212> TYPE: DNA
<213> ORGANISM: Homo sapiens
<220> FEATURE:
<221> NAME/KEY: CDS
<222> LOCATION: (204)..(614)

<400> SEQUENCE: 1

actcagctct ctcaccatgc gattgccctg caacaccttg gaactctgca gagagtcccc      60

agcaggaagg tctcacctga ggtgaacctt cgaccttgga cttctcagcc tccagaatga     120

agaatggcaa ccatcaaatc aagaaattgg cccaaagccc tacagtctgc aaacatcata     180

acaattcatc ctgaagtttc tcc atg aat tgt gat gct ttg cta cat cat tct     233
                          Met Asn Cys Asp Ala Leu Leu His His Ser
                          1               5                   10
```

-continued

```
gca atc cca gaa gat ttt ttg cat att ttt ttg cta tta cag aaa atc       281
Ala Ile Pro Glu Asp Phe Leu His Ile Phe Leu Leu Leu Gln Lys Ile
                15                  20                  25

tca gtc tcc ctc cct ctc tct ctc tct caa tct gtg tgt ctc ttt tac       329
Ser Val Ser Leu Pro Leu Ser Leu Ser Gln Ser Val Cys Leu Phe Tyr
            30                  35                  40

tcc ata tct ctg tgt gtg tct ctt tta ctc cat atc tct ctg tgt gtg       377
Ser Ile Ser Leu Cys Val Ser Leu Leu Leu His Ile Ser Leu Cys Val
        45                  50                  55

tct gtt tat gtc tct ctc tct ctc tca tcc ttc cca tgt ttc tct ctc       425
Ser Val Tyr Val Ser Leu Ser Leu Ser Ser Phe Pro Cys Phe Ser Leu
    60                  65                  70

aca cac aca cac act cat tca cag ctt tca aaa gac acg tct gtc ctt       473
Thr His Thr His Thr His Ser Gln Leu Ser Lys Asp Thr Ser Val Leu
75                  80                  85                  90

acc ttc act ttt tgt ttt aaa cag cac act cac ttt act ctg aac tat       521
Thr Phe Thr Phe Cys Phe Lys Gln His Thr His Phe Thr Leu Asn Tyr
                95                  100                 105

acc tca cat gca cac gag ctt tct gct cca tct gtt cat ccc aca tgt       569
Thr Ser His Ala His Glu Leu Ser Ala Pro Ser Val His Pro Thr Cys
            110                 115                 120

gtc ttc aca ttc aaa gca gca cct tcc cca aga cca gct acc taa           614
Val Phe Thr Phe Lys Ala Ala Pro Ser Pro Arg Pro Ala Thr
        125                 130                 135

ccacctccca cctccacccc atccctagtc agaggaaggc ctggttccca cctgaattca    674

gctttgtcaa agagcctcct ggaaagctgt catcttcagt tagtagggat aatgggatta    734

ttctatctgt gtaataataa catgttcaat ttaaagaaaa aaatctgaag ccacttaaaa    794

gctactgttt ggcaccgata cattattcca gtaatgaata atcattaaag atattattct    854

ggatgcagtt accatgcagt gatgtgaata aaatgcatta gatggaaaat tgtatttcaa    914

gtaaatatat gcactggtag aaatgtatta ccacccacta atatgtatta attcaaaacc    974

aaatgccaac tggagttcgc ctacacgggt ttgaatggca ggcagtgatt tggaagtggg   1034

aggaaatagg tttggatttg gtcaaataga ctgagaagtg atagtggggg cgggggttta   1094

tgactcaaac tttaacaggt gagaagacta tgccatggac agaacaggca tgaggggctc   1154

ccctcctacg cctctttaag agatttttat ctctgactaa ggattactgg tagttgttga   1214

catttctgaa gcagtggatc tttttccttt ttcactatct gcatcttcaa atattctttt   1274

ctgaagaaag ttaaaaggaa gcctgtacat tttttgctaa ggtaaatgcc ttgccatctt   1334

atttcatttt ctcatttttt tcttcagtgc acaacataag caactgtcct ccttgtcata   1394

ctcaagatga gcttggcata tctgaaatct gcagggattt tctcattagc acagggttcc   1454

aagcccaaac cgtgaagatg gagttttcat ttttaaatgg cacatcttca agttcttgcc   1514

ctgtcctcac tttagtatgc cccagaggaa gtcaaagata tggacactct aagactcaga   1574

agaactttct caggcattca ttttcctatc tattttgagc cattttattt aaaaggttac   1634

aattttaaac ctctctttaa ttaaaagata ccagagttac aatgcaatac tatttggcaa   1694

tcaaaactaa tgaagcacag atgcatgcta caacacgaat gaactttgaa acgttgtgtt   1754

aagtgaaata aaccagttat tatacaaggc c                                   1785

<210> SEQ ID NO 2
<211> LENGTH: 136
<212> TYPE: PRT
<213> ORGANISM: Homo sapiens

<400> SEQUENCE: 2
```

```
Met Asn Cys Asp Ala Leu Leu His His Ser Ala Ile Pro Glu Asp Phe
1               5                   10                  15

Leu His Ile Phe Leu Leu Leu Gln Lys Ile Ser Val Ser Leu Pro Leu
            20                  25                  30

Ser Leu Ser Gln Ser Val Cys Leu Phe Tyr Ser Ile Ser Leu Cys Val
        35                  40                  45

Ser Leu Leu Leu His Ile Ser Leu Cys Val Ser Val Tyr Val Ser Leu
    50                  55                  60

Ser Leu Ser Ser Phe Pro Cys Phe Ser Leu Thr His Thr His Thr His
65                  70                  75                  80

Ser Gln Leu Ser Lys Asp Thr Ser Val Leu Thr Phe Thr Phe Cys Phe
                85                  90                  95

Lys Gln His Thr His Phe Thr Leu Asn Tyr Thr Ser His Ala His Glu
            100                 105                 110

Leu Ser Ala Pro Ser Val His Pro Thr Cys Val Phe Thr Phe Lys Ala
        115                 120                 125

Ala Pro Ser Pro Arg Pro Ala Thr
    130                 135


<210> SEQ ID NO 3
<211> LENGTH: 3336
<212> TYPE: DNA
<213> ORGANISM: Homo sapiens
<220> FEATURE:
<221> NAME/KEY: CDS
<222> LOCATION: (84)..(3083)

<400> SEQUENCE: 3

ttttcttaga cattaactgc agacggctgg caggatagaa gcagcggctc acttggactt      60

tttcaccagg gaaatcagag aca atg atg ggg ctc ttc ccc aga act aca ggg     113
                          Met Met Gly Leu Phe Pro Arg Thr Thr Gly
                          1               5                   10

gct ctg gcc atc ttc gtg gtg gtc ata ttg gtt cat gga gaa ttg cga       161
Ala Leu Ala Ile Phe Val Val Val Ile Leu Val His Gly Glu Leu Arg
                15                  20                  25

ata gag act aaa ggt caa tat gat gaa gaa gag atg act atg caa caa       209
Ile Glu Thr Lys Gly Gln Tyr Asp Glu Glu Glu Met Thr Met Gln Gln
            30                  35                  40

gct aaa aga agg caa aaa cgt gaa tgg gtg aaa ttt gcc aaa ccc tgc       257
Ala Lys Arg Arg Gln Lys Arg Glu Trp Val Lys Phe Ala Lys Pro Cys
        45                  50                  55

aga gaa gga gaa gat aac tca aaa aga aac cca att gcc aag att act       305
Arg Glu Gly Glu Asp Asn Ser Lys Arg Asn Pro Ile Ala Lys Ile Thr
    60                  65                  70

tca gat tac caa gca acc cag aaa atc acc tac cga atc tct gga gtg       353
Ser Asp Tyr Gln Ala Thr Gln Lys Ile Thr Tyr Arg Ile Ser Gly Val
75                  80                  85                  90

gga atc gat cag ccg cct ttt gga atc ttt gtt gtt gac aaa aac act       401
Gly Ile Asp Gln Pro Pro Phe Gly Ile Phe Val Val Asp Lys Asn Thr
                95                  100                 105

gga gat att aac ata aca gct ata gtc gac cgg gag gaa act cca agc       449
Gly Asp Ile Asn Ile Thr Ala Ile Val Asp Arg Glu Glu Thr Pro Ser
            110                 115                 120

ttc ctg atc aca tgt cgg gct cta aat gcc caa gga cta gat gta gag       497
Phe Leu Ile Thr Cys Arg Ala Leu Asn Ala Gln Gly Leu Asp Val Glu
        125                 130                 135

aaa cca ctt ata cta acg gtt aaa att ttg gat att aat gat aat cct       545
Lys Pro Leu Ile Leu Thr Val Lys Ile Leu Asp Ile Asn Asp Asn Pro
```

-continued

```
    140                 145                 150

cca gta ttt tca caa caa att ttc atg ggt gaa att gaa gaa aat agt      593
Pro Val Phe Ser Gln Gln Ile Phe Met Gly Glu Ile Glu Glu Asn Ser
155                 160                 165                 170

gcc tca aac tca ctg gtg atg ata cta aat gcc aca gat gca gat gaa      641
Ala Ser Asn Ser Leu Val Met Ile Leu Asn Ala Thr Asp Ala Asp Glu
                175                 180                 185

cca aac cac ttg aat tct aaa att gcc ttc aaa att gtc tct cag gaa      689
Pro Asn His Leu Asn Ser Lys Ile Ala Phe Lys Ile Val Ser Gln Glu
            190                 195                 200

cca gca ggc aca ccc atg ttc ctc cta agc aga aac act ggg gaa gtc      737
Pro Ala Gly Thr Pro Met Phe Leu Leu Ser Arg Asn Thr Gly Glu Val
        205                 210                 215

cgt act ttg acc aat tct ctt gac cga gag caa gct agc agc tat cgt      785
Arg Thr Leu Thr Asn Ser Leu Asp Arg Glu Gln Ala Ser Ser Tyr Arg
    220                 225                 230

ctg gtt gtg agt ggt gca gac aaa gat gga gaa gga cta tca act caa      833
Leu Val Val Ser Gly Ala Asp Lys Asp Gly Glu Gly Leu Ser Thr Gln
235                 240                 245                 250

tgt gaa tgt aat att aaa gtg aaa gat gtc aac gat aac ttc cca atg      881
Cys Glu Cys Asn Ile Lys Val Lys Asp Val Asn Asp Asn Phe Pro Met
                255                 260                 265

ttt aga gac tct cag tat tca gca cgt att gaa gaa aat att tta agt      929
Phe Arg Asp Ser Gln Tyr Ser Ala Arg Ile Glu Glu Asn Ile Leu Ser
            270                 275                 280

tct gaa tta ctt cga ttt caa gta aca gat ttg gat gaa gag tac aca      977
Ser Glu Leu Leu Arg Phe Gln Val Thr Asp Leu Asp Glu Glu Tyr Thr
        285                 290                 295

gat aat tgg ctt gca gta tat ttc ttt acc tct ggg aat gaa gga aat     1025
Asp Asn Trp Leu Ala Val Tyr Phe Phe Thr Ser Gly Asn Glu Gly Asn
    300                 305                 310

tgg ttt gaa ata caa act gat cct aga act aat gaa ggc atc ctg aaa     1073
Trp Phe Glu Ile Gln Thr Asp Pro Arg Thr Asn Glu Gly Ile Leu Lys
315                 320                 325                 330

gtg gtg aag gct cta gat tat gaa caa cta caa agc gtg aaa ctt agt     1121
Val Val Lys Ala Leu Asp Tyr Glu Gln Leu Gln Ser Val Lys Leu Ser
                335                 340                 345

att gct gtc aaa aac aaa gct gaa ttt cac caa tca gtt atc tct cga     1169
Ile Ala Val Lys Asn Lys Ala Glu Phe His Gln Ser Val Ile Ser Arg
            350                 355                 360

tac cga gtt cag tca acc cca gtc aca att cag gta ata aat gta aga     1217
Tyr Arg Val Gln Ser Thr Pro Val Thr Ile Gln Val Ile Asn Val Arg
        365                 370                 375

gaa gga att gca ttc cgt cct gct tcc aag aca ttt act gtg caa aaa     1265
Glu Gly Ile Ala Phe Arg Pro Ala Ser Lys Thr Phe Thr Val Gln Lys
    380                 385                 390

ggc ata agt agc aaa aaa ttg gtg gat tat atc ctg gga aca tat caa     1313
Gly Ile Ser Ser Lys Lys Leu Val Asp Tyr Ile Leu Gly Thr Tyr Gln
395                 400                 405                 410

gcc atc gat gag gac act aac aaa gct gcc tca aat gtc aaa tat gtc     1361
Ala Ile Asp Glu Asp Thr Asn Lys Ala Ala Ser Asn Val Lys Tyr Val
                415                 420                 425

atg gga cgt aac gat ggt gga tac cta atg att gat tca aaa act gct     1409
Met Gly Arg Asn Asp Gly Gly Tyr Leu Met Ile Asp Ser Lys Thr Ala
            430                 435                 440

gaa atc aaa ttt gtc aaa aat atg aac cga gat tct act ttc ata gtt     1457
Glu Ile Lys Phe Val Lys Asn Met Asn Arg Asp Ser Thr Phe Ile Val
        445                 450                 455

aac aaa aca atc aca gct gag gtt ctg gcc ata gat gaa tac acg ggt     1505
```

-continued

```
Asn Lys Thr Ile Thr Ala Glu Val Leu Ala Ile Asp Glu Tyr Thr Gly
    460                 465                 470

aaa act tct aca ggc acg gta tat gtt aga gta ccc gat ttc aat gac      1553
Lys Thr Ser Thr Gly Thr Val Tyr Val Arg Val Pro Asp Phe Asn Asp
475                 480                 485                 490

aat tgt cca aca gct gtc ctc gaa aaa gat gca gtt tgc agt tct tca      1601
Asn Cys Pro Thr Ala Val Leu Glu Lys Asp Ala Val Cys Ser Ser Ser
                495                 500                 505

cct tcc gtg gtt gtc tcc gct aga aca ctg aat aat aga tac act ggc      1649
Pro Ser Val Val Val Ser Ala Arg Thr Leu Asn Asn Arg Tyr Thr Gly
            510                 515                 520

ccc tat aca ttt gca ctg gaa gat caa cct gta aag ttg cct gcc gta      1697
Pro Tyr Thr Phe Ala Leu Glu Asp Gln Pro Val Lys Leu Pro Ala Val
        525                 530                 535

tgg agt atc aca acc ctc aat gct acc tcg gcc ctc ctc aga gcc cag      1745
Trp Ser Ile Thr Thr Leu Asn Ala Thr Ser Ala Leu Leu Arg Ala Gln
    540                 545                 550

gaa cag ata cct cct gga gta tac cac atc tcc ctg gta ctt aca gac      1793
Glu Gln Ile Pro Pro Gly Val Tyr His Ile Ser Leu Val Leu Thr Asp
555                 560                 565                 570

agt cag aac aat cgg tgt gag atg cca cgc agc ttg aca ctg gaa gtc      1841
Ser Gln Asn Asn Arg Cys Glu Met Pro Arg Ser Leu Thr Leu Glu Val
                575                 580                 585

tgt cag tgt gac aac agg ggc atc tgt gga act tct tac cca acc aca      1889
Cys Gln Cys Asp Asn Arg Gly Ile Cys Gly Thr Ser Tyr Pro Thr Thr
            590                 595                 600

agc cct ggg acc agg tat ggc agg ccg cac tca ggg agg ctg ggg cct      1937
Ser Pro Gly Thr Arg Tyr Gly Arg Pro His Ser Gly Arg Leu Gly Pro
        605                 610                 615

gcc gcc atc ggc ctg ctg ctc ctt ggt ctc ctg ctg ctg ctg ttg gcc      1985
Ala Ala Ile Gly Leu Leu Leu Leu Gly Leu Leu Leu Leu Leu Leu Ala
    620                 625                 630

ccc ctt ctg ctg ttg acc tgt gac tgt ggg gca ggt tct act ggg gga      2033
Pro Leu Leu Leu Leu Thr Cys Asp Cys Gly Ala Gly Ser Thr Gly Gly
635                 640                 645                 650

gtg aca ggt ggt ttt atc cca gtt cct gat ggc tca gaa gga aca att      2081
Val Thr Gly Gly Phe Ile Pro Val Pro Asp Gly Ser Glu Gly Thr Ile
                655                 660                 665

cat cag tgg gga att gaa gga gcc cat cct gaa gac aag gaa atc aca      2129
His Gln Trp Gly Ile Glu Gly Ala His Pro Glu Asp Lys Glu Ile Thr
            670                 675                 680

aat att tgt gtg cct cct gta aca gcc aat gga gcc gat ttc atg gaa      2177
Asn Ile Cys Val Pro Pro Val Thr Ala Asn Gly Ala Asp Phe Met Glu
        685                 690                 695

agt tct gaa gtt tgt aca aat acg tat gcc aga ggc aca gcg gtg gaa      2225
Ser Ser Glu Val Cys Thr Asn Thr Tyr Ala Arg Gly Thr Ala Val Glu
    700                 705                 710

ggc act tca gga atg gaa atg acc act aag ctt gga gca gcc act gaa      2273
Gly Thr Ser Gly Met Glu Met Thr Thr Lys Leu Gly Ala Ala Thr Glu
715                 720                 725                 730

tct gga ggt gct gca ggc ttt gca aca ggg aca gtg tca gga gct gct      2321
Ser Gly Gly Ala Ala Gly Phe Ala Thr Gly Thr Val Ser Gly Ala Ala
                735                 740                 745

tca gga ttc gga gca gcc act gga gtt ggc atc tgt tcc tca ggg cag      2369
Ser Gly Phe Gly Ala Ala Thr Gly Val Gly Ile Cys Ser Ser Gly Gln
            750                 755                 760

tct gga acc atg aga aca agg cat tcc act gga gga acc aat aag gac      2417
Ser Gly Thr Met Arg Thr Arg His Ser Thr Gly Gly Thr Asn Lys Asp
        765                 770                 775
```

```
tac gct gat ggg gcg ata agc atg aat ttt ctg gac tcc tac ttt tct     2465
Tyr Ala Asp Gly Ala Ile Ser Met Asn Phe Leu Asp Ser Tyr Phe Ser
    780                 785                 790

cag aaa gca ttt gcc tgt gcg gag gaa gac gat ggc cag gaa gca aat     2513
Gln Lys Ala Phe Ala Cys Ala Glu Glu Asp Asp Gly Gln Glu Ala Asn
795                 800                 805                 810

gac tgc ttg ttg atc tat gat aat gaa ggc gca gat gcc act ggt tct     2561
Asp Cys Leu Leu Ile Tyr Asp Asn Glu Gly Ala Asp Ala Thr Gly Ser
                815                 820                 825

cct gtg ggc tcc gtg ggt tgt tgc agt ttt att gct gat gac ctg gat     2609
Pro Val Gly Ser Val Gly Cys Cys Ser Phe Ile Ala Asp Asp Leu Asp
            830                 835                 840

gac agc ttc ttg gac tca ctt gga ccc aaa ttt aaa aaa ctt gca gag     2657
Asp Ser Phe Leu Asp Ser Leu Gly Pro Lys Phe Lys Lys Leu Ala Glu
        845                 850                 855

ata agc ctt ggt gtt gat ggt gaa ggc aaa gaa gtt cag cca ccc tct     2705
Ile Ser Leu Gly Val Asp Gly Glu Gly Lys Glu Val Gln Pro Pro Ser
    860                 865                 870

aaa gac agc ggt tat ggg att gaa tcc tgt ggc cat ccc ata gaa gtc     2753
Lys Asp Ser Gly Tyr Gly Ile Glu Ser Cys Gly His Pro Ile Glu Val
875                 880                 885                 890

cag cag aca gga ttt gtt aag tgc cag act ttg tca gga agt caa gga     2801
Gln Gln Thr Gly Phe Val Lys Cys Gln Thr Leu Ser Gly Ser Gln Gly
                895                 900                 905

gct tct gct ttg tcc gcc tct ggg tct gtc cag cca gct gtt tcc atc     2849
Ala Ser Ala Leu Ser Ala Ser Gly Ser Val Gln Pro Ala Val Ser Ile
            910                 915                 920

cct gac cct ctg cag cat ggt aac tat tta gta acg gag act tac tcg     2897
Pro Asp Pro Leu Gln His Gly Asn Tyr Leu Val Thr Glu Thr Tyr Ser
        925                 930                 935

gct tct ggt tcc ctc gtg caa cct tcc act gca ggc ttt gat cca ctt     2945
Ala Ser Gly Ser Leu Val Gln Pro Ser Thr Ala Gly Phe Asp Pro Leu
    940                 945                 950

ctc aca caa aat gtg ata gtg aca gaa agg gtg atc tgt ccc att tcc     2993
Leu Thr Gln Asn Val Ile Val Thr Glu Arg Val Ile Cys Pro Ile Ser
955                 960                 965                 970

agt gtt cct ggc aac cta gct ggc cca acg cag cta cga ggg tca cat     3041
Ser Val Pro Gly Asn Leu Ala Gly Pro Thr Gln Leu Arg Gly Ser His
                975                 980                 985

act atg ctc tgt aca gag gat cct tgc tcc cgt cta ata tga             3083
Thr Met Leu Cys Thr Glu Asp Pro Cys Ser Arg Leu Ile
            990                 995

ccagaatgag ctggaatacc acactgacca aatctggatc tttggactaa agtattcaaa   3143

atagcatagc aaagctcact gtattgggct aataatttgg cacttattag cttctctcat   3203

aaactgatca cgattataaa ttaaatgttt gggttcatac cccaaaagca atatgttgtc   3263

actcctaatt ctcaagtact attcaaattg tagtaaatct taaagttttt caaaacccta   3323

aaatcatatt cgc                                                      3336


<210> SEQ ID NO 4
<211> LENGTH: 999
<212> TYPE: PRT
<213> ORGANISM: Homo sapiens

<400> SEQUENCE: 4

Met Met Gly Leu Phe Pro Arg Thr Thr Gly Ala Leu Ala Ile Phe Val
1               5                   10                  15

Val Val Ile Leu Val His Gly Glu Leu Arg Ile Glu Thr Lys Gly Gln
            20                  25                  30
```

-continued

```
Tyr Asp Glu Glu Glu Met Thr Met Gln Gln Ala Lys Arg Arg Gln Lys
        35                  40                  45

Arg Glu Trp Val Lys Phe Ala Lys Pro Cys Arg Glu Gly Glu Asp Asn
    50                  55                  60

Ser Lys Arg Asn Pro Ile Ala Lys Ile Thr Ser Asp Tyr Gln Ala Thr
65                  70                  75                  80

Gln Lys Ile Thr Tyr Arg Ile Ser Gly Val Gly Ile Asp Gln Pro Pro
                85                  90                  95

Phe Gly Ile Phe Val Val Asp Lys Asn Thr Gly Asp Ile Asn Ile Thr
            100                 105                 110

Ala Ile Val Asp Arg Glu Glu Thr Pro Ser Phe Leu Ile Thr Cys Arg
        115                 120                 125

Ala Leu Asn Ala Gln Gly Leu Asp Val Glu Lys Pro Leu Ile Leu Thr
    130                 135                 140

Val Lys Ile Leu Asp Ile Asn Asp Asn Pro Pro Val Phe Ser Gln Gln
145                 150                 155                 160

Ile Phe Met Gly Glu Ile Glu Glu Asn Ser Ala Ser Asn Ser Leu Val
                165                 170                 175

Met Ile Leu Asn Ala Thr Asp Ala Asp Glu Pro Asn His Leu Asn Ser
            180                 185                 190

Lys Ile Ala Phe Lys Ile Val Ser Gln Glu Pro Ala Gly Thr Pro Met
        195                 200                 205

Phe Leu Leu Ser Arg Asn Thr Gly Glu Val Arg Thr Leu Thr Asn Ser
    210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
            260                 265                 270

Ser Ala Arg Ile Glu Glu Asn Ile Leu Ser Ser Glu Leu Leu Arg Phe
        275                 280                 285

Gln Val Thr Asp Leu Asp Glu Glu Tyr Thr Asp Asn Trp Leu Ala Val
    290                 295                 300

Tyr Phe Phe Thr Ser Gly Asn Glu Gly Asn Trp Phe Glu Ile Gln Thr
305                 310                 315                 320

Asp Pro Arg Thr Asn Glu Gly Ile Leu Lys Val Val Lys Ala Leu Asp
                325                 330                 335

Tyr Glu Gln Leu Gln Ser Val Lys Leu Ser Ile Ala Val Lys Asn Lys
            340                 345                 350

Ala Glu Phe His Gln Ser Val Ile Ser Arg Tyr Arg Val Gln Ser Thr
        355                 360                 365

Pro Val Thr Ile Gln Val Ile Asn Val Arg Glu Gly Ile Ala Phe Arg
    370                 375                 380

Pro Ala Ser Lys Thr Phe Thr Val Gln Lys Gly Ile Ser Ser Lys Lys
385                 390                 395                 400

Leu Val Asp Tyr Ile Leu Gly Thr Tyr Gln Ala Ile Asp Glu Asp Thr
                405                 410                 415

Asn Lys Ala Ala Ser Asn Val Lys Tyr Val Met Gly Arg Asn Asp Gly
            420                 425                 430

Gly Tyr Leu Met Ile Asp Ser Lys Thr Ala Glu Ile Lys Phe Val Lys
        435                 440                 445
```

-continued

```
Asn Met Asn Arg Asp Ser Thr Phe Ile Val Asn Lys Thr Ile Thr Ala
    450                 455                 460

Glu Val Leu Ala Ile Asp Glu Tyr Thr Gly Lys Thr Ser Thr Gly Thr
465                 470                 475                 480

Val Tyr Val Arg Val Pro Asp Phe Asn Asp Asn Cys Pro Thr Ala Val
                485                 490                 495

Leu Glu Lys Asp Ala Val Cys Ser Ser Ser Pro Ser Val Val Val Ser
            500                 505                 510

Ala Arg Thr Leu Asn Asn Arg Tyr Thr Gly Pro Tyr Thr Phe Ala Leu
        515                 520                 525

Glu Asp Gln Pro Val Lys Leu Pro Ala Val Trp Ser Ile Thr Thr Leu
    530                 535                 540

Asn Ala Thr Ser Ala Leu Leu Arg Ala Gln Glu Gln Ile Pro Pro Gly
545                 550                 555                 560

Val Tyr His Ile Ser Leu Val Leu Thr Asp Ser Gln Asn Asn Arg Cys
                565                 570                 575

Glu Met Pro Arg Ser Leu Thr Leu Glu Val Cys Gln Cys Asp Asn Arg
            580                 585                 590

Gly Ile Cys Gly Thr Ser Tyr Pro Thr Thr Ser Pro Gly Thr Arg Tyr
        595                 600                 605

Gly Arg Pro His Ser Gly Arg Leu Gly Pro Ala Ala Ile Gly Leu Leu
    610                 615                 620

Leu Leu Gly Leu Leu Leu Leu Leu Leu Ala Pro Leu Leu Leu Leu Thr
625                 630                 635                 640

Cys Asp Cys Gly Ala Gly Ser Thr Gly Gly Val Thr Gly Gly Phe Ile
                645                 650                 655

Pro Val Pro Asp Gly Ser Glu Gly Thr Ile His Gln Trp Gly Ile Glu
            660                 665                 670

Gly Ala His Pro Glu Asp Lys Glu Ile Thr Asn Ile Cys Val Pro Pro
        675                 680                 685

Val Thr Ala Asn Gly Ala Asp Phe Met Glu Ser Ser Glu Val Cys Thr
    690                 695                 700

Asn Thr Tyr Ala Arg Gly Thr Ala Val Glu Gly Thr Ser Gly Met Glu
705                 710                 715                 720

Met Thr Thr Lys Leu Gly Ala Ala Thr Glu Ser Gly Gly Ala Ala Gly
                725                 730                 735

Phe Ala Thr Gly Thr Val Ser Gly Ala Ala Ser Gly Phe Gly Ala Ala
            740                 745                 750

Thr Gly Val Gly Ile Cys Ser Ser Gly Gln Ser Gly Thr Met Arg Thr
        755                 760                 765

Arg His Ser Thr Gly Gly Thr Asn Lys Asp Tyr Ala Asp Gly Ala Ile
    770                 775                 780

Ser Met Asn Phe Leu Asp Ser Tyr Phe Ser Gln Lys Ala Phe Ala Cys
785                 790                 795                 800

Ala Glu Glu Asp Asp Gly Gln Glu Ala Asn Asp Cys Leu Leu Ile Tyr
                805                 810                 815

Asp Asn Glu Gly Ala Asp Ala Thr Gly Ser Pro Val Gly Ser Val Gly
            820                 825                 830

Cys Cys Ser Phe Ile Ala Asp Asp Leu Asp Asp Ser Phe Leu Asp Ser
        835                 840                 845

Leu Gly Pro Lys Phe Lys Lys Leu Ala Glu Ile Ser Leu Gly Val Asp
    850                 855                 860

Gly Glu Gly Lys Glu Val Gln Pro Pro Ser Lys Asp Ser Gly Tyr Gly
```

```
865                 870                 875                 880

Ile Glu Ser Cys Gly His Pro Ile Glu Val Gln Gln Thr Gly Phe Val
                885                 890                 895

Lys Cys Gln Thr Leu Ser Gly Ser Gln Gly Ala Ser Ala Leu Ser Ala
            900                 905                 910

Ser Gly Ser Val Gln Pro Ala Val Ser Ile Pro Asp Pro Leu Gln His
        915                 920                 925

Gly Asn Tyr Leu Val Thr Glu Thr Tyr Ser Ala Ser Gly Ser Leu Val
    930                 935                 940

Gln Pro Ser Thr Ala Gly Phe Asp Pro Leu Leu Thr Gln Asn Val Ile
945                 950                 955                 960

Val Thr Glu Arg Val Ile Cys Pro Ile Ser Ser Val Pro Gly Asn Leu
                965                 970                 975

Ala Gly Pro Thr Gln Leu Arg Gly Ser His Thr Met Leu Cys Thr Glu
            980                 985                 990

Asp Pro Cys Ser Arg Leu Ile
        995


<210> SEQ ID NO 5
<211> LENGTH: 3946
<212> TYPE: DNA
<213> ORGANISM: Homo sapiens
<220> FEATURE:
<221> NAME/KEY: CDS
<222> LOCATION: (129)..(1991)

<400> SEQUENCE: 5

accgctccgg agcgggaggg gaggcttcgc ggaacgctct cggcgccagg actcgcgtgc      60

aaagcccagg cccgggcggc cagaccaaga gggaagaagc acagaattcc tcaactccca     120

gtgtgccc atg agt aag agc aaa tgc tcc gtg gga ctc atg tct tcc gtg      170
         Met Ser Lys Ser Lys Cys Ser Val Gly Leu Met Ser Ser Val
         1               5                   10

gtg gcc ccg gct aag gag ccc aat gcc gtg ggc ccg aag gag gtg gag       218
Val Ala Pro Ala Lys Glu Pro Asn Ala Val Gly Pro Lys Glu Val Glu
15                  20                  25                  30

ctc atc ctt gtc aag gag cag aac gga gtg cag ctc acc agc tcc acc       266
Leu Ile Leu Val Lys Glu Gln Asn Gly Val Gln Leu Thr Ser Ser Thr
                35                  40                  45

ctc acc aac ccg cgg cag agc ccc gtg gag gcc cag gat cgg gag acc       314
Leu Thr Asn Pro Arg Gln Ser Pro Val Glu Ala Gln Asp Arg Glu Thr
            50                  55                  60

tgg ggc aag aag atc gac ttt ctc ctg tcc gtc att ggc ttt gct gtg       362
Trp Gly Lys Lys Ile Asp Phe Leu Leu Ser Val Ile Gly Phe Ala Val
        65                  70                  75

gac ctg gcc aac gtc tgg cgg ttc ccc tac ctg tgc tac aaa aat ggt       410
Asp Leu Ala Asn Val Trp Arg Phe Pro Tyr Leu Cys Tyr Lys Asn Gly
    80                  85                  90

ggc ggt gcc ttc ctg gtc ccc tac ctg ctc ttc atg gtc att gct ggg       458
Gly Gly Ala Phe Leu Val Pro Tyr Leu Leu Phe Met Val Ile Ala Gly
95                  100                 105                 110

atg cca ctt ttc tac atg gag ctg gcc ctc ggc cag ttc aac agg gaa       506
Met Pro Leu Phe Tyr Met Glu Leu Ala Leu Gly Gln Phe Asn Arg Glu
                115                 120                 125

ggg gcc gct ggt gtc tgg aag atc tgc ccc ata ctg aaa ggt gtg ggc       554
Gly Ala Ala Gly Val Trp Lys Ile Cys Pro Ile Leu Lys Gly Val Gly
            130                 135                 140

ttc acg gtc atc ctc atc tca ctg tat gtc ggc ttc ttc tac aac gtc       602
Phe Thr Val Ile Leu Ile Ser Leu Tyr Val Gly Phe Phe Tyr Asn Val
```

-continued

```
        145                 150                 155

atc atc gcc tgg gcg ctg cac tat ctc ttc tcc tcc ttc acc acg gag      650
Ile Ile Ala Trp Ala Leu His Tyr Leu Phe Ser Ser Phe Thr Thr Glu
    160                 165                 170

ctc ccc tgg atc cac tgc aac aac tcc tgg aac agc ccc aac tgc tcg      698
Leu Pro Trp Ile His Cys Asn Asn Ser Trp Asn Ser Pro Asn Cys Ser
175                 180                 185                 190

gat gcc cat cct ggt gac tcc agt gga gac agc tcg ggc ctc aac gac      746
Asp Ala His Pro Gly Asp Ser Ser Gly Asp Ser Ser Gly Leu Asn Asp
                195                 200                 205

act ttt ggg acc aca cct gct gcc gag tac ttt gaa cgt ggc gtg ctg      794
Thr Phe Gly Thr Thr Pro Ala Ala Glu Tyr Phe Glu Arg Gly Val Leu
            210                 215                 220

cac ctc cac cag agc cat ggc atc gac gac ctg ggg cct ccg cgg tgg      842
His Leu His Gln Ser His Gly Ile Asp Asp Leu Gly Pro Pro Arg Trp
        225                 230                 235

cag ctc aca gcc tgc ctg gtg ctg gtc atc gtg ctg ctc tac ttc agc      890
Gln Leu Thr Ala Cys Leu Val Leu Val Ile Val Leu Leu Tyr Phe Ser
    240                 245                 250

ctc tgg aag ggc gtg aag acc tca ggg aag gtg gta tgg atc aca gcc      938
Leu Trp Lys Gly Val Lys Thr Ser Gly Lys Val Val Trp Ile Thr Ala
255                 260                 265                 270

acc atg cca tac gtg gtc ctc act gcc ctg ctc ctg cgt ggg gtc acc      986
Thr Met Pro Tyr Val Val Leu Thr Ala Leu Leu Leu Arg Gly Val Thr
                275                 280                 285

ctc cct gga gcc ata gac ggc atc aga gca tac ctg agc gtt gac ttc     1034
Leu Pro Gly Ala Ile Asp Gly Ile Arg Ala Tyr Leu Ser Val Asp Phe
            290                 295                 300

tac cgg ctc tgc gag gcg tct gtt tgg att gac gcg gcc acc cag gtg     1082
Tyr Arg Leu Cys Glu Ala Ser Val Trp Ile Asp Ala Ala Thr Gln Val
        305                 310                 315

tgc ttc tcc ctg ggc gtg ggg ttc ggg gtg ctg atc gcc ttc tcc agc     1130
Cys Phe Ser Leu Gly Val Gly Phe Gly Val Leu Ile Ala Phe Ser Ser
    320                 325                 330

tac aac aag ttc acc aac aac tgc tac agg gac gcg att gtc acc acc     1178
Tyr Asn Lys Phe Thr Asn Asn Cys Tyr Arg Asp Ala Ile Val Thr Thr
335                 340                 345                 350

tcc atc aac tcc ctg acg agc ttc tcc tcc ggc ttc gtc gtc ttc tcc     1226
Ser Ile Asn Ser Leu Thr Ser Phe Ser Ser Gly Phe Val Val Phe Ser
                355                 360                 365

ttc ctg ggg tac atg gca cag aag cac agt gtg ccc atc ggg gac gtg     1274
Phe Leu Gly Tyr Met Ala Gln Lys His Ser Val Pro Ile Gly Asp Val
            370                 375                 380

gcc aag gac ggg cca ggg ctg atc ttc atc atc tac ccg gaa gcc atc     1322
Ala Lys Asp Gly Pro Gly Leu Ile Phe Ile Ile Tyr Pro Glu Ala Ile
        385                 390                 395

gcc acg ctc cct ctg tcc tca gcc tgg gcc gtg gtc ttc ttc atc atg     1370
Ala Thr Leu Pro Leu Ser Ser Ala Trp Ala Val Val Phe Phe Ile Met
    400                 405                 410

ctg ctc acc ctg ggt atc gac agc gcc atg ggt ggt atg gag tca gtg     1418
Leu Leu Thr Leu Gly Ile Asp Ser Ala Met Gly Gly Met Glu Ser Val
415                 420                 425                 430

atc acc ggg ctc atc gat gag ttc cag ctg ctg cac aga cac cgt gag     1466
Ile Thr Gly Leu Ile Asp Glu Phe Gln Leu Leu His Arg His Arg Glu
                435                 440                 445

ctc ttc acg ctc ttc atc gtc ctg gcg acc ttc ctc ctg tcc ctg ttc     1514
Leu Phe Thr Leu Phe Ile Val Leu Ala Thr Phe Leu Leu Ser Leu Phe
            450                 455                 460

tgc gtc acc aac ggt ggc atc tac gtc ttc acg ctc ctg gac cat ttt     1562
```

-continued

```
Cys Val Thr Asn Gly Gly Ile Tyr Val Phe Thr Leu Leu Asp His Phe
        465                 470                 475

gca gcc ggc acg tcc atc ctc ttt gga gtg ctc atc gaa gcc atc gga      1610
Ala Ala Gly Thr Ser Ile Leu Phe Gly Val Leu Ile Glu Ala Ile Gly
    480                 485                 490

gtg gcc tgg ttc tat ggt gtt ggg cag ttc agc gac gac atc cag cag      1658
Val Ala Trp Phe Tyr Gly Val Gly Gln Phe Ser Asp Asp Ile Gln Gln
495                 500                 505                 510

atg acc ggg cag cgg ccc agc ctg tac tgg cgg ctg tgc tgg aag ctg      1706
Met Thr Gly Gln Arg Pro Ser Leu Tyr Trp Arg Leu Cys Trp Lys Leu
                515                 520                 525

gtc agc ccc tgc ttt ctc ctg ttc gtg gtc gtg gtc agc att gtg acc      1754
Val Ser Pro Cys Phe Leu Leu Phe Val Val Val Val Ser Ile Val Thr
            530                 535                 540

ttc aga ccc ccc cac tac gga gcc tac atc ttc ccc gac tgg gcc aac      1802
Phe Arg Pro Pro His Tyr Gly Ala Tyr Ile Phe Pro Asp Trp Ala Asn
        545                 550                 555

gcg ctg ggc tgg gtc atc gcc aca tcc tcc atg gcc atg gtg ccc atc      1850
Ala Leu Gly Trp Val Ile Ala Thr Ser Ser Met Ala Met Val Pro Ile
    560                 565                 570

tat gcg gcc tac aag ttc tgc agc ctg cct ggg tcc ttt cga gag aaa      1898
Tyr Ala Ala Tyr Lys Phe Cys Ser Leu Pro Gly Ser Phe Arg Glu Lys
575                 580                 585                 590

ctg gcc tac gcc att gca ccc gag aag gac cgt gag ctg gtg gac aga      1946
Leu Ala Tyr Ala Ile Ala Pro Glu Lys Asp Arg Glu Leu Val Asp Arg
                595                 600                 605

ggg gag gtg cgc cag ttc acg ctc cgc cac tgg ctc aag gtg tag          1991
Gly Glu Val Arg Gln Phe Thr Leu Arg His Trp Leu Lys Val
            610                 615                 620

agggagcaga gacgaagacc ccaggaagtc atcctgcaat gggagagaca cgaacaaacc   2051

aaggaaatct aagtttcgag agaaaggagg gcaacttcta ctcttcaacc tctactgaaa   2111

acacaaacaa caaagcagaa gactcctctc ttctgactgt ttacaccttt ccgtgccggg   2171

agcgcacctc gccgtgtctt gtgttgctgt aataacgacg tagatctgtg cagcgaggtc   2231

caccccgttg ttgtccctgc agggcagaaa aacgtctaac ttcatgctgt ctgtgtgagg   2291

ctccctccct ccctgctccc tgctcccggc tctgaggctg ccccaggggc actgtgttct   2351

caggcgggga tcacgatcct tgtagacgca cctgctgaga atccccgtgc tcacagtagc   2411

ttcctagacc atttactttg cccatattaa aaagccaagt gtcctgcttg gtttagctgt   2471

gcagaaggtg aaatggagga aaccacaaat tcatgcaaag tcctttcccg atgcgtggct   2531

cccagcagag gccgtaaatt gagcgttcag ttgacacatt gcacacacag tctgttcaga   2591

ggcattggag gatgggggtc ctggtatgtc tcaccaggaa attctgttta tgttcttgca   2651

gcagagagaa ataaaactcc ttgaaaccag ctcaggctac tgccactcag gcagcctgtg   2711

ggtccttgtg gtgtagggaa cggcctgaga ggagcgtgtc ctatccccgg acgcatgcag   2771

ggcccccaca ggagcgtgtc ctatccccgg acgcatgcag ggcccccaca ggagcatgtc   2831

ctatccctgg acgcatgcag ggcccccaca ggagcgtgta ctaccccaga acgcatgcag   2891

ggcccccaca ggagcgtgta ctaccccagg acgcatgcag ggcccccact ggagcgtgta   2951

ctaccccagg acgcatgcag ggcccccaca ggagcgtgtc ctatccccgg accggacgca   3011

tgcagggccc ccacaggagc gtgtactacc ccaggacgca tgcagggccc ccacaggagc   3071

gtgtactacc ccaggatgca tgcagggccc ccacaggagc gtgtactacc ccaggacgca   3131

tgcagggccc ccatgcaggc agcctgcaga ccaacactct gcctggcctt gagccgtgac   3191
```

-continued

```
ctccaggaag ggaccccact ggaattttat ttctctcagg tgcgtgccac atcaataaca   3251

acagttttta tgtttgcgaa tggcttttta aaatcatatt tacctgtgaa tcaaaacaaa   3311

ttcaagaatg cagtatccgc gagcctgctt gctgatattg cagtttttgt ttacaagaat   3371

aattagcaat actgagtgaa ggatgttggc caaaagctgc tttccatggc acactgccct   3431

ctgccactga caggaaagtg gatgccatag tttgaattca tgcctcaagt cggtgggcct   3491

gcctacgtgc tgcccgaggg caggggccgt gcagggccag tcatggctgt cccctgcaag   3551

tggacgtggg ctccagggac tggagtgtaa tgctcggtgg gagccgtcag cctgtgaact   3611

gccaggcagc tgcagttagc acagaggatg gcttccccat tgccttctgg ggagggacac   3671

agaggacggc ttccccatcg ccttctggcc gctgcagtca gcacagagag cggcttcccc   3731

attgccttct ggggagggac acagaggaca gtttccccat cgccttctgg ttgttgaaga   3791

cagcacagag agcggcttcc ccatcgcctt ctggggaggg gctccgtgta gcaacccagg   3851

tgttgtccgt gtctgttgac caatctctat tcagcatcgt gtgggtccct aagcacaata   3911

aaagacatcc acaatggaaa aaaaaaaagg aattc                              3946
```

```
<210> SEQ ID NO 6
<211> LENGTH: 620
<212> TYPE: PRT
<213> ORGANISM: Homo sapiens

<400> SEQUENCE: 6

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
        115                 120                 125

Ala Gly Val Trp Lys Ile Cys Pro Ile Leu Lys Gly Val Gly Phe Thr
    130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
            180                 185                 190

His Pro Gly Asp Ser Ser Gly Asp Ser Ser Gly Leu Asn Asp Thr Phe
        195                 200                 205

Gly Thr Thr Pro Ala Ala Glu Tyr Phe Glu Arg Gly Val Leu His Leu
    210                 215                 220

His Gln Ser His Gly Ile Asp Asp Leu Gly Pro Pro Arg Trp Gln Leu
225                 230                 235                 240
```

```
Thr Ala Cys Leu Val Leu Val Ile Val Leu Leu Tyr Phe Ser Leu Trp
                245                 250                 255

Lys Gly Val Lys Thr Ser Gly Lys Val Val Trp Ile Thr Ala Thr Met
            260                 265                 270

Pro Tyr Val Val Leu Thr Ala Leu Leu Leu Arg Gly Val Thr Leu Pro
        275                 280                 285

Gly Ala Ile Asp Gly Ile Arg Ala Tyr Leu Ser Val Asp Phe Tyr Arg
    290                 295                 300

Leu Cys Glu Ala Ser Val Trp Ile Asp Ala Ala Thr Gln Val Cys Phe
305                 310                 315                 320

Ser Leu Gly Val Gly Phe Gly Val Leu Ile Ala Phe Ser Ser Tyr Asn
                325                 330                 335

Lys Phe Thr Asn Asn Cys Tyr Arg Asp Ala Ile Val Thr Thr Ser Ile
            340                 345                 350

Asn Ser Leu Thr Ser Phe Ser Ser Gly Phe Val Val Phe Ser Phe Leu
        355                 360                 365

Gly Tyr Met Ala Gln Lys His Ser Val Pro Ile Gly Asp Val Ala Lys
    370                 375                 380

Asp Gly Pro Gly Leu Ile Phe Ile Ile Tyr Pro Glu Ala Ile Ala Thr
385                 390                 395                 400

Leu Pro Leu Ser Ser Ala Trp Ala Val Val Phe Phe Ile Met Leu Leu
                405                 410                 415

Thr Leu Gly Ile Asp Ser Ala Met Gly Gly Met Glu Ser Val Ile Thr
            420                 425                 430

Gly Leu Ile Asp Glu Phe Gln Leu Leu His Arg His Arg Glu Leu Phe
        435                 440                 445

Thr Leu Phe Ile Val Leu Ala Thr Phe Leu Leu Ser Leu Phe Cys Val
    450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
                485                 490                 495

Trp Phe Tyr Gly Val Gly Gln Phe Ser Asp Asp Ile Gln Gln Met Thr
            500                 505                 510

Gly Gln Arg Pro Ser Leu Tyr Trp Arg Leu Cys Trp Lys Leu Val Ser
        515                 520                 525

Pro Cys Phe Leu Leu Phe Val Val Val Val Ser Ile Val Thr Phe Arg
    530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
        595                 600                 605

Val Arg Gln Phe Thr Leu Arg His Trp Leu Lys Val
    610                 615                 620
```

<210> SEQ ID NO 7
<211> LENGTH: 3321
<212> TYPE: DNA
<213> ORGANISM: Homo sapiens
<220> FEATURE:
<221> NAME/KEY: CDS -continued

```
<222> LOCATION: (58)..(2784)

<400> SEQUENCE: 7

tgctgtgttg caagaataaa ctttgggtct tggattgcaa taccacctgt ggagaaa        57

atg gta tgc gag gga aag cga tca gcc tct tgc cct tgt ttc ttc ctc      105
Met Val Cys Glu Gly Lys Arg Ser Ala Ser Cys Pro Cys Phe Phe Leu
1               5                   10                  15

ttg acc gcc aag ttc tac tgg atc ctc aca atg atg caa aga act cac      153
Leu Thr Ala Lys Phe Tyr Trp Ile Leu Thr Met Met Gln Arg Thr His
            20                  25                  30

agc cag gag tat gcc cat tcc ata cgg gtg gat ggg gac att att ttg      201
Ser Gln Glu Tyr Ala His Ser Ile Arg Val Asp Gly Asp Ile Ile Leu
        35                  40                  45

ggg ggt ctc ttc cct gtc cac gca aag gga gag aga ggg gtg cct tgt      249
Gly Gly Leu Phe Pro Val His Ala Lys Gly Glu Arg Gly Val Pro Cys
    50                  55                  60

ggg gag ctg aag aag gaa aag ggg att cac aga ctg gag gcc atg ctt      297
Gly Glu Leu Lys Lys Glu Lys Gly Ile His Arg Leu Glu Ala Met Leu
65                  70                  75                  80

tat gca att gac cag att aac aag gac cct gat ctc ctt tcc aac atc      345
Tyr Ala Ile Asp Gln Ile Asn Lys Asp Pro Asp Leu Leu Ser Asn Ile
                85                  90                  95

act ctg ggt gtc cgc atc ctc gac acg tgc tct agg gac acc tat gct      393
Thr Leu Gly Val Arg Ile Leu Asp Thr Cys Ser Arg Asp Thr Tyr Ala
            100                 105                 110

ttg gag cag tct cta aca ttc gtg cag gca tta ata gag aaa gat gct      441
Leu Glu Gln Ser Leu Thr Phe Val Gln Ala Leu Ile Glu Lys Asp Ala
        115                 120                 125

tcg gat gtg aag tgt gct aat gga gat cca ccc att ttc acc aag ccc      489
Ser Asp Val Lys Cys Ala Asn Gly Asp Pro Pro Ile Phe Thr Lys Pro
    130                 135                 140

gac aag att tct ggc gtc ata ggt gct gca gca agc tcc gtg tcc atc      537
Asp Lys Ile Ser Gly Val Ile Gly Ala Ala Ala Ser Ser Val Ser Ile
145                 150                 155                 160

atg gtt gct aac att tta aga ctt ttt aag ata cct caa atc agc tat      585
Met Val Ala Asn Ile Leu Arg Leu Phe Lys Ile Pro Gln Ile Ser Tyr
                165                 170                 175

gca tcc aca gcc cca gag cta agt gat aac acc agg tat gac ttt ttc      633
Ala Ser Thr Ala Pro Glu Leu Ser Asp Asn Thr Arg Tyr Asp Phe Phe
            180                 185                 190

tct cga gtg gtt ccg cct gac tcc tac caa gcc caa gcc atg gtg gac      681
Ser Arg Val Val Pro Pro Asp Ser Tyr Gln Ala Gln Ala Met Val Asp
        195                 200                 205

atc gtg aca gca ctg gga tgg aat tat gtt tcg aca ctg gct tct gag      729
Ile Val Thr Ala Leu Gly Trp Asn Tyr Val Ser Thr Leu Ala Ser Glu
    210                 215                 220

ggg aac tat ggt gag agc ggt gtg gag gcc ttc acc cag atc tcg agg      777
Gly Asn Tyr Gly Glu Ser Gly Val Glu Ala Phe Thr Gln Ile Ser Arg
225                 230                 235                 240

gag att ggt ggt gtt tgc att gct cag tca cag aaa atc cca cgt gaa      825
Glu Ile Gly Gly Val Cys Ile Ala Gln Ser Gln Lys Ile Pro Arg Glu
                245                 250                 255

cca aga cct gga gaa ttt gaa aaa att atc aaa cgc ctg cta gaa aca      873
Pro Arg Pro Gly Glu Phe Glu Lys Ile Ile Lys Arg Leu Leu Glu Thr
            260                 265                 270

cct aat gct cga gca gtg att atg ttt gcc aat gag gat gac atc agg      921
Pro Asn Ala Arg Ala Val Ile Met Phe Ala Asn Glu Asp Asp Ile Arg
        275                 280                 285

agg ata ttg gaa gca gca aaa aaa cta aac caa agt ggg cat ttt ctc      969
```

-continued

```
Arg Ile Leu Glu Ala Ala Lys Lys Leu Asn Gln Ser Gly His Phe Leu
    290                 295                 300

tgg att ggc tca gat agt tgg gga tcc aaa ata gca cct gtc tat cag     1017
Trp Ile Gly Ser Asp Ser Trp Gly Ser Lys Ile Ala Pro Val Tyr Gln
305                 310                 315                 320

caa gag gag att gca gaa ggg gct gtg aca att ttg ccc aaa cga gca     1065
Gln Glu Glu Ile Ala Glu Gly Ala Val Thr Ile Leu Pro Lys Arg Ala
                325                 330                 335

tca att gat gga ttt gat cga tac ttt aga agc cga act ctt gcc aat     1113
Ser Ile Asp Gly Phe Asp Arg Tyr Phe Arg Ser Arg Thr Leu Ala Asn
            340                 345                 350

aat cga aga aat gtg tgg ttt gca gaa ttc tgg gag gag aat ttt ggc     1161
Asn Arg Arg Asn Val Trp Phe Ala Glu Phe Trp Glu Glu Asn Phe Gly
        355                 360                 365

tgc aag tta gga tca cat ggg aaa agg aac agt cat ata aag aaa tgc     1209
Cys Lys Leu Gly Ser His Gly Lys Arg Asn Ser His Ile Lys Lys Cys
    370                 375                 380

aca ggg ctg gag cga att gct cgg gat tca tct tat gaa cag gaa gga     1257
Thr Gly Leu Glu Arg Ile Ala Arg Asp Ser Ser Tyr Glu Gln Glu Gly
385                 390                 395                 400

aag gtc caa ttt gta att gat gct gta tat tcc atg gct tac gcc ctg     1305
Lys Val Gln Phe Val Ile Asp Ala Val Tyr Ser Met Ala Tyr Ala Leu
                405                 410                 415

cac aat atg cac aaa gat ctc tgc cct gga tac att ggc ctt tgt cca     1353
His Asn Met His Lys Asp Leu Cys Pro Gly Tyr Ile Gly Leu Cys Pro
            420                 425                 430

cga atg agt acc att gat ggg aaa gag cta ctt ggt tat att cgg gct     1401
Arg Met Ser Thr Ile Asp Gly Lys Glu Leu Leu Gly Tyr Ile Arg Ala
        435                 440                 445

gta aat ttt aat ggc agt gct ggc act cct gtc act ttt aat gaa aac     1449
Val Asn Phe Asn Gly Ser Ala Gly Thr Pro Val Thr Phe Asn Glu Asn
    450                 455                 460

gga gat gct cct gga cgt tat gat atc ttc cag tat caa ata acc aac     1497
Gly Asp Ala Pro Gly Arg Tyr Asp Ile Phe Gln Tyr Gln Ile Thr Asn
465                 470                 475                 480

aaa agc aca gag tac aaa gtc atc ggc cac tgg acc aat cag ctt cat     1545
Lys Ser Thr Glu Tyr Lys Val Ile Gly His Trp Thr Asn Gln Leu His
                485                 490                 495

cta aaa gtg gaa gac atg cag tgg gct cat aga gaa cat act cac ccg     1593
Leu Lys Val Glu Asp Met Gln Trp Ala His Arg Glu His Thr His Pro
            500                 505                 510

gcg tct gtc tgc agc ctg ccg tgt aag cca ggg gag agg aag aaa acg     1641
Ala Ser Val Cys Ser Leu Pro Cys Lys Pro Gly Glu Arg Lys Lys Thr
        515                 520                 525

gtg aaa ggg gtc cct tgc tgc tgg cac tgt gaa cgc tgt gaa ggt tac     1689
Val Lys Gly Val Pro Cys Cys Trp His Cys Glu Arg Cys Glu Gly Tyr
    530                 535                 540

aac tac cag gtg gat gag ctg tcc tgt gaa ctt tgc cct ctg gat cag     1737
Asn Tyr Gln Val Asp Glu Leu Ser Cys Glu Leu Cys Pro Leu Asp Gln
545                 550                 555                 560

aga ccc aac atg aac cgc aca ggc tgc cag ctt atc ccc atc atc aaa     1785
Arg Pro Asn Met Asn Arg Thr Gly Cys Gln Leu Ile Pro Ile Ile Lys
                565                 570                 575

ttg gag tgg cat tct ccc tgg gct gtg gtg cct gtg ttt gtt gca ata     1833
Leu Glu Trp His Ser Pro Trp Ala Val Val Pro Val Phe Val Ala Ile
            580                 585                 590

ttg gga atc atc gcc acc acc ttt gtg atc gtg acc ttt gtc cgc tat     1881
Leu Gly Ile Ile Ala Thr Thr Phe Val Ile Val Thr Phe Val Arg Tyr
        595                 600                 605
```

-continued aat gac aca cct atc gtg agg gct tca gga cgc gaa ctt agt tac gtg 1929
Asn Asp Thr Pro Ile Val Arg Ala Ser Gly Arg Glu Leu Ser Tyr Val
610 615 620 ctc cta acg ggg att ttt ctc tgt tat tca atc acg ttt tta atg att 1977
Leu Leu Thr Gly Ile Phe Leu Cys Tyr Ser Ile Thr Phe Leu Met Ile
625 630 635 640 gca gca cca gat aca atc ata tgc tcc ttc cga cgg gtc ttc cta gga 2025
Ala Ala Pro Asp Thr Ile Ile Cys Ser Phe Arg Arg Val Phe Leu Gly
645 650 655 ctt ggc atg tgt ttc agc tat gca gcc ctt ctg acc aaa aca aac cgt 2073
Leu Gly Met Cys Phe Ser Tyr Ala Ala Leu Leu Thr Lys Thr Asn Arg
660 665 670 atc cac cga ata ttt gag cag ggg aag aaa tct gtc aca gcg ccc aag 2121
Ile His Arg Ile Phe Glu Gln Gly Lys Lys Ser Val Thr Ala Pro Lys
675 680 685 ttc att agt cca gca tct cag ctg gtg atc acc ttc agc ctc atc tcc 2169
Phe Ile Ser Pro Ala Ser Gln Leu Val Ile Thr Phe Ser Leu Ile Ser
690 695 700 gtc cag ctc ctt gga gtg ttt gtc tgg ttt gtt gtg gat ccc ccc cac 2217
Val Gln Leu Leu Gly Val Phe Val Trp Phe Val Val Asp Pro Pro His
705 710 715 720 atc atc att gac tat gga gag cag cgg aca cta gat cca gag aag gcc 2265
Ile Ile Ile Asp Tyr Gly Glu Gln Arg Thr Leu Asp Pro Glu Lys Ala
725 730 735 agg gga gtg ctc aag tgt gac att tct gat ctc tca ctc att tgt tca 2313
Arg Gly Val Leu Lys Cys Asp Ile Ser Asp Leu Ser Leu Ile Cys Ser
740 745 750 ctt gga tac agt atc ctc ttg atg gtc act tgt act gtt tat gcc aat 2361
Leu Gly Tyr Ser Ile Leu Leu Met Val Thr Cys Thr Val Tyr Ala Asn
755 760 765 aaa acg aga ggt gtc cca gag act ttc aat gaa gcc aaa cct att gga 2409
Lys Thr Arg Gly Val Pro Glu Thr Phe Asn Glu Ala Lys Pro Ile Gly
770 775 780 ttt acc atg tat acc acc tgc atc att tgg tta gct ttc atc ccc atc 2457
Phe Thr Met Tyr Thr Thr Cys Ile Ile Trp Leu Ala Phe Ile Pro Ile
785 790 795 800 ttt ttt ggt aca gcc cag tca gca gaa aag atg tac atc cag aca aca 2505
Phe Phe Gly Thr Ala Gln Ser Ala Glu Lys Met Tyr Ile Gln Thr Thr
805 810 815 aca ctt act gtc tcc atg agt tta agt gct tca gta tct ctg ggc atg 2553
Thr Leu Thr Val Ser Met Ser Leu Ser Ala Ser Val Ser Leu Gly Met
820 825 830 ctc tat atg ccc aag gtt tat att ata att ttt cat cca gaa cag aat 2601
Leu Tyr Met Pro Lys Val Tyr Ile Ile Ile Phe His Pro Glu Gln Asn
835 840 845 gtt caa aaa cgc aag agg agc ttc aag gct gtg gtg aca gct gcc acc 2649
Val Gln Lys Arg Lys Arg Ser Phe Lys Ala Val Val Thr Ala Ala Thr
850 855 860 atg caa agc aaa ctg atc caa aaa gga aat gac aga cca aat ggc gag 2697
Met Gln Ser Lys Leu Ile Gln Lys Gly Asn Asp Arg Pro Asn Gly Glu
865 870 875 880 gtg aaa agt gaa ctc tgt gag agt ctt gaa acc aac act tcc tct acc 2745
Val Lys Ser Glu Leu Cys Glu Ser Leu Glu Thr Asn Thr Ser Ser Thr
885 890 895 aag aca aca tat atc agt tac agc aat cat tca atc tga aacagggaaa 2794
Lys Thr Thr Tyr Ile Ser Tyr Ser Asn His Ser Ile
900 905 tggcacaatc tgaagagacg tggtatatga tcttaaatga tgaacatgag accgcaaaaa 2854 ttcactcctg gagatctccg tagactacaa tcaatcaaat caatagtcag tcttgtaagg 2914

```
aacaaaaatt agccatgagc caaaagtatc aataaacggg gagtgaagaa acccgtttta   2974

tacaataaaa ccaatgagtg tcaagctaaa gtattgctta ttcatgagca gttaaaacaa   3034

atcacaaaag gaaaactaat gttagctcgt gaaaaaaatg ctgttgaaat aaataatgtc   3094

tgatgttatt cttgtatttt tctgtgattg tgagaactcc cgttcctgtc ccacattgtt   3154

taacttgtat aagacaatga gtctgtttct tgtaatggct gaccagattg aagccctggg   3214

ttgtgctaaa aataaatgca atgattgatg catgcaattt tttatacaaa taatttattt   3274

ctaataataa aggaatgttt tgcaaaaaaa aaaaaaaaaa actcgag                 3321


<210> SEQ ID NO 8
<211> LENGTH: 908
<212> TYPE: PRT
<213> ORGANISM: Homo sapiens

<400> SEQUENCE: 8

Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
        35                  40                  45

Gly Gly Leu Phe Pro Val His Ala Lys Gly Glu Arg Gly Val Pro Cys
    50                  55                  60

Gly Glu Leu Lys Lys Glu Lys Gly Ile His Arg Leu Glu Ala Met Leu
65                  70                  75                  80

Tyr Ala Ile Asp Gln Ile Asn Lys Asp Pro Asp Leu Leu Ser Asn Ile
                85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
        115                 120                 125

Ser Asp Val Lys Cys Ala Asn Gly Asp Pro Pro Ile Phe Thr Lys Pro
    130                 135                 140

Asp Lys Ile Ser Gly Val Ile Gly Ala Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
        195                 200                 205

Ile Val Thr Ala Leu Gly Trp Asn Tyr Val Ser Thr Leu Ala Ser Glu
    210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
        275                 280                 285

Arg Ile Leu Glu Ala Ala Lys Lys Leu Asn Gln Ser Gly His Phe Leu
    290                 295                 300
```

-continued

```
Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
        355                 360                 365

Cys Lys Leu Gly Ser His Gly Lys Arg Asn Ser His Ile Lys Lys Cys
    370                 375                 380

Thr Gly Leu Glu Arg Ile Ala Arg Asp Ser Ser Tyr Glu Gln Glu Gly
385                 390                 395                 400

Lys Val Gln Phe Val Ile Asp Ala Val Tyr Ser Met Ala Tyr Ala Leu
                405                 410                 415

His Asn Met His Lys Asp Leu Cys Pro Gly Tyr Ile Gly Leu Cys Pro
            420                 425                 430

Arg Met Ser Thr Ile Asp Gly Lys Glu Leu Leu Gly Tyr Ile Arg Ala
        435                 440                 445

Val Asn Phe Asn Gly Ser Ala Gly Thr Pro Val Thr Phe Asn Glu Asn
    450                 455                 460

Gly Asp Ala Pro Gly Arg Tyr Asp Ile Phe Gln Tyr Gln Ile Thr Asn
465                 470                 475                 480

Lys Ser Thr Glu Tyr Lys Val Ile Gly His Trp Thr Asn Gln Leu His
                485                 490                 495

Leu Lys Val Glu Asp Met Gln Trp Ala His Arg Glu His Thr His Pro
            500                 505                 510

Ala Ser Val Cys Ser Leu Pro Cys Lys Pro Gly Glu Arg Lys Lys Thr
        515                 520                 525

Val Lys Gly Val Pro Cys Cys Trp His Cys Glu Arg Cys Glu Gly Tyr
    530                 535                 540

Asn Tyr Gln Val Asp Glu Leu Ser Cys Glu Leu Cys Pro Leu Asp Gln
545                 550                 555                 560

Arg Pro Asn Met Asn Arg Thr Gly Cys Gln Leu Ile Pro Ile Ile Lys
                565                 570                 575

Leu Glu Trp His Ser Pro Trp Ala Val Val Pro Val Phe Val Ala Ile
            580                 585                 590

Leu Gly Ile Ile Ala Thr Thr Phe Val Ile Val Thr Phe Val Arg Tyr
        595                 600                 605

Asn Asp Thr Pro Ile Val Arg Ala Ser Gly Arg Glu Leu Ser Tyr Val
    610                 615                 620

Leu Leu Thr Gly Ile Phe Leu Cys Tyr Ser Ile Thr Phe Leu Met Ile
625                 630                 635                 640

Ala Ala Pro Asp Thr Ile Ile Cys Ser Phe Arg Arg Val Phe Leu Gly
                645                 650                 655

Leu Gly Met Cys Phe Ser Tyr Ala Ala Leu Leu Thr Lys Thr Asn Arg
            660                 665                 670

Ile His Arg Ile Phe Glu Gln Gly Lys Lys Ser Val Thr Ala Pro Lys
        675                 680                 685

Phe Ile Ser Pro Ala Ser Gln Leu Val Ile Thr Phe Ser Leu Ile Ser
    690                 695                 700

Val Gln Leu Leu Gly Val Phe Val Trp Phe Val Val Asp Pro Pro His
705                 710                 715                 720
```

```
Ile Ile Ile Asp Tyr Gly Glu Gln Arg Thr Leu Asp Pro Glu Lys Ala
            725                 730                 735

Arg Gly Val Leu Lys Cys Asp Ile Ser Asp Leu Ser Leu Ile Cys Ser
            740                 745                 750

Leu Gly Tyr Ser Ile Leu Leu Met Val Thr Cys Thr Val Tyr Ala Asn
        755                 760                 765

Lys Thr Arg Gly Val Pro Glu Thr Phe Asn Glu Ala Lys Pro Ile Gly
    770                 775                 780

Phe Thr Met Tyr Thr Thr Cys Ile Ile Trp Leu Ala Phe Ile Pro Ile
785                 790                 795                 800

Phe Phe Gly Thr Ala Gln Ser Ala Glu Lys Met Tyr Ile Gln Thr Thr
            805                 810                 815

Thr Leu Thr Val Ser Met Ser Leu Ser Ala Ser Val Ser Leu Gly Met
            820                 825                 830

Leu Tyr Met Pro Lys Val Tyr Ile Ile Ile Phe His Pro Glu Gln Asn
        835                 840                 845

Val Gln Lys Arg Lys Arg Ser Phe Lys Ala Val Val Thr Ala Ala Thr
    850                 855                 860

Met Gln Ser Lys Leu Ile Gln Lys Gly Asn Asp Arg Pro Asn Gly Glu
865                 870                 875                 880

Val Lys Ser Glu Leu Cys Glu Ser Leu Glu Thr Asn Thr Ser Ser Thr
            885                 890                 895

Lys Thr Thr Tyr Ile Ser Tyr Ser Asn His Ser Ile
            900                 905


<210> SEQ ID NO 9
<211> LENGTH: 3697
<212> TYPE: DNA
<213> ORGANISM: Homo sapiens
<220> FEATURE:
<221> NAME/KEY: CDS
<222> LOCATION: (121)..(2619)

<400> SEQUENCE: 9

agggagtgtt cccgggggag atactccagt cgtagcaaga gtctcgacca ctgaatggaa      60

gaaaaggact tttaaccacc attttgtgac ttacagaaag gaatttgaat aaagaaaact     120

atg ata ctt cag gcc cat ctt cac tcc ctg tgt ctt ctt atg ctt tat       168
Met Ile Leu Gln Ala His Leu His Ser Leu Cys Leu Leu Met Leu Tyr
1               5                   10                  15

ttg gca act gga tat ggc caa gag ggg aag ttt agt gga ccc ctg aaa       216
Leu Ala Thr Gly Tyr Gly Gln Glu Gly Lys Phe Ser Gly Pro Leu Lys
            20                  25                  30

ccc atg aca ttt tct att tat gaa ggc caa gaa ccg agt caa att ata       264
Pro Met Thr Phe Ser Ile Tyr Glu Gly Gln Glu Pro Ser Gln Ile Ile
        35                  40                  45

ttc cag ttt aag gcc aat cct cct gct gtg act ttt gaa cta act ggg       312
Phe Gln Phe Lys Ala Asn Pro Pro Ala Val Thr Phe Glu Leu Thr Gly
    50                  55                  60

gag aca gac aac ata ttt gtg ata gaa cgg gag gga ctt ctg tat tac       360
Glu Thr Asp Asn Ile Phe Val Ile Glu Arg Glu Gly Leu Leu Tyr Tyr
65                  70                  75                  80

aac aga gcc ttg gac agg gaa aca aga tct act cac aat ctc cag gtt       408
Asn Arg Ala Leu Asp Arg Glu Thr Arg Ser Thr His Asn Leu Gln Val
            85                  90                  95

gca gcc ctg gac gct aat gga att ata gtg gag ggt cca gtc cct atc       456
Ala Ala Leu Asp Ala Asn Gly Ile Ile Val Glu Gly Pro Val Pro Ile
            100                 105                 110
```

-continued

```
acc ata gaa gtg aag gac atc aac gac aat cga ccc acg ttt ctc cag      504
Thr Ile Glu Val Lys Asp Ile Asn Asp Asn Arg Pro Thr Phe Leu Gln
        115                 120                 125

tca aag tac gaa ggc tca gta agg cag aac tct cgc cca gga aag ccc      552
Ser Lys Tyr Glu Gly Ser Val Arg Gln Asn Ser Arg Pro Gly Lys Pro
    130                 135                 140

ttc ttg tat gtc aat gcc aca gac ctg gat gat ccg gcc act ccc aat      600
Phe Leu Tyr Val Asn Ala Thr Asp Leu Asp Asp Pro Ala Thr Pro Asn
145                 150                 155                 160

ggc cag ctt tat tac cag att gtc atc cag ctt ccc atg atc aac aat      648
Gly Gln Leu Tyr Tyr Gln Ile Val Ile Gln Leu Pro Met Ile Asn Asn
                165                 170                 175

gtc atg tac ttt cag atc aac aac aaa acg gga gcc atc tct ctt acc      696
Val Met Tyr Phe Gln Ile Asn Asn Lys Thr Gly Ala Ile Ser Leu Thr
            180                 185                 190

cga gag gga tct cag gaa ttg aat cct gct aag aat cct tcc tat aat      744
Arg Glu Gly Ser Gln Glu Leu Asn Pro Ala Lys Asn Pro Ser Tyr Asn
        195                 200                 205

ctg gtg atc tca gtg aag gac atg gga ggc cag agt gag aat tcc ttc      792
Leu Val Ile Ser Val Lys Asp Met Gly Gly Gln Ser Glu Asn Ser Phe
    210                 215                 220

agt gat acc aca tct gtg gat atc ata gtg aca gag aat att tgg aaa      840
Ser Asp Thr Thr Ser Val Asp Ile Ile Val Thr Glu Asn Ile Trp Lys
225                 230                 235                 240

gca cca aaa cct gtg gag atg gtg gaa aac tca act gat cct cac ccc      888
Ala Pro Lys Pro Val Glu Met Val Glu Asn Ser Thr Asp Pro His Pro
                245                 250                 255

atc aaa atc act cag gtg cgg tgg aat gat ccc ggt gca caa tat tcc      936
Ile Lys Ile Thr Gln Val Arg Trp Asn Asp Pro Gly Ala Gln Tyr Ser
            260                 265                 270

tta gtt gac aaa gag aag ctg cca aga ttc cca ttt tca att gac cag      984
Leu Val Asp Lys Glu Lys Leu Pro Arg Phe Pro Phe Ser Ile Asp Gln
        275                 280                 285

gaa gga gat att tac gtg act cag ccc ttg gac cga gaa gaa aag gat     1032
Glu Gly Asp Ile Tyr Val Thr Gln Pro Leu Asp Arg Glu Glu Lys Asp
    290                 295                 300

gca tat gtt ttt tat gca gtt gca aag gat gag tac gga aaa cca ctt     1080
Ala Tyr Val Phe Tyr Ala Val Ala Lys Asp Glu Tyr Gly Lys Pro Leu
305                 310                 315                 320

tca tat ccg ctg gaa att cat gta aaa gtt aaa gat att aat gat aat     1128
Ser Tyr Pro Leu Glu Ile His Val Lys Val Lys Asp Ile Asn Asp Asn
                325                 330                 335

cca cct aca tgt ccg tca cca gta acc gta ttt gag gtc cag gag aat     1176
Pro Pro Thr Cys Pro Ser Pro Val Thr Val Phe Glu Val Gln Glu Asn
            340                 345                 350

gaa cga ctg ggt aac agt atc ggg acc ctt act gca cat gac agg gat     1224
Glu Arg Leu Gly Asn Ser Ile Gly Thr Leu Thr Ala His Asp Arg Asp
        355                 360                 365

gaa gaa aat act gcc aac agt ttt cta aac tac agg att gtg gag caa     1272
Glu Glu Asn Thr Ala Asn Ser Phe Leu Asn Tyr Arg Ile Val Glu Gln
    370                 375                 380

act ccc aaa ctt ccc atg gat gga ctc ttc cta atc caa acc tat gct     1320
Thr Pro Lys Leu Pro Met Asp Gly Leu Phe Leu Ile Gln Thr Tyr Ala
385                 390                 395                 400

gga atg tta cag tta gct aaa cag tcc ttg aag aag caa gat act cct     1368
Gly Met Leu Gln Leu Ala Lys Gln Ser Leu Lys Lys Gln Asp Thr Pro
                405                 410                 415

cag tac aac tta acg ata gag gtg tct gac aaa gat ttc aag acc ctt     1416
Gln Tyr Asn Leu Thr Ile Glu Val Ser Asp Lys Asp Phe Lys Thr Leu
            420                 425                 430
```

-continued

```
tgt ttt gtg caa atc aac gtt att gat atc aat gat cag atc ccc atc     1464
Cys Phe Val Gln Ile Asn Val Ile Asp Ile Asn Asp Gln Ile Pro Ile
        435                 440                 445

ttt gaa aaa tca gat tat gga aac ctg act ctt gct gaa gac aca aac     1512
Phe Glu Lys Ser Asp Tyr Gly Asn Leu Thr Leu Ala Glu Asp Thr Asn
    450                 455                 460

att ggg tcc acc atc tta acc atc cag gcc act gat gct gat gag cca     1560
Ile Gly Ser Thr Ile Leu Thr Ile Gln Ala Thr Asp Ala Asp Glu Pro
465                 470                 475                 480

ttt act ggg agt tct aaa att ctg tat cat atc ata aag gga gac agt     1608
Phe Thr Gly Ser Ser Lys Ile Leu Tyr His Ile Ile Lys Gly Asp Ser
                485                 490                 495

gag gga cgc ctg ggg gtt gac aca gat ccc cat acc aac acc gga tat     1656
Glu Gly Arg Leu Gly Val Asp Thr Asp Pro His Thr Asn Thr Gly Tyr
            500                 505                 510

gtc ata att aaa aag cct ctt gat ttt gaa aca gca gct gtt tcc aac     1704
Val Ile Ile Lys Lys Pro Leu Asp Phe Glu Thr Ala Ala Val Ser Asn
        515                 520                 525

att gtg ttc aaa gca gaa aat cct gag cct cta gtg ttt ggt gtg aag     1752
Ile Val Phe Lys Ala Glu Asn Pro Glu Pro Leu Val Phe Gly Val Lys
    530                 535                 540

tac aat gca agt tct ttt gcc aag ttc acg ctt att gtg aca gat gtg     1800
Tyr Asn Ala Ser Ser Phe Ala Lys Phe Thr Leu Ile Val Thr Asp Val
545                 550                 555                 560

aat gaa gca cct caa ttt tcc caa cac gta ttc caa gcg aaa gtc agt     1848
Asn Glu Ala Pro Gln Phe Ser Gln His Val Phe Gln Ala Lys Val Ser
                565                 570                 575

gag gat gta gct ata ggc act aaa gtg ggc aat gtg act gcc aag gat     1896
Glu Asp Val Ala Ile Gly Thr Lys Val Gly Asn Val Thr Ala Lys Asp
            580                 585                 590

cca gaa ggt ctg gac ata agc tat tca ctg agg gga gac aca aga ggt     1944
Pro Glu Gly Leu Asp Ile Ser Tyr Ser Leu Arg Gly Asp Thr Arg Gly
        595                 600                 605

tgg ctt aaa att gac cac gtg act ggt gag atc ttt agt gtg gct cca     1992
Trp Leu Lys Ile Asp His Val Thr Gly Glu Ile Phe Ser Val Ala Pro
    610                 615                 620

ttg gac aga gaa gcc gga agt cca tat cgg gta caa gtg gtg gcc aca     2040
Leu Asp Arg Glu Ala Gly Ser Pro Tyr Arg Val Gln Val Val Ala Thr
625                 630                 635                 640

gaa gta ggg ggg tct tcc ttg agc tct gtg tca gag ttc cac ctg atc     2088
Glu Val Gly Gly Ser Ser Leu Ser Ser Val Ser Glu Phe His Leu Ile
                645                 650                 655

ctt atg gat gtg aat gac aac cct ccc agg cta gcc aag gac tac acg     2136
Leu Met Asp Val Asn Asp Asn Pro Pro Arg Leu Ala Lys Asp Tyr Thr
            660                 665                 670

ggc ttg ttc ttc tgc cat ccc ctc agt gca cct gga agt ctc att ttc     2184
Gly Leu Phe Phe Cys His Pro Leu Ser Ala Pro Gly Ser Leu Ile Phe
        675                 680                 685

gag gct act gat gat gat cag cac tta ttt cgg ggt ccc cat ttt aca     2232
Glu Ala Thr Asp Asp Asp Gln His Leu Phe Arg Gly Pro His Phe Thr
    690                 695                 700

ttt tcc ctc ggc agt gga agc tta caa aac gac tgg gaa gtt tcc aaa     2280
Phe Ser Leu Gly Ser Gly Ser Leu Gln Asn Asp Trp Glu Val Ser Lys
705                 710                 715                 720

atc aat ggt act cat gcc cga ctg tct acc agg cac aca gag ttt gag     2328
Ile Asn Gly Thr His Ala Arg Leu Ser Thr Arg His Thr Glu Phe Glu
                725                 730                 735

gag agg gag tat gtc gtc ttg atc cgc atc aat gat ggg ggt cgg cca     2376
Glu Arg Glu Tyr Val Val Leu Ile Arg Ile Asn Asp Gly Gly Arg Pro
```

-continued 740 745 750 ccc ttg gaa ggc att gtt tct tta cca gtt aca ttc tgc agt tgt gtg 2424
Pro Leu Glu Gly Ile Val Ser Leu Pro Val Thr Phe Cys Ser Cys Val
755 760 765 gaa gga agt tgt ttc cgg cca gca ggt cac cag act ggg ata ccc act 2472
Glu Gly Ser Cys Phe Arg Pro Ala Gly His Gln Thr Gly Ile Pro Thr
770 775 780 gtg ggc atg gca gtt ggt ata ctg ctg acc acc ctt ctg gtg att ggt 2520
Val Gly Met Ala Val Gly Ile Leu Leu Thr Thr Leu Leu Val Ile Gly
785 790 795 800 ata att tta gca gtt gtg ttt atc cgc ata aag aag gat aaa ggc aaa 2568
Ile Ile Leu Ala Val Val Phe Ile Arg Ile Lys Lys Asp Lys Gly Lys
805 810 815 gat aat gtt gaa agt gct caa gca tct gaa gtc aaa cct ctg aga agc 2616
Asp Asn Val Glu Ser Ala Gln Ala Ser Glu Val Lys Pro Leu Arg Ser
820 825 830 tga atttgaaaag gaatgtttga atttatatag caagtgctat ttcagcaaca 2669 accatctcat cctattactt ttcatctaac gtgcattata attttttaaa cagatattcc 2729 ctcttgtcct ttaatatttg ctaaatattt ctttttttgag gtggagtctt gctctgtcgc 2789 ccaggctgga gtacagtggt gtgatcccag ctcactgcaa cctccgcctc ctgggttcac 2849 atgattctcc tgcctcagct tcctaagtag ctgggtttac aggcacccac caccatgccc 2909 agctaatttt tgtattttta atagagacgg ggtttcgcca tttggccagg ctggtcttga 2969 actcctgacg tcaagtgatc tgcctgcctt ggtctcccaa tacaggcatg aaccactgca 3029 cccacctact tagatatttc atgtgctata gacattagag agatttttca tttttccatg 3089 acatttttcc tctctgcaaa tggcttagct acttgtgttt ttccctttttg gggcaagaca 3149 gactcattaa atattctgta catttttttct ttatcaagga gatatatcag tgttgtctca 3209 tagaactgcc tggattccat ttatgttttt tctgattcca tcctgtgtcc ccttcatcct 3269 tgactccttt ggtatttcac tgaatttcaa acatttgtca gagaagaaaa acgtgaggac 3329 tcaggaaaaa taaataaata aaagaacagc cttttccctt agtattaaca gaaatgtttc 3389 tgtgtcatta accatcttta atcaatgtga catgttgctc tttggctgaa attcttcaac 3449 ttggaaatga cacagaccca cagaaggtgt tcaaacacaa cctactctgc aaaccttggt 3509 aaaggaacca gtcagctggc cagatttcct cactacctgc catgcataca tgctgcgcat 3569 gttttcttca ttcgtatgtt agtaaagttt tggttattat atatttaaca tgtggaagaa 3629 aacaagacat gaaaagagtg gtgacaaatc aagaataaac actggttgta gtcagttttg 3689 tttgttaa 3697

<210> SEQ ID NO 10
<211> LENGTH: 832
<212> TYPE: PRT
<213> ORGANISM: Homo sapiens

<400> SEQUENCE: 10

Met Ile Leu Gln Ala His Leu His Ser Leu Cys Leu Leu Met Leu Tyr
1 5 10 15

Leu Ala Thr Gly Tyr Gly Gln Glu Gly Lys Phe Ser Gly Pro Leu Lys
20 25 30

Pro Met Thr Phe Ser Ile Tyr Glu Gly Gln Glu Pro Ser Gln Ile Ile
35 40 45

Phe Gln Phe Lys Ala Asn Pro Pro Ala Val Thr Phe Glu Leu Thr Gly
50 55 60

```
Glu Thr Asp Asn Ile Phe Val Ile Glu Arg Glu Gly Leu Leu Tyr Tyr
65                  70                  75                  80

Asn Arg Ala Leu Asp Arg Glu Thr Arg Ser Thr His Asn Leu Gln Val
                85                  90                  95

Ala Ala Leu Asp Ala Asn Gly Ile Ile Val Glu Gly Pro Val Pro Ile
            100                 105                 110

Thr Ile Glu Val Lys Asp Ile Asn Asp Asn Arg Pro Thr Phe Leu Gln
        115                 120                 125

Ser Lys Tyr Glu Gly Ser Val Arg Gln Asn Ser Arg Pro Gly Lys Pro
    130                 135                 140

Phe Leu Tyr Val Asn Ala Thr Asp Leu Asp Asp Pro Ala Thr Pro Asn
145                 150                 155                 160

Gly Gln Leu Tyr Tyr Gln Ile Val Ile Gln Leu Pro Met Ile Asn Asn
                165                 170                 175

Val Met Tyr Phe Gln Ile Asn Asn Lys Thr Gly Ala Ile Ser Leu Thr
            180                 185                 190

Arg Glu Gly Ser Gln Glu Leu Asn Pro Ala Lys Asn Pro Ser Tyr Asn
        195                 200                 205

Leu Val Ile Ser Val Lys Asp Met Gly Gly Gln Ser Glu Asn Ser Phe
    210                 215                 220

Ser Asp Thr Thr Ser Val Asp Ile Ile Val Thr Glu Asn Ile Trp Lys
225                 230                 235                 240

Ala Pro Lys Pro Val Glu Met Val Glu Asn Ser Thr Asp Pro His Pro
                245                 250                 255

Ile Lys Ile Thr Gln Val Arg Trp Asn Asp Pro Gly Ala Gln Tyr Ser
            260                 265                 270

Leu Val Asp Lys Glu Lys Leu Pro Arg Phe Pro Phe Ser Ile Asp Gln
        275                 280                 285

Glu Gly Asp Ile Tyr Val Thr Gln Pro Leu Asp Arg Glu Glu Lys Asp
    290                 295                 300

Ala Tyr Val Phe Tyr Ala Val Ala Lys Asp Glu Tyr Gly Lys Pro Leu
305                 310                 315                 320

Ser Tyr Pro Leu Glu Ile His Val Lys Val Lys Asp Ile Asn Asp Asn
                325                 330                 335

Pro Pro Thr Cys Pro Ser Pro Val Thr Val Phe Glu Val Gln Glu Asn
            340                 345                 350

Glu Arg Leu Gly Asn Ser Ile Gly Thr Leu Thr Ala His Asp Arg Asp
        355                 360                 365

Glu Glu Asn Thr Ala Asn Ser Phe Leu Asn Tyr Arg Ile Val Glu Gln
    370                 375                 380

Thr Pro Lys Leu Pro Met Asp Gly Leu Phe Leu Ile Gln Thr Tyr Ala
385                 390                 395                 400

Gly Met Leu Gln Leu Ala Lys Gln Ser Leu Lys Lys Gln Asp Thr Pro
                405                 410                 415

Gln Tyr Asn Leu Thr Ile Glu Val Ser Asp Lys Asp Phe Lys Thr Leu
            420                 425                 430

Cys Phe Val Gln Ile Asn Val Ile Asp Ile Asn Asp Gln Ile Pro Ile
        435                 440                 445

Phe Glu Lys Ser Asp Tyr Gly Asn Leu Thr Leu Ala Glu Asp Thr Asn
    450                 455                 460

Ile Gly Ser Thr Ile Leu Thr Ile Gln Ala Thr Asp Ala Asp Glu Pro
465                 470                 475                 480
```

-continued

```
Phe Thr Gly Ser Ser Lys Ile Leu Tyr His Ile Ile Lys Gly Asp Ser
                485                 490                 495

Glu Gly Arg Leu Gly Val Asp Thr Asp Pro His Thr Asn Thr Gly Tyr
            500                 505                 510

Val Ile Ile Lys Lys Pro Leu Asp Phe Glu Thr Ala Ala Val Ser Asn
        515                 520                 525

Ile Val Phe Lys Ala Glu Asn Pro Glu Pro Leu Val Phe Gly Val Lys
    530                 535                 540

Tyr Asn Ala Ser Ser Phe Ala Lys Phe Thr Leu Ile Val Thr Asp Val
545                 550                 555                 560

Asn Glu Ala Pro Gln Phe Ser Gln His Val Phe Gln Ala Lys Val Ser
                565                 570                 575

Glu Asp Val Ala Ile Gly Thr Lys Val Gly Asn Val Thr Ala Lys Asp
            580                 585                 590

Pro Glu Gly Leu Asp Ile Ser Tyr Ser Leu Arg Gly Asp Thr Arg Gly
        595                 600                 605

Trp Leu Lys Ile Asp His Val Thr Gly Glu Ile Phe Ser Val Ala Pro
    610                 615                 620

Leu Asp Arg Glu Ala Gly Ser Pro Tyr Arg Val Gln Val Val Ala Thr
625                 630                 635                 640

Glu Val Gly Gly Ser Ser Leu Ser Ser Val Ser Glu Phe His Leu Ile
                645                 650                 655

Leu Met Asp Val Asn Asp Asn Pro Pro Arg Leu Ala Lys Asp Tyr Thr
            660                 665                 670

Gly Leu Phe Phe Cys His Pro Leu Ser Ala Pro Gly Ser Leu Ile Phe
        675                 680                 685

Glu Ala Thr Asp Asp Asp Gln His Leu Phe Arg Gly Pro His Phe Thr
    690                 695                 700

Phe Ser Leu Gly Ser Gly Ser Leu Gln Asn Asp Trp Glu Val Ser Lys
705                 710                 715                 720

Ile Asn Gly Thr His Ala Arg Leu Ser Thr Arg His Thr Glu Phe Glu
                725                 730                 735

Glu Arg Glu Tyr Val Val Leu Ile Arg Ile Asn Asp Gly Gly Arg Pro
            740                 745                 750

Pro Leu Glu Gly Ile Val Ser Leu Pro Val Thr Phe Cys Ser Cys Val
        755                 760                 765

Glu Gly Ser Cys Phe Arg Pro Ala Gly His Gln Thr Gly Ile Pro Thr
    770                 775                 780

Val Gly Met Ala Val Gly Ile Leu Leu Thr Thr Leu Leu Val Ile Gly
785                 790                 795                 800

Ile Ile Leu Ala Val Val Phe Ile Arg Ile Lys Lys Asp Lys Gly Lys
                805                 810                 815

Asp Asn Val Glu Ser Ala Gln Ala Ser Glu Val Lys Pro Leu Arg Ser
            820                 825                 830


<210> SEQ ID NO 11
<211> LENGTH: 4231
<212> TYPE: DNA
<213> ORGANISM: Homo sapiens
<220> FEATURE:
<221> NAME/KEY: CDS
<222> LOCATION: (116)..(4093)

<400> SEQUENCE: 11

ggacaggcgt ggcggccgga gccccagcat ccctgcttga ggtccaggag cggagcccgc      60
```

-continued

```
ggccaccgcc gcctgatcag cgcgaccccg gcccgcgccc gccccgcccg gcaag atg      118
                                                             Met
                                                             1

ctg ccc gtg tac cag gag gtg aag ccc aac ccg ctg cag gac gcg aac      166
Leu Pro Val Tyr Gln Glu Val Lys Pro Asn Pro Leu Gln Asp Ala Asn
            5                   10                  15

atc tgc tca cgc gtg ttc ttc tgg tgg ctc aat ccc ttg ttt aaa att      214
Ile Cys Ser Arg Val Phe Phe Trp Trp Leu Asn Pro Leu Phe Lys Ile
        20                  25                  30

ggc cat aaa cgg aga tta gag gaa gat gat atg tat tca gtg ctg cca      262
Gly His Lys Arg Arg Leu Glu Glu Asp Asp Met Tyr Ser Val Leu Pro
    35                  40                  45

gaa gac cgc tca cag cac ctt gga gag gag ttg caa ggg ttc tgg gat      310
Glu Asp Arg Ser Gln His Leu Gly Glu Glu Leu Gln Gly Phe Trp Asp
50                  55                  60                  65

aaa gaa gtt tta aga gct gag aat gac gca cag aag cct tct tta aca      358
Lys Glu Val Leu Arg Ala Glu Asn Asp Ala Gln Lys Pro Ser Leu Thr
                70                  75                  80

aga gca atc ata aag tgt tac tgg aaa tct tat tta gtt ttg gga att      406
Arg Ala Ile Ile Lys Cys Tyr Trp Lys Ser Tyr Leu Val Leu Gly Ile
            85                  90                  95

ttt acg tta att gag gaa agt gcc aaa gta atc cag ccc ata ttt ttg      454
Phe Thr Leu Ile Glu Glu Ser Ala Lys Val Ile Gln Pro Ile Phe Leu
        100                 105                 110

gga aaa att att aat tat ttt gaa aat tat gat ccc atg gat tct gtg      502
Gly Lys Ile Ile Asn Tyr Phe Glu Asn Tyr Asp Pro Met Asp Ser Val
    115                 120                 125

gct ttg aac aca gcg tac gcc tat gcc acg gtg ctg act ttt tgc acg      550
Ala Leu Asn Thr Ala Tyr Ala Tyr Ala Thr Val Leu Thr Phe Cys Thr
130                 135                 140                 145

ctc att ttg gct ata ctg cat cac tta tat ttt tat cac gtt cag tgt      598
Leu Ile Leu Ala Ile Leu His His Leu Tyr Phe Tyr His Val Gln Cys
                150                 155                 160

gct ggg atg agg tta cga gta gcc atg tgc cat atg att tat cgg aag      646
Ala Gly Met Arg Leu Arg Val Ala Met Cys His Met Ile Tyr Arg Lys
            165                 170                 175

gca ctt cgt ctt agt aac atg gcc atg ggg aag aca acc aca ggc cag      694
Ala Leu Arg Leu Ser Asn Met Ala Met Gly Lys Thr Thr Thr Gly Gln
        180                 185                 190

ata gtc aat ctg ctg tcc aat gat gtg aac aag ttt gat cag gtg aca      742
Ile Val Asn Leu Leu Ser Asn Asp Val Asn Lys Phe Asp Gln Val Thr
    195                 200                 205

gtg ttc tta cac ttc ctg tgg gca gga cca ctg cag gcg atc gca gtg      790
Val Phe Leu His Phe Leu Trp Ala Gly Pro Leu Gln Ala Ile Ala Val
210                 215                 220                 225

act gcc cta ctc tgg atg gag ata gga ata tcg tgc ctt gct ggg atg      838
Thr Ala Leu Leu Trp Met Glu Ile Gly Ile Ser Cys Leu Ala Gly Met
                230                 235                 240

gca gtt cta atc att ctc ctg ccc ttg caa agc tgt ttt ggg aag ttg      886
Ala Val Leu Ile Ile Leu Leu Pro Leu Gln Ser Cys Phe Gly Lys Leu
            245                 250                 255

ttc tca tca ctg agg agt aaa act gca act ttc acg gat gcc agg atc      934
Phe Ser Ser Leu Arg Ser Lys Thr Ala Thr Phe Thr Asp Ala Arg Ile
        260                 265                 270

agg acc atg aat gaa gtt ata act ggt ata agg ata ata aaa atg tac      982
Arg Thr Met Asn Glu Val Ile Thr Gly Ile Arg Ile Ile Lys Met Tyr
    275                 280                 285

gcc tgg gaa aag tca ttt tca aat ctt att acc aat ttg aga aag aag     1030
Ala Trp Glu Lys Ser Phe Ser Asn Leu Ile Thr Asn Leu Arg Lys Lys
290                 295                 300                 305
```

-continued

```
gag att tcc aag att ctg aga agt tcc tgc ctc agg ggg atg aat ttg     1078
Glu Ile Ser Lys Ile Leu Arg Ser Ser Cys Leu Arg Gly Met Asn Leu
                310                 315                 320

gct tcg ttt ttc agt gca agc aaa atc atc gtg ttt gtg acc ttc acc     1126
Ala Ser Phe Phe Ser Ala Ser Lys Ile Ile Val Phe Val Thr Phe Thr
            325                 330                 335

acc tac gtg ctc ctc ggc agt gtg atc aca gcc agc cgc gtg ttc gtg     1174
Thr Tyr Val Leu Leu Gly Ser Val Ile Thr Ala Ser Arg Val Phe Val
        340                 345                 350

gca gtg acg ctg tat ggg gct gtg cgg ctg acg gtt acc ctc ttc ttc     1222
Ala Val Thr Leu Tyr Gly Ala Val Arg Leu Thr Val Thr Leu Phe Phe
    355                 360                 365

ccc tca gcc att gag agg gtg tca gag gca atc gtc agc atc cga aga     1270
Pro Ser Ala Ile Glu Arg Val Ser Glu Ala Ile Val Ser Ile Arg Arg
370                 375                 380                 385

atc cag acc ttt ttg cta ctt gat gag ata tca cag cgc aac cgt cag     1318
Ile Gln Thr Phe Leu Leu Leu Asp Glu Ile Ser Gln Arg Asn Arg Gln
                390                 395                 400

ctg ccg tca gat ggt aaa aag atg gtg cat gtg cag gat ttt act gct     1366
Leu Pro Ser Asp Gly Lys Lys Met Val His Val Gln Asp Phe Thr Ala
            405                 410                 415

ttt tgg gat aag gca tca gag acc cca act cta caa ggc ctt tcc ttt     1414
Phe Trp Asp Lys Ala Ser Glu Thr Pro Thr Leu Gln Gly Leu Ser Phe
        420                 425                 430

act gtc aga cct ggc gaa ttg tta gct gtg gtc ggc ccc gtg gga gca     1462
Thr Val Arg Pro Gly Glu Leu Leu Ala Val Val Gly Pro Val Gly Ala
    435                 440                 445

ggg aag tca tca ctg tta agt gcc gtg ctc ggg gaa ttg gcc cca agt     1510
Gly Lys Ser Ser Leu Leu Ser Ala Val Leu Gly Glu Leu Ala Pro Ser
450                 455                 460                 465

cac ggg ctg gtc agc gtg cat gga aga att gcc tat gtg tct cag cag     1558
His Gly Leu Val Ser Val His Gly Arg Ile Ala Tyr Val Ser Gln Gln
                470                 475                 480

ccc tgg gtg ttc tcg gga act ctg agg agt aat att tta ttt ggg aag     1606
Pro Trp Val Phe Ser Gly Thr Leu Arg Ser Asn Ile Leu Phe Gly Lys
            485                 490                 495

aaa tat gaa aag gaa cga tat gaa aaa gtc ata aag gct tgt gct ctg     1654
Lys Tyr Glu Lys Glu Arg Tyr Glu Lys Val Ile Lys Ala Cys Ala Leu
        500                 505                 510

aaa aag gat tta cag ctg ttg gag gat ggt gat ctg act gtg ata gga     1702
Lys Lys Asp Leu Gln Leu Leu Glu Asp Gly Asp Leu Thr Val Ile Gly
    515                 520                 525

gat cgg gga acc acg ctg agt gga ggg cag aaa gca cgg gta aac ctt     1750
Asp Arg Gly Thr Thr Leu Ser Gly Gly Gln Lys Ala Arg Val Asn Leu
530                 535                 540                 545

gca aga gca gtg tat caa gat gct gac atc tat ctc ctg gac gat cct     1798
Ala Arg Ala Val Tyr Gln Asp Ala Asp Ile Tyr Leu Leu Asp Asp Pro
                550                 555                 560

ctc agt gca gta gat gcg gaa gtt agc aga cac ttg ttc gaa ctg tgt     1846
Leu Ser Ala Val Asp Ala Glu Val Ser Arg His Leu Phe Glu Leu Cys
            565                 570                 575

att tgt caa att ttg cat gag aag atc aca att tta gtg act cat cag     1894
Ile Cys Gln Ile Leu His Glu Lys Ile Thr Ile Leu Val Thr His Gln
        580                 585                 590

ttg cag tac ctc aaa gct gca agt cag att ctg ata ttg aaa gat ggt     1942
Leu Gln Tyr Leu Lys Ala Ala Ser Gln Ile Leu Ile Leu Lys Asp Gly
    595                 600                 605

aaa atg gtg cag aag ggg act tac act gag ttc cta aaa tct ggt ata     1990
Lys Met Val Gln Lys Gly Thr Tyr Thr Glu Phe Leu Lys Ser Gly Ile
```

-continued

```
610                 615                 620                 625

gat ttt ggc tcc ctt tta aag aag gat aat gag gaa agt gaa caa cct      2038
Asp Phe Gly Ser Leu Leu Lys Lys Asp Asn Glu Glu Ser Glu Gln Pro
                630                 635                 640

cca gtt cca gga act ccc aca cta agg aat cgt acc ttc tca gag tct      2086
Pro Val Pro Gly Thr Pro Thr Leu Arg Asn Arg Thr Phe Ser Glu Ser
            645                 650                 655

tcg gtt tgg tct caa caa tct tct aga ccc tcc ttg aaa gat ggt gct      2134
Ser Val Trp Ser Gln Gln Ser Ser Arg Pro Ser Leu Lys Asp Gly Ala
        660                 665                 670

ctg gag agc caa gat aca gag aat gtc cca gtt aca cta tca gag gag      2182
Leu Glu Ser Gln Asp Thr Glu Asn Val Pro Val Thr Leu Ser Glu Glu
    675                 680                 685

aac cgt tct gaa gga aaa gtt ggt ttt cag gcc tat aag aat tac ttc      2230
Asn Arg Ser Glu Gly Lys Val Gly Phe Gln Ala Tyr Lys Asn Tyr Phe
690                 695                 700                 705

aga gct ggt gct cac tgg att gtc ttc att ttc ctt att ctc cta aac      2278
Arg Ala Gly Ala His Trp Ile Val Phe Ile Phe Leu Ile Leu Leu Asn
                710                 715                 720

act gca gct cag gtt gcc tat gtg ctt caa gat tgg tgg ctt tca tac      2326
Thr Ala Ala Gln Val Ala Tyr Val Leu Gln Asp Trp Trp Leu Ser Tyr
            725                 730                 735

tgg gca aac aaa caa agt atg cta aat gtc act gta aat gga gga gga      2374
Trp Ala Asn Lys Gln Ser Met Leu Asn Val Thr Val Asn Gly Gly Gly
        740                 745                 750

aat gta acc gag aag cta gat ctt aac tgg tac tta gga att tat tca      2422
Asn Val Thr Glu Lys Leu Asp Leu Asn Trp Tyr Leu Gly Ile Tyr Ser
    755                 760                 765

ggt tta act gta gct acc gtt ctt ttt ggc ata gca aga tct cta ttg      2470
Gly Leu Thr Val Ala Thr Val Leu Phe Gly Ile Ala Arg Ser Leu Leu
770                 775                 780                 785

gta ttc tac gtc ctt gtt aac tct tca caa act ttg cac aac aaa atg      2518
Val Phe Tyr Val Leu Val Asn Ser Ser Gln Thr Leu His Asn Lys Met
                790                 795                 800

ttt gag tca att ctg aaa gct ccg gta tta ttc ttt gat aga aat cca      2566
Phe Glu Ser Ile Leu Lys Ala Pro Val Leu Phe Phe Asp Arg Asn Pro
            805                 810                 815

ata gga aga att tta aat cgt ttc tcc aaa gac att gga cac ttg gat      2614
Ile Gly Arg Ile Leu Asn Arg Phe Ser Lys Asp Ile Gly His Leu Asp
        820                 825                 830

gat ttg ctg ccg ctg acg ttt tta gat ttc atc cag aca ttg cta caa      2662
Asp Leu Leu Pro Leu Thr Phe Leu Asp Phe Ile Gln Thr Leu Leu Gln
    835                 840                 845

gtg gtt ggt gtg gtc tct gtg gct gtg gcc gtg att cct tgg atc gca      2710
Val Val Gly Val Val Ser Val Ala Val Ala Val Ile Pro Trp Ile Ala
850                 855                 860                 865

ata ccc ttg gtt ccc ctt gga atc att ttc att ttt ctt cgg cga tat      2758
Ile Pro Leu Val Pro Leu Gly Ile Ile Phe Ile Phe Leu Arg Arg Tyr
                870                 875                 880

ttt ttg gaa acg tca aga gat gtg aag cgc ctg gaa tct aca act cgg      2806
Phe Leu Glu Thr Ser Arg Asp Val Lys Arg Leu Glu Ser Thr Thr Arg
            885                 890                 895

agt cca gtg ttt tcc cac ttg tca tct tct ctc cag ggg ctc tgg acc      2854
Ser Pro Val Phe Ser His Leu Ser Ser Ser Leu Gln Gly Leu Trp Thr
        900                 905                 910

atc cgg gca tac aaa gca gaa gag agg tgt cag gaa ctg ttt gat gca      2902
Ile Arg Ala Tyr Lys Ala Glu Glu Arg Cys Gln Glu Leu Phe Asp Ala
    915                 920                 925

cac cag gat tta cat tca gag gct tgg ttc ttg ttt ttg aca acg tcc      2950
```

-continued

```
His Gln Asp Leu His Ser Glu Ala Trp Phe Leu Phe Leu Thr Thr Ser
930                 935                 940                 945

cgc tgg ttc gcc gtc cgt ctg gat gcc atc tgt gcc atg ttt gtc atc      2998
Arg Trp Phe Ala Val Arg Leu Asp Ala Ile Cys Ala Met Phe Val Ile
                950                 955                 960

atc gtt gcc ttt ggg tcc ctg att ctg gca aaa act ctg gat gcc ggg      3046
Ile Val Ala Phe Gly Ser Leu Ile Leu Ala Lys Thr Leu Asp Ala Gly
            965                 970                 975

cag gtt ggt ttg gca ctg tcc tat gcc ctc acg ctc atg ggg atg ttt      3094
Gln Val Gly Leu Ala Leu Ser Tyr Ala Leu Thr Leu Met Gly Met Phe
        980                 985                 990

cag tgg tgt gtt cga caa agt  gct gaa gtt gag aat  atg atg atc tca    3142
Gln Trp Cys Val Arg Gln Ser  Ala Glu Val Glu Asn  Met Met Ile Ser
    995                 1000                 1005

gta  gaa agg gtc att gaa  tac aca gac ctt gaa  aaa gaa gca cct      3187
Val  Glu Arg Val Ile Glu  Tyr Thr Asp Leu Glu  Lys Glu Ala Pro
1010                 1015                 1020

tgg  gaa tat cag aaa cgc  cca cca cca gcc tgg  ccc cat gaa gga      3232
Trp  Glu Tyr Gln Lys Arg  Pro Pro Pro Ala Trp  Pro His Glu Gly
1025                 1030                 1035

gtg  ata atc ttt gac aat  gtg aac ttc atg tac  agt cca ggt ggg      3277
Val  Ile Ile Phe Asp Asn  Val Asn Phe Met Tyr  Ser Pro Gly Gly
1040                 1045                 1050

cct  ctg gta ctg aag cat  ctg aca gca ctc att  aaa tca caa gaa      3322
Pro  Leu Val Leu Lys His  Leu Thr Ala Leu Ile  Lys Ser Gln Glu
1055                 1060                 1065

aag  gtt ggc att gtg gga  aga acc gga gct gga  aaa agt tcc ctc      3367
Lys  Val Gly Ile Val Gly  Arg Thr Gly Ala Gly  Lys Ser Ser Leu
1070                 1075                 1080

atc  tca gcc ctt ttt aga  ttg tca gaa ccc gaa  ggt aaa att tgg      3412
Ile  Ser Ala Leu Phe Arg  Leu Ser Glu Pro Glu  Gly Lys Ile Trp
1085                 1090                 1095

att  gat aag atc ttg aca  act gaa att gga ctt  cac gat tta agg      3457
Ile  Asp Lys Ile Leu Thr  Thr Glu Ile Gly Leu  His Asp Leu Arg
1100                 1105                 1110

aag  aaa atg tca atc ata  cct cag gaa cct gtt  ttg ttc act gga      3502
Lys  Lys Met Ser Ile Ile  Pro Gln Glu Pro Val  Leu Phe Thr Gly
1115                 1120                 1125

aca  atg agg aaa aac ctg  gat ccc ttt aag gag  cac acg gat gag      3547
Thr  Met Arg Lys Asn Leu  Asp Pro Phe Lys Glu  His Thr Asp Glu
1130                 1135                 1140

gaa  ctg tgg aat gcc tta  caa gag gta caa ctt  aaa gaa acc att      3592
Glu  Leu Trp Asn Ala Leu  Gln Glu Val Gln Leu  Lys Glu Thr Ile
1145                 1150                 1155

gaa  gat ctt cct ggt aaa  atg gat act gaa tta  gca gaa tca gga      3637
Glu  Asp Leu Pro Gly Lys  Met Asp Thr Glu Leu  Ala Glu Ser Gly
1160                 1165                 1170

tcc  aat ttt agt gtt gga  caa aga caa ctg gtg  tgc ctt gcc agg      3682
Ser  Asn Phe Ser Val Gly  Gln Arg Gln Leu Val  Cys Leu Ala Arg
1175                 1180                 1185

gca  att ctc agg aaa aat  cag ata ttg att att  gat gaa gcg acg      3727
Ala  Ile Leu Arg Lys Asn  Gln Ile Leu Ile Ile  Asp Glu Ala Thr
1190                 1195                 1200

gca  aat gtg gat cca aga  act gat gag tta ata  caa aaa aaa atc      3772
Ala  Asn Val Asp Pro Arg  Thr Asp Glu Leu Ile  Gln Lys Lys Ile
1205                 1210                 1215

cgg  gag aaa ttt gcc cac  tgc acc gtg cta acc  att gca cac aga      3817
Arg  Glu Lys Phe Ala His  Cys Thr Val Leu Thr  Ile Ala His Arg
1220                 1225                 1230
```

```
ttg  aac acc att att gac  agc gac aag ata atg  gtt tta gat tca      3862
Leu  Asn Thr Ile Ile Asp  Ser Asp Lys Ile Met  Val Leu Asp Ser
1235                 1240                 1245

gga  aga ctg aaa gaa tat  gat gag ccg tat gtt  ttg ctg caa aat      3907
Gly  Arg Leu Lys Glu Tyr  Asp Glu Pro Tyr Val  Leu Leu Gln Asn
1250                 1255                 1260

aaa  gag agc cta ttt tac  aag atg gtg caa caa  ctg ggc aag gca      3952
Lys  Glu Ser Leu Phe Tyr  Lys Met Val Gln Gln  Leu Gly Lys Ala
1265                 1270                 1275

gaa  gcc gct gcc ctc act  gaa aca gca aaa cag  gta tac ttc aaa      3997
Glu  Ala Ala Ala Leu Thr  Glu Thr Ala Lys Gln  Val Tyr Phe Lys
1280                 1285                 1290

aga  aat tat cca cat att  ggt cac act gac cac  atg gtt aca aac      4042
Arg  Asn Tyr Pro His Ile  Gly His Thr Asp His  Met Val Thr Asn
1295                 1300                 1305

act  tcc aat gga cag ccc  tcg acc tta act att  ttc gag aca gca      4087
Thr  Ser Asn Gly Gln Pro  Ser Thr Leu Thr Ile  Phe Glu Thr Ala
1310                 1315                 1320

ctg  tga atccaaccaa aatgtcaagt ccgttccgaa ggcattttcc actagttttt     4143
Leu
1325

ggactatgta aaccacattg tacttttttt tactttggca acaaatattt atacatacaa   4203

gatgctagtt catttgaata tttctccc                                      4231


<210> SEQ ID NO 12
<211> LENGTH: 1325
<212> TYPE: PRT
<213> ORGANISM: Homo sapiens

<400> SEQUENCE: 12

Met Leu Pro Val Tyr Gln Glu Val Lys Pro Asn Pro Leu Gln Asp Ala
1               5                   10                  15

Asn Ile Cys Ser Arg Val Phe Phe Trp Trp Leu Asn Pro Leu Phe Lys
            20                  25                  30

Ile Gly His Lys Arg Arg Leu Glu Glu Asp Asp Met Tyr Ser Val Leu
        35                  40                  45

Pro Glu Asp Arg Ser Gln His Leu Gly Glu Glu Leu Gln Gly Phe Trp
    50                  55                  60

Asp Lys Glu Val Leu Arg Ala Glu Asn Asp Ala Gln Lys Pro Ser Leu
65                  70                  75                  80

Thr Arg Ala Ile Ile Lys Cys Tyr Trp Lys Ser Tyr Leu Val Leu Gly
                85                  90                  95

Ile Phe Thr Leu Ile Glu Glu Ser Ala Lys Val Ile Gln Pro Ile Phe
            100                 105                 110

Leu Gly Lys Ile Ile Asn Tyr Phe Glu Asn Tyr Asp Pro Met Asp Ser
        115                 120                 125

Val Ala Leu Asn Thr Ala Tyr Ala Tyr Ala Thr Val Leu Thr Phe Cys
    130                 135                 140

Thr Leu Ile Leu Ala Ile Leu His His Leu Tyr Phe Tyr His Val Gln
145                 150                 155                 160

Cys Ala Gly Met Arg Leu Arg Val Ala Met Cys His Met Ile Tyr Arg
                165                 170                 175

Lys Ala Leu Arg Leu Ser Asn Met Ala Met Gly Lys Thr Thr Thr Gly
            180                 185                 190

Gln Ile Val Asn Leu Leu Ser Asn Asp Val Asn Lys Phe Asp Gln Val
        195                 200                 205
```

```
Thr Val Phe Leu His Phe Leu Trp Ala Gly Pro Leu Gln Ala Ile Ala
    210                 215                 220

Val Thr Ala Leu Leu Trp Met Glu Ile Gly Ile Ser Cys Leu Ala Gly
225                 230                 235                 240

Met Ala Val Leu Ile Ile Leu Leu Pro Leu Gln Ser Cys Phe Gly Lys
                245                 250                 255

Leu Phe Ser Ser Leu Arg Ser Lys Thr Ala Thr Phe Thr Asp Ala Arg
            260                 265                 270

Ile Arg Thr Met Asn Glu Val Ile Thr Gly Ile Arg Ile Ile Lys Met
        275                 280                 285

Tyr Ala Trp Glu Lys Ser Phe Ser Asn Leu Ile Thr Asn Leu Arg Lys
    290                 295                 300

Lys Glu Ile Ser Lys Ile Leu Arg Ser Ser Cys Leu Arg Gly Met Asn
305                 310                 315                 320

Leu Ala Ser Phe Phe Ser Ala Ser Lys Ile Ile Val Phe Val Thr Phe
                325                 330                 335

Thr Thr Tyr Val Leu Leu Gly Ser Val Ile Thr Ala Ser Arg Val Phe
            340                 345                 350

Val Ala Val Thr Leu Tyr Gly Ala Val Arg Leu Thr Val Thr Leu Phe
        355                 360                 365

Phe Pro Ser Ala Ile Glu Arg Val Ser Glu Ala Ile Val Ser Ile Arg
    370                 375                 380

Arg Ile Gln Thr Phe Leu Leu Leu Asp Glu Ile Ser Gln Arg Asn Arg
385                 390                 395                 400

Gln Leu Pro Ser Asp Gly Lys Lys Met Val His Val Gln Asp Phe Thr
                405                 410                 415

Ala Phe Trp Asp Lys Ala Ser Glu Thr Pro Thr Leu Gln Gly Leu Ser
            420                 425                 430

Phe Thr Val Arg Pro Gly Glu Leu Leu Ala Val Val Gly Pro Val Gly
        435                 440                 445

Ala Gly Lys Ser Ser Leu Leu Ser Ala Val Leu Gly Glu Leu Ala Pro
    450                 455                 460

Ser His Gly Leu Val Ser Val His Gly Arg Ile Ala Tyr Val Ser Gln
465                 470                 475                 480

Gln Pro Trp Val Phe Ser Gly Thr Leu Arg Ser Asn Ile Leu Phe Gly
                485                 490                 495

Lys Lys Tyr Glu Lys Glu Arg Tyr Glu Lys Val Ile Lys Ala Cys Ala
            500                 505                 510

Leu Lys Lys Asp Leu Gln Leu Leu Glu Asp Gly Asp Leu Thr Val Ile
        515                 520                 525

Gly Asp Arg Gly Thr Thr Leu Ser Gly Gly Gln Lys Ala Arg Val Asn
    530                 535                 540

Leu Ala Arg Ala Val Tyr Gln Asp Ala Asp Ile Tyr Leu Leu Asp Asp
545                 550                 555                 560

Pro Leu Ser Ala Val Asp Ala Glu Val Ser Arg His Leu Phe Glu Leu
                565                 570                 575

Cys Ile Cys Gln Ile Leu His Glu Lys Ile Thr Ile Leu Val Thr His
            580                 585                 590

Gln Leu Gln Tyr Leu Lys Ala Ala Ser Gln Ile Leu Ile Leu Lys Asp
        595                 600                 605

Gly Lys Met Val Gln Lys Gly Thr Tyr Thr Glu Phe Leu Lys Ser Gly
    610                 615                 620

Ile Asp Phe Gly Ser Leu Leu Lys Lys Asp Asn Glu Glu Ser Glu Gln
```

-continued

```
625                 630                 635                 640

Pro Pro Val Pro Gly Thr Pro Thr Leu Arg Asn Arg Thr Phe Ser Glu
                645                 650                 655

Ser Ser Val Trp Ser Gln Gln Ser Ser Arg Pro Ser Leu Lys Asp Gly
            660                 665                 670

Ala Leu Glu Ser Gln Asp Thr Glu Asn Val Pro Val Thr Leu Ser Glu
        675                 680                 685

Glu Asn Arg Ser Glu Gly Lys Val Gly Phe Gln Ala Tyr Lys Asn Tyr
    690                 695                 700

Phe Arg Ala Gly Ala His Trp Ile Val Phe Ile Phe Leu Ile Leu Leu
705                 710                 715                 720

Asn Thr Ala Ala Gln Val Ala Tyr Val Leu Gln Asp Trp Trp Leu Ser
                725                 730                 735

Tyr Trp Ala Asn Lys Gln Ser Met Leu Asn Val Thr Val Asn Gly Gly
            740                 745                 750

Gly Asn Val Thr Glu Lys Leu Asp Leu Asn Trp Tyr Leu Gly Ile Tyr
        755                 760                 765

Ser Gly Leu Thr Val Ala Thr Val Leu Phe Gly Ile Ala Arg Ser Leu
    770                 775                 780

Leu Val Phe Tyr Val Leu Val Asn Ser Ser Gln Thr Leu His Asn Lys
785                 790                 795                 800

Met Phe Glu Ser Ile Leu Lys Ala Pro Val Leu Phe Phe Asp Arg Asn
                805                 810                 815

Pro Ile Gly Arg Ile Leu Asn Arg Phe Ser Lys Asp Ile Gly His Leu
            820                 825                 830

Asp Asp Leu Leu Pro Leu Thr Phe Leu Asp Phe Ile Gln Thr Leu Leu
        835                 840                 845

Gln Val Val Gly Val Val Ser Val Ala Val Ala Val Ile Pro Trp Ile
    850                 855                 860

Ala Ile Pro Leu Val Pro Leu Gly Ile Ile Phe Ile Phe Leu Arg Arg
865                 870                 875                 880

Tyr Phe Leu Glu Thr Ser Arg Asp Val Lys Arg Leu Glu Ser Thr Thr
                885                 890                 895

Arg Ser Pro Val Phe Ser His Leu Ser Ser Ser Leu Gln Gly Leu Trp
            900                 905                 910

Thr Ile Arg Ala Tyr Lys Ala Glu Glu Arg Cys Gln Glu Leu Phe Asp
        915                 920                 925

Ala His Gln Asp Leu His Ser Glu Ala Trp Phe Leu Phe Leu Thr Thr
    930                 935                 940

Ser Arg Trp Phe Ala Val Arg Leu Asp Ala Ile Cys Ala Met Phe Val
945                 950                 955                 960

Ile Ile Val Ala Phe Gly Ser Leu Ile Leu Ala Lys Thr Leu Asp Ala
                965                 970                 975

Gly Gln Val Gly Leu Ala Leu Ser Tyr Ala Leu Thr Leu Met Gly Met
            980                 985                 990

Phe Gln Trp Cys Val Arg Gln Ser  Ala Glu Val Glu Asn  Met Met Ile
        995                 1000                1005

Ser Val  Glu Arg Val Ile Glu  Tyr Thr Asp Leu Glu  Lys Glu Ala
    1010                1015                1020

Pro Trp  Glu Tyr Gln Lys Arg  Pro Pro Pro Ala Trp  Pro His Glu
    1025                1030                1035

Gly Val  Ile Ile Phe Asp Asn  Val Asn Phe Met Tyr  Ser Pro Gly
    1040                1045                1050
```

```
Gly Pro  Leu Val Leu Lys His  Leu Thr Ala Leu Ile  Lys Ser Gln
    1055                 1060                 1065

Glu Lys  Val Gly Ile Val Gly  Arg Thr Gly Ala Gly  Lys Ser Ser
    1070                 1075                 1080

Leu Ile  Ser Ala Leu Phe Arg  Leu Ser Glu Pro Glu  Gly Lys Ile
    1085                 1090                 1095

Trp Ile  Asp Lys Ile Leu Thr  Thr Glu Ile Gly Leu  His Asp Leu
    1100                 1105                 1110

Arg Lys  Lys Met Ser Ile Ile  Pro Gln Glu Pro Val  Leu Phe Thr
    1115                 1120                 1125

Gly Thr  Met Arg Lys Asn Leu  Asp Pro Phe Lys Glu  His Thr Asp
    1130                 1135                 1140

Glu Glu  Leu Trp Asn Ala Leu  Gln Glu Val Gln Leu  Lys Glu Thr
    1145                 1150                 1155

Ile Glu  Asp Leu Pro Gly Lys  Met Asp Thr Glu Leu  Ala Glu Ser
    1160                 1165                 1170

Gly Ser  Asn Phe Ser Val Gly  Gln Arg Gln Leu Val  Cys Leu Ala
    1175                 1180                 1185

Arg Ala  Ile Leu Arg Lys Asn  Gln Ile Leu Ile Ile  Asp Glu Ala
    1190                 1195                 1200

Thr Ala  Asn Val Asp Pro Arg  Thr Asp Glu Leu Ile  Gln Lys Lys
    1205                 1210                 1215

Ile Arg  Glu Lys Phe Ala His  Cys Thr Val Leu Thr  Ile Ala His
    1220                 1225                 1230

Arg Leu  Asn Thr Ile Ile Asp  Ser Asp Lys Ile Met  Val Leu Asp
    1235                 1240                 1245

Ser Gly  Arg Leu Lys Glu Tyr  Asp Glu Pro Tyr Val  Leu Leu Gln
    1250                 1255                 1260

Asn Lys  Glu Ser Leu Phe Tyr  Lys Met Val Gln Gln  Leu Gly Lys
    1265                 1270                 1275

Ala Glu  Ala Ala Ala Leu Thr  Glu Thr Ala Lys Gln  Val Tyr Phe
    1280                 1285                 1290

Lys Arg  Asn Tyr Pro His Ile  Gly His Thr Asp His  Met Val Thr
    1295                 1300                 1305

Asn Thr  Ser Asn Gly Gln Pro  Ser Thr Leu Thr Ile  Phe Glu Thr
    1310                 1315                 1320

Ala Leu
    1325


<210> SEQ ID NO 13
<211> LENGTH: 2702
<212> TYPE: DNA
<213> ORGANISM: Homo sapiens
<220> FEATURE:
<221> NAME/KEY: CDS
<222> LOCATION: (25)..(2508)

<400> SEQUENCE: 13

cattctcccc caggctcact cacc atg acc aag ctg agc gcc caa gtc aaa        51
                           Met Thr Lys Leu Ser Ala Gln Val Lys
                           1               5

ggc tct ctc aac atc acc acc ccg ggg ctg cag ata tgg agg atc gag       99
Gly Ser Leu Asn Ile Thr Thr Pro Gly Leu Gln Ile Trp Arg Ile Glu
10                  15                  20                  25

gcc atg cag atg gtg cct gtt cct tcc agc acc ttt gga agc ttc ttc      147
Ala Met Gln Met Val Pro Val Pro Ser Ser Thr Phe Gly Ser Phe Phe
```

-continued

```
            30                  35                  40

gat ggt gac tgc tac atc atc ctg gct atc cac aag aca gcc agc agc      195
Asp Gly Asp Cys Tyr Ile Ile Leu Ala Ile His Lys Thr Ala Ser Ser
            45                  50                  55

ctg tcc tat gac atc cac tac tgg att ggc cag gac tca tcc ctg gat      243
Leu Ser Tyr Asp Ile His Tyr Trp Ile Gly Gln Asp Ser Ser Leu Asp
        60                  65                  70

gag cag ggg gca gct gcc atc tac acc aca cag atg gat gac ttc ctg      291
Glu Gln Gly Ala Ala Ala Ile Tyr Thr Thr Gln Met Asp Asp Phe Leu
    75                  80                  85

aag ggc cgg gct gtg cag cac cgc gag gtc cag ggc aac gag agc gag      339
Lys Gly Arg Ala Val Gln His Arg Glu Val Gln Gly Asn Glu Ser Glu
90                  95                  100                 105

gcc ttc cga ggc tac ttc aag caa ggc ctt gtg atc cgg aaa ggg ggc      387
Ala Phe Arg Gly Tyr Phe Lys Gln Gly Leu Val Ile Arg Lys Gly Gly
            110                 115                 120

gtg gct tct ggc atg aag cac gtg gag acc aac tcc tat gac gtc cag      435
Val Ala Ser Gly Met Lys His Val Glu Thr Asn Ser Tyr Asp Val Gln
            125                 130                 135

agg ctg ctg cat gtc aag ggc aag agg aac gtg gta gct gga gag gta      483
Arg Leu Leu His Val Lys Gly Lys Arg Asn Val Val Ala Gly Glu Val
        140                 145                 150

gag atg tcc tgg aag agt ttc aac cga ggg gat gtt ttc ctc ctg gac      531
Glu Met Ser Trp Lys Ser Phe Asn Arg Gly Asp Val Phe Leu Leu Asp
    155                 160                 165

ctt ggg aag ctt atc atc cag tgg aat gga ccg gaa agc acc cgt atg      579
Leu Gly Lys Leu Ile Ile Gln Trp Asn Gly Pro Glu Ser Thr Arg Met
170                 175                 180                 185

gag aga ctc agg ggc atg act ctg gcc aag gag atc cga gac cag gag      627
Glu Arg Leu Arg Gly Met Thr Leu Ala Lys Glu Ile Arg Asp Gln Glu
            190                 195                 200

cgg gga ggg cgc acc tat gta ggc gtg gtg gac gga gag aat gaa ttg      675
Arg Gly Gly Arg Thr Tyr Val Gly Val Val Asp Gly Glu Asn Glu Leu
            205                 210                 215

gca tcc ccg aag ctg atg gag gtg atg aac cac gtg ctg ggc aag cgc      723
Ala Ser Pro Lys Leu Met Glu Val Met Asn His Val Leu Gly Lys Arg
        220                 225                 230

agg gag ctg aag gcg gcc gtg ccc gac acg gtg gtg gag ccg gca ctc      771
Arg Glu Leu Lys Ala Ala Val Pro Asp Thr Val Val Glu Pro Ala Leu
    235                 240                 245

aag gct gca ctc aaa ctg tac cat gtg tct gac tcc gag ggg aat ctg      819
Lys Ala Ala Leu Lys Leu Tyr His Val Ser Asp Ser Glu Gly Asn Leu
250                 255                 260                 265

gtg gtg agg gaa gtc gcc aca cgg cca ctg aca cag gac ctg ctc agt      867
Val Val Arg Glu Val Ala Thr Arg Pro Leu Thr Gln Asp Leu Leu Ser
            270                 275                 280

cac gag gac tgt tac atc ctg gac cag ggg ggc ctg aag atc tac gtg      915
His Glu Asp Cys Tyr Ile Leu Asp Gln Gly Gly Leu Lys Ile Tyr Val
            285                 290                 295

tgg aaa ggg aag aaa gcc aat gag cag gag aag aag gga gcc atg agc      963
Trp Lys Gly Lys Lys Ala Asn Glu Gln Glu Lys Lys Gly Ala Met Ser
        300                 305                 310

cat gcg ctg aac ttc atc aaa gcc aag cag tac cca cca agc aca cag     1011
His Ala Leu Asn Phe Ile Lys Ala Lys Gln Tyr Pro Pro Ser Thr Gln
    315                 320                 325

gtg gag gtg cag aat gat ggg gct gag tcg gcc gtc ttt cag cag ctc     1059
Val Glu Val Gln Asn Asp Gly Ala Glu Ser Ala Val Phe Gln Gln Leu
330                 335                 340                 345

ttc cag aag tgg aca gcg tcc aac cgg acc tca ggc cta ggc aaa acc     1107
```

-continued

```
Phe Gln Lys Trp Thr Ala Ser Asn Arg Thr Ser Gly Leu Gly Lys Thr
                350                 355                 360

cac act gtg ggc tcc gtg gcc aaa gtg gaa cag gtg aag ttc gat gcc      1155
His Thr Val Gly Ser Val Ala Lys Val Glu Gln Val Lys Phe Asp Ala
            365                 370                 375

aca tcc atg cat gtc aag cct cag gtg gct gcc cag cag aag atg gta      1203
Thr Ser Met His Val Lys Pro Gln Val Ala Ala Gln Gln Lys Met Val
        380                 385                 390

gat gat ggg agt ggg gaa gtg cag gtg tgg cgc att gag aac cta gag      1251
Asp Asp Gly Ser Gly Glu Val Gln Val Trp Arg Ile Glu Asn Leu Glu
    395                 400                 405

ctg gta cct gtg gat tcc aag tgg cta ggc cac ttc tat ggg ggc gac      1299
Leu Val Pro Val Asp Ser Lys Trp Leu Gly His Phe Tyr Gly Gly Asp
410                 415                 420                 425

tgc tac ctg ctg ctc tac acc tac ctc atc ggc gag aag cag cat tac      1347
Cys Tyr Leu Leu Leu Tyr Thr Tyr Leu Ile Gly Glu Lys Gln His Tyr
                430                 435                 440

ctg ctc tac gtt tgg cag ggc agc cag gcc agc caa gat gaa att aca      1395
Leu Leu Tyr Val Trp Gln Gly Ser Gln Ala Ser Gln Asp Glu Ile Thr
            445                 450                 455

gca tca gct tat caa gcc gtc atc ctg gac cag aag tac aat ggt gaa      1443
Ala Ser Ala Tyr Gln Ala Val Ile Leu Asp Gln Lys Tyr Asn Gly Glu
        460                 465                 470

cca gtc cag atc cgg gtc cca atg ggc aag gag cca cct cat ctt atg      1491
Pro Val Gln Ile Arg Val Pro Met Gly Lys Glu Pro Pro His Leu Met
    475                 480                 485

tcc atc ttc aag gga cgc atg gtg gtc tac cag gga ggc acc tcc cga      1539
Ser Ile Phe Lys Gly Arg Met Val Val Tyr Gln Gly Gly Thr Ser Arg
490                 495                 500                 505

act aac aac ttg gag acc ggg ccc tcc aca cgg ctg ttc cag gtc cag      1587
Thr Asn Asn Leu Glu Thr Gly Pro Ser Thr Arg Leu Phe Gln Val Gln
                510                 515                 520

gga act ggc gcc aac aac acc aag gcc ttt gag gtc cca gcg cgg gcc      1635
Gly Thr Gly Ala Asn Asn Thr Lys Ala Phe Glu Val Pro Ala Arg Ala
            525                 530                 535

aat ttc ctc aat tcc aat gat gtc ttt gtc ctc aag acc cag tct tgc      1683
Asn Phe Leu Asn Ser Asn Asp Val Phe Val Leu Lys Thr Gln Ser Cys
        540                 545                 550

tgc tat cta tgg tgt ggg aag ggt tgt agc ggg gac gag cgg gag atg      1731
Cys Tyr Leu Trp Cys Gly Lys Gly Cys Ser Gly Asp Glu Arg Glu Met
    555                 560                 565

gcc aag atg gtt gct gac acc atc tcc cgg acg gag aag caa gtg gtg      1779
Ala Lys Met Val Ala Asp Thr Ile Ser Arg Thr Glu Lys Gln Val Val
570                 575                 580                 585

gtg gaa ggg cag gag cca gcc aac ttc tgg atg gcc ctg ggt ggg aag      1827
Val Glu Gly Gln Glu Pro Ala Asn Phe Trp Met Ala Leu Gly Gly Lys
                590                 595                 600

gcc ccc tat gcc aac acc aag aga cta cag gaa gaa aac ctg gtc atc      1875
Ala Pro Tyr Ala Asn Thr Lys Arg Leu Gln Glu Glu Asn Leu Val Ile
            605                 610                 615

acc ccc cgg ctc ttt gag tgt tcc aac aag act ggg cgc ttc ctg gcc      1923
Thr Pro Arg Leu Phe Glu Cys Ser Asn Lys Thr Gly Arg Phe Leu Ala
        620                 625                 630

aca gag atc cct gac ttc aat cag gat gac ttg gaa gag gat gat gtg      1971
Thr Glu Ile Pro Asp Phe Asn Gln Asp Asp Leu Glu Glu Asp Asp Val
    635                 640                 645

ttc cta cta gat gtc tgg gac cag gtc ttc ttc tgg att ggg aaa cat      2019
Phe Leu Leu Asp Val Trp Asp Gln Val Phe Phe Trp Ile Gly Lys His
650                 655                 660                 665
```

```
gcc aac gag gag gag aag aag gcc gca gca acc act gca cag gaa tac      2067
Ala Asn Glu Glu Glu Lys Lys Ala Ala Ala Thr Thr Ala Gln Glu Tyr
                670                 675                 680

ctc aag acc cat ccc agc ggg cgt gac cct gag acc ccc atc att gtg      2115
Leu Lys Thr His Pro Ser Gly Arg Asp Pro Glu Thr Pro Ile Ile Val
            685                 690                 695

gtg aag cag gga cac gag ccc ccc acc ttc aca ggc tgg ttc ctg gct      2163
Val Lys Gln Gly His Glu Pro Pro Thr Phe Thr Gly Trp Phe Leu Ala
        700                 705                 710

tgg gat ccc ttc aag tgg agt aac acc aaa tcc tat gag gac ctg aag      2211
Trp Asp Pro Phe Lys Trp Ser Asn Thr Lys Ser Tyr Glu Asp Leu Lys
    715                 720                 725

gcg gag tct ggc aac ctt agg gac tgg agc cag atc act gct gag gtc      2259
Ala Glu Ser Gly Asn Leu Arg Asp Trp Ser Gln Ile Thr Ala Glu Val
730                 735                 740                 745

aca agc ccc aaa gtg gac gtg ttc aat gct aac agc aac ctc agt tct      2307
Thr Ser Pro Lys Val Asp Val Phe Asn Ala Asn Ser Asn Leu Ser Ser
                750                 755                 760

ggg cct ctg ccc atc ttc ccc ctg gag cag cta gtg aac aag cct gta      2355
Gly Pro Leu Pro Ile Phe Pro Leu Glu Gln Leu Val Asn Lys Pro Val
            765                 770                 775

gag gag ctc ccc gag ggt gtg gac ccc agc agg aag gag gaa cac ctg      2403
Glu Glu Leu Pro Glu Gly Val Asp Pro Ser Arg Lys Glu Glu His Leu
        780                 785                 790

tcc att gaa gat ttc act cag gcc ttt ggg atg act cca gct gcc ttc      2451
Ser Ile Glu Asp Phe Thr Gln Ala Phe Gly Met Thr Pro Ala Ala Phe
    795                 800                 805

tct gct ctg cct cga tgg aag caa caa aac ctc aag aaa gaa aaa gga      2499
Ser Ala Leu Pro Arg Trp Lys Gln Gln Asn Leu Lys Lys Glu Lys Gly
810                 815                 820                 825

cta ttt tga gaagagtagc tgtggttgta aagcagtacc ctaccctgat              2548
Leu Phe

tgtagggtct cattttctca ccgatattag tcctacacca attgaagtga aattttgcag   2608

atgtgcctat gagcacaaac ttctgtggca aatgccagtt ttgtttaata atgtacctat   2668

tccttcagaa agatgatacc ccaaaaaaaa aaaa                                2702


<210> SEQ ID NO 14
<211> LENGTH: 827
<212> TYPE: PRT
<213> ORGANISM: Homo sapiens

<400> SEQUENCE: 14

Met Thr Lys Leu Ser Ala Gln Val Lys Gly Ser Leu Asn Ile Thr Thr
1               5                   10                  15

Pro Gly Leu Gln Ile Trp Arg Ile Glu Ala Met Gln Met Val Pro Val
            20                  25                  30

Pro Ser Ser Thr Phe Gly Ser Phe Phe Asp Gly Asp Cys Tyr Ile Ile
        35                  40                  45

Leu Ala Ile His Lys Thr Ala Ser Ser Leu Ser Tyr Asp Ile His Tyr
    50                  55                  60

Trp Ile Gly Gln Asp Ser Ser Leu Asp Glu Gln Gly Ala Ala Ala Ile
65                  70                  75                  80

Tyr Thr Thr Gln Met Asp Asp Phe Leu Lys Gly Arg Ala Val Gln His
                85                  90                  95

Arg Glu Val Gln Gly Asn Glu Ser Glu Ala Phe Arg Gly Tyr Phe Lys
            100                 105                 110

Gln Gly Leu Val Ile Arg Lys Gly Gly Val Ala Ser Gly Met Lys His
```

-continued

```
        115                 120                 125

Val Glu Thr Asn Ser Tyr Asp Val Gln Arg Leu Leu His Val Lys Gly
    130                 135                 140

Lys Arg Asn Val Val Ala Gly Glu Val Glu Met Ser Trp Lys Ser Phe
145                 150                 155                 160

Asn Arg Gly Asp Val Phe Leu Leu Asp Leu Gly Lys Leu Ile Ile Gln
                165                 170                 175

Trp Asn Gly Pro Glu Ser Thr Arg Met Glu Arg Leu Arg Gly Met Thr
            180                 185                 190

Leu Ala Lys Glu Ile Arg Asp Gln Glu Arg Gly Gly Arg Thr Tyr Val
        195                 200                 205

Gly Val Val Asp Gly Glu Asn Glu Leu Ala Ser Pro Lys Leu Met Glu
    210                 215                 220

Val Met Asn His Val Leu Gly Lys Arg Arg Glu Leu Lys Ala Ala Val
225                 230                 235                 240

Pro Asp Thr Val Val Glu Pro Ala Leu Lys Ala Ala Leu Lys Leu Tyr
                245                 250                 255

His Val Ser Asp Ser Glu Gly Asn Leu Val Val Arg Glu Val Ala Thr
            260                 265                 270

Arg Pro Leu Thr Gln Asp Leu Leu Ser His Glu Asp Cys Tyr Ile Leu
        275                 280                 285

Asp Gln Gly Gly Leu Lys Ile Tyr Val Trp Lys Gly Lys Lys Ala Asn
    290                 295                 300

Glu Gln Glu Lys Lys Gly Ala Met Ser His Ala Leu Asn Phe Ile Lys
305                 310                 315                 320

Ala Lys Gln Tyr Pro Pro Ser Thr Gln Val Glu Val Gln Asn Asp Gly
                325                 330                 335

Ala Glu Ser Ala Val Phe Gln Gln Leu Phe Gln Lys Trp Thr Ala Ser
            340                 345                 350

Asn Arg Thr Ser Gly Leu Gly Lys Thr His Thr Val Gly Ser Val Ala
        355                 360                 365

Lys Val Glu Gln Val Lys Phe Asp Ala Thr Ser Met His Val Lys Pro
    370                 375                 380

Gln Val Ala Ala Gln Gln Lys Met Val Asp Asp Gly Ser Gly Glu Val
385                 390                 395                 400

Gln Val Trp Arg Ile Glu Asn Leu Glu Leu Val Pro Val Asp Ser Lys
                405                 410                 415

Trp Leu Gly His Phe Tyr Gly Gly Asp Cys Tyr Leu Leu Leu Tyr Thr
            420                 425                 430

Tyr Leu Ile Gly Glu Lys Gln His Tyr Leu Leu Tyr Val Trp Gln Gly
        435                 440                 445

Ser Gln Ala Ser Gln Asp Glu Ile Thr Ala Ser Ala Tyr Gln Ala Val
    450                 455                 460

Ile Leu Asp Gln Lys Tyr Asn Gly Glu Pro Val Gln Ile Arg Val Pro
465                 470                 475                 480

Met Gly Lys Glu Pro Pro His Leu Met Ser Ile Phe Lys Gly Arg Met
                485                 490                 495

Val Val Tyr Gln Gly Gly Thr Ser Arg Thr Asn Asn Leu Glu Thr Gly
            500                 505                 510

Pro Ser Thr Arg Leu Phe Gln Val Gln Gly Thr Gly Ala Asn Asn Thr
        515                 520                 525

Lys Ala Phe Glu Val Pro Ala Arg Ala Asn Phe Leu Asn Ser Asn Asp
    530                 535                 540
```

```
Val Phe Val Leu Lys Thr Gln Ser Cys Cys Tyr Leu Trp Cys Gly Lys
545                 550                 555                 560

Gly Cys Ser Gly Asp Glu Arg Glu Met Ala Lys Met Val Ala Asp Thr
                565                 570                 575

Ile Ser Arg Thr Glu Lys Gln Val Val Val Glu Gly Gln Glu Pro Ala
            580                 585                 590

Asn Phe Trp Met Ala Leu Gly Gly Lys Ala Pro Tyr Ala Asn Thr Lys
        595                 600                 605

Arg Leu Gln Glu Glu Asn Leu Val Ile Thr Pro Arg Leu Phe Glu Cys
    610                 615                 620

Ser Asn Lys Thr Gly Arg Phe Leu Ala Thr Glu Ile Pro Asp Phe Asn
625                 630                 635                 640

Gln Asp Asp Leu Glu Glu Asp Asp Val Phe Leu Leu Asp Val Trp Asp
                645                 650                 655

Gln Val Phe Phe Trp Ile Gly Lys His Ala Asn Glu Glu Glu Lys Lys
            660                 665                 670

Ala Ala Ala Thr Thr Ala Gln Glu Tyr Leu Lys Thr His Pro Ser Gly
        675                 680                 685

Arg Asp Pro Glu Thr Pro Ile Ile Val Val Lys Gln Gly His Glu Pro
    690                 695                 700

Pro Thr Phe Thr Gly Trp Phe Leu Ala Trp Asp Pro Phe Lys Trp Ser
705                 710                 715                 720

Asn Thr Lys Ser Tyr Glu Asp Leu Lys Ala Glu Ser Gly Asn Leu Arg
                725                 730                 735

Asp Trp Ser Gln Ile Thr Ala Glu Val Thr Ser Pro Lys Val Asp Val
            740                 745                 750

Phe Asn Ala Asn Ser Asn Leu Ser Ser Gly Pro Leu Pro Ile Phe Pro
        755                 760                 765

Leu Glu Gln Leu Val Asn Lys Pro Val Glu Glu Leu Pro Glu Gly Val
    770                 775                 780

Asp Pro Ser Arg Lys Glu Glu His Leu Ser Ile Glu Asp Phe Thr Gln
785                 790                 795                 800

Ala Phe Gly Met Thr Pro Ala Ala Phe Ser Ala Leu Pro Arg Trp Lys
                805                 810                 815

Gln Gln Asn Leu Lys Lys Glu Lys Gly Leu Phe
            820                 825


<210> SEQ ID NO 15
<211> LENGTH: 2307
<212> TYPE: DNA
<213> ORGANISM: Homo sapiens
<220> FEATURE:
<221> NAME/KEY: CDS
<222> LOCATION: (123)..(2282)

<400> SEQUENCE: 15

agcgggggag gttcagtgtt gatggagtta ttgaagaaat gatggagtaa gagactcttt      60

tctaagcaac tcaagtttgc agtgattcag gcctacttct gaagagacag ccttttatct     120

ca atg aat gac aca gaa aaa cca gca gat act ccc tct gag gaa gag        167
   Met Asn Asp Thr Glu Lys Pro Ala Asp Thr Pro Ser Glu Glu Glu
   1               5                   10                  15

gac ttt ggt gat cca agg aca tat gac cca gat ttc aag ggg cct gtt       215
Asp Phe Gly Asp Pro Arg Thr Tyr Asp Pro Asp Phe Lys Gly Pro Val
                20                  25                  30

gcc aac agg agt tgt aca gat gtt ctg tgc tgt atg atc ttc cta ctg       263
```

-continued

```
Ala Asn Arg Ser Cys Thr Asp Val Leu Cys Cys Met Ile Phe Leu Leu
            35                  40                  45

tgt att att ggc tac att gtt tta gga ctt gtg gcc tgg gta cat ggg      311
Cys Ile Ile Gly Tyr Ile Val Leu Gly Leu Val Ala Trp Val His Gly
        50                  55                  60

gac ccc aga aga gca gcc tat cct aca gac agc cag ggc cac ttt tgt      359
Asp Pro Arg Arg Ala Ala Tyr Pro Thr Asp Ser Gln Gly His Phe Cys
    65                  70                  75

ggc cag aag ggc act ccc aat gag aac aag acc att ttg ttt tac ttt      407
Gly Gln Lys Gly Thr Pro Asn Glu Asn Lys Thr Ile Leu Phe Tyr Phe
80                  85                  90                  95

aac ctg tta cgc tgt acc agt ccc tcc gta ttg cta aac cta cag tgc      455
Asn Leu Leu Arg Cys Thr Ser Pro Ser Val Leu Leu Asn Leu Gln Cys
                100                 105                 110

cct acc aca cag atc tgt gtc tcc aag tgc cca gaa aaa ttt tta acc      503
Pro Thr Thr Gln Ile Cys Val Ser Lys Cys Pro Glu Lys Phe Leu Thr
            115                 120                 125

tat gtg gaa atg caa ctt ttg tac aca aaa gac aaa agc tac tgg gaa      551
Tyr Val Glu Met Gln Leu Leu Tyr Thr Lys Asp Lys Ser Tyr Trp Glu
        130                 135                 140

gac tac cgt cag ttc tgt aag acc act gct aag cct gtg aag tct ctc      599
Asp Tyr Arg Gln Phe Cys Lys Thr Thr Ala Lys Pro Val Lys Ser Leu
    145                 150                 155

aca cag ctt tta ctg gat gat gat tgt cca aca gcg att ttt ccc agc      647
Thr Gln Leu Leu Leu Asp Asp Asp Cys Pro Thr Ala Ile Phe Pro Ser
160                 165                 170                 175

aaa cct ttt ctc cag aga tgt ttc cct gac ttc tct acc aaa aat ggc      695
Lys Pro Phe Leu Gln Arg Cys Phe Pro Asp Phe Ser Thr Lys Asn Gly
                180                 185                 190

act tta aca ata gga agt aag atg atg ttt caa gat gga aat gga ggg      743
Thr Leu Thr Ile Gly Ser Lys Met Met Phe Gln Asp Gly Asn Gly Gly
            195                 200                 205

aca aga agt gtt gta gaa ctc ggg att gct gca aat ggt atc aat aaa      791
Thr Arg Ser Val Val Glu Leu Gly Ile Ala Ala Asn Gly Ile Asn Lys
        210                 215                 220

ctt ctt gat gca aag tca ctt gga ttg aaa gtg ttt gaa gac tat gca      839
Leu Leu Asp Ala Lys Ser Leu Gly Leu Lys Val Phe Glu Asp Tyr Ala
    225                 230                 235

aga act tgg tat tgg att ctc att ggc ctg acg att gcc atg gtc ctt      887
Arg Thr Trp Tyr Trp Ile Leu Ile Gly Leu Thr Ile Ala Met Val Leu
240                 245                 250                 255

agt tgg ata ttt ttg ata ctt ctg agg ttc ata gct gga tgc ctc ttc      935
Ser Trp Ile Phe Leu Ile Leu Leu Arg Phe Ile Ala Gly Cys Leu Phe
                260                 265                 270

tgg gtc ttc atg att ggt gtg att gga att ata ggt tat gga ata tgg      983
Trp Val Phe Met Ile Gly Val Ile Gly Ile Ile Gly Tyr Gly Ile Trp
            275                 280                 285

cac tgt tac cag cag tac acc aat ctt cag gaa cgc cca agt tct gta     1031
His Cys Tyr Gln Gln Tyr Thr Asn Leu Gln Glu Arg Pro Ser Ser Val
        290                 295                 300

tta act atc tat gac atc ggg att cag act aac ata agc atg tac ttt     1079
Leu Thr Ile Tyr Asp Ile Gly Ile Gln Thr Asn Ile Ser Met Tyr Phe
    305                 310                 315

gaa ctg caa caa aca tgg ttc aca ttt atg ata ata ctc tgc atc att     1127
Glu Leu Gln Gln Thr Trp Phe Thr Phe Met Ile Ile Leu Cys Ile Ile
320                 325                 330                 335

gaa gtg att gtc atc ctc atg ctg atc ttc ctc agg aat cga atc cga     1175
Glu Val Ile Val Ile Leu Met Leu Ile Phe Leu Arg Asn Arg Ile Arg
                340                 345                 350
```

-continued

```
gtc gcc att atc ctg ctg aag gaa gga agc aaa gcc att gga tat gtt      1223
Val Ala Ile Ile Leu Leu Lys Glu Gly Ser Lys Ala Ile Gly Tyr Val
            355                 360                 365

cct agt aca tta gtc tat cca gct tta act ttc att ttg ctc tca atc      1271
Pro Ser Thr Leu Val Tyr Pro Ala Leu Thr Phe Ile Leu Leu Ser Ile
        370                 375                 380

tgc att tgc tac tgg gtc gtg aca gca gtt ttc ttg gcg aca tcg ggg      1319
Cys Ile Cys Tyr Trp Val Val Thr Ala Val Phe Leu Ala Thr Ser Gly
    385                 390                 395

gta cct gta tac aaa gtc ata gct cca ggg ggg cat tgt ata cat gaa      1367
Val Pro Val Tyr Lys Val Ile Ala Pro Gly Gly His Cys Ile His Glu
400                 405                 410                 415

aat caa acc tgt gac cca gag att ttt aat aca act gaa att gcc aaa      1415
Asn Gln Thr Cys Asp Pro Glu Ile Phe Asn Thr Thr Glu Ile Ala Lys
                420                 425                 430

gct tgc cct ggg gct ctg tgt aac ttt gct ttc tat ggt gga aag agc      1463
Ala Cys Pro Gly Ala Leu Cys Asn Phe Ala Phe Tyr Gly Gly Lys Ser
            435                 440                 445

ttg tac cat cag tac atc cct acc ttc cat gta tac aac tta ttt gtc      1511
Leu Tyr His Gln Tyr Ile Pro Thr Phe His Val Tyr Asn Leu Phe Val
        450                 455                 460

ttt ctc tgg ctt ata aac ttc gtc att gca tta ggt cag tgc gcc ctt      1559
Phe Leu Trp Leu Ile Asn Phe Val Ile Ala Leu Gly Gln Cys Ala Leu
    465                 470                 475

gct ggt gca ttc gct act tat tac tgg gcc atg aaa aaa cct gat gac      1607
Ala Gly Ala Phe Ala Thr Tyr Tyr Trp Ala Met Lys Lys Pro Asp Asp
480                 485                 490                 495

atc cca cga tat cca ctt ttt act gca ttt gga cga gcc ata cga tat      1655
Ile Pro Arg Tyr Pro Leu Phe Thr Ala Phe Gly Arg Ala Ile Arg Tyr
                500                 505                 510

cac aca gga tcc cta gca ttt gga tct tta att att gca tta att caa      1703
His Thr Gly Ser Leu Ala Phe Gly Ser Leu Ile Ile Ala Leu Ile Gln
            515                 520                 525

atg ttt aaa att gta cta gaa tac ttg gac cac cgt ctt aaa cgt acc      1751
Met Phe Lys Ile Val Leu Glu Tyr Leu Asp His Arg Leu Lys Arg Thr
        530                 535                 540

cag aac aca ttg tct aaa ttc cta cag tgc tgc ctg aga tgc tgc ttc      1799
Gln Asn Thr Leu Ser Lys Phe Leu Gln Cys Cys Leu Arg Cys Cys Phe
    545                 550                 555

tgg tgt ttg gaa aat gca ata aag ttt tta aac aga aat gcc tat att      1847
Trp Cys Leu Glu Asn Ala Ile Lys Phe Leu Asn Arg Asn Ala Tyr Ile
560                 565                 570                 575

atg att gca ata tat ggc aga aac ttc tgc agg tca gca aaa gat gct      1895
Met Ile Ala Ile Tyr Gly Arg Asn Phe Cys Arg Ser Ala Lys Asp Ala
                580                 585                 590

ttc aat ctg ctg atg aga aat gtt ttg aaa gtt gca gtt aca gat gaa      1943
Phe Asn Leu Leu Met Arg Asn Val Leu Lys Val Ala Val Thr Asp Glu
            595                 600                 605

gtt aca tac ttt gta tta ttc ctg ggg aaa ctt cta gtt gct gga agt      1991
Val Thr Tyr Phe Val Leu Phe Leu Gly Lys Leu Leu Val Ala Gly Ser
        610                 615                 620

ata ggt gtt ctg gcc ttc cta ttc ttc aca caa aga ctg cca gtg att      2039
Ile Gly Val Leu Ala Phe Leu Phe Phe Thr Gln Arg Leu Pro Val Ile
    625                 630                 635

gca caa gga cca gca tct tta tat tac tac tgg gta cct ttg ctg aca      2087
Ala Gln Gly Pro Ala Ser Leu Tyr Tyr Tyr Trp Val Pro Leu Leu Thr
640                 645                 650                 655

gtc att ttt ggg tct tac ctg att gca cat ggg ttc ttc agc gtc tat      2135
Val Ile Phe Gly Ser Tyr Leu Ile Ala His Gly Phe Phe Ser Val Tyr
                660                 665                 670
```

```
gca atg tgt gtt gaa aca att ttc atc tgc ttc tgt gaa gat ctg gaa      2183
Ala Met Cys Val Glu Thr Ile Phe Ile Cys Phe Cys Glu Asp Leu Glu
            675                 680                 685

aga aat gat gga tcc aca gaa aaa ccc tac ttc gta acc cct aac ctg      2231
Arg Asn Asp Gly Ser Thr Glu Lys Pro Tyr Phe Val Thr Pro Asn Leu
        690                 695                 700

cat gga att ctg atc aag aag caa cta gtt ccc cag aag cag aaa gag      2279
His Gly Ile Leu Ile Lys Lys Gln Leu Val Pro Gln Lys Gln Lys Glu
    705                 710                 715

tag aaaagctcca aaaaaaaaaa aaaaa                                      2307


<210> SEQ ID NO 16
<211> LENGTH: 719
<212> TYPE: PRT
<213> ORGANISM: Homo sapiens

<400> SEQUENCE: 16

Met Asn Asp Thr Glu Lys Pro Ala Asp Thr Pro Ser Glu Glu Glu Asp
1               5                   10                  15

Phe Gly Asp Pro Arg Thr Tyr Asp Pro Asp Phe Lys Gly Pro Val Ala
            20                  25                  30

Asn Arg Ser Cys Thr Asp Val Leu Cys Cys Met Ile Phe Leu Leu Cys
        35                  40                  45

Ile Ile Gly Tyr Ile Val Leu Gly Leu Val Ala Trp Val His Gly Asp
    50                  55                  60

Pro Arg Arg Ala Ala Tyr Pro Thr Asp Ser Gln Gly His Phe Cys Gly
65                  70                  75                  80

Gln Lys Gly Thr Pro Asn Glu Asn Lys Thr Ile Leu Phe Tyr Phe Asn
                85                  90                  95

Leu Leu Arg Cys Thr Ser Pro Ser Val Leu Leu Asn Leu Gln Cys Pro
            100                 105                 110

Thr Thr Gln Ile Cys Val Ser Lys Cys Pro Glu Lys Phe Leu Thr Tyr
        115                 120                 125

Val Glu Met Gln Leu Leu Tyr Thr Lys Asp Lys Ser Tyr Trp Glu Asp
    130                 135                 140

Tyr Arg Gln Phe Cys Lys Thr Thr Ala Lys Pro Val Lys Ser Leu Thr
145                 150                 155                 160

Gln Leu Leu Leu Asp Asp Asp Cys Pro Thr Ala Ile Phe Pro Ser Lys
                165                 170                 175

Pro Phe Leu Gln Arg Cys Phe Pro Asp Phe Ser Thr Lys Asn Gly Thr
            180                 185                 190

Leu Thr Ile Gly Ser Lys Met Met Phe Gln Asp Gly Asn Gly Gly Thr
        195                 200                 205

Arg Ser Val Val Glu Leu Gly Ile Ala Ala Asn Gly Ile Asn Lys Leu
    210                 215                 220

Leu Asp Ala Lys Ser Leu Gly Leu Lys Val Phe Glu Asp Tyr Ala Arg
225                 230                 235                 240

Thr Trp Tyr Trp Ile Leu Ile Gly Leu Thr Ile Ala Met Val Leu Ser
                245                 250                 255

Trp Ile Phe Leu Ile Leu Leu Arg Phe Ile Ala Gly Cys Leu Phe Trp
            260                 265                 270

Val Phe Met Ile Gly Val Ile Gly Ile Ile Gly Tyr Gly Ile Trp His
        275                 280                 285

Cys Tyr Gln Gln Tyr Thr Asn Leu Gln Glu Arg Pro Ser Ser Val Leu
    290                 295                 300
```

Thr Ile Tyr Asp Ile Gly Ile Gln Thr Asn Ile Ser Met Tyr Phe Glu
305 310 315 320

Leu Gln Gln Thr Trp Phe Thr Phe Met Ile Ile Leu Cys Ile Ile Glu
325 330 335

Val Ile Val Ile Leu Met Leu Ile Phe Leu Arg Asn Arg Ile Arg Val
340 345 350

Ala Ile Ile Leu Leu Lys Glu Gly Ser Lys Ala Ile Gly Tyr Val Pro
355 360 365

Ser Thr Leu Val Tyr Pro Ala Leu Thr Phe Ile Leu Leu Ser Ile Cys
370 375 380

Ile Cys Tyr Trp Val Val Thr Ala Val Phe Leu Ala Thr Ser Gly Val
385 390 395 400

Pro Val Tyr Lys Val Ile Ala Pro Gly Gly His Cys Ile His Glu Asn
405 410 415

Gln Thr Cys Asp Pro Glu Ile Phe Asn Thr Thr Glu Ile Ala Lys Ala
420 425 430

Cys Pro Gly Ala Leu Cys Asn Phe Ala Phe Tyr Gly Gly Lys Ser Leu
435 440 445

Tyr His Gln Tyr Ile Pro Thr Phe His Val Tyr Asn Leu Phe Val Phe
450 455 460

Leu Trp Leu Ile Asn Phe Val Ile Ala Leu Gly Gln Cys Ala Leu Ala
465 470 475 480

Gly Ala Phe Ala Thr Tyr Tyr Trp Ala Met Lys Lys Pro Asp Asp Ile
485 490 495

Pro Arg Tyr Pro Leu Phe Thr Ala Phe Gly Arg Ala Ile Arg Tyr His
500 505 510

Thr Gly Ser Leu Ala Phe Gly Ser Leu Ile Ile Ala Leu Ile Gln Met
515 520 525

Phe Lys Ile Val Leu Glu Tyr Leu Asp His Arg Leu Lys Arg Thr Gln
530 535 540

Asn Thr Leu Ser Lys Phe Leu Gln Cys Cys Leu Arg Cys Cys Phe Trp
545 550 555 560

Cys Leu Glu Asn Ala Ile Lys Phe Leu Asn Arg Asn Ala Tyr Ile Met
565 570 575

Ile Ala Ile Tyr Gly Arg Asn Phe Cys Arg Ser Ala Lys Asp Ala Phe
580 585 590

Asn Leu Leu Met Arg Asn Val Leu Lys Val Ala Val Thr Asp Glu Val
595 600 605

Thr Tyr Phe Val Leu Phe Leu Gly Lys Leu Leu Val Ala Gly Ser Ile
610 615 620

Gly Val Leu Ala Phe Leu Phe Phe Thr Gln Arg Leu Pro Val Ile Ala
625 630 635 640

Gln Gly Pro Ala Ser Leu Tyr Tyr Tyr Trp Val Pro Leu Leu Thr Val
645 650 655

Ile Phe Gly Ser Tyr Leu Ile Ala His Gly Phe Phe Ser Val Tyr Ala
660 665 670

Met Cys Val Glu Thr Ile Phe Ile Cys Phe Cys Glu Asp Leu Glu Arg
675 680 685

Asn Asp Gly Ser Thr Glu Lys Pro Tyr Phe Val Thr Pro Asn Leu His
690 695 700

Gly Ile Leu Ile Lys Lys Gln Leu Val Pro Gln Lys Gln Lys Glu
705 710 715

<210> SEQ ID NO 17
<211> LENGTH: 3696
<212> TYPE: DNA
<213> ORGANISM: Homo sapiens
<220> FEATURE:
<221> NAME/KEY: CDS
<222> LOCATION: (41)..(3100)

<400> SEQUENCE: 17

```
accagacagt tcttaaatta gcaagccttc aaaaccaaaa atg ggg tcg aaa aga       55
                                            Met Gly Ser Lys Arg
                                            1               5

ggc ata tct tct agg cat cat tct ctc agc tcc tat gaa atc atg ttt      103
Gly Ile Ser Ser Arg His His Ser Leu Ser Ser Tyr Glu Ile Met Phe
                10                  15                  20

gca gct ctc ttt gcc ata ttg gta gtg ctc tgt gct gga tta att gca      151
Ala Ala Leu Phe Ala Ile Leu Val Val Leu Cys Ala Gly Leu Ile Ala
            25                  30                  35

gta tcc tgc ctg aca atc aag gaa tcc caa cga ggt gca gca ctt gga      199
Val Ser Cys Leu Thr Ile Lys Glu Ser Gln Arg Gly Ala Ala Leu Gly
        40                  45                  50

cag agt cat gaa gcc aga gcg aca ttt aaa ata aca tcc gga gtt aca      247
Gln Ser His Glu Ala Arg Ala Thr Phe Lys Ile Thr Ser Gly Val Thr
    55                  60                  65

tat aat cct aat ttg caa gac aaa ctc tca gtg gat ttc aaa gtt ctt      295
Tyr Asn Pro Asn Leu Gln Asp Lys Leu Ser Val Asp Phe Lys Val Leu
70                  75                  80                  85

gct ttt gac ctt cag caa atg ata gat gag atc ttt cta tca agc aat      343
Ala Phe Asp Leu Gln Gln Met Ile Asp Glu Ile Phe Leu Ser Ser Asn
                90                  95                  100

ctg aag aat gaa tat aag aac tca aga gtt tta caa ttt gaa aat ggc      391
Leu Lys Asn Glu Tyr Lys Asn Ser Arg Val Leu Gln Phe Glu Asn Gly
            105                 110                 115

agc att ata gtc gta ttt gac ctt ttc ttt gcc cag tgg gtg tca gat      439
Ser Ile Ile Val Val Phe Asp Leu Phe Phe Ala Gln Trp Val Ser Asp
        120                 125                 130

caa aat gta aaa gaa gaa ctg att caa ggc ctt gaa gca aat aaa tcc      487
Gln Asn Val Lys Glu Glu Leu Ile Gln Gly Leu Glu Ala Asn Lys Ser
    135                 140                 145

agc caa ctg gtc act ttc cat att gat ttg aac agc gtt gat atc cta      535
Ser Gln Leu Val Thr Phe His Ile Asp Leu Asn Ser Val Asp Ile Leu
150                 155                 160                 165

gac aag cta aca acc acc agt cat ctg gca act cca gga aat gtc tca      583
Asp Lys Leu Thr Thr Thr Ser His Leu Ala Thr Pro Gly Asn Val Ser
                170                 175                 180

ata gag tgc ctg cct ggt tca agt cct tgt act gat gct cta acg tgt      631
Ile Glu Cys Leu Pro Gly Ser Ser Pro Cys Thr Asp Ala Leu Thr Cys
            185                 190                 195

ata aaa gct gat tta ttt tgt gat gga gaa gta aac tgt cca gat ggt      679
Ile Lys Ala Asp Leu Phe Cys Asp Gly Glu Val Asn Cys Pro Asp Gly
        200                 205                 210

tct gac gaa gac aat aaa atg tgt gcc aca gtt tgt gat gga aga ttt      727
Ser Asp Glu Asp Asn Lys Met Cys Ala Thr Val Cys Asp Gly Arg Phe
    215                 220                 225

ttg tta act gga tca tct ggg tct ttc cag gct act cat tat cca aaa      775
Leu Leu Thr Gly Ser Ser Gly Ser Phe Gln Ala Thr His Tyr Pro Lys
230                 235                 240                 245

cct tct gaa aca agt gtt gtc tgc cag tgg atc ata cgt gta aac caa      823
Pro Ser Glu Thr Ser Val Val Cys Gln Trp Ile Ile Arg Val Asn Gln
                250                 255                 260
```

-continued

```
gga ctt tcc att aaa ctg agc ttc gat gat ttt aat aca tat tat aca      871
Gly Leu Ser Ile Lys Leu Ser Phe Asp Asp Phe Asn Thr Tyr Tyr Thr
            265                 270                 275

gat ata tta gat att tat gaa ggt gta gga tca agc aag att tta aga      919
Asp Ile Leu Asp Ile Tyr Glu Gly Val Gly Ser Ser Lys Ile Leu Arg
        280                 285                 290

gct tct att tgg gaa act aat cct ggc aca ata aga att ttt tcc aac      967
Ala Ser Ile Trp Glu Thr Asn Pro Gly Thr Ile Arg Ile Phe Ser Asn
    295                 300                 305

caa gtt act gcc acc ttt ctt ata gaa tct gat gaa agt gat tat gtt     1015
Gln Val Thr Ala Thr Phe Leu Ile Glu Ser Asp Glu Ser Asp Tyr Val
310                 315                 320                 325

ggc ttt aat gca aca tat act gca ttt aac agc agt gag ctt aat aat     1063
Gly Phe Asn Ala Thr Tyr Thr Ala Phe Asn Ser Ser Glu Leu Asn Asn
                330                 335                 340

tat gag aaa att aat tgt aac ttt gag gat ggc ttt tgt ttc tgg gtc     1111
Tyr Glu Lys Ile Asn Cys Asn Phe Glu Asp Gly Phe Cys Phe Trp Val
            345                 350                 355

cag gat cta aat gat gat aat gaa tgg gaa agg att cag gga agc acc     1159
Gln Asp Leu Asn Asp Asp Asn Glu Trp Glu Arg Ile Gln Gly Ser Thr
        360                 365                 370

ttt tct cct ttt act gga ccc aat ttt gac cac act ttt ggc aat gct     1207
Phe Ser Pro Phe Thr Gly Pro Asn Phe Asp His Thr Phe Gly Asn Ala
    375                 380                 385

tca gga ttt tac att tct acc cca act gga cca gga ggg aga caa gaa     1255
Ser Gly Phe Tyr Ile Ser Thr Pro Thr Gly Pro Gly Gly Arg Gln Glu
390                 395                 400                 405

cga gtg ggg ctt tta agc ctc cct ttg gac ccc act ttg gag cca gct     1303
Arg Val Gly Leu Leu Ser Leu Pro Leu Asp Pro Thr Leu Glu Pro Ala
                410                 415                 420

tgc ctt agt ttc tgg tat cat atg tat ggt gaa aat gtc cat aaa tta     1351
Cys Leu Ser Phe Trp Tyr His Met Tyr Gly Glu Asn Val His Lys Leu
            425                 430                 435

agc att aat atc agc aat gac caa aat atg gag aag aca gtt ttc caa     1399
Ser Ile Asn Ile Ser Asn Asp Gln Asn Met Glu Lys Thr Val Phe Gln
        440                 445                 450

aag gaa gga aat tat gga gac aat tgg aat tat gga caa gta acc cta     1447
Lys Glu Gly Asn Tyr Gly Asp Asn Trp Asn Tyr Gly Gln Val Thr Leu
    455                 460                 465

aat gaa aca gtt aaa ttt aag gtt gct ttt aat gct ttt aaa aac aag     1495
Asn Glu Thr Val Lys Phe Lys Val Ala Phe Asn Ala Phe Lys Asn Lys
470                 475                 480                 485

atc ctg agt gat att gcg ttg gat gac att agc cta aca tat ggg att     1543
Ile Leu Ser Asp Ile Ala Leu Asp Asp Ile Ser Leu Thr Tyr Gly Ile
                490                 495                 500

tgc aat ggg agt ctt tat cca gaa cca act ttg gtg cca act cct cca     1591
Cys Asn Gly Ser Leu Tyr Pro Glu Pro Thr Leu Val Pro Thr Pro Pro
            505                 510                 515

cca gaa ctt cct acg gac tgt gga gga cct ttt gag ctg tgg gag cca     1639
Pro Glu Leu Pro Thr Asp Cys Gly Gly Pro Phe Glu Leu Trp Glu Pro
        520                 525                 530

aat aca aca ttc agt tct acg aac ttt cca aac agc tac cct aat ctg     1687
Asn Thr Thr Phe Ser Ser Thr Asn Phe Pro Asn Ser Tyr Pro Asn Leu
    535                 540                 545

gct ttc tgt gtt tgg att tta aat gca caa aaa gga aag aat ata caa     1735
Ala Phe Cys Val Trp Ile Leu Asn Ala Gln Lys Gly Lys Asn Ile Gln
550                 555                 560                 565

ctt cat ttt caa gaa ttt gac tta gaa aat att aac gat gta gtt gaa     1783
Leu His Phe Gln Glu Phe Asp Leu Glu Asn Ile Asn Asp Val Val Glu
                570                 575                 580
```

```
ata aga gat ggt gaa gaa gct gat tcc ttg ctc tta gct gtg tac aca      1831
Ile Arg Asp Gly Glu Glu Ala Asp Ser Leu Leu Leu Ala Val Tyr Thr
            585                 590                 595

ggg cct ggc cca gta aag gat gtg ttc tct acc acc aac aga atg act      1879
Gly Pro Gly Pro Val Lys Asp Val Phe Ser Thr Thr Asn Arg Met Thr
        600                 605                 610

gtg ctt ctc atc act aac gat gtg ttg gca aga gga ggg ttt aaa gca      1927
Val Leu Leu Ile Thr Asn Asp Val Leu Ala Arg Gly Gly Phe Lys Ala
    615                 620                 625

aac ttt act act ggc tat cac ttg ggg att cca gag cca tgc aag gca      1975
Asn Phe Thr Thr Gly Tyr His Leu Gly Ile Pro Glu Pro Cys Lys Ala
630                 635                 640                 645

gac cat ttt caa tgt aaa aat gga gag tgt gtt cca ctg gtg aat ctc      2023
Asp His Phe Gln Cys Lys Asn Gly Glu Cys Val Pro Leu Val Asn Leu
                650                 655                 660

tgt gac ggt cat ctg cac tgt gag gat ggc tca gat gaa gca gat tgt      2071
Cys Asp Gly His Leu His Cys Glu Asp Gly Ser Asp Glu Ala Asp Cys
            665                 670                 675

gtg cgt ttt ttc aat ggc aca acg aac aac aat ggt tta gtg cgg ttc      2119
Val Arg Phe Phe Asn Gly Thr Thr Asn Asn Asn Gly Leu Val Arg Phe
        680                 685                 690

aga atc cag agc ata tgg cat aca gct tgt gct gag aac tgg acc acc      2167
Arg Ile Gln Ser Ile Trp His Thr Ala Cys Ala Glu Asn Trp Thr Thr
    695                 700                 705

cag att tca aat gat gtt tgt caa ctg ctg gga cta ggg agt gga aac      2215
Gln Ile Ser Asn Asp Val Cys Gln Leu Leu Gly Leu Gly Ser Gly Asn
710                 715                 720                 725

tca tca aag cca atc ttc tct acc gat ggt gga cca ttt gtc aaa tta      2263
Ser Ser Lys Pro Ile Phe Ser Thr Asp Gly Gly Pro Phe Val Lys Leu
                730                 735                 740

aac aca gca cct gat ggc cac tta ata cta aca ccc agt caa cag tgt      2311
Asn Thr Ala Pro Asp Gly His Leu Ile Leu Thr Pro Ser Gln Gln Cys
            745                 750                 755

tta cag gat tcc ttg att cgg tta cag tgt aac cat aaa tct tgt gga      2359
Leu Gln Asp Ser Leu Ile Arg Leu Gln Cys Asn His Lys Ser Cys Gly
        760                 765                 770

aaa aaa ctg gca gct caa gac atc acc cca aag att gtt gga gga agt      2407
Lys Lys Leu Ala Ala Gln Asp Ile Thr Pro Lys Ile Val Gly Gly Ser
    775                 780                 785

aat gcc aaa gaa ggg gcc tgg ccc tgg gtt gtg ggt ctg tat tat ggc      2455
Asn Ala Lys Glu Gly Ala Trp Pro Trp Val Val Gly Leu Tyr Tyr Gly
790                 795                 800                 805

ggc cga ctg ctc tgc ggc gca tct ctc gtc agc agt gac tgg ctg gtg      2503
Gly Arg Leu Leu Cys Gly Ala Ser Leu Val Ser Ser Asp Trp Leu Val
                810                 815                 820

tcc gcc gca cac tgc gtg tat ggg aga aac tta gag cca tcc aag tgg      2551
Ser Ala Ala His Cys Val Tyr Gly Arg Asn Leu Glu Pro Ser Lys Trp
            825                 830                 835

aca gca atc cta ggc ctg cat atg aaa tca aat ctg acc tct cct caa      2599
Thr Ala Ile Leu Gly Leu His Met Lys Ser Asn Leu Thr Ser Pro Gln
        840                 845                 850

aca gtc cct cga tta ata gat gaa att gtc ata aac cct cat tac aat      2647
Thr Val Pro Arg Leu Ile Asp Glu Ile Val Ile Asn Pro His Tyr Asn
    855                 860                 865

agg cga aga aag gac aac gac att gcc atg atg cat ctg gaa ttt aaa      2695
Arg Arg Arg Lys Asp Asn Asp Ile Ala Met Met His Leu Glu Phe Lys
870                 875                 880                 885

gtg aat tac aca gat tac ata caa cct att tgt tta ccg gaa gaa aat      2743
Val Asn Tyr Thr Asp Tyr Ile Gln Pro Ile Cys Leu Pro Glu Glu Asn
```

```
                890                 895                 900

caa gtt ttt cct cca gga aga aat tgt tct att gct ggt tgg ggg acg     2791
Gln Val Phe Pro Pro Gly Arg Asn Cys Ser Ile Ala Gly Trp Gly Thr
            905                 910                 915

gtt gta tat caa ggt act act gca aac ata ttg caa gaa gct gat gtt     2839
Val Val Tyr Gln Gly Thr Thr Ala Asn Ile Leu Gln Glu Ala Asp Val
        920                 925                 930

cct ctt cta tca aat gag aga tgc caa cag cag atg cca gaa tat aac     2887
Pro Leu Leu Ser Asn Glu Arg Cys Gln Gln Gln Met Pro Glu Tyr Asn
    935                 940                 945

att act gaa aat atg ata tgt gca ggc tat gaa gaa gga gga ata gat     2935
Ile Thr Glu Asn Met Ile Cys Ala Gly Tyr Glu Glu Gly Gly Ile Asp
950                 955                 960                 965

tct tgt cag ggg gat tca gga gga cca tta atg tgc caa gaa aac aac     2983
Ser Cys Gln Gly Asp Ser Gly Gly Pro Leu Met Cys Gln Glu Asn Asn
                970                 975                 980

agg tgg ttc ctt gct ggt gtg acc tca ttt gga tac aag tgt gcc ctg     3031
Arg Trp Phe Leu Ala Gly Val Thr Ser Phe Gly Tyr Lys Cys Ala Leu
            985                 990                 995

cct aat cgc  ccc gga gtg tat gcc  agg gtc tca agg ttt  acc gaa      3076
Pro Asn Arg  Pro Gly Val Tyr Ala  Arg Val Ser Arg Phe  Thr Glu
        1000                1005                1010

tgg ata caa  agt ttt cta cat tag cgcatttctt aaactaaaca ggaaagtcgc   3130
Trp Ile Gln  Ser Phe Leu His
        1015

attattttcc cattctactc tagaaagcat ggaaattaag tgtttcgtac aaaaatttta   3190

aaaagttacc aaaggttttt attcttacct atgtcaatga aatgctaggg ggccagggaa   3250

acaaaatttt aaaaataata aaattcacca tagcaataca gaataacttt aaaataccat   3310

taaatacatt tgtatttcat tgtgaacagg tatttcttca cagatctcat ttttaaaatt   3370

cttaatgatt atttttatta cttactgttg tttaaaggga tgttatttta aagcatatac   3430

catacactta agaaatttga gcagaattta aaaaagaaag aaaataaatt gtttttccca   3490

aagtatgtca ctgttggaaa taaactgcca taaattttct agttccagtt tagtttgctg   3550

ctattagcag aaactcaatt gtttctctgt cttttctatc aaaattttca acatatgcat   3610

aaccttagta ttttcccaac caatagaaac tatttattgt aagcttatgt cacaggcctg   3670

gactaaattg attttacgtt cctctt                                        3696


<210> SEQ ID NO 18
<211> LENGTH: 1019
<212> TYPE: PRT
<213> ORGANISM: Homo sapiens

<400> SEQUENCE: 18

Met Gly Ser Lys Arg Gly Ile Ser Ser Arg His His Ser Leu Ser Ser
1               5                   10                  15

Tyr Glu Ile Met Phe Ala Ala Leu Phe Ala Ile Leu Val Val Leu Cys
            20                  25                  30

Ala Gly Leu Ile Ala Val Ser Cys Leu Thr Ile Lys Glu Ser Gln Arg
        35                  40                  45

Gly Ala Ala Leu Gly Gln Ser His Glu Ala Arg Ala Thr Phe Lys Ile
    50                  55                  60

Thr Ser Gly Val Thr Tyr Asn Pro Asn Leu Gln Asp Lys Leu Ser Val
65                  70                  75                  80

Asp Phe Lys Val Leu Ala Phe Asp Leu Gln Gln Met Ile Asp Glu Ile
                85                  90                  95
```

-continued

```
Phe Leu Ser Ser Asn Leu Lys Asn Glu Tyr Lys Asn Ser Arg Val Leu
            100                 105                 110

Gln Phe Glu Asn Gly Ser Ile Ile Val Val Phe Asp Leu Phe Phe Ala
        115                 120                 125

Gln Trp Val Ser Asp Gln Asn Val Lys Glu Glu Leu Ile Gln Gly Leu
    130                 135                 140

Glu Ala Asn Lys Ser Ser Gln Leu Val Thr Phe His Ile Asp Leu Asn
145                 150                 155                 160

Ser Val Asp Ile Leu Asp Lys Leu Thr Thr Thr Ser His Leu Ala Thr
                165                 170                 175

Pro Gly Asn Val Ser Ile Glu Cys Leu Pro Gly Ser Ser Pro Cys Thr
            180                 185                 190

Asp Ala Leu Thr Cys Ile Lys Ala Asp Leu Phe Cys Asp Gly Glu Val
        195                 200                 205

Asn Cys Pro Asp Gly Ser Asp Glu Asp Asn Lys Met Cys Ala Thr Val
    210                 215                 220

Cys Asp Gly Arg Phe Leu Leu Thr Gly Ser Ser Gly Ser Phe Gln Ala
225                 230                 235                 240

Thr His Tyr Pro Lys Pro Ser Glu Thr Ser Val Val Cys Gln Trp Ile
                245                 250                 255

Ile Arg Val Asn Gln Gly Leu Ser Ile Lys Leu Ser Phe Asp Asp Phe
            260                 265                 270

Asn Thr Tyr Tyr Thr Asp Ile Leu Asp Ile Tyr Glu Gly Val Gly Ser
        275                 280                 285

Ser Lys Ile Leu Arg Ala Ser Ile Trp Glu Thr Asn Pro Gly Thr Ile
    290                 295                 300

Arg Ile Phe Ser Asn Gln Val Thr Ala Thr Phe Leu Ile Glu Ser Asp
305                 310                 315                 320

Glu Ser Asp Tyr Val Gly Phe Asn Ala Thr Tyr Thr Ala Phe Asn Ser
                325                 330                 335

Ser Glu Leu Asn Asn Tyr Glu Lys Ile Asn Cys Asn Phe Glu Asp Gly
            340                 345                 350

Phe Cys Phe Trp Val Gln Asp Leu Asn Asp Asp Asn Glu Trp Glu Arg
        355                 360                 365

Ile Gln Gly Ser Thr Phe Ser Pro Phe Thr Gly Pro Asn Phe Asp His
    370                 375                 380

Thr Phe Gly Asn Ala Ser Gly Phe Tyr Ile Ser Thr Pro Thr Gly Pro
385                 390                 395                 400

Gly Gly Arg Gln Glu Arg Val Gly Leu Leu Ser Leu Pro Leu Asp Pro
                405                 410                 415

Thr Leu Glu Pro Ala Cys Leu Ser Phe Trp Tyr His Met Tyr Gly Glu
            420                 425                 430

Asn Val His Lys Leu Ser Ile Asn Ile Ser Asn Asp Gln Asn Met Glu
        435                 440                 445

Lys Thr Val Phe Gln Lys Glu Gly Asn Tyr Gly Asp Asn Trp Asn Tyr
    450                 455                 460

Gly Gln Val Thr Leu Asn Glu Thr Val Lys Phe Lys Val Ala Phe Asn
465                 470                 475                 480

Ala Phe Lys Asn Lys Ile Leu Ser Asp Ile Ala Leu Asp Asp Ile Ser
                485                 490                 495

Leu Thr Tyr Gly Ile Cys Asn Gly Ser Leu Tyr Pro Glu Pro Thr Leu
            500                 505                 510
```

-continued

```
Val Pro Thr Pro Pro Pro Glu Leu Pro Thr Asp Cys Gly Gly Pro Phe
        515                 520                 525

Glu Leu Trp Glu Pro Asn Thr Thr Phe Ser Ser Thr Asn Phe Pro Asn
    530                 535                 540

Ser Tyr Pro Asn Leu Ala Phe Cys Val Trp Ile Leu Asn Ala Gln Lys
545                 550                 555                 560

Gly Lys Asn Ile Gln Leu His Phe Gln Glu Phe Asp Leu Glu Asn Ile
                565                 570                 575

Asn Asp Val Val Glu Ile Arg Asp Gly Glu Glu Ala Asp Ser Leu Leu
            580                 585                 590

Leu Ala Val Tyr Thr Gly Pro Gly Pro Val Lys Asp Val Phe Ser Thr
        595                 600                 605

Thr Asn Arg Met Thr Val Leu Leu Ile Thr Asn Asp Val Leu Ala Arg
    610                 615                 620

Gly Gly Phe Lys Ala Asn Phe Thr Thr Gly Tyr His Leu Gly Ile Pro
625                 630                 635                 640

Glu Pro Cys Lys Ala Asp His Phe Gln Cys Lys Asn Gly Glu Cys Val
                645                 650                 655

Pro Leu Val Asn Leu Cys Asp Gly His Leu His Cys Glu Asp Gly Ser
            660                 665                 670

Asp Glu Ala Asp Cys Val Arg Phe Phe Asn Gly Thr Thr Asn Asn Asn
        675                 680                 685

Gly Leu Val Arg Phe Arg Ile Gln Ser Ile Trp His Thr Ala Cys Ala
    690                 695                 700

Glu Asn Trp Thr Thr Gln Ile Ser Asn Asp Val Cys Gln Leu Leu Gly
705                 710                 715                 720

Leu Gly Ser Gly Asn Ser Ser Lys Pro Ile Phe Ser Thr Asp Gly Gly
                725                 730                 735

Pro Phe Val Lys Leu Asn Thr Ala Pro Asp Gly His Leu Ile Leu Thr
            740                 745                 750

Pro Ser Gln Gln Cys Leu Gln Asp Ser Leu Ile Arg Leu Gln Cys Asn
        755                 760                 765

His Lys Ser Cys Gly Lys Lys Leu Ala Ala Gln Asp Ile Thr Pro Lys
    770                 775                 780

Ile Val Gly Gly Ser Asn Ala Lys Glu Gly Ala Trp Pro Trp Val Val
785                 790                 795                 800

Gly Leu Tyr Tyr Gly Gly Arg Leu Leu Cys Gly Ala Ser Leu Val Ser
                805                 810                 815

Ser Asp Trp Leu Val Ser Ala Ala His Cys Val Tyr Gly Arg Asn Leu
            820                 825                 830

Glu Pro Ser Lys Trp Thr Ala Ile Leu Gly Leu His Met Lys Ser Asn
        835                 840                 845

Leu Thr Ser Pro Gln Thr Val Pro Arg Leu Ile Asp Glu Ile Val Ile
    850                 855                 860

Asn Pro His Tyr Asn Arg Arg Arg Lys Asp Asn Asp Ile Ala Met Met
865                 870                 875                 880

His Leu Glu Phe Lys Val Asn Tyr Thr Asp Tyr Ile Gln Pro Ile Cys
                885                 890                 895

Leu Pro Glu Glu Asn Gln Val Phe Pro Pro Gly Arg Asn Cys Ser Ile
            900                 905                 910

Ala Gly Trp Gly Thr Val Val Tyr Gln Gly Thr Thr Ala Asn Ile Leu
        915                 920                 925

Gln Glu Ala Asp Val Pro Leu Leu Ser Asn Glu Arg Cys Gln Gln Gln
```

```
    930                 935                 940

Met Pro Glu Tyr Asn Ile Thr Glu Asn Met Ile Cys Ala Gly Tyr Glu
945                 950                 955                 960

Glu Gly Gly Ile Asp Ser Cys Gln Gly Asp Ser Gly Gly Pro Leu Met
                965                 970                 975

Cys Gln Glu Asn Asn Arg Trp Phe Leu Ala Gly Val Thr Ser Phe Gly
            980                 985                 990

Tyr Lys Cys Ala Leu Pro Asn Arg  Pro Gly Val Tyr Ala  Arg Val Ser
        995                 1000                1005

Arg Phe  Thr Glu Trp Ile Gln  Ser Phe Leu His
    1010                1015


<210> SEQ ID NO 19
<211> LENGTH: 3669
<212> TYPE: DNA
<213> ORGANISM: Homo sapiens
<220> FEATURE:
<221> NAME/KEY: CDS
<222> LOCATION: (109)..(2940)

<400> SEQUENCE: 19

acctaaaacc ttgcaagttc aggaagaaac catctgcatc catattgaaa acctgacaca      60

atgtatgcag caggctcagt gtgagtgaac tggaggcttc tctacaac atg acc caa      117
                                                     Met Thr Gln
                                                     1

agg agc att gca ggt cct att tgc aac ctg aag ttt gtg act ctc ctg      165
Arg Ser Ile Ala Gly Pro Ile Cys Asn Leu Lys Phe Val Thr Leu Leu
    5                   10                  15

gtt gcc tta agt tca gaa ctc cca ttc ctg gga gct gga gta cag ctt      213
Val Ala Leu Ser Ser Glu Leu Pro Phe Leu Gly Ala Gly Val Gln Leu
20                  25                  30                  35

caa gac aat ggg tat aat gga ttg ctc att gca att aat cct cag gta      261
Gln Asp Asn Gly Tyr Asn Gly Leu Leu Ile Ala Ile Asn Pro Gln Val
                40                  45                  50

cct gag aat cag aac ctc atc tca aac att aag gaa atg ata act gaa      309
Pro Glu Asn Gln Asn Leu Ile Ser Asn Ile Lys Glu Met Ile Thr Glu
            55                  60                  65

gct tca ttt tac cta ttt aat gct acc aag aga aga gta ttt ttc aga      357
Ala Ser Phe Tyr Leu Phe Asn Ala Thr Lys Arg Arg Val Phe Phe Arg
        70                  75                  80

aat ata aag att tta ata cct gcc aca tgg aaa gct aat aat aac agc      405
Asn Ile Lys Ile Leu Ile Pro Ala Thr Trp Lys Ala Asn Asn Asn Ser
    85                  90                  95

aaa ata aaa caa gaa tca tat gaa aag gca aat gtc ata gtg act gac      453
Lys Ile Lys Gln Glu Ser Tyr Glu Lys Ala Asn Val Ile Val Thr Asp
100                 105                 110                 115

tgg tat ggg gca cat gga gat gat cca tac acc cta caa tac aga ggg      501
Trp Tyr Gly Ala His Gly Asp Asp Pro Tyr Thr Leu Gln Tyr Arg Gly
                120                 125                 130

tgt gga aaa gag gga aaa tac att cat ttc aca cct aat ttc cta ctg      549
Cys Gly Lys Glu Gly Lys Tyr Ile His Phe Thr Pro Asn Phe Leu Leu
            135                 140                 145

aat gat aac tta aca gct ggc tac gga tca cga ggc cga gtg ttt gtc      597
Asn Asp Asn Leu Thr Ala Gly Tyr Gly Ser Arg Gly Arg Val Phe Val
        150                 155                 160

cat gaa tgg gcc cac ctc cgt tgg ggt gtg ttc gat gag tat aac aat      645
His Glu Trp Ala His Leu Arg Trp Gly Val Phe Asp Glu Tyr Asn Asn
    165                 170                 175

gac aaa cct ttc tac ata aat ggg caa aat caa att aaa gtg aca agg      693
```

-continued

```
Asp Lys Pro Phe Tyr Ile Asn Gly Gln Asn Gln Ile Lys Val Thr Arg
180                 185                 190                 195

tgt tca tct gac atc aca ggc att ttt gtg tgt gaa aaa ggt cct tgc      741
Cys Ser Ser Asp Ile Thr Gly Ile Phe Val Cys Glu Lys Gly Pro Cys
                200                 205                 210

ccc caa gaa aac tgt att att agt aag ctt ttt aaa gaa gga tgc acc      789
Pro Gln Glu Asn Cys Ile Ile Ser Lys Leu Phe Lys Glu Gly Cys Thr
            215                 220                 225

ttt atc tac aat agc acc caa aat gca act gca tca ata atg ttc atg      837
Phe Ile Tyr Asn Ser Thr Gln Asn Ala Thr Ala Ser Ile Met Phe Met
        230                 235                 240

caa agt tta tct tct gtg gtt gaa ttt tgt aat gca agt acc cac aac      885
Gln Ser Leu Ser Ser Val Val Glu Phe Cys Asn Ala Ser Thr His Asn
    245                 250                 255

caa gaa gca cca aac cta cag aac cag atg tgc agc ctc aga agt gca      933
Gln Glu Ala Pro Asn Leu Gln Asn Gln Met Cys Ser Leu Arg Ser Ala
260                 265                 270                 275

tgg gat gta atc aca gac tct gct gac ttt cac cac agc ttt ccc atg      981
Trp Asp Val Ile Thr Asp Ser Ala Asp Phe His His Ser Phe Pro Met
                280                 285                 290

aat ggg act gag ctt cca cct cct ccc aca ttc tcg ctt gta cag gct     1029
Asn Gly Thr Glu Leu Pro Pro Pro Pro Thr Phe Ser Leu Val Gln Ala
            295                 300                 305

ggt gac aaa gtg gtc tgt tta gtg ctg gat gtg tcc agc aag atg gca     1077
Gly Asp Lys Val Val Cys Leu Val Leu Asp Val Ser Ser Lys Met Ala
        310                 315                 320

gag gct gac aga ctc ctt caa cta caa caa gcc gca gaa ttt tat ttg     1125
Glu Ala Asp Arg Leu Leu Gln Leu Gln Gln Ala Ala Glu Phe Tyr Leu
    325                 330                 335

atg cag att gtt gaa att cat acc ttc gtg ggc att gcc agt ttc gac     1173
Met Gln Ile Val Glu Ile His Thr Phe Val Gly Ile Ala Ser Phe Asp
340                 345                 350                 355

agc aaa gga gag atc aga gcc cag cta cac caa att aac agc aat gat     1221
Ser Lys Gly Glu Ile Arg Ala Gln Leu His Gln Ile Asn Ser Asn Asp
                360                 365                 370

gat cga aag ttg ctg gtt tca tat ctg ccc acc act gta tca gct aaa     1269
Asp Arg Lys Leu Leu Val Ser Tyr Leu Pro Thr Thr Val Ser Ala Lys
            375                 380                 385

aca gac atc agc att tgt tca ggg ctt aag aaa gga ttt gag gtg gtt     1317
Thr Asp Ile Ser Ile Cys Ser Gly Leu Lys Lys Gly Phe Glu Val Val
        390                 395                 400

gaa aaa ctg aat gga aaa gct tat ggc tct gtg atg ata tta gtg acc     1365
Glu Lys Leu Asn Gly Lys Ala Tyr Gly Ser Val Met Ile Leu Val Thr
    405                 410                 415

agc gga gat gat aag ctt ctt ggc aat tgc tta ccc act gtg ctc agc     1413
Ser Gly Asp Asp Lys Leu Leu Gly Asn Cys Leu Pro Thr Val Leu Ser
420                 425                 430                 435

agt ggt tca aca att cac tcc att gcc ctg ggt tca tct gca gcc cca     1461
Ser Gly Ser Thr Ile His Ser Ile Ala Leu Gly Ser Ser Ala Ala Pro
                440                 445                 450

aat ctg gag gaa tta tca cgt ctt aca gga ggt tta aag ttc ttt gtt     1509
Asn Leu Glu Glu Leu Ser Arg Leu Thr Gly Gly Leu Lys Phe Phe Val
            455                 460                 465

cca gat ata tca aac tcc aat agc atg att gat gct ttc agt aga att     1557
Pro Asp Ile Ser Asn Ser Asn Ser Met Ile Asp Ala Phe Ser Arg Ile
        470                 475                 480

tcc tct gga act gga gac att ttc cag caa cat att cag ctt gaa agt     1605
Ser Ser Gly Thr Gly Asp Ile Phe Gln Gln His Ile Gln Leu Glu Ser
    485                 490                 495
```

-continued

```
aca ggt gaa aat gtc aaa cct cac cat caa ttg aaa aac aca gtg act      1653
Thr Gly Glu Asn Val Lys Pro His His Gln Leu Lys Asn Thr Val Thr
500                 505                 510                 515

gtg gat aat act gtg ggc aac gac act atg ttt cta gtt acg tgg cag      1701
Val Asp Asn Thr Val Gly Asn Asp Thr Met Phe Leu Val Thr Trp Gln
                520                 525                 530

gcc agt ggt cct cct gag att ata tta ttt gat cct gat gga cga aaa      1749
Ala Ser Gly Pro Pro Glu Ile Ile Leu Phe Asp Pro Asp Gly Arg Lys
            535                 540                 545

tac tac aca aat aat ttt atc acc aat cta act ttt cgg aca gct agt      1797
Tyr Tyr Thr Asn Asn Phe Ile Thr Asn Leu Thr Phe Arg Thr Ala Ser
        550                 555                 560

ctt tgg att cca gga aca gct aag cct ggg cac tgg act tac acc ctg      1845
Leu Trp Ile Pro Gly Thr Ala Lys Pro Gly His Trp Thr Tyr Thr Leu
    565                 570                 575

aac aat acc cat cat tct ctg caa gcc ctg aaa gtg aca gtg acc tct      1893
Asn Asn Thr His His Ser Leu Gln Ala Leu Lys Val Thr Val Thr Ser
580                 585                 590                 595

cgc gcc tcc aac tca gct gtg ccc cca gcc act gtg gaa gcc ttt gtg      1941
Arg Ala Ser Asn Ser Ala Val Pro Pro Ala Thr Val Glu Ala Phe Val
                600                 605                 610

gaa aga gac agc ctc cat ttt cct cat cct gtg atg att tat gcc aat      1989
Glu Arg Asp Ser Leu His Phe Pro His Pro Val Met Ile Tyr Ala Asn
            615                 620                 625

gtg aaa cag gga ttt tat ccc att ctt aat gcc act gtc act gcc aca      2037
Val Lys Gln Gly Phe Tyr Pro Ile Leu Asn Ala Thr Val Thr Ala Thr
        630                 635                 640

gtt gag cca gag act gga gat cct gtt acg ctg aga ctc ctt gat gat      2085
Val Glu Pro Glu Thr Gly Asp Pro Val Thr Leu Arg Leu Leu Asp Asp
    645                 650                 655

gga gca ggt gct gat gtt ata aaa aat gat gga att tac tcg agg tat      2133
Gly Ala Gly Ala Asp Val Ile Lys Asn Asp Gly Ile Tyr Ser Arg Tyr
660                 665                 670                 675

ttt ttc tcc ttt gct gca aat ggt aga tat agc ttg aaa gtg cat gtc      2181
Phe Phe Ser Phe Ala Ala Asn Gly Arg Tyr Ser Leu Lys Val His Val
                680                 685                 690

aat cac tct ccc agc ata agc acc cca gcc cac tct att cca ggg agt      2229
Asn His Ser Pro Ser Ile Ser Thr Pro Ala His Ser Ile Pro Gly Ser
            695                 700                 705

cat gct atg tat gta cca ggt tac aca gca aac ggt aat att cag atg      2277
His Ala Met Tyr Val Pro Gly Tyr Thr Ala Asn Gly Asn Ile Gln Met
        710                 715                 720

aat gct cca agg aaa tca gta ggc aga aat gag gag gag cga aag tgg      2325
Asn Ala Pro Arg Lys Ser Val Gly Arg Asn Glu Glu Glu Arg Lys Trp
    725                 730                 735

ggc ttt agc cga gtc agc tca gga ggc tcc ttt tca gtg ctg gga gtt      2373
Gly Phe Ser Arg Val Ser Ser Gly Gly Ser Phe Ser Val Leu Gly Val
740                 745                 750                 755

cca gct ggc ccc cac cct gat gtg ttt cca cca tgc aaa att att gac      2421
Pro Ala Gly Pro His Pro Asp Val Phe Pro Pro Cys Lys Ile Ile Asp
                760                 765                 770

ctg gaa gct gta aaa gta gaa gag gaa ttg acc cta tct tgg aca gca      2469
Leu Glu Ala Val Lys Val Glu Glu Glu Leu Thr Leu Ser Trp Thr Ala
            775                 780                 785

cct gga gaa gac ttt gat cag ggc cag gct aca agc tat gaa ata aga      2517
Pro Gly Glu Asp Phe Asp Gln Gly Gln Ala Thr Ser Tyr Glu Ile Arg
        790                 795                 800

atg agt aaa agt cta cag aat atc caa gat gac ttt aac aat gct att      2565
Met Ser Lys Ser Leu Gln Asn Ile Gln Asp Asp Phe Asn Asn Ala Ile
    805                 810                 815
```

-continued

```
tta gta aat aca tca aag cga aat cct cag caa gct ggc atc agg gag     2613
Leu Val Asn Thr Ser Lys Arg Asn Pro Gln Gln Ala Gly Ile Arg Glu
820                 825                 830                 835

ata ttt acg ttc tca ccc cag att tcc acg aat gga cct gaa cat cag     2661
Ile Phe Thr Phe Ser Pro Gln Ile Ser Thr Asn Gly Pro Glu His Gln
                840                 845                 850

cca aat gga gaa aca cat gaa agc cac aga att tat gtt gca ata cga     2709
Pro Asn Gly Glu Thr His Glu Ser His Arg Ile Tyr Val Ala Ile Arg
            855                 860                 865

gca atg gat agg aac tcc tta cag tct gct gta tct aac att gcc cag     2757
Ala Met Asp Arg Asn Ser Leu Gln Ser Ala Val Ser Asn Ile Ala Gln
        870                 875                 880

gcg cct ctg ttt att ccc ccc aat tct gat cct gta cct gcc aga gat     2805
Ala Pro Leu Phe Ile Pro Pro Asn Ser Asp Pro Val Pro Ala Arg Asp
    885                 890                 895

tat ctt ata ttg aaa gga gtt tta aca gca atg ggt ttg ata gga atc     2853
Tyr Leu Ile Leu Lys Gly Val Leu Thr Ala Met Gly Leu Ile Gly Ile
900                 905                 910                 915

att tgc ctt att ata gtt gtg aca cat cat act tta agc agg aaa aag     2901
Ile Cys Leu Ile Ile Val Val Thr His His Thr Leu Ser Arg Lys Lys
                920                 925                 930

aga gca gac aag aaa gag aat gga aca aaa tta tta taa ataaatatcc      2950
Arg Ala Asp Lys Lys Glu Asn Gly Thr Lys Leu Leu
            935                 940

aaagtgtctt ccttcttaga tataagaccc atggccttcg actacaaaaa catactaaca   3010

aagtcaaatt aacatcaaaa ctgtattaaa atgcattgag tttttgtaca atacagataa   3070

gatttttaca tggtagatca acaattcttt ttgggggtag attagaaaac ccttacactt   3130

tggctatgaa caaataataa aaattattct ttaaagtaat gtctttaaag gcaaagggaa   3190

gggtaaagtc ggaccagtgt caaggaaagt ttgttttatt gaggtggaaa aatagcccca   3250

agcagagaaa aggagggtag gtctgcatta taactgtctg tgtgaagcaa tcatttagtt   3310

actttgatta atttttcttt tctccttatc tgtgcagaac aggttgcttg tttacaactg   3370

aagatcatgc tatattttat atatgaagcc cctaatgcaa agctctttac ctcttgctat   3430

tttgttatat atattacaga tgaaatctca ctgctaatgc tcagagatct tttttcactg   3490

taagaggtaa cctttaacaa tatgggtatt acctttgtct cttcataccg gttttatgac   3550

aaaggtctat tgaatttatt tgtttgtaag tttctactcc catcaaagca gctttctaag   3610

ttattgcctt ggttattatg gatgatagtt atagccctta taatgcctta cctaggaaa    3669
```

```
<210> SEQ ID NO 20
<211> LENGTH: 943
<212> TYPE: PRT
<213> ORGANISM: Homo sapiens

<400> SEQUENCE: 20

Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65                  70                  75                  80
```

```
Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Pro Thr Phe Ser Leu
    290                 295                 300

Val Gln Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495
```

```
Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
            580                 585                 590

Val Thr Ser Arg Ala Ser Asn Ser Ala Val Pro Pro Ala Thr Val Glu
        595                 600                 605

Ala Phe Val Glu Arg Asp Ser Leu His Phe Pro His Pro Val Met Ile
    610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
            660                 665                 670

Ser Arg Tyr Phe Phe Ser Phe Ala Ala Asn Gly Arg Tyr Ser Leu Lys
        675                 680                 685

Val His Val Asn His Ser Pro Ser Ile Ser Thr Pro Ala His Ser Ile
    690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser Val
            740                 745                 750

Leu Gly Val Pro Ala Gly Pro His Pro Asp Val Phe Pro Pro Cys Lys
        755                 760                 765

Ile Ile Asp Leu Glu Ala Val Lys Val Glu Glu Glu Leu Thr Leu Ser
    770                 775                 780

Trp Thr Ala Pro Gly Glu Asp Phe Asp Gln Gly Gln Ala Thr Ser Tyr
785                 790                 795                 800

Glu Ile Arg Met Ser Lys Ser Leu Gln Asn Ile Gln Asp Asp Phe Asn
                805                 810                 815

Asn Ala Ile Leu Val Asn Thr Ser Lys Arg Asn Pro Gln Gln Ala Gly
            820                 825                 830

Ile Arg Glu Ile Phe Thr Phe Ser Pro Gln Ile Ser Thr Asn Gly Pro
        835                 840                 845

Glu His Gln Pro Asn Gly Glu Thr His Glu Ser His Arg Ile Tyr Val
    850                 855                 860

Ala Ile Arg Ala Met Asp Arg Asn Ser Leu Gln Ser Ala Val Ser Asn
865                 870                 875                 880

Ile Ala Gln Ala Pro Leu Phe Ile Pro Pro Asn Ser Asp Pro Val Pro
                885                 890                 895

Ala Arg Asp Tyr Leu Ile Leu Lys Gly Val Leu Thr Ala Met Gly Leu
            900                 905                 910

Ile Gly Ile Ile Cys Leu Ile Ile Val Val Thr His His Thr Leu Ser
```

```
        915                 920                 925

Arg Lys Lys Arg Ala Asp Lys Lys Glu Asn Gly Thr Lys Leu Leu
    930                 935                 940


<210> SEQ ID NO 21
<211> LENGTH: 1428
<212> TYPE: DNA
<213> ORGANISM: Homo sapiens
<220> FEATURE:
<221> NAME/KEY: CDS
<222> LOCATION: (232)..(840)

<400> SEQUENCE: 21

cttcaggtca gggagaatgt ataaatgtcc attgccatcg aggttctgct atttttgaga      60

agctgaagca actccaagga cacagttcac agaaatttgg ttctcagccc caaaatactg     120

attgaattgg agacaattac aaggactctc tggccaaaaa cccttgaaga ggccccgtga     180

aggaggcagt gaggagcttt tgattgctga cctgtgtcgt accaccccag a atg tgc      237
                                                         Met Cys
                                                         1

act ggg ggc tgt gcc aga tgc ctg ggg ggg acc ctc att ccc ctt gct       285
Thr Gly Gly Cys Ala Arg Cys Leu Gly Gly Thr Leu Ile Pro Leu Ala
        5                   10                  15

ttt ttt ggc ttc ctg gct aac atc ctg tta ttt ttt cct gga gga aaa       333
Phe Phe Gly Phe Leu Ala Asn Ile Leu Leu Phe Phe Pro Gly Gly Lys
    20                  25                  30

gtg ata gat gac aac gac cac ctt tcc caa gag atc tgg ttt ttc gga       381
Val Ile Asp Asp Asn Asp His Leu Ser Gln Glu Ile Trp Phe Phe Gly
35                  40                  45                  50

gga ata tta gga agc ggt gtc ttg atg atc ttc cct gcg ctg gtg ttc       429
Gly Ile Leu Gly Ser Gly Val Leu Met Ile Phe Pro Ala Leu Val Phe
                55                  60                  65

ttg ggc ctg aag aac aat gac tgc tgt ggg tgc tgc ggc aac gag ggc       477
Leu Gly Leu Lys Asn Asn Asp Cys Cys Gly Cys Cys Gly Asn Glu Gly
            70                  75                  80

tgt ggg aag cga ttt gcg atg ttc acc tcc acg ata ttt gct gtg gtt       525
Cys Gly Lys Arg Phe Ala Met Phe Thr Ser Thr Ile Phe Ala Val Val
        85                  90                  95

gga ttc ttg gga gct gga tac tcg ttt atc atc tca gcc att tca atc       573
Gly Phe Leu Gly Ala Gly Tyr Ser Phe Ile Ile Ser Ala Ile Ser Ile
    100                 105                 110

aac aag ggt cct aaa tgc ctc atg gcc aat agt aca tgg ggc tac ccc       621
Asn Lys Gly Pro Lys Cys Leu Met Ala Asn Ser Thr Trp Gly Tyr Pro
115                 120                 125                 130

ttc cac gac ggg gat tat ctc aat gat gag gcc tta tgg aac aag tgc       669
Phe His Asp Gly Asp Tyr Leu Asn Asp Glu Ala Leu Trp Asn Lys Cys
                135                 140                 145

cga gag cct ctc aat gtg gtt ccc tgg aat ctg acc ctc ttc tcc atc       717
Arg Glu Pro Leu Asn Val Val Pro Trp Asn Leu Thr Leu Phe Ser Ile
            150                 155                 160

ctg ctg gtc gta gga gga atc cag atg gtt ctc tgc gcc atc cag gtg       765
Leu Leu Val Val Gly Gly Ile Gln Met Val Leu Cys Ala Ile Gln Val
        165                 170                 175

gtc aat ggc ctc ctg ggg acc ctc tgt ggg gac tgc cag tgt tgt ggc       813
Val Asn Gly Leu Leu Gly Thr Leu Cys Gly Asp Cys Gln Cys Cys Gly
    180                 185                 190

tgc tgt ggg gga gat gga ccc gtt taa acctccgaga tgagctgctc             860
Cys Cys Gly Gly Asp Gly Pro Val
195                 200

agactctaca gcatgacgac tacaatttct tttcataaaa cttcttctct tcttggaatt     920
```

```
attaattcct atctgcttcc tagctgataa agcttagaaa aggcagttat tccttctttc    980

caaccagctt tgctcgagtt agaattttgt tattttcaaa taaaaaatag tttggccact   1040

taacaaattt gatttataaa tctttcaaat tagttccttt ttagaattta ccaacaggtt   1100

caaagcatac ttttcatgat ttttttatta caaatgtaaa atgtataaag tcacatgtac   1160

tgccatacta cttctttgta tataaagatg tttatatctt tggaagtttt acataaatca   1220

aaggaagaaa gcacatttaa aatgagaaac taagaccaat ttctgttttt aagaggaaaa   1280

agaatgattg atgtatccta agtattgtta tttgttgtct ttttttgctg ccttgcttga   1340

gttgcttgtg actgatcttt tgaggctgtc atcatggcta gggttctttt atgtatgtta   1400

aattaaaacc tgaattcaga ggtaacgt                                      1428
```

<210> SEQ ID NO 22
<211> LENGTH: 202
<212> TYPE: PRT
<213> ORGANISM: Homo sapiens

<400> SEQUENCE: 22

```
Met Cys Thr Gly Gly Cys Ala Arg Cys Leu Gly Gly Thr Leu Ile Pro
1               5                   10                  15

Leu Ala Phe Phe Gly Phe Leu Ala Asn Ile Leu Leu Phe Phe Pro Gly
            20                  25                  30

Gly Lys Val Ile Asp Asp Asn Asp His Leu Ser Gln Glu Ile Trp Phe
        35                  40                  45

Phe Gly Gly Ile Leu Gly Ser Gly Val Leu Met Ile Phe Pro Ala Leu
    50                  55                  60

Val Phe Leu Gly Leu Lys Asn Asn Asp Cys Cys Gly Cys Cys Gly Asn
65                  70                  75                  80

Glu Gly Cys Gly Lys Arg Phe Ala Met Phe Thr Ser Thr Ile Phe Ala
                85                  90                  95

Val Val Gly Phe Leu Gly Ala Gly Tyr Ser Phe Ile Ile Ser Ala Ile
            100                 105                 110

Ser Ile Asn Lys Gly Pro Lys Cys Leu Met Ala Asn Ser Thr Trp Gly
        115                 120                 125

Tyr Pro Phe His Asp Gly Asp Tyr Leu Asn Asp Glu Ala Leu Trp Asn
    130                 135                 140

Lys Cys Arg Glu Pro Leu Asn Val Val Pro Trp Asn Leu Thr Leu Phe
145                 150                 155                 160

Ser Ile Leu Leu Val Val Gly Gly Ile Gln Met Val Leu Cys Ala Ile
                165                 170                 175

Gln Val Val Asn Gly Leu Leu Gly Thr Leu Cys Gly Asp Cys Gln Cys
            180                 185                 190

Cys Gly Cys Cys Gly Gly Asp Gly Pro Val
        195                 200
```

<210> SEQ ID NO 23
<211> LENGTH: 2859
<212> TYPE: DNA
<213> ORGANISM: Homo sapiens
<220> FEATURE:
<221> NAME/KEY: CDS
<222> LOCATION: (192)..(866)

<400> SEQUENCE: 23

```
attctggagt ccagagccac tgcctttgct ccagccgctg ccgccgcacc acctctcctt     60
```

-continued

```
ctctgcctct gaccctcctt ctcgctgctc cccctgccca gctgctcctc ccacctggcc    120

atgaccaaag cccctgctgg caccctggcc cagctctgag tcctgggacc ctcggtcctc    180

tctcctgggc c atg gcc aac tca ggc ctc cag ctc ctg ggc tac ttc ttg     230
             Met Ala Asn Ser Gly Leu Gln Leu Leu Gly Tyr Phe Leu
             1               5                   10

gcc ctg ggt ggc tgg gtg ggc atc att gct agc aca gcc ctg cca cag      278
Ala Leu Gly Gly Trp Val Gly Ile Ile Ala Ser Thr Ala Leu Pro Gln
    15                  20                  25

tgg aag cag tct tcc tac gca ggc gac gcc atc atc act gcc gtg ggc      326
Trp Lys Gln Ser Ser Tyr Ala Gly Asp Ala Ile Ile Thr Ala Val Gly
30                  35                  40                  45

ccc tat gaa ggg ctc tgg atg tcc tgc gcc tcc cag agc act ggg caa      374
Pro Tyr Glu Gly Leu Trp Met Ser Cys Ala Ser Gln Ser Thr Gly Gln
                50                  55                  60

gtg cag tgc aag ctc tac gac tcg ctg ctc gcc ctg gac ggt cac atc      422
Val Gln Cys Lys Leu Tyr Asp Ser Leu Leu Ala Leu Asp Gly His Ile
            65                  70                  75

caa tca gcg cgg gcc ctg atg gtg gtg gcc gtg ctc ctg ggc ttc gtg      470
Gln Ser Ala Arg Ala Leu Met Val Val Ala Val Leu Leu Gly Phe Val
        80                  85                  90

gcc atg gtc ctc agc gta gtt ggc atg aag tgt acg cgg gtg gga gac      518
Ala Met Val Leu Ser Val Val Gly Met Lys Cys Thr Arg Val Gly Asp
    95                  100                 105

agc aac ccc att gcc aag ggc cgt gtt gcc atc gcc ggg gga gcc ctc      566
Ser Asn Pro Ile Ala Lys Gly Arg Val Ala Ile Ala Gly Gly Ala Leu
110                 115                 120                 125

ttc atc ctg gca ggc ctc tgc act ttg act gct gtc tcg tgg tat gcc      614
Phe Ile Leu Ala Gly Leu Cys Thr Leu Thr Ala Val Ser Trp Tyr Ala
                130                 135                 140

acc ctg gtg acc cag gag ttc ttc aac cca agc aca cct gtc aat gcc      662
Thr Leu Val Thr Gln Glu Phe Phe Asn Pro Ser Thr Pro Val Asn Ala
            145                 150                 155

agg tat gaa ttt ggc cca gcc ctg ttc gtg ggc tgg gcc tca gct ggc      710
Arg Tyr Glu Phe Gly Pro Ala Leu Phe Val Gly Trp Ala Ser Ala Gly
        160                 165                 170

ctg gcc gtg ctg ggc ggc tcc ttc ctc tgc tgc aca tgc ccg gag cca      758
Leu Ala Val Leu Gly Gly Ser Phe Leu Cys Cys Thr Cys Pro Glu Pro
    175                 180                 185

gag aga ccc aac agc agc cca cag ccc tat cgg cct gga ccc tct gct      806
Glu Arg Pro Asn Ser Ser Pro Gln Pro Tyr Arg Pro Gly Pro Ser Ala
190                 195                 200                 205

gct gcc cga gaa cca gtt gtt aaa ttg ccc gcc tcc gcc aag ggc ccc      854
Ala Ala Arg Glu Pro Val Val Lys Leu Pro Ala Ser Ala Lys Gly Pro
                210                 215                 220

ctg ggt gtg taa tgtccagtcc ccagccaggc tctgtcccct gccataccta          906
Leu Gly Val

gactgtgtgt ttcatatttt tttggaaaga gaagtgaaca tccagcccca atcatggtat    966

cattcggtct gtcctcagcg tggcttggac ggggcctgtg tcagagtggt cagtgctgac   1026

ccctggggct cttgggcaga aagatgagga gacagaggtc cagggtgggt tacatagcac   1086

atccagggct gagcaagaaa taattcagag gtcctaccct ctgtctaggg acccccctcc   1146

caagcctggc cttggccttg gcacaaagtc ctccttgata ggagatccca ctcactcctg   1206

gaggctgccc ctgaggcttg gcccagctct aggagcagtc cccagggtca gggagcccct   1266

ggtgtggaaa gaggccccaa ggtagtaaac cctgcccctg ttactgtgct ccagagacct   1326

cctaagggaa gggacagttc ctggaaggcc ctccagctgg atgctgggga tcagcgatag   1386
```

-continued

```
gtgaggggac acagtgtagg agctccccat gtagaaaagg gaatgtgggg agggcgttag   1446

gagcttgcag gcattaggac tgtcctgagc aaggtctgca gcccccagct ctgctcaccc   1506

cgaatcctgc cccttgtttc cacacctacc attcctcctc tcctgatccc cagcatccag   1566

ctgaggtcca aggtctttgt cctagaatca gagtggggag gggacagcct ggggctgccc   1626

agagactgtg ggtggagctg cctgctgcac tcagcagtgc ggtcagagaa gggcttttgg   1686

tcttgaagtc caggtaccat ccccccttag catacagggg gaagggcctg agaggaatgt   1746

aaggaaacca gcccagatca gtcccaaggc cagagtcctt tgtcctacat ctccctgaac   1806

cagagtgtgc cctgcccctc atgctcagac ctctcccacc ccaaaccctc tcccgggact   1866

cagtctccct ggccactgcg tatcaggctt ctggggaaag catccatcac agaacctccc   1926

cttccctgcc acgcaccttc cttggccagc tccattctgg cctcctccac cacctgcctt   1986

gtgaccacat ctcccaccac gtccccagat ctcaagaacg cagctcagct tctccttcga   2046

gcttgactct gagagggaaa gtgacggaaa ccaagtcaga tgagatgact gccatgtaca   2106

ctgcagtcaa gggcagggag gggaggaatg acacaaatgg cagggagctg ctggggggact   2166

gacccctcgg cgcctggcct ggccggtgct gcacatccac cggggcacaa cagggacttg   2226

tccagcctct ggtcagagga tgtggccacc tgaccctaaa taggttcccc agagtcctgc   2286

ccctctaatg aatgagaact gcaggagttt ctcctctggg tgcctgaagc tatagtgcaa   2346

tggttcccaa ccctgcatgc acattcgaat cacctggggg cacaatgcct aggctccaac   2406

cccagacact cttatttcat tggtctgggt ggacctggca tcagaagtca tgtagctcct   2466

caggggactg tagtgtgtgg tcagcactga gggctcctct atgaggcctc aagcccaggt   2526

gactctgtga ggtctgcaga gggagaaaag aacccacaag ggaagaggtg gaggtcaggc   2586

acggtggctc acgcttgtaa tcccagcact ttgggaggcc gaggtgggta gatacctgaa   2646

gtcaggagtt cgagactagc ctggccaata tggtaaaacc ccgtgtctat taaaaataca   2706

aaaattagct ggctgtggtg gtgggcacct gtaatcccag ctactcggga ggctgaggca   2766

ggagaatcgc ttgaactcgg gaggtggagg ttgcagtcag ccaagatcgt gccactgcac   2826

accatcctgg atgacagagc aagactccat cac                                2859
```

<210> SEQ ID NO 24
<211> LENGTH: 224
<212> TYPE: PRT
<213> ORGANISM: Homo sapiens

<400> SEQUENCE: 24

```
Met Ala Asn Ser Gly Leu Gln Leu Leu Gly Tyr Phe Leu Ala Leu Gly
1               5                   10                  15

Gly Trp Val Gly Ile Ile Ala Ser Thr Ala Leu Pro Gln Trp Lys Gln
            20                  25                  30

Ser Ser Tyr Ala Gly Asp Ala Ile Ile Thr Ala Val Gly Pro Tyr Glu
        35                  40                  45

Gly Leu Trp Met Ser Cys Ala Ser Gln Ser Thr Gly Gln Val Gln Cys
    50                  55                  60

Lys Leu Tyr Asp Ser Leu Leu Ala Leu Asp Gly His Ile Gln Ser Ala
65                  70                  75                  80

Arg Ala Leu Met Val Val Ala Val Leu Leu Gly Phe Val Ala Met Val
                85                  90                  95

Leu Ser Val Val Gly Met Lys Cys Thr Arg Val Gly Asp Ser Asn Pro
            100                 105                 110
```

-continued

```
Ile Ala Lys Gly Arg Val Ala Ile Ala Gly Gly Ala Leu Phe Ile Leu
        115                 120                 125

Ala Gly Leu Cys Thr Leu Thr Ala Val Ser Trp Tyr Ala Thr Leu Val
    130                 135                 140

Thr Gln Glu Phe Phe Asn Pro Ser Thr Pro Val Asn Ala Arg Tyr Glu
145                 150                 155                 160

Phe Gly Pro Ala Leu Phe Val Gly Trp Ala Ser Ala Gly Leu Ala Val
                165                 170                 175

Leu Gly Gly Ser Phe Leu Cys Cys Thr Cys Pro Glu Pro Glu Arg Pro
            180                 185                 190

Asn Ser Ser Pro Gln Pro Tyr Arg Pro Gly Pro Ser Ala Ala Ala Arg
        195                 200                 205

Glu Pro Val Val Lys Leu Pro Ala Ser Ala Lys Gly Pro Leu Gly Val
    210                 215                 220


<210> SEQ ID NO 25
<211> LENGTH: 2485
<212> TYPE: DNA
<213> ORGANISM: Homo sapiens
<220> FEATURE:
<221> NAME/KEY: CDS
<222> LOCATION: (53)..(1651)

<400> SEQUENCE: 25

catactccat acctgggatt tccgcctcgc cgctctccga ctgcttccag ac atg cag      58
                                                          Met Gln
                                                          1

ggg ccc tgg gtg ctg ctc ctg ctg ggc ctg agg cta cag ctc tcc ctg      106
Gly Pro Trp Val Leu Leu Leu Leu Gly Leu Arg Leu Gln Leu Ser Leu
        5                   10                  15

ggc atc atc cca gtt gag gag gag aac ccg gac ttc tgg aac cgc cag      154
Gly Ile Ile Pro Val Glu Glu Glu Asn Pro Asp Phe Trp Asn Arg Gln
    20                  25                  30

gca gcc gag gcc ctg ggt gcc gcc aag aag ctg cag cct gca cag aca      202
Ala Ala Glu Ala Leu Gly Ala Ala Lys Lys Leu Gln Pro Ala Gln Thr
35                  40                  45                  50

gcc gcc aag aac ctc atc atc ttc ctg ggt gac ggg atg ggg gtg tct      250
Ala Ala Lys Asn Leu Ile Ile Phe Leu Gly Asp Gly Met Gly Val Ser
                55                  60                  65

acg gtg aca gct gcc agg atc cta aaa ggg cag aag aag gac aaa ctg      298
Thr Val Thr Ala Ala Arg Ile Leu Lys Gly Gln Lys Lys Asp Lys Leu
            70                  75                  80

ggg cct gag acc ttc ctg gcc atg gac cgc ttc ccg tac gtg gct ctg      346
Gly Pro Glu Thr Phe Leu Ala Met Asp Arg Phe Pro Tyr Val Ala Leu
        85                  90                  95

tcc aag aca tac agt gta gac aag cat gtg cca gac agt gga gcc aca      394
Ser Lys Thr Tyr Ser Val Asp Lys His Val Pro Asp Ser Gly Ala Thr
    100                 105                 110

gcc acg gcc tac ctg tgc ggg gtc aag ggc aac ttc cag acc att ggc      442
Ala Thr Ala Tyr Leu Cys Gly Val Lys Gly Asn Phe Gln Thr Ile Gly
115                 120                 125                 130

ttg agt gca gcc gcc cgc ttt aac cag tgc aac acg aca cgc ggc aac      490
Leu Ser Ala Ala Ala Arg Phe Asn Gln Cys Asn Thr Thr Arg Gly Asn
                135                 140                 145

gag gtc atc tcc gtg gtg aat cgg gcc aag aaa gca gga aag tca gtg      538
Glu Val Ile Ser Val Val Asn Arg Ala Lys Lys Ala Gly Lys Ser Val
            150                 155                 160

gga gtg gta acc acc aca cgg gtg cag cat gcc tcg cca gcc ggc acc      586
Gly Val Val Thr Thr Thr Arg Val Gln His Ala Ser Pro Ala Gly Thr
        165                 170                 175
```

-continued

```
tac gcc cac acg gtg aac cgc aac tgg tac tcg gat gcc gac gtg cct      634
Tyr Ala His Thr Val Asn Arg Asn Trp Tyr Ser Asp Ala Asp Val Pro
    180                 185                 190

gcc tcg gcc cgc cag gag ggg tgc cag gac atc gcc acg cag ctc atc      682
Ala Ser Ala Arg Gln Glu Gly Cys Gln Asp Ile Ala Thr Gln Leu Ile
195                 200                 205                 210

tcc aac atg gac att gat gtg atc cta ggt gga ggc cga aag tac atg      730
Ser Asn Met Asp Ile Asp Val Ile Leu Gly Gly Gly Arg Lys Tyr Met
                215                 220                 225

ttt ccc atg ggg acc cca gac cct gag tac cca gat gac tac agc caa      778
Phe Pro Met Gly Thr Pro Asp Pro Glu Tyr Pro Asp Asp Tyr Ser Gln
            230                 235                 240

ggt ggg acc agg ctg gac ggg aag aat ctg gtg cag gaa tgg ctg gcg      826
Gly Gly Thr Arg Leu Asp Gly Lys Asn Leu Val Gln Glu Trp Leu Ala
        245                 250                 255

aag cac cag ggt gcc cgg tac gtg tgg aac cgc act gag ctc ctg cag      874
Lys His Gln Gly Ala Arg Tyr Val Trp Asn Arg Thr Glu Leu Leu Gln
    260                 265                 270

gct tcc ctg gac ccg tct gtg acc cat ctc atg ggt ctc ttt gag cct      922
Ala Ser Leu Asp Pro Ser Val Thr His Leu Met Gly Leu Phe Glu Pro
275                 280                 285                 290

gga gac atg aaa tac gag atc cac cga gac tcc aca ctg gac ccc tcc      970
Gly Asp Met Lys Tyr Glu Ile His Arg Asp Ser Thr Leu Asp Pro Ser
                295                 300                 305

ctg atg gag atg aca gag gct gcc ctg cgc ctg ctg agc agg aac ccc     1018
Leu Met Glu Met Thr Glu Ala Ala Leu Arg Leu Leu Ser Arg Asn Pro
            310                 315                 320

cgc ggc ttc ttc ctc ttc gtg gag ggt ggt cgc atc gac cat ggt cat     1066
Arg Gly Phe Phe Leu Phe Val Glu Gly Gly Arg Ile Asp His Gly His
        325                 330                 335

cat gaa agc agg gct tac cgg gca ctg act gag acg atc atg ttc gac     1114
His Glu Ser Arg Ala Tyr Arg Ala Leu Thr Glu Thr Ile Met Phe Asp
    340                 345                 350

gac gcc att gag agg gcg ggc cag ctc acc agc gag gag gac acg ctg     1162
Asp Ala Ile Glu Arg Ala Gly Gln Leu Thr Ser Glu Glu Asp Thr Leu
355                 360                 365                 370

agc ctc gtc act gcc gac cac tcc cac gtc ttc tcc ttc gga ggc tac     1210
Ser Leu Val Thr Ala Asp His Ser His Val Phe Ser Phe Gly Gly Tyr
                375                 380                 385

ccc ctg cga ggg agc tcc atc ttc ggg ctg gcc cct ggc aag gcc cgg     1258
Pro Leu Arg Gly Ser Ser Ile Phe Gly Leu Ala Pro Gly Lys Ala Arg
            390                 395                 400

gac agg aag gcc tac acg gtc ctc cta tac gga aac ggt cca ggc tat     1306
Asp Arg Lys Ala Tyr Thr Val Leu Leu Tyr Gly Asn Gly Pro Gly Tyr
        405                 410                 415

gtg ctc aag gac ggc gcc cgg ccg gat gtt acc gag agc gag agc ggg     1354
Val Leu Lys Asp Gly Ala Arg Pro Asp Val Thr Glu Ser Glu Ser Gly
    420                 425                 430

agc ccc gag tat cgg cag cag tca gca gtg ccc ctg gac gga gag acc     1402
Ser Pro Glu Tyr Arg Gln Gln Ser Ala Val Pro Leu Asp Gly Glu Thr
435                 440                 445                 450

cac gca ggc gag gac gtg gcg gtg ttc gcg cgc ggc ccg cag gcg cac     1450
His Ala Gly Glu Asp Val Ala Val Phe Ala Arg Gly Pro Gln Ala His
                455                 460                 465

ctg gtt cac ggc gtg cag gag cag acc ttc ata gcg cac gtc atg gcc     1498
Leu Val His Gly Val Gln Glu Gln Thr Phe Ile Ala His Val Met Ala
            470                 475                 480

ttc gcc gcc tgc ctg gag ccc tac acc gcc tgc gac ctg gcg ccc ccc     1546
Phe Ala Ala Cys Leu Glu Pro Tyr Thr Ala Cys Asp Leu Ala Pro Pro
```

-continued

```
        485                 490                 495

gcc ggc acc acc gac gcc gcg cac ccg ggg ccg tcc gtg gtc ccc gcg      1594
Ala Gly Thr Thr Asp Ala Ala His Pro Gly Pro Ser Val Val Pro Ala
    500                 505                 510

ttg ctt cct ctg ctg gca ggg acc ttg ctg ctg ctg ggg acg gcc act      1642
Leu Leu Pro Leu Leu Ala Gly Thr Leu Leu Leu Leu Gly Thr Ala Thr
515                 520                 525                 530

gct ccc tga gtgtcccgtc cctgggggct cctgcttccc catcccggag              1691
Ala Pro

ttcccctgct ccccacctcc agttctgcct gccggacctc cacctggagc tgtcaccccc    1751

ggagtcgcca cacagactgt cctgccatgg aaccttccct cccggtgcac cctggggacc    1811

gagcccttga caccacgccc tttgctttat cttgctctta aattttggcc ccaactccag    1871

ggactgggga tttgtgcctg gcagctgcct gcatttcagg aaaagaggag gctcagacca    1931

tccagccccc cgcccatatc ctgaggtgga tcaggcaggc tctctccccg gggacatgag    1991

gcacccatac ctaggacccc ctgcgccttt tttagcttca gtcatggcag cacctgaggg    2051

acacaaggac ttgggtgcat caggacgcct tggagaagcg tggcttcctg ccaccctgca    2111

acccaccctc ccagccaagg aggctgctgt ggtggggatc cccaggggct ttgacacagt    2171

cctctgctgt ccctccactg ggctaattct acacccctgt cgcctcctag ggcccatga     2231

gtcagagagg cttgccccaa gtcacagcca ctcagatgtt cgacgccccc taaggtccat    2291

tccagcaccc acctgagttc cgaggagcac ctgggaagct ctgggtgcag gatagcagtc    2351

cagagtccat ggccccgcct aggccatctg ggtgctgggc atggatttct cagcaaggaa    2411

gactcattac cttccctccc tggcctcca ttcttctggg aaacacaaag caataataaa     2471

aggaagtgtt agac                                                      2485


<210> SEQ ID NO 26
<211> LENGTH: 532
<212> TYPE: PRT
<213> ORGANISM: Homo sapiens

<400> SEQUENCE: 26

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Val Asn Arg Ala Lys Lys Ala Gly Lys
145                 150                 155                 160
```

-continued

```
Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
    290                 295                 300

Pro Ser Leu Met Glu Met Thr Glu Ala Ala Leu Arg Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
        355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
    450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Pro Ala Gly Thr Thr Asp Ala Ala His Pro Gly Pro Ser Val Val
            500                 505                 510

Pro Ala Leu Leu Pro Leu Leu Ala Gly Thr Leu Leu Leu Leu Gly Thr
        515                 520                 525

Ala Thr Ala Pro
    530
```

<210> SEQ ID NO 27
<211> LENGTH: 4665
<212> TYPE: DNA
<213> ORGANISM: Homo sapiens
<220> FEATURE:
<221> NAME/KEY: CDS

```
<222> LOCATION: (73)..(3117)

<400> SEQUENCE: 27

agccagcccg aggacgcgag cggcaggtgt gcacagaggt tctccacttt gttttctgaa      60

ctcgcggtca gg atg gtt ttc tct gtc agg cag tgt ggc cat gtt ggc aga     111
              Met Val Phe Ser Val Arg Gln Cys Gly His Val Gly Arg
              1               5                   10

act gaa gaa gtt tta ctg acg ttc aag ata ttc ctt gtc atc att tgt      159
Thr Glu Glu Val Leu Leu Thr Phe Lys Ile Phe Leu Val Ile Ile Cys
    15                  20                  25

ctt cat gtc gtt ctg gta aca tcc ctg gaa gaa gat act gat aat tcc      207
Leu His Val Val Leu Val Thr Ser Leu Glu Glu Asp Thr Asp Asn Ser
30                  35                  40                  45

agt ttg tca cca cca cct gct aaa tta tct gtt gtc agt ttt gcc ccc      255
Ser Leu Ser Pro Pro Pro Ala Lys Leu Ser Val Val Ser Phe Ala Pro
                50                  55                  60

tcc tcc aat gag gtt gaa aca aca agc ctc aat gat gtt act tta agc      303
Ser Ser Asn Glu Val Glu Thr Thr Ser Leu Asn Asp Val Thr Leu Ser
            65                  70                  75

tta ctc cct tca aac gaa aca gaa aaa act aaa atc act ata gta aaa      351
Leu Leu Pro Ser Asn Glu Thr Glu Lys Thr Lys Ile Thr Ile Val Lys
        80                  85                  90

acc ttc aat gct tca ggc gtc aaa ccc cag aga aat atc tgc aat ttg      399
Thr Phe Asn Ala Ser Gly Val Lys Pro Gln Arg Asn Ile Cys Asn Leu
    95                  100                 105

tca tct att tgc aat gac tca gca ttt ttt aga ggt gag atc atg ttt      447
Ser Ser Ile Cys Asn Asp Ser Ala Phe Phe Arg Gly Glu Ile Met Phe
110                 115                 120                 125

caa tat gat aaa gaa agc act gtt ccc cag aat caa cat ata acg aat      495
Gln Tyr Asp Lys Glu Ser Thr Val Pro Gln Asn Gln His Ile Thr Asn
                130                 135                 140

ggc acc tta act gga gtc ctg tct cta agt gaa tta aaa cgc tca gag      543
Gly Thr Leu Thr Gly Val Leu Ser Leu Ser Glu Leu Lys Arg Ser Glu
            145                 150                 155

ctc aac aaa acc ctg caa acc cta agt gag act tac ttt ata atg tgt      591
Leu Asn Lys Thr Leu Gln Thr Leu Ser Glu Thr Tyr Phe Ile Met Cys
        160                 165                 170

gct aca gca gag gcc caa agc aca tta aat tgt aca ttc aca ata aaa      639
Ala Thr Ala Glu Ala Gln Ser Thr Leu Asn Cys Thr Phe Thr Ile Lys
    175                 180                 185

ctg aat aat aca atg aat gca tgt gct gca ata gcc gct ttg gaa aga      687
Leu Asn Asn Thr Met Asn Ala Cys Ala Ala Ile Ala Ala Leu Glu Arg
190                 195                 200                 205

gta aag att cga cca atg gaa cac tgc tgc tgt tct gtc agg ata ccc      735
Val Lys Ile Arg Pro Met Glu His Cys Cys Cys Ser Val Arg Ile Pro
                210                 215                 220

tgc cct tcc tcc cca gaa gag ttg gga aag ctt cag tgt gac ctg cag      783
Cys Pro Ser Ser Pro Glu Glu Leu Gly Lys Leu Gln Cys Asp Leu Gln
            225                 230                 235

gat ccc att gtc tgt ctt gct gac cat cca cgt ggc cca cca ttt tct      831
Asp Pro Ile Val Cys Leu Ala Asp His Pro Arg Gly Pro Pro Phe Ser
        240                 245                 250

tcc agc caa tcc atc cca gtg gtg cct cgg gcc act gtg ctt tcc cag      879
Ser Ser Gln Ser Ile Pro Val Val Pro Arg Ala Thr Val Leu Ser Gln
    255                 260                 265

gtc ccc aaa gct acc tct ttt gct gag cct cca gat tat tca cct gtg      927
Val Pro Lys Ala Thr Ser Phe Ala Glu Pro Pro Asp Tyr Ser Pro Val
270                 275                 280                 285

acc cac aat gtt ccc tct cca ata ggg gag att caa ccc ctt tca ccc      975
```

-continued

```
Thr His Asn Val Pro Ser Pro Ile Gly Glu Ile Gln Pro Leu Ser Pro
                290                 295                 300

cag cct tca gct ccc ata gct tcc agc cct gcc att gac atg ccc cca      1023
Gln Pro Ser Ala Pro Ile Ala Ser Ser Pro Ala Ile Asp Met Pro Pro
            305                 310                 315

cag tct gaa acg atc tct tcc cct atg ccc caa acc cat gtc tcc ggc      1071
Gln Ser Glu Thr Ile Ser Ser Pro Met Pro Gln Thr His Val Ser Gly
        320                 325                 330

acc cca cct cct gtg aaa gcc tca ttt tcc tct ccc acc gtg tct gcc      1119
Thr Pro Pro Pro Val Lys Ala Ser Phe Ser Ser Pro Thr Val Ser Ala
    335                 340                 345

cct gcg aat gtc aac act acc agc gca cct cct gtc cag aca gac atc      1167
Pro Ala Asn Val Asn Thr Thr Ser Ala Pro Pro Val Gln Thr Asp Ile
350                 355                 360                 365

gtc aac acc agc agt att tct gat ctt gag aac caa gtg ttg cag atg      1215
Val Asn Thr Ser Ser Ile Ser Asp Leu Glu Asn Gln Val Leu Gln Met
                370                 375                 380

gag aag gct ctg tcc ttg ggc agc ctg gag cct aac ctc gca gga gaa      1263
Glu Lys Ala Leu Ser Leu Gly Ser Leu Glu Pro Asn Leu Ala Gly Glu
            385                 390                 395

atg atc aac caa gtc agc aga ctc ctt cat tcc ccg cct gac atg ctg      1311
Met Ile Asn Gln Val Ser Arg Leu Leu His Ser Pro Pro Asp Met Leu
        400                 405                 410

gcc cct ctg gct caa aga ttg ctg aaa gta gtg gat gac att ggc cta      1359
Ala Pro Leu Ala Gln Arg Leu Leu Lys Val Val Asp Asp Ile Gly Leu
    415                 420                 425

cag ctg aac ttt tca aac acg act ata agt cta acc tcc cct tct ttg      1407
Gln Leu Asn Phe Ser Asn Thr Thr Ile Ser Leu Thr Ser Pro Ser Leu
430                 435                 440                 445

gct ctg gct gtg atc aga gtg aat gcc agt agt ttc aac aca act acc      1455
Ala Leu Ala Val Ile Arg Val Asn Ala Ser Ser Phe Asn Thr Thr Thr
                450                 455                 460

ttt gtg gcc caa gac cct gca aat ctt cag gtt tct ctg gaa acc caa      1503
Phe Val Ala Gln Asp Pro Ala Asn Leu Gln Val Ser Leu Glu Thr Gln
            465                 470                 475

gct cct gag aac agt att ggc aca att act ctt cct tca tcg ctg atg      1551
Ala Pro Glu Asn Ser Ile Gly Thr Ile Thr Leu Pro Ser Ser Leu Met
        480                 485                 490

aat aat tta cca gct cat gac atg gag cta gct tcc agg gtt cag ttc      1599
Asn Asn Leu Pro Ala His Asp Met Glu Leu Ala Ser Arg Val Gln Phe
    495                 500                 505

aat ttt ttt gaa aca cct gct ttg ttt cag gat cct tcc ctg gag aac      1647
Asn Phe Phe Glu Thr Pro Ala Leu Phe Gln Asp Pro Ser Leu Glu Asn
510                 515                 520                 525

ctc tct ctg atc agc tac gtc ata tca tcg agt gtt gca aac ctg acc      1695
Leu Ser Leu Ile Ser Tyr Val Ile Ser Ser Ser Val Ala Asn Leu Thr
                530                 535                 540

gtc agg aac ttg aca aga aac gtg aca gtc aca tta aag cac atc aac      1743
Val Arg Asn Leu Thr Arg Asn Val Thr Val Thr Leu Lys His Ile Asn
            545                 550                 555

ccg agc cag gat gag tta aca gtg aga tgt gta ttt tgg gac ttg ggc      1791
Pro Ser Gln Asp Glu Leu Thr Val Arg Cys Val Phe Trp Asp Leu Gly
        560                 565                 570

aga aat ggt ggc aga gga ggc tgg tca gac aat ggc tgc tct gtc aaa      1839
Arg Asn Gly Gly Arg Gly Gly Trp Ser Asp Asn Gly Cys Ser Val Lys
    575                 580                 585

gac agg aga ttg aat gaa acc atc tgt acc tgt agc cat cta aca agc      1887
Asp Arg Arg Leu Asn Glu Thr Ile Cys Thr Cys Ser His Leu Thr Ser
590                 595                 600                 605
```

-continued

```
ttc ggc gtt ctg ctg gac cta tct agg aca tct gtg ctg cct gct caa      1935
Phe Gly Val Leu Leu Asp Leu Ser Arg Thr Ser Val Leu Pro Ala Gln
                610                 615                 620

atg atg gct ctg acg ttc att aca tat att ggt tgt ggg ctt tca tca      1983
Met Met Ala Leu Thr Phe Ile Thr Tyr Ile Gly Cys Gly Leu Ser Ser
            625                 630                 635

att ttt ctg tca gtg act ctt gta acc tac ata gct ttt gaa aag atc      2031
Ile Phe Leu Ser Val Thr Leu Val Thr Tyr Ile Ala Phe Glu Lys Ile
        640                 645                 650

cgg agg gat tac cct tcc aaa atc ctc atc cag ctg tgt gct gct ctg      2079
Arg Arg Asp Tyr Pro Ser Lys Ile Leu Ile Gln Leu Cys Ala Ala Leu
    655                 660                 665

ctt ctg ctg aac ctg gtc ttc ctc ctg gac tcg tgg att gct ctg tat      2127
Leu Leu Leu Asn Leu Val Phe Leu Leu Asp Ser Trp Ile Ala Leu Tyr
670                 675                 680                 685

aag atg caa ggc ctc tgc atc tca gtg gct gta ttt ctt cat tat ttt      2175
Lys Met Gln Gly Leu Cys Ile Ser Val Ala Val Phe Leu His Tyr Phe
                690                 695                 700

ctc ttg gtc tca ttc aca tgg atg ggc cta gaa gca ttc cat atg tac      2223
Leu Leu Val Ser Phe Thr Trp Met Gly Leu Glu Ala Phe His Met Tyr
            705                 710                 715

ctg gcc ctt gtc aaa gta ttt aat act tac atc cga aaa tac atc ctt      2271
Leu Ala Leu Val Lys Val Phe Asn Thr Tyr Ile Arg Lys Tyr Ile Leu
        720                 725                 730

aaa ttc tgc att gtc ggt tgg ggg gta cca gct gtg gtt gtg acc atc      2319
Lys Phe Cys Ile Val Gly Trp Gly Val Pro Ala Val Val Val Thr Ile
    735                 740                 745

atc ctg act ata tcc cca gat aac tat ggg ctt gga tcc tat ggg aaa      2367
Ile Leu Thr Ile Ser Pro Asp Asn Tyr Gly Leu Gly Ser Tyr Gly Lys
750                 755                 760                 765

ttc ccc aat ggt tca ccg gat gac ttc tgc tgg atc aac aac aat gca      2415
Phe Pro Asn Gly Ser Pro Asp Asp Phe Cys Trp Ile Asn Asn Asn Ala
                770                 775                 780

gta ttc tac att acg gtg gtg gga tat ttc tgt gtg ata ttt ttg ctg      2463
Val Phe Tyr Ile Thr Val Val Gly Tyr Phe Cys Val Ile Phe Leu Leu
            785                 790                 795

aac gtc agc atg ttc att gtg gtc ctg gtt cag ctc tgt cga att aaa      2511
Asn Val Ser Met Phe Ile Val Val Leu Val Gln Leu Cys Arg Ile Lys
        800                 805                 810

aag aag aag caa ctg gga gcc cag cga aaa acc agt att caa gac ctc      2559
Lys Lys Lys Gln Leu Gly Ala Gln Arg Lys Thr Ser Ile Gln Asp Leu
    815                 820                 825

agg agt atc gct ggc ctt aca ttt tta ctg gga ata act tgg ggc ttt      2607
Arg Ser Ile Ala Gly Leu Thr Phe Leu Leu Gly Ile Thr Trp Gly Phe
830                 835                 840                 845

gcc ttc ttt gcc tgg gga cca gtt aac gtg acc ttc atg tat ctg ttt      2655
Ala Phe Phe Ala Trp Gly Pro Val Asn Val Thr Phe Met Tyr Leu Phe
                850                 855                 860

gcc atc ttt aat acc tta caa gga ttt ttc ata ttc atc ttt tac tgt      2703
Ala Ile Phe Asn Thr Leu Gln Gly Phe Phe Ile Phe Ile Phe Tyr Cys
            865                 870                 875

gtg gcc aaa gaa aat gtc agg aag caa tgg agg cgg tat ctt tgt tgt      2751
Val Ala Lys Glu Asn Val Arg Lys Gln Trp Arg Arg Tyr Leu Cys Cys
        880                 885                 890

gga aag tta cgg ctg gct gaa aat tct gac tgg agt aaa act gct act      2799
Gly Lys Leu Arg Leu Ala Glu Asn Ser Asp Trp Ser Lys Thr Ala Thr
    895                 900                 905

aat ggt tta aag aag cag act gta aac caa gga gtg tcc agc tct tca      2847
Asn Gly Leu Lys Lys Gln Thr Val Asn Gln Gly Val Ser Ser Ser Ser
910                 915                 920                 925
```

```
aat tcc tta cag tca agc agt aac tcc act aac tcc acc aca ctg cta     2895
Asn Ser Leu Gln Ser Ser Ser Asn Ser Thr Asn Ser Thr Thr Leu Leu
                930                 935                 940

gtg aat aat gat tgc tca gta cac gca agc ggg aat gga aat gct tct     2943
Val Asn Asn Asp Cys Ser Val His Ala Ser Gly Asn Gly Asn Ala Ser
            945                 950                 955

aca gag agg aat ggg gtc tct ttt agt gtt cag aat gga gat gtg tgc     2991
Thr Glu Arg Asn Gly Val Ser Phe Ser Val Gln Asn Gly Asp Val Cys
        960                 965                 970

ctt cac gat ttc act gga aaa cag cac atg ttt aac gag aag gaa gat     3039
Leu His Asp Phe Thr Gly Lys Gln His Met Phe Asn Glu Lys Glu Asp
    975                 980                 985

tcc tgc aat ggg aaa ggc cgt atg gct ctc aga  agg act tca aag cgg    3087
Ser Cys Asn Gly Lys Gly Arg Met Ala Leu Arg  Arg Thr Ser Lys Arg
990                 995                 1000                1005

gga agc tta cac ttt  att gag caa atg tga ttcctttctt ctaaaatcaa      3137
Gly Ser Leu His Phe  Ile Glu Gln Met
                1010

agcatgatgc ttgacagtgt gaaatgtcca attttacctt ttacacaatg tgagatgtat   3197

gaaaatcaac tcattttatt ctcggcaaca tctggagaag cataagctaa ttaagggcga   3257

tgattattat tacaagaaga aaccaagaca ttacaccatg gtttttagac atttctgatt   3317

tggtttctta tctttcattt tataagaagg ttggttttaa acaatacact aagaatgact   3377

cctataaaga aaacaaaaaa aggtagtgaa ctttcagcta ccttttaaag aggctaagtt   3437

atctttgata acatcatata aagcaactgt tgacttcagc ctgttggtga gtttagttgt   3497

gcatgccttt gttgtatata agctaaattc tagtgaccca tgtgtcaaaa atcttacttc   3557

tacatttttt tgtatttatt ttctactgtg taaatgtatt cctttgtaga atcatggttg   3617

ttttgtctca cgtgataatt cagaaaatcc ttgctcgttc cgcaaatcct aaagctcctt   3677

ttggagatga tataggatgt gaaatacaga aacctcagtg aaatcaagaa ataatgatcc   3737

cagccagact gagaaaatgt aagcagacag tgccacagtt agctcataca gtgcctttga   3797

gcaagttagg aaaagatgcc ccactgggc agacacagcc ctatgggtca tggtttgaca    3857

aacagagtga gagaccatat tttagcccca ctcaccctct tgggtgcacg acctgtacag   3917

ccaaacacag catccaatat gaatacccat cccctgaccg catccccagt agtcagatta   3977

tagaatctgc accaagatgt ttagctttat accttggcca cagagaggga tgaactgtca   4037

tccagaccat gtgtcaggaa aattgtgaac gtagatgagg tacatacact gccgcttctc   4097

aaatccccag agcctttagg aacaggagag tagactagga ttccttctct taaaaaggta   4157

catatatatg gaaaaaaatc atattgccgt tctttaaaag gcaactgcat ggtacattgt   4217

tgattgttat gactggtaca ctctggccca gccagagcta taattgtttt ttaaatgtgt   4277

cttgaagaat gcacagtgac aaggggagta gctattggga acagggaact gtcctacact   4337

gctattgttg ctacatgtat cgagccttga ttgctcctag ttatatacag ggtctatctt   4397

gcttcctacc tacatctgct tgagcagtgc ctcaagtaca tccttattag gaacatttca   4457

aacccctttt agttaagtct ttcactaagg ttctcttgca tatatttcaa gtgaatgttg   4517

gatctcagac taaccatagt aataatacac atttctgtga gtgctgactt gtctttgcaa   4577

tatttctttt ctgatttatt taattttctt gtatttatat gttaaaatca aaaatgttaa   4637

aatcaatgaa ataaatttgc agttaaga                                      4665
```

<210> SEQ ID NO 28

<211> LENGTH: 1014
<212> TYPE: PRT
<213> ORGANISM: Homo sapiens

<400> SEQUENCE: 28

```
Met Val Phe Ser Val Arg Gln Cys Gly His Val Gly Arg Thr Glu Glu
1               5                   10                  15

Val Leu Leu Thr Phe Lys Ile Phe Leu Val Ile Ile Cys Leu His Val
            20                  25                  30

Val Leu Val Thr Ser Leu Glu Glu Asp Thr Asp Asn Ser Ser Leu Ser
        35                  40                  45

Pro Pro Pro Ala Lys Leu Ser Val Val Ser Phe Ala Pro Ser Ser Asn
    50                  55                  60

Glu Val Glu Thr Thr Ser Leu Asn Asp Val Thr Leu Ser Leu Leu Pro
65                  70                  75                  80

Ser Asn Glu Thr Glu Lys Thr Lys Ile Thr Ile Val Lys Thr Phe Asn
                85                  90                  95

Ala Ser Gly Val Lys Pro Gln Arg Asn Ile Cys Asn Leu Ser Ser Ile
            100                 105                 110

Cys Asn Asp Ser Ala Phe Phe Arg Gly Glu Ile Met Phe Gln Tyr Asp
        115                 120                 125

Lys Glu Ser Thr Val Pro Gln Asn Gln His Ile Thr Asn Gly Thr Leu
    130                 135                 140

Thr Gly Val Leu Ser Leu Ser Glu Leu Lys Arg Ser Glu Leu Asn Lys
145                 150                 155                 160

Thr Leu Gln Thr Leu Ser Glu Thr Tyr Phe Ile Met Cys Ala Thr Ala
                165                 170                 175

Glu Ala Gln Ser Thr Leu Asn Cys Thr Phe Thr Ile Lys Leu Asn Asn
            180                 185                 190

Thr Met Asn Ala Cys Ala Ala Ile Ala Ala Leu Glu Arg Val Lys Ile
        195                 200                 205

Arg Pro Met Glu His Cys Cys Cys Ser Val Arg Ile Pro Cys Pro Ser
    210                 215                 220

Ser Pro Glu Glu Leu Gly Lys Leu Gln Cys Asp Leu Gln Asp Pro Ile
225                 230                 235                 240

Val Cys Leu Ala Asp His Pro Arg Gly Pro Pro Phe Ser Ser Ser Gln
                245                 250                 255

Ser Ile Pro Val Val Pro Arg Ala Thr Val Leu Ser Gln Val Pro Lys
            260                 265                 270

Ala Thr Ser Phe Ala Glu Pro Pro Asp Tyr Ser Pro Val Thr His Asn
        275                 280                 285

Val Pro Ser Pro Ile Gly Glu Ile Gln Pro Leu Ser Pro Gln Pro Ser
    290                 295                 300

Ala Pro Ile Ala Ser Ser Pro Ala Ile Asp Met Pro Pro Gln Ser Glu
305                 310                 315                 320

Thr Ile Ser Ser Pro Met Pro Gln Thr His Val Ser Gly Thr Pro Pro
                325                 330                 335

Pro Val Lys Ala Ser Phe Ser Ser Pro Thr Val Ser Ala Pro Ala Asn
            340                 345                 350

Val Asn Thr Thr Ser Ala Pro Pro Val Gln Thr Asp Ile Val Asn Thr
        355                 360                 365

Ser Ser Ile Ser Asp Leu Glu Asn Gln Val Leu Gln Met Glu Lys Ala
    370                 375                 380

Leu Ser Leu Gly Ser Leu Glu Pro Asn Leu Ala Gly Glu Met Ile Asn
```

-continued

```
385                 390                 395                 400

Gln Val Ser Arg Leu Leu His Ser Pro Pro Asp Met Leu Ala Pro Leu
                405                 410                 415

Ala Gln Arg Leu Leu Lys Val Val Asp Asp Ile Gly Leu Gln Leu Asn
            420                 425                 430

Phe Ser Asn Thr Thr Ile Ser Leu Thr Ser Pro Ser Leu Ala Leu Ala
        435                 440                 445

Val Ile Arg Val Asn Ala Ser Ser Phe Asn Thr Thr Thr Phe Val Ala
    450                 455                 460

Gln Asp Pro Ala Asn Leu Gln Val Ser Leu Glu Thr Gln Ala Pro Glu
465                 470                 475                 480

Asn Ser Ile Gly Thr Ile Thr Leu Pro Ser Ser Leu Met Asn Asn Leu
                485                 490                 495

Pro Ala His Asp Met Glu Leu Ala Ser Arg Val Gln Phe Asn Phe Phe
            500                 505                 510

Glu Thr Pro Ala Leu Phe Gln Asp Pro Ser Leu Glu Asn Leu Ser Leu
        515                 520                 525

Ile Ser Tyr Val Ile Ser Ser Ser Val Ala Asn Leu Thr Val Arg Asn
    530                 535                 540

Leu Thr Arg Asn Val Thr Val Thr Leu Lys His Ile Asn Pro Ser Gln
545                 550                 555                 560

Asp Glu Leu Thr Val Arg Cys Val Phe Trp Asp Leu Gly Arg Asn Gly
                565                 570                 575

Gly Arg Gly Gly Trp Ser Asp Asn Gly Cys Ser Val Lys Asp Arg Arg
            580                 585                 590

Leu Asn Glu Thr Ile Cys Thr Cys Ser His Leu Thr Ser Phe Gly Val
        595                 600                 605

Leu Leu Asp Leu Ser Arg Thr Ser Val Leu Pro Ala Gln Met Met Ala
    610                 615                 620

Leu Thr Phe Ile Thr Tyr Ile Gly Cys Gly Leu Ser Ser Ile Phe Leu
625                 630                 635                 640

Ser Val Thr Leu Val Thr Tyr Ile Ala Phe Glu Lys Ile Arg Arg Asp
                645                 650                 655

Tyr Pro Ser Lys Ile Leu Ile Gln Leu Cys Ala Ala Leu Leu Leu Leu
            660                 665                 670

Asn Leu Val Phe Leu Leu Asp Ser Trp Ile Ala Leu Tyr Lys Met Gln
        675                 680                 685

Gly Leu Cys Ile Ser Val Ala Val Phe Leu His Tyr Phe Leu Leu Val
    690                 695                 700

Ser Phe Thr Trp Met Gly Leu Glu Ala Phe His Met Tyr Leu Ala Leu
705                 710                 715                 720

Val Lys Val Phe Asn Thr Tyr Ile Arg Lys Tyr Ile Leu Lys Phe Cys
                725                 730                 735

Ile Val Gly Trp Gly Val Pro Ala Val Val Val Thr Ile Ile Leu Thr
            740                 745                 750

Ile Ser Pro Asp Asn Tyr Gly Leu Gly Ser Tyr Gly Lys Phe Pro Asn
        755                 760                 765

Gly Ser Pro Asp Asp Phe Cys Trp Ile Asn Asn Asn Ala Val Phe Tyr
    770                 775                 780

Ile Thr Val Val Gly Tyr Phe Cys Val Ile Phe Leu Leu Asn Val Ser
785                 790                 795                 800

Met Phe Ile Val Val Leu Val Gln Leu Cys Arg Ile Lys Lys Lys Lys
                805                 810                 815
```

```
Gln Leu Gly Ala Gln Arg Lys Thr Ser Ile Gln Asp Leu Arg Ser Ile
            820                 825                 830

Ala Gly Leu Thr Phe Leu Leu Gly Ile Thr Trp Gly Phe Ala Phe Phe
        835                 840                 845

Ala Trp Gly Pro Val Asn Val Thr Phe Met Tyr Leu Phe Ala Ile Phe
    850                 855                 860

Asn Thr Leu Gln Gly Phe Phe Ile Phe Ile Phe Tyr Cys Val Ala Lys
865                 870                 875                 880

Glu Asn Val Arg Lys Gln Trp Arg Arg Tyr Leu Cys Cys Gly Lys Leu
                885                 890                 895

Arg Leu Ala Glu Asn Ser Asp Trp Ser Lys Thr Ala Thr Asn Gly Leu
            900                 905                 910

Lys Lys Gln Thr Val Asn Gln Gly Val Ser Ser Ser Ser Asn Ser Leu
        915                 920                 925

Gln Ser Ser Ser Asn Ser Thr Asn Ser Thr Thr Leu Leu Val Asn Asn
    930                 935                 940

Asp Cys Ser Val His Ala Ser Gly Asn Gly Asn Ala Ser Thr Glu Arg
945                 950                 955                 960

Asn Gly Val Ser Phe Ser Val Gln Asn Gly Asp Val Cys Leu His Asp
                965                 970                 975

Phe Thr Gly Lys Gln His Met Phe Asn Glu Lys Glu Asp Ser Cys Asn
            980                 985                 990

Gly Lys Gly Arg Met Ala Leu Arg  Arg Thr Ser Lys Arg  Gly Ser Leu
        995                 1000                1005

His Phe  Ile Glu Gln Met
    1010


<210> SEQ ID NO 29
<211> LENGTH: 3362
<212> TYPE: DNA
<213> ORGANISM: Homo sapiens
<220> FEATURE:
<221> NAME/KEY: CDS
<222> LOCATION: (20)..(3319)

<400> SEQUENCE: 29

aaaaaatcaa ttttggaag atg tca ctg aac aac tct tcc aat gta ttt ctg      52
                     Met Ser Leu Asn Asn Ser Ser Asn Val Phe Leu
                     1               5                   10

gat tca gtg ccc agt aat acc aat cgc ttt caa gtt agt gtc ata aat      100
Asp Ser Val Pro Ser Asn Thr Asn Arg Phe Gln Val Ser Val Ile Asn
            15                  20                  25

gag aac cat gag agc agt gca gct gca gat gac aat act gac cca cca      148
Glu Asn His Glu Ser Ser Ala Ala Ala Asp Asp Asn Thr Asp Pro Pro
        30                  35                  40

cat tat gaa gaa acc tct ttt ggg gat gaa gct cag aaa aga ctc aga      196
His Tyr Glu Glu Thr Ser Phe Gly Asp Glu Ala Gln Lys Arg Leu Arg
    45                  50                  55

atc agc ttt agg cct ggg aat cag gag tgc tat gac aat ttc ctc cac      244
Ile Ser Phe Arg Pro Gly Asn Gln Glu Cys Tyr Asp Asn Phe Leu His
60                  65                  70                  75

agt gga gaa act gct aaa aca gat gcc agt ttt cac gct tat gat tct      292
Ser Gly Glu Thr Ala Lys Thr Asp Ala Ser Phe His Ala Tyr Asp Ser
                80                  85                  90

cac aca aac aca tac tat cta caa act ttt ggc cac aac acc atg gat      340
His Thr Asn Thr Tyr Tyr Leu Gln Thr Phe Gly His Asn Thr Met Asp
            95                  100                 105
```

-continued

```
gcc gtt ccc aag ata gag tac tat cgt aac acc ggc agc atc agt ggg      388
Ala Val Pro Lys Ile Glu Tyr Tyr Arg Asn Thr Gly Ser Ile Ser Gly
        110                 115                 120

ccc aag gtc aac cga ccc agc ctg ctt gag att cac gag caa ctc gca      436
Pro Lys Val Asn Arg Pro Ser Leu Leu Glu Ile His Glu Gln Leu Ala
    125                 130                 135

aag aat gtg gca gtc acc cca agt tca gct gac aga gtt gct aac ggt      484
Lys Asn Val Ala Val Thr Pro Ser Ser Ala Asp Arg Val Ala Asn Gly
140                 145                 150                 155

gat ggg ata cct gga gat gaa caa gct gaa aat aag gaa gat gat caa      532
Asp Gly Ile Pro Gly Asp Glu Gln Ala Glu Asn Lys Glu Asp Asp Gln
                160                 165                 170

gct ggt gtt gtg aag ttt gga tgg gtg aaa ggt gtg ctg gta aga tgc      580
Ala Gly Val Val Lys Phe Gly Trp Val Lys Gly Val Leu Val Arg Cys
            175                 180                 185

atg ctg aac atc tgg gga gtc atg ctc ttc att cgc ctc tcc tgg att      628
Met Leu Asn Ile Trp Gly Val Met Leu Phe Ile Arg Leu Ser Trp Ile
        190                 195                 200

gtt gga gaa gct gga att ggt ctt gga gtt atc atc att ggc cta tcc      676
Val Gly Glu Ala Gly Ile Gly Leu Gly Val Ile Ile Ile Gly Leu Ser
    205                 210                 215

acc ata gta acg aca atc aca ggt atg tcc acg tct gct att gcc acg      724
Thr Ile Val Thr Thr Ile Thr Gly Met Ser Thr Ser Ala Ile Ala Thr
220                 225                 230                 235

aac gga gtt gtt aga gga ggt ggg gcc tac tat ctt att tcc aga agt      772
Asn Gly Val Val Arg Gly Gly Gly Ala Tyr Tyr Leu Ile Ser Arg Ser
                240                 245                 250

tta ggg ccc gag ttc ggt ggg tca ata ggc ctg atc ttt gct ttt gct      820
Leu Gly Pro Glu Phe Gly Gly Ser Ile Gly Leu Ile Phe Ala Phe Ala
            255                 260                 265

aat gca gtg gct gtt gct atg tat gtg gtg gga ttc gct gaa act gta      868
Asn Ala Val Ala Val Ala Met Tyr Val Val Gly Phe Ala Glu Thr Val
        270                 275                 280

gta gat cta ctt aag gag agt gat tcg atg atg gtg gat cca acc aat      916
Val Asp Leu Leu Lys Glu Ser Asp Ser Met Met Val Asp Pro Thr Asn
    285                 290                 295

gac atc cgg att ata ggc tcc atc aca gtg gtg att ctt cta gga att      964
Asp Ile Arg Ile Ile Gly Ser Ile Thr Val Val Ile Leu Leu Gly Ile
300                 305                 310                 315

tca gta gct gga atg gaa tgg gag gca aag gcc caa gtc att ctt ctg     1012
Ser Val Ala Gly Met Glu Trp Glu Ala Lys Ala Gln Val Ile Leu Leu
                320                 325                 330

gtc att ctt cta att gct att gca aac ttc ttc att gga act gtc att     1060
Val Ile Leu Leu Ile Ala Ile Ala Asn Phe Phe Ile Gly Thr Val Ile
            335                 340                 345

cca tcc aac aat gag aaa aag tcc aga ggt ttc ttt aat tac caa gca     1108
Pro Ser Asn Asn Glu Lys Lys Ser Arg Gly Phe Phe Asn Tyr Gln Ala
        350                 355                 360

tca ata ttt gca gaa aac ttt ggg cca cgc ttc aca aag ggt gaa ggc     1156
Ser Ile Phe Ala Glu Asn Phe Gly Pro Arg Phe Thr Lys Gly Glu Gly
    365                 370                 375

ttc ttc tct gtc ttt gcc att ttt ttc cca gca gct act ggg att ctt     1204
Phe Phe Ser Val Phe Ala Ile Phe Phe Pro Ala Ala Thr Gly Ile Leu
380                 385                 390                 395

gct ggt gcc aat atc tca gga gat ttg gag gat ccc caa gat gcc atc     1252
Ala Gly Ala Asn Ile Ser Gly Asp Leu Glu Asp Pro Gln Asp Ala Ile
                400                 405                 410

ccc aga gga acc atg ctg gcc att ttc atc acc act gtt gcc tac tta     1300
Pro Arg Gly Thr Met Leu Ala Ile Phe Ile Thr Thr Val Ala Tyr Leu
            415                 420                 425
```

```
ggg gtt gca att tgt gta ggg gcc tgt gtg gtc cga gat gcc acc ggg      1348
Gly Val Ala Ile Cys Val Gly Ala Cys Val Val Arg Asp Ala Thr Gly
        430                 435                 440

aac atg aat gac acc atc att tct ggg atg aac tgc aat ggt tca gca      1396
Asn Met Asn Asp Thr Ile Ile Ser Gly Met Asn Cys Asn Gly Ser Ala
    445                 450                 455

gca tgt ggg ttg ggc tat gac ttc tca aga tgt cga cat gaa cca tgt      1444
Ala Cys Gly Leu Gly Tyr Asp Phe Ser Arg Cys Arg His Glu Pro Cys
460                 465                 470                 475

cag tac ggg ctg atg aac aat ttc cag gtc atg agc atg gta tca ggg      1492
Gln Tyr Gly Leu Met Asn Asn Phe Gln Val Met Ser Met Val Ser Gly
                480                 485                 490

ttc ggc ccc ctc atc act gcg gga atc ttt tct gca aca ctc tcc tcc      1540
Phe Gly Pro Leu Ile Thr Ala Gly Ile Phe Ser Ala Thr Leu Ser Ser
            495                 500                 505

gcc ctg gcc tcc ctt gtc agc gca ccc aaa gtg ttc cag gct ctg tgc      1588
Ala Leu Ala Ser Leu Val Ser Ala Pro Lys Val Phe Gln Ala Leu Cys
        510                 515                 520

aag gac aac atc tac aaa gcc ctg cag ttt ttt gca aag gga tat ggg      1636
Lys Asp Asn Ile Tyr Lys Ala Leu Gln Phe Phe Ala Lys Gly Tyr Gly
    525                 530                 535

aaa aac aat gaa ccc ctg aga gga tat att ctc act ttt ctt ata gcc      1684
Lys Asn Asn Glu Pro Leu Arg Gly Tyr Ile Leu Thr Phe Leu Ile Ala
540                 545                 550                 555

atg gca ttt att ctt att gcg gaa ctg aac acc att gct ccc atc atc      1732
Met Ala Phe Ile Leu Ile Ala Glu Leu Asn Thr Ile Ala Pro Ile Ile
                560                 565                 570

tcc aac ttt ttc ctg gcc tca tat gca ctt att aat ttc tcc tgc ttc      1780
Ser Asn Phe Phe Leu Ala Ser Tyr Ala Leu Ile Asn Phe Ser Cys Phe
            575                 580                 585

cat gcc tct tat gcc aaa tct cca gga tgg aga cct gcg tat gga att      1828
His Ala Ser Tyr Ala Lys Ser Pro Gly Trp Arg Pro Ala Tyr Gly Ile
        590                 595                 600

tac aac atg tgg gta tct ctt ttt gga gct gtt ttg tgc tgt gca gtc      1876
Tyr Asn Met Trp Val Ser Leu Phe Gly Ala Val Leu Cys Cys Ala Val
    605                 610                 615

atg ttt gtc atc aac tgg tgg gca gct gtc atc acc tat gtc att gaa      1924
Met Phe Val Ile Asn Trp Trp Ala Ala Val Ile Thr Tyr Val Ile Glu
620                 625                 630                 635

ttc ttc ctt tac gtc tat gtg act tgt aag aag cca gat gtg aac tgg      1972
Phe Phe Leu Tyr Val Tyr Val Thr Cys Lys Lys Pro Asp Val Asn Trp
                640                 645                 650

ggc tcc tcc aca cag gct ctt tcc tac gtg agt gct tta gac aat gct      2020
Gly Ser Ser Thr Gln Ala Leu Ser Tyr Val Ser Ala Leu Asp Asn Ala
            655                 660                 665

ctg gaa tta acc aca gtg gaa gac cac gta aaa aac ttc agg ccc cag      2068
Leu Glu Leu Thr Thr Val Glu Asp His Val Lys Asn Phe Arg Pro Gln
        670                 675                 680

tgc att gtc tta aca ggg gga ccc atg aca aga cct gct ctc ctg gac      2116
Cys Ile Val Leu Thr Gly Gly Pro Met Thr Arg Pro Ala Leu Leu Asp
    685                 690                 695

ata act cac gcc ttt acc aag aac agt ggc ctt tgc atc tgc tgt gaa      2164
Ile Thr His Ala Phe Thr Lys Asn Ser Gly Leu Cys Ile Cys Cys Glu
700                 705                 710                 715

gtc ttt gtg gga ccg cgc aaa ctg tgt gtt aag gag atg aac agt ggc      2212
Val Phe Val Gly Pro Arg Lys Leu Cys Val Lys Glu Met Asn Ser Gly
                720                 725                 730

atg gcg aaa aaa cag gcc tgg ctt ata aag aac aaa atc aag gct ttt      2260
Met Ala Lys Lys Gln Ala Trp Leu Ile Lys Asn Lys Ile Lys Ala Phe
```

-continued 735 740 745 tat gct gca gtg gcg gca gac tgt ttc agg gat ggt gtc cga agt ctt 2308
Tyr Ala Ala Val Ala Ala Asp Cys Phe Arg Asp Gly Val Arg Ser Leu
750 755 760 ctt cag gcc tca ggc tta gga aga atg aaa cca aac act ctg gtg att 2356
Leu Gln Ala Ser Gly Leu Gly Arg Met Lys Pro Asn Thr Leu Val Ile
765 770 775 gga tat aag aaa aac tgg agg aaa gct ccc ttg aca gag att gag aac 2404
Gly Tyr Lys Lys Asn Trp Arg Lys Ala Pro Leu Thr Glu Ile Glu Asn
780 785 790 795 tac gtg gga atc ata cat gat gca ttt gat ttt gag att ggc gtg gtt 2452
Tyr Val Gly Ile Ile His Asp Ala Phe Asp Phe Glu Ile Gly Val Val
800 805 810 ata gtc aga atc agc caa gga ttt gac atc tct cag gtt ctt cag gtg 2500
Ile Val Arg Ile Ser Gln Gly Phe Asp Ile Ser Gln Val Leu Gln Val
815 820 825 caa gag gaa tta gag aga tta gaa cag gag aga cta gca ttg gaa gcg 2548
Gln Glu Glu Leu Glu Arg Leu Glu Gln Glu Arg Leu Ala Leu Glu Ala
830 835 840 act atc aaa gat aat gag tgt gaa gag gaa agt gga ggc atc cga ggc 2596
Thr Ile Lys Asp Asn Glu Cys Glu Glu Glu Ser Gly Gly Ile Arg Gly
845 850 855 ttg ttt aaa aaa gct ggc aag ttg aac att act aag aca acg cct aaa 2644
Leu Phe Lys Lys Ala Gly Lys Leu Asn Ile Thr Lys Thr Thr Pro Lys
860 865 870 875 aaa gat ggc agc att aac aca agc cag tcg atg cat gtg gga gag ttc 2692
Lys Asp Gly Ser Ile Asn Thr Ser Gln Ser Met His Val Gly Glu Phe
880 885 890 aac cag aaa ctg gtg gaa gcc agc act caa ttt aaa aag aaa caa gaa 2740
Asn Gln Lys Leu Val Glu Ala Ser Thr Gln Phe Lys Lys Lys Gln Glu
895 900 905 aaa ggc aca att gat gtt tgg tgg ttg ttt gat gat gga ggg tta aca 2788
Lys Gly Thr Ile Asp Val Trp Trp Leu Phe Asp Asp Gly Gly Leu Thr
910 915 920 ctt ctt atc ccc tat atc tta act ctc aga aaa aaa tgg aaa gac tgt 2836
Leu Leu Ile Pro Tyr Ile Leu Thr Leu Arg Lys Lys Trp Lys Asp Cys
925 930 935 aaa tta aga atc tat gtg gga ggg aag atc aac cgc att gaa gaa gaa 2884
Lys Leu Arg Ile Tyr Val Gly Gly Lys Ile Asn Arg Ile Glu Glu Glu
940 945 950 955 aaa att gca atg gct tcc ctt ctg agc aaa ttt agg ata aaa ttt gca 2932
Lys Ile Ala Met Ala Ser Leu Leu Ser Lys Phe Arg Ile Lys Phe Ala
960 965 970 gac atc cat atc atc ggt gac atc aac att agg cca aac aaa gag agc 2980
Asp Ile His Ile Ile Gly Asp Ile Asn Ile Arg Pro Asn Lys Glu Ser
975 980 985 tgg aaa gtc ttt gaa gag atg att gaa cca tat cgt ctc cat gaa agc 3028
Trp Lys Val Phe Glu Glu Met Ile Glu Pro Tyr Arg Leu His Glu Ser
990 995 1000 tgc aaa gat tta aca act gct gag aaa tta aaa aga gaa act ccg 3073
Cys Lys Asp Leu Thr Thr Ala Glu Lys Leu Lys Arg Glu Thr Pro
1005 1010 1015 tgg aaa att aca gat gca gaa ctg gaa gca gtc aag gaa aag agt 3118
Trp Lys Ile Thr Asp Ala Glu Leu Glu Ala Val Lys Glu Lys Ser
1020 1025 1030 tac cgc caa gtt cga ctg aat gaa ctc tta cag gag cac tcc aga 3163
Tyr Arg Gln Val Arg Leu Asn Glu Leu Leu Gln Glu His Ser Arg
1035 1040 1045 gct gct aat ctc att gtc ctg agc ctt ccc gtg gca aga aag gga 3208

-continued

```
Ala Ala  Asn Leu Ile Val Leu  Ser Leu Pro Val Ala  Arg Lys Gly
    1050                1055                1060

tcc ata  tcg gat ttg ttg tat  atg gct tgg ttg gaa  atc ctc aca      3253
Ser Ile  Ser Asp Leu Leu Tyr  Met Ala Trp Leu Glu  Ile Leu Thr
    1065                1070                1075

aag aac  ctc cca cct gtc tta  cta gtt aga gga aat  cac aaa aat      3298
Lys Asn  Leu Pro Pro Val Leu  Leu Val Arg Gly Asn  His Lys Asn
    1080                1085                1090

gtc ttg  aca ttt tac tct taa aacatgaaag attggaatac attttaactt       3349
Val Leu  Thr Phe Tyr Ser
    1095

aatgtaatgc ata                                                      3362


<210> SEQ ID NO 30
<211> LENGTH: 1099
<212> TYPE: PRT
<213> ORGANISM: Homo sapiens

<400> SEQUENCE: 30

Met Ser Leu Asn Asn Ser Ser Asn Val Phe Leu Asp Ser Val Pro Ser
1               5                   10                  15

Asn Thr Asn Arg Phe Gln Val Ser Val Ile Asn Glu Asn His Glu Ser
            20                  25                  30

Ser Ala Ala Ala Asp Asp Asn Thr Asp Pro Pro His Tyr Glu Glu Thr
        35                  40                  45

Ser Phe Gly Asp Glu Ala Gln Lys Arg Leu Arg Ile Ser Phe Arg Pro
    50                  55                  60

Gly Asn Gln Glu Cys Tyr Asp Asn Phe Leu His Ser Gly Glu Thr Ala
65                  70                  75                  80

Lys Thr Asp Ala Ser Phe His Ala Tyr Asp Ser His Thr Asn Thr Tyr
                85                  90                  95

Tyr Leu Gln Thr Phe Gly His Asn Thr Met Asp Ala Val Pro Lys Ile
            100                 105                 110

Glu Tyr Tyr Arg Asn Thr Gly Ser Ile Ser Gly Pro Lys Val Asn Arg
        115                 120                 125

Pro Ser Leu Leu Glu Ile His Glu Gln Leu Ala Lys Asn Val Ala Val
    130                 135                 140

Thr Pro Ser Ser Ala Asp Arg Val Ala Asn Gly Asp Gly Ile Pro Gly
145                 150                 155                 160

Asp Glu Gln Ala Glu Asn Lys Glu Asp Asp Gln Ala Gly Val Val Lys
                165                 170                 175

Phe Gly Trp Val Lys Gly Val Leu Val Arg Cys Met Leu Asn Ile Trp
            180                 185                 190

Gly Val Met Leu Phe Ile Arg Leu Ser Trp Ile Val Gly Glu Ala Gly
        195                 200                 205

Ile Gly Leu Gly Val Ile Ile Ile Gly Leu Ser Thr Ile Val Thr Thr
    210                 215                 220

Ile Thr Gly Met Ser Thr Ser Ala Ile Ala Thr Asn Gly Val Val Arg
225                 230                 235                 240

Gly Gly Gly Ala Tyr Tyr Leu Ile Ser Arg Ser Leu Gly Pro Glu Phe
                245                 250                 255

Gly Gly Ser Ile Gly Leu Ile Phe Ala Phe Ala Asn Ala Val Ala Val
            260                 265                 270

Ala Met Tyr Val Val Gly Phe Ala Glu Thr Val Val Asp Leu Leu Lys
        275                 280                 285
```

-continued

```
Glu Ser Asp Ser Met Met Val Asp Pro Thr Asn Asp Ile Arg Ile Ile
    290                 295                 300

Gly Ser Ile Thr Val Val Ile Leu Leu Gly Ile Ser Val Ala Gly Met
305                 310                 315                 320

Glu Trp Glu Ala Lys Ala Gln Val Ile Leu Leu Val Ile Leu Leu Ile
                325                 330                 335

Ala Ile Ala Asn Phe Phe Ile Gly Thr Val Ile Pro Ser Asn Asn Glu
            340                 345                 350

Lys Lys Ser Arg Gly Phe Phe Asn Tyr Gln Ala Ser Ile Phe Ala Glu
        355                 360                 365

Asn Phe Gly Pro Arg Phe Thr Lys Gly Glu Gly Phe Phe Ser Val Phe
    370                 375                 380

Ala Ile Phe Phe Pro Ala Ala Thr Gly Ile Leu Ala Gly Ala Asn Ile
385                 390                 395                 400

Ser Gly Asp Leu Glu Asp Pro Gln Asp Ala Ile Pro Arg Gly Thr Met
                405                 410                 415

Leu Ala Ile Phe Ile Thr Thr Val Ala Tyr Leu Gly Val Ala Ile Cys
            420                 425                 430

Val Gly Ala Cys Val Val Arg Asp Ala Thr Gly Asn Met Asn Asp Thr
        435                 440                 445

Ile Ile Ser Gly Met Asn Cys Asn Gly Ser Ala Ala Cys Gly Leu Gly
    450                 455                 460

Tyr Asp Phe Ser Arg Cys Arg His Glu Pro Cys Gln Tyr Gly Leu Met
465                 470                 475                 480

Asn Asn Phe Gln Val Met Ser Met Val Ser Gly Phe Gly Pro Leu Ile
                485                 490                 495

Thr Ala Gly Ile Phe Ser Ala Thr Leu Ser Ser Ala Leu Ala Ser Leu
            500                 505                 510

Val Ser Ala Pro Lys Val Phe Gln Ala Leu Cys Lys Asp Asn Ile Tyr
        515                 520                 525

Lys Ala Leu Gln Phe Phe Ala Lys Gly Tyr Gly Lys Asn Asn Glu Pro
    530                 535                 540

Leu Arg Gly Tyr Ile Leu Thr Phe Leu Ile Ala Met Ala Phe Ile Leu
545                 550                 555                 560

Ile Ala Glu Leu Asn Thr Ile Ala Pro Ile Ile Ser Asn Phe Phe Leu
                565                 570                 575

Ala Ser Tyr Ala Leu Ile Asn Phe Ser Cys Phe His Ala Ser Tyr Ala
            580                 585                 590

Lys Ser Pro Gly Trp Arg Pro Ala Tyr Gly Ile Tyr Asn Met Trp Val
        595                 600                 605

Ser Leu Phe Gly Ala Val Leu Cys Cys Ala Val Met Phe Val Ile Asn
    610                 615                 620

Trp Trp Ala Ala Val Ile Thr Tyr Val Ile Glu Phe Phe Leu Tyr Val
625                 630                 635                 640

Tyr Val Thr Cys Lys Lys Pro Asp Val Asn Trp Gly Ser Ser Thr Gln
                645                 650                 655

Ala Leu Ser Tyr Val Ser Ala Leu Asp Asn Ala Leu Glu Leu Thr Thr
            660                 665                 670

Val Glu Asp His Val Lys Asn Phe Arg Pro Gln Cys Ile Val Leu Thr
        675                 680                 685

Gly Gly Pro Met Thr Arg Pro Ala Leu Leu Asp Ile Thr His Ala Phe
    690                 695                 700

Thr Lys Asn Ser Gly Leu Cys Ile Cys Cys Glu Val Phe Val Gly Pro
```

-continued

```
705                 710                 715                 720

Arg Lys Leu Cys Val Lys Glu Met Asn Ser Gly Met Ala Lys Lys Gln
                725                 730                 735

Ala Trp Leu Ile Lys Asn Lys Ile Lys Ala Phe Tyr Ala Ala Val Ala
            740                 745                 750

Ala Asp Cys Phe Arg Asp Gly Val Arg Ser Leu Leu Gln Ala Ser Gly
        755                 760                 765

Leu Gly Arg Met Lys Pro Asn Thr Leu Val Ile Gly Tyr Lys Lys Asn
    770                 775                 780

Trp Arg Lys Ala Pro Leu Thr Glu Ile Glu Asn Tyr Val Gly Ile Ile
785                 790                 795                 800

His Asp Ala Phe Asp Phe Glu Ile Gly Val Val Ile Val Arg Ile Ser
                805                 810                 815

Gln Gly Phe Asp Ile Ser Gln Val Leu Gln Val Gln Glu Glu Leu Glu
            820                 825                 830

Arg Leu Glu Gln Glu Arg Leu Ala Leu Glu Ala Thr Ile Lys Asp Asn
        835                 840                 845

Glu Cys Glu Glu Glu Ser Gly Gly Ile Arg Gly Leu Phe Lys Lys Ala
    850                 855                 860

Gly Lys Leu Asn Ile Thr Lys Thr Thr Pro Lys Lys Asp Gly Ser Ile
865                 870                 875                 880

Asn Thr Ser Gln Ser Met His Val Gly Glu Phe Asn Gln Lys Leu Val
                885                 890                 895

Glu Ala Ser Thr Gln Phe Lys Lys Lys Gln Glu Lys Gly Thr Ile Asp
            900                 905                 910

Val Trp Trp Leu Phe Asp Asp Gly Gly Leu Thr Leu Leu Ile Pro Tyr
        915                 920                 925

Ile Leu Thr Leu Arg Lys Lys Trp Lys Asp Cys Lys Leu Arg Ile Tyr
    930                 935                 940

Val Gly Gly Lys Ile Asn Arg Ile Glu Glu Glu Lys Ile Ala Met Ala
945                 950                 955                 960

Ser Leu Leu Ser Lys Phe Arg Ile Lys Phe Ala Asp Ile His Ile Ile
                965                 970                 975

Gly Asp Ile Asn Ile Arg Pro Asn Lys Glu Ser Trp Lys Val Phe Glu
            980                 985                 990

Glu Met Ile Glu Pro Tyr Arg Leu  His Glu Ser Cys Lys  Asp Leu Thr
        995                 1000                 1005

Thr Ala  Glu Lys Leu Lys Arg  Glu Thr Pro Trp Lys  Ile Thr Asp
    1010                 1015                 1020

Ala Glu  Leu Glu Ala Val Lys  Glu Lys Ser Tyr Arg  Gln Val Arg
    1025                 1030                 1035

Leu Asn  Glu Leu Leu Gln Glu  His Ser Arg Ala Ala  Asn Leu Ile
    1040                 1045                 1050

Val Leu  Ser Leu Pro Val Ala  Arg Lys Gly Ser Ile  Ser Asp Leu
    1055                 1060                 1065

Leu Tyr  Met Ala Trp Leu Glu  Ile Leu Thr Lys Asn  Leu Pro Pro
    1070                 1075                 1080

Val Leu  Leu Val Arg Gly Asn  His Lys Asn Val Leu  Thr Phe Tyr
    1085                 1090                 1095

Ser
```

<210> SEQ ID NO 31
<211> LENGTH: 21

<212> TYPE: DNA
<213> ORGANISM: Artificial Sequence
<220> FEATURE:
<223> OTHER INFORMATION: Description fo the artificial sequence:
Oligonucleotide

<400> SEQUENCE: 31
cagcctccag aatgaagaat g 21

<210> SEQ ID NO 32
<211> LENGTH: 18
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 32
ggagggagac tgagattt 18

<210> SEQ ID NO 33
<211> LENGTH: 22
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 33
gcggctcact tggacttttt ca 22

<210> SEQ ID NO 34
<211> LENGTH: 20
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 34
gcatagtcat ctcttcttca 20

<210> SEQ ID NO 35
<211> LENGTH: 20
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 35
catactgaaa ggtgtgggct 20

<210> SEQ ID NO 36
<211> LENGTH: 18
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 36
ggtcccaaaa gtgtcgtt 18

<210> SEQ ID NO 37
<211> LENGTH: 19
<212> TYPE: DNA

```
<213> ORGANISM: Artificial Sequence
<220> FEATURE:
<223> OTHER INFORMATION: Description fo the artificial sequence:
      Oligonucleotide

<400> SEQUENCE: 37

gagggagatt ggtggtgtt                                                19


<210> SEQ ID NO 38
<211> LENGTH: 18
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 38

ccagagaaaa tgcccact                                                 18


<210> SEQ ID NO 39
<211> LENGTH: 20
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 39

aatgaacgac tgggtaacag                                               20


<210> SEQ ID NO 40
<211> LENGTH: 21
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 40

gaggagtatc ttgcttcttc a                                             21


<210> SEQ ID NO 41
<211> LENGTH: 22
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 41

gtgttcttct ggtggctcaa tc                                            22


<210> SEQ ID NO 42
<211> LENGTH: 16
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 42

ggcttctgtg cgtcat                                                   16


<210> SEQ ID NO 43
<211> LENGTH: 21
<212> TYPE: DNA
<213> ORGANISM: Artificial Sequence
```

<220> FEATURE:
<223> OTHER INFORMATION: Description fo the artificial sequence:
      Oligonucleotide

<400> SEQUENCE: 43
gctacatcat cctggctatc c 21

<210> SEQ ID NO 44
<211> LENGTH: 17
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 44
gcctcgctct cgttgcc 17

<210> SEQ ID NO 45
<211> LENGTH: 22
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 45
acagtgccct accacacaga tc 22

<210> SEQ ID NO 46
<211> LENGTH: 18
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 46
gggaaaaatc gctgttgg 18

<210> SEQ ID NO 47
<211> LENGTH: 20
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 47
aatagagtgc ctgcctggtt 20

<210> SEQ ID NO 48
<211> LENGTH: 20
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 48
tggataatga gtagcctgga 20

<210> SEQ ID NO 49
<211> LENGTH: 20
<212> TYPE: DNA
<213> ORGANISM: Artificial Sequence
<220> FEATURE:

<223> OTHER INFORMATION: Description fo the artificial sequence:
Oligonucleotide

<400> SEQUENCE: 49
ccacaaccaa gaagcaccaa 20

<210> SEQ ID NO 50
<211> LENGTH: 20
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 50
tgcggcttgt tgtagttgaa 20

<210> SEQ ID NO 51
<211> LENGTH: 17
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 51
ttggcttcct ggctaac 17

<210> SEQ ID NO 52
<211> LENGTH: 20
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 52
tggaggtgaa catcgcaaat 20

<210> SEQ ID NO 53
<211> LENGTH: 20
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 53
actgctgtct cgtggtatgc 20

<210> SEQ ID NO 54
<211> LENGTH: 25
<212> TYPE: DNA
<213> ORGANISM: Artificial Sequence
<220> FEATURE:
<223> OTHER INFORMATION: Description fo the artificial sequence:
Oligonucleotide

<400> SEQUENCE: 54
ggcaatttaa caactggttc tcggg 25

<210> SEQ ID NO 55
<211> LENGTH: 20
<212> TYPE: DNA
<213> ORGANISM: Artificial Sequence
<220> FEATURE:
<223> OTHER INFORMATION: Description fo the artificial sequence:

Oligonucleotide

<400> SEQUENCE: 55
ctaaaagggc agaagaagga 20

<210> SEQ ID NO 56
<211> LENGTH: 25
<212> TYPE: DNA
<213> ORGANISM: Artificial Sequence
<220> FEATURE:
<223> OTHER INFORMATION: Description fo the artificial sequence: Oligonucleotide

<400> SEQUENCE: 56
ctcccactga ctttcctgct ttctt 25

<210> SEQ ID NO 57
<211> LENGTH: 15
<212> TYPE: DNA
<213> ORGANISM: Artificial Sequence
<220> FEATURE:
<223> OTHER INFORMATION: Description fo the artificial sequence: Oligonucleotide

<400> SEQUENCE: 57
ttctcttggt ctcat 15

<210> SEQ ID NO 58
<211> LENGTH: 18
<212> TYPE: DNA
<213> ORGANISM: Artificial Sequence
<220> FEATURE:
<223> OTHER INFORMATION: Description fo the artificial sequence: Oligonucleotide

<400> SEQUENCE: 58
atccagcaga agtcatcc 18

<210> SEQ ID NO 59
<211> LENGTH: 19
<212> TYPE: DNA
<213> ORGANISM: Artificial Sequence
<220> FEATURE:
<223> OTHER INFORMATION: Description fo the artificial sequence: Oligonucleotide

<400> SEQUENCE: 59
catttattct tattgcgga 19

<210> SEQ ID NO 60
<211> LENGTH: 19
<212> TYPE: DNA
<213> ORGANISM: Artificial Sequence
<220> FEATURE:
<223> OTHER INFORMATION: Description fo the artificial sequence: Oligonucleotide

<400> SEQUENCE: 60
caaaaagaga tacccacat 19

<210> SEQ ID NO 61
<211> LENGTH: 15
<212> TYPE: PRT
<213> ORGANISM: Homo sapiens

<400> SEQUENCE: 61

Lys Ile Ser Val Ser Leu Pro Leu Ser Leu Ser Gln Ser Val Cys
1 5 10 15

<210> SEQ ID NO 62
<211> LENGTH: 14
<212> TYPE: PRT
<213> ORGANISM: Homo sapiens

<400> SEQUENCE: 62

Gln Leu Ser Lys Asp Thr Ser Val Leu Thr Phe Thr Phe Cys
1 5 10

<210> SEQ ID NO 63
<211> LENGTH: 17
<212> TYPE: PRT
<213> ORGANISM: Homo sapiens

<400> SEQUENCE: 63

Cys Ser Asp Ala His Pro Gly Asp Ser Ser Gly Asp Ser Ser Gly Leu
1 5 10 15

Asn

<210> SEQ ID NO 64
<211> LENGTH: 15
<212> TYPE: PRT
<213> ORGANISM: Homo sapiens

<400> SEQUENCE: 64

Arg Gly Glu Val Arg Gln Phe Thr Leu Arg His Trp Leu Lys Val
1 5 10 15

<210> SEQ ID NO 65
<211> LENGTH: 13
<212> TYPE: PRT
<213> ORGANISM: Homo sapiens

<400> SEQUENCE: 65

Gly Asp Tyr Leu Asn Asp Glu Ala Leu Trp Asn Lys Cys
1 5 10

<210> SEQ ID NO 66
<211> LENGTH: 15
<212> TYPE: PRT
<213> ORGANISM: Homo sapiens

<400> SEQUENCE: 66

Gly Lys Val Ile Asp Asp Asn Asp His Leu Ser Gln Glu Ile Cys
1 5 10 15

<210> SEQ ID NO 67
<211> LENGTH: 14
<212> TYPE: PRT
<213> ORGANISM: Homo sapiens

<400> SEQUENCE: 67

Leu Met Ala Asn Ser Thr Trp Gly Tyr Pro Phe His Asp Gly
1 5 10

<210> SEQ ID NO 68
<211> LENGTH: 14
<212> TYPE: PRT
<213> ORGANISM: Homo sapiens

<400> SEQUENCE: 68

```
Leu Asn Val Val Pro Trp Asn Leu Thr Leu Phe Ser Ile Leu
1               5                   10


<210> SEQ ID NO 69
<211> LENGTH: 303
<212> TYPE: DNA
<213> ORGANISM: Homo sapiens
<220> FEATURE:
<221> NAME/KEY: CDS
<222> LOCATION: (1)..(303)

<400> SEQUENCE: 69

atg ctt tgc tac atc att ctg caa tcc cag aag att ttt tgc ata ttt       48
Met Leu Cys Tyr Ile Ile Leu Gln Ser Gln Lys Ile Phe Cys Ile Phe
1               5                   10                  15

ttt tgc tat tac aga aaa tct cag tct ccc tcc ctc tct ctc tct ctc       96
Phe Cys Tyr Tyr Arg Lys Ser Gln Ser Pro Ser Leu Ser Leu Ser Leu
            20                  25                  30

aat ctg tgt gtc tct ttt act cca tat ctc tgt gtg tgt ctc ttt tac      144
Asn Leu Cys Val Ser Phe Thr Pro Tyr Leu Cys Val Cys Leu Phe Tyr
        35                  40                  45

tcc ata tct ctc tgt gtg tgt ctg ttt atg tct ctc tct ctc tct cat      192
Ser Ile Ser Leu Cys Val Cys Leu Phe Met Ser Leu Ser Leu Ser His
    50                  55                  60

cct tcc cat gtt tct ctc tca cac aca cac aca ctc att cac agc ttt      240
Pro Ser His Val Ser Leu Ser His Thr His Thr Leu Ile His Ser Phe
65                  70                  75                  80

caa aag aca cgt ctg tcc tta cct tca ctt ttt gtt tta aac agc aca      288
Gln Lys Thr Arg Leu Ser Leu Pro Ser Leu Phe Val Leu Asn Ser Thr
                85                  90                  95

ctc act tta ctc tga                                                  303
Leu Thr Leu Leu
            100


<210> SEQ ID NO 70
<211> LENGTH: 100
<212> TYPE: PRT
<213> ORGANISM: Homo sapiens

<400> SEQUENCE: 70

Met Leu Cys Tyr Ile Ile Leu Gln Ser Gln Lys Ile Phe Cys Ile Phe
1               5                   10                  15

Phe Cys Tyr Tyr Arg Lys Ser Gln Ser Pro Ser Leu Ser Leu Ser Leu
            20                  25                  30

Asn Leu Cys Val Ser Phe Thr Pro Tyr Leu Cys Val Cys Leu Phe Tyr
        35                  40                  45

Ser Ile Ser Leu Cys Val Cys Leu Phe Met Ser Leu Ser Leu Ser His
    50                  55                  60

Pro Ser His Val Ser Leu Ser His Thr His Thr Leu Ile His Ser Phe
65                  70                  75                  80

Gln Lys Thr Arg Leu Ser Leu Pro Ser Leu Phe Val Leu Asn Ser Thr
                85                  90                  95

Leu Thr Leu Leu
            100


<210> SEQ ID NO 71
<211> LENGTH: 1786
<212> TYPE: DNA
<213> ORGANISM: Homo sapiens
<220> FEATURE:
<221> NAME/KEY: CDS
<222> LOCATION: (204)..(494)
```

<400> SEQUENCE: 71

```
actcagctct ctcaccatgc gattgccctg caacaccttg gaactctgca gagagtcccc     60

agcaggaagg tctcacctga ggtgaacctt cgaccttgga cttctcagcc tccagaatga    120

agaatggcaa ccatcaaatc aagaaattgg cccaaagccc tacagtctgc aaacatcata    180

acaattcatc ctgaagtttc tcc atg aat tgt gat gct ttg cta cat cat tct    233
                          Met Asn Cys Asp Ala Leu Leu His His Ser
                          1               5                   10

gca atc cca gaa gat ttt ttg cat att ttt ttg cta tta cag aaa aat      281
Ala Ile Pro Glu Asp Phe Leu His Ile Phe Leu Leu Leu Gln Lys Asn
                15                  20                  25

ctc agt ctc cct ccc tct ctc tct ctc tca atc tgt gtg tct ctt tta      329
Leu Ser Leu Pro Pro Ser Leu Ser Leu Ser Ile Cys Val Ser Leu Leu
            30                  35                  40

ctc cat atc tct gtg tgt gtc tct ttt act cca tat ctc tct gtg tgt      377
Leu His Ile Ser Val Cys Val Ser Phe Thr Pro Tyr Leu Ser Val Cys
        45                  50                  55

gtc tgt tta tgt ctc tct ctc tct ctc atc ctt ccc atg ttt ctc tct      425
Val Cys Leu Cys Leu Ser Leu Ser Leu Ile Leu Pro Met Phe Leu Ser
    60                  65                  70

cac aca cac aca cac tca ttc aca gct ttc aaa aga cac gtc tgt cct      473
His Thr His Thr His Ser Phe Thr Ala Phe Lys Arg His Val Cys Pro
75                  80                  85                  90

tac ctt cac ttt ttg ttt taa acagcacact cactttactc tgaactatac         524
Tyr Leu His Phe Leu Phe
                95

ctcacatgca cacgagcttt ctgctccatc tgttcatccc acatgtgtct tcacattcaa    584

agcagcacct tccccaagac cagctaccta accacctccc acctccaccc catccctagt    644

cagaggaagg cctggttccc acctgaattc agctttgtca aagagcctcc tggaaagctg    704

tcatcttcag ttagtaggga taatgggatt attctatctg tgtaataata acatgttcaa    764

tttaaagaaa aaaatctgaa gccacttaaa agctactgtt tggcaccgat acattattcc    824

agtaatgaat aatcattaaa gatattattc tggatgcagt taccatgcag tgatgtgaat    884

aaaatgcatt agatggaaaa ttgtatttca agtaaatata tgcactggta gaaatgtatt    944

accacccact aatatgtatt aattcaaaac caaatgccaa ctggagttcg cctacacggg   1004

tttgaatggc aggcagtgat ttggaagtgg gaggaaatag gtttggattt ggtcaaatag   1064

actgagaagt gatagtgggg gcgggggttt atgactcaaa ctttaacagg tgagaagact   1124

atgccatgga cagaacaggc atgaggggct cccctcctac gcctctttaa gagattttta   1184

tctctgacta aggattactg gtagttgttg acatttctga agcagtggat ctttttcctt   1244

tttcactatc tgcatcttca aatattcttt tctgaagaaa gttaaaagga agcctgtaca   1304

ttttttgcta aggtaaatgc cttgccatct tatttcattt tctcattttt ttcttcagtg   1364

cacaacataa gcaactgtcc tccttgtcat actcaagatg agcttggcat atctgaaatc   1424

tgcagggatt ttctcattag cacagggttc caagcccaaa ccgtgaagat ggagttttca   1484

tttttaaatg gcacatcttc aagttcttgc cctgtcctca ctttagtatg ccccagagga   1544

agtcaaagat atggacactc taagactcag aagaactttc tcaggcattc attttcctat   1604

ctattttgag ccattttatt taaaaggtta caattttaaa cctctcttta attaaaagat   1664

accagagtta caatgcaata ctatttggca atcaaaacta atgaagcaca gatgcatgct   1724

acaacacgaa tgaactttga aacgttgtgt taagtgaaat aaaccagtta ttatacaagg   1784
```

```
cc                                                                    1786


<210> SEQ ID NO 72
<211> LENGTH: 96
<212> TYPE: PRT
<213> ORGANISM: Homo sapiens

<400> SEQUENCE: 72

Met Asn Cys Asp Ala Leu Leu His His Ser Ala Ile Pro Glu Asp Phe
1               5                   10                  15

Leu His Ile Phe Leu Leu Leu Gln Lys Asn Leu Ser Leu Pro Pro Ser
            20                  25                  30

Leu Ser Leu Ser Ile Cys Val Ser Leu Leu Leu His Ile Ser Val Cys
        35                  40                  45

Val Ser Phe Thr Pro Tyr Leu Ser Val Cys Val Cys Leu Cys Leu Ser
    50                  55                  60

Leu Ser Leu Ile Leu Pro Met Phe Leu Ser His Thr His Thr His Ser
65                  70                  75                  80

Phe Thr Ala Phe Lys Arg His Val Cys Pro Tyr Leu His Phe Leu Phe
                85                  90                  95


<210> SEQ ID NO 73
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 73

atg ctt tgc tac atc att ctg caa tcc cag aag att ttt tgc ata ttt       48
Met Leu Cys Tyr Ile Ile Leu Gln Ser Gln Lys Ile Phe Cys Ile Phe
1               5                   10                  15

ttt tgc tat tac aga aaa atc tca gtc tcc ctc cct ctc tct ctc tct       96
Phe Cys Tyr Tyr Arg Lys Ile Ser Val Ser Leu Pro Leu Ser Leu Ser
            20                  25                  30

caa tct gtg tgt ctc ttt tac tcc ata tct ctg tgt gtg tct ctt tta      144
Gln Ser Val Cys Leu Phe Tyr Ser Ile Ser Leu Cys Val Ser Leu Leu
        35                  40                  45

ctc cat atc tct ctg tgt gtg tct gtt tat gtc tct ctc tct ctc tca      192
Leu His Ile Ser Leu Cys Val Ser Val Tyr Val Ser Leu Ser Leu Ser
    50                  55                  60

tcc ttc cca tgt ttc tct ctc aca cac aca cac act cat tca cag ctt      240
Ser Phe Pro Cys Phe Ser Leu Thr His Thr His Thr His Ser Gln Leu
65                  70                  75                  80

tca aaa gac acg tct gtc ctt acc ttc act ttt tgt ttt aaa cag cac      288
Ser Lys Asp Thr Ser Val Leu Thr Phe Thr Phe Cys Phe Lys Gln His
                85                  90                  95

act cac ttt act ctg aac tat acc tca cat gca cac gag ctt tct gct      336
Thr His Phe Thr Leu Asn Tyr Thr Ser His Ala His Glu Leu Ser Ala
            100                 105                 110

cca tct gtt cat ccc aca tgt gtc ttc aca ttc aaa gca gca cct tcc      384
Pro Ser Val His Pro Thr Cys Val Phe Thr Phe Lys Ala Ala Pro Ser
        115                 120                 125

cca aga cca gct acc taa                                              402
Pro Arg Pro Ala Thr
    130


<210> SEQ ID NO 74
<211> LENGTH: 133
<212> TYPE: PRT
```

<213> ORGANISM: Homo sapiens

<400> SEQUENCE: 74

```
Met Leu Cys Tyr Ile Ile Leu Gln Ser Gln Lys Ile Phe Cys Ile Phe
1               5                   10                  15

Phe Cys Tyr Tyr Arg Lys Ile Ser Val Ser Leu Pro Leu Ser Leu Ser
            20                  25                  30

Gln Ser Val Cys Leu Phe Tyr Ser Ile Ser Leu Cys Val Ser Leu Leu
        35                  40                  45

Leu His Ile Ser Leu Cys Val Ser Val Tyr Val Ser Leu Ser Leu Ser
    50                  55                  60

Ser Phe Pro Cys Phe Ser Leu Thr His Thr His Thr His Ser Gln Leu
65                  70                  75                  80

Ser Lys Asp Thr Ser Val Leu Thr Phe Thr Phe Cys Phe Lys Gln His
                85                  90                  95

Thr His Phe Thr Leu Asn Tyr Thr Ser His Ala His Glu Leu Ser Ala
            100                 105                 110

Pro Ser Val His Pro Thr Cys Val Phe Thr Phe Lys Ala Ala Pro Ser
        115                 120                 125

Pro Arg Pro Ala Thr
    130
```

<210> SEQ ID NO 75
<211> LENGTH: 3579
<212> TYPE: DNA
<213> ORGANISM: Homo sapiens
<220> FEATURE:
<221> NAME/KEY: CDS
<222> LOCATION: (136)..(3258)

<400> SEQUENCE: 75

```
caccacagtt atcacccatg ccctcctaaa agggtgtctc aaagcatatc tttctgtaga      60

gcagaattcg gaactgagaa gacgagggct caaattgaat ctcacaggat ttgcgtgcaa     120

gagaaaccca aagga atg gat tgg ctc ttc ttc aga aac att tgc ctt ttg      171
                 Met Asp Trp Leu Phe Phe Arg Asn Ile Cys Leu Leu
                 1               5                   10

atc att cta atg gtg gtg atg gaa gta aac agt gaa ttt att gtt gag      219
Ile Ile Leu Met Val Val Met Glu Val Asn Ser Glu Phe Ile Val Glu
        15                  20                  25

gtg aag gaa ttt gac att gaa aat ggc act aca aaa tgg caa aca gtc      267
Val Lys Glu Phe Asp Ile Glu Asn Gly Thr Thr Lys Trp Gln Thr Val
    30                  35                  40

aga aga caa aag cgg gag tgg atc aag ttt gcc gca gcc tgt cga gaa      315
Arg Arg Gln Lys Arg Glu Trp Ile Lys Phe Ala Ala Ala Cys Arg Glu
45                  50                  55                  60

gga gag gac aac tcg aag agg aac ccc att gcc aaa att cga tca gac      363
Gly Glu Asp Asn Ser Lys Arg Asn Pro Ile Ala Lys Ile Arg Ser Asp
                65                  70                  75

tgc gaa tcg aac cag aag ata aca tac cgg att tct gga gta ggg att      411
Cys Glu Ser Asn Gln Lys Ile Thr Tyr Arg Ile Ser Gly Val Gly Ile
            80                  85                  90

gat cga cca cca tat ggg gta ttc acc att aat cct cgc act ggg gaa      459
Asp Arg Pro Pro Tyr Gly Val Phe Thr Ile Asn Pro Arg Thr Gly Glu
        95                  100                 105

att aac atc act tca gtg gta gac aga gaa ata act cca ctt ttc ttg      507
Ile Asn Ile Thr Ser Val Val Asp Arg Glu Ile Thr Pro Leu Phe Leu
    110                 115                 120

atc tat tgc cgg gct ctg aat tca cgg ggt gaa gat tta gaa agg cct      555
```

-continued

```
Ile Tyr Cys Arg Ala Leu Asn Ser Arg Gly Glu Asp Leu Glu Arg Pro
125                 130                 135                 140

ctt gag ctt aga gtc aaa gtt atg gac ata aat gat aac gct cca gtc      603
Leu Glu Leu Arg Val Lys Val Met Asp Ile Asn Asp Asn Ala Pro Val
                145                 150                 155

ttt tcg caa agt gta tac aca gcc agc att gaa gaa aat agt gat gcc      651
Phe Ser Gln Ser Val Tyr Thr Ala Ser Ile Glu Glu Asn Ser Asp Ala
            160                 165                 170

aat aca ttg gta gta aag tta tgt gcc aca gat gca gat gaa gaa aat      699
Asn Thr Leu Val Val Lys Leu Cys Ala Thr Asp Ala Asp Glu Glu Asn
        175                 180                 185

cat ctg aat tct aaa att gcc tac aag atc gtc tct cag gag cca tca      747
His Leu Asn Ser Lys Ile Ala Tyr Lys Ile Val Ser Gln Glu Pro Ser
    190                 195                 200

ggt gca ccc atg ttc att ctg aat agg tac act gga gaa gtc tgc acc      795
Gly Ala Pro Met Phe Ile Leu Asn Arg Tyr Thr Gly Glu Val Cys Thr
205                 210                 215                 220

atg tcc agt ttc ttg gac aga gag caa cac agt atg tac aac ctg gtt      843
Met Ser Ser Phe Leu Asp Arg Glu Gln His Ser Met Tyr Asn Leu Val
                225                 230                 235

gtg aga ggc tca gat cgg gat gga gct gca gat gga ctg tct tct gag      891
Val Arg Gly Ser Asp Arg Asp Gly Ala Ala Asp Gly Leu Ser Ser Glu
            240                 245                 250

tgt gac tgt aga atc aag gtt tta gac gtc aac gat aat ttc ccc acc      939
Cys Asp Cys Arg Ile Lys Val Leu Asp Val Asn Asp Asn Phe Pro Thr
        255                 260                 265

tta gag aaa act tca tac tca gcc agt att gaa gag aat tgt tta agt      987
Leu Glu Lys Thr Ser Tyr Ser Ala Ser Ile Glu Glu Asn Cys Leu Ser
    270                 275                 280

tcg gaa ctg ata cga tta caa gca att gat ctt gat gaa gaa ggc act     1035
Ser Glu Leu Ile Arg Leu Gln Ala Ile Asp Leu Asp Glu Glu Gly Thr
285                 290                 295                 300

gat aac tgg ttg gct caa tat tta att ctc tct gga aat gat ggg aat     1083
Asp Asn Trp Leu Ala Gln Tyr Leu Ile Leu Ser Gly Asn Asp Gly Asn
                305                 310                 315

tgg ttc gat att caa aca gat cca caa acc aat gaa ggc att ttg aaa     1131
Trp Phe Asp Ile Gln Thr Asp Pro Gln Thr Asn Glu Gly Ile Leu Lys
            320                 325                 330

gtt gtc aag atg ctg gat tat gaa caa gca cct aac att cag ctt agt     1179
Val Val Lys Met Leu Asp Tyr Glu Gln Ala Pro Asn Ile Gln Leu Ser
        335                 340                 345

atc gga gtt aaa aac caa gct gat ttt cac tac tcc gtt gct tct caa     1227
Ile Gly Val Lys Asn Gln Ala Asp Phe His Tyr Ser Val Ala Ser Gln
    350                 355                 360

ttc caa atg cac cca acc cct gtg aga att caa gtt gtt gat gtg aga     1275
Phe Gln Met His Pro Thr Pro Val Arg Ile Gln Val Val Asp Val Arg
365                 370                 375                 380

gaa gga cct gca ttt cat cca agt act atg gct ttt agt gtg cgg gaa     1323
Glu Gly Pro Ala Phe His Pro Ser Thr Met Ala Phe Ser Val Arg Glu
                385                 390                 395

gga ata aaa gga agt tcc tta ttg aat tat gtg ctt ggc aca tat aca     1371
Gly Ile Lys Gly Ser Ser Leu Leu Asn Tyr Val Leu Gly Thr Tyr Thr
            400                 405                 410

gcc ata gat ttg gac aca gga aac cct gca aca gat gtc aga tat atc     1419
Ala Ile Asp Leu Asp Thr Gly Asn Pro Ala Thr Asp Val Arg Tyr Ile
        415                 420                 425

ata ggg cat gat gca ggc agc tgg tta aaa att gat tca aga act ggt     1467
Ile Gly His Asp Ala Gly Ser Trp Leu Lys Ile Asp Ser Arg Thr Gly
    430                 435                 440
```

```
gag ata caa ttt tct aga gaa ttt gat aag aag tca aaa tat att atc      1515
Glu Ile Gln Phe Ser Arg Glu Phe Asp Lys Lys Ser Lys Tyr Ile Ile
445                 450                 455                 460

aat ggg ata tac aca gca gag atc ctg gct ata gat gat ggc tct gga      1563
Asn Gly Ile Tyr Thr Ala Glu Ile Leu Ala Ile Asp Asp Gly Ser Gly
                465                 470                 475

aaa aca gct aca gga acc ata tgt att gag gtt cct gat atc aat gat      1611
Lys Thr Ala Thr Gly Thr Ile Cys Ile Glu Val Pro Asp Ile Asn Asp
            480                 485                 490

tat tgt cca aac att ttt cct gaa aga aga acc atc tgc att gac tct      1659
Tyr Cys Pro Asn Ile Phe Pro Glu Arg Arg Thr Ile Cys Ile Asp Ser
        495                 500                 505

cca tca gtc ctt atc tct gtt aat gaa cat tct tat ggg tct ccg ttt      1707
Pro Ser Val Leu Ile Ser Val Asn Glu His Ser Tyr Gly Ser Pro Phe
    510                 515                 520

act ttc tgt gtt gtt gat gag cca cca gga ata gct gac atg tgg gat      1755
Thr Phe Cys Val Val Asp Glu Pro Pro Gly Ile Ala Asp Met Trp Asp
525                 530                 535                 540

gtc aga tca aca aat gct acc tcg gca atc ctt acg gct aag cag gtt      1803
Val Arg Ser Thr Asn Ala Thr Ser Ala Ile Leu Thr Ala Lys Gln Val
                545                 550                 555

tta tct cca gga ttt tat gaa atc cca atc ctg gtg aag gac agc tat      1851
Leu Ser Pro Gly Phe Tyr Glu Ile Pro Ile Leu Val Lys Asp Ser Tyr
            560                 565                 570

aac aga gca tgt gaa ttg gca caa atg gtg cag tta tat gcc tgt gat      1899
Asn Arg Ala Cys Glu Leu Ala Gln Met Val Gln Leu Tyr Ala Cys Asp
        575                 580                 585

tgc gat gac aac cac atg tgc ctg gac tct ggt gcc gcg ggc atc tac      1947
Cys Asp Asp Asn His Met Cys Leu Asp Ser Gly Ala Ala Gly Ile Tyr
    590                 595                 600

aca gag gac ata act ggt gac acg tat ggg cct gtc act gaa gac caa      1995
Thr Glu Asp Ile Thr Gly Asp Thr Tyr Gly Pro Val Thr Glu Asp Gln
605                 610                 615                 620

gct gga gtt tca aat gtt ggt ctt gga cca gca ggg att ggc atg atg      2043
Ala Gly Val Ser Asn Val Gly Leu Gly Pro Ala Gly Ile Gly Met Met
                625                 630                 635

gtt ctg ggc atc ctg cta ctg att ttg gct cca ctc ttg ctg ctc ctg      2091
Val Leu Gly Ile Leu Leu Leu Ile Leu Ala Pro Leu Leu Leu Leu Leu
            640                 645                 650

tgt tgc tgc aaa cag aga cag cca gaa ggc ctg gga aca aga ttt gct      2139
Cys Cys Cys Lys Gln Arg Gln Pro Glu Gly Leu Gly Thr Arg Phe Ala
        655                 660                 665

cct gtg cct gag ggc gga gaa gga gtg atg cag tct tgg aga att gaa      2187
Pro Val Pro Glu Gly Gly Glu Gly Val Met Gln Ser Trp Arg Ile Glu
    670                 675                 680

ggg gcc cat ccc gag gac agg gat gtg tca aat ata tgt gca ccc atg      2235
Gly Ala His Pro Glu Asp Arg Asp Val Ser Asn Ile Cys Ala Pro Met
685                 690                 695                 700

aca gcc tca aat acc cag gat cgg atg gat tcc tct gaa atc tac acc      2283
Thr Ala Ser Asn Thr Gln Asp Arg Met Asp Ser Ser Glu Ile Tyr Thr
                705                 710                 715

aac acc tat gca gcc ggg ggc acg gtg gaa gga ggt gta tcg gga gtg      2331
Asn Thr Tyr Ala Ala Gly Gly Thr Val Glu Gly Gly Val Ser Gly Val
            720                 725                 730

gag ctc aac aca ggt atg ggg aca gcc gtt ggc ctc atg gcc gca ggg      2379
Glu Leu Asn Thr Gly Met Gly Thr Ala Val Gly Leu Met Ala Ala Gly
        735                 740                 745

gcc gca gga gcc tca ggg gcc gca agg aag agg agc tct acc atg gga      2427
Ala Ala Gly Ala Ser Gly Ala Ala Arg Lys Arg Ser Ser Thr Met Gly
    750                 755                 760
```

```
acc ctg cgg gac tac gct gac gca gac atc aac atg gct ttc ttg gac     2475
Thr Leu Arg Asp Tyr Ala Asp Ala Asp Ile Asn Met Ala Phe Leu Asp
765                 770                 775                 780

agc tac ttc tcg gag aaa gcg tat gct tat gca gat gaa gat gaa ggt     2523
Ser Tyr Phe Ser Glu Lys Ala Tyr Ala Tyr Ala Asp Glu Asp Glu Gly
                785                 790                 795

cga cca gcc aat gac tgc ttg ctc att tat gac cac gag gga gtc ggg     2571
Arg Pro Ala Asn Asp Cys Leu Leu Ile Tyr Asp His Glu Gly Val Gly
            800                 805                 810

tct ccc gta ggc tct att ggt tgt tgc agt tgg att gtg gat gac tta     2619
Ser Pro Val Gly Ser Ile Gly Cys Cys Ser Trp Ile Val Asp Asp Leu
        815                 820                 825

gat gaa agc tgc atg gaa act tta gat cca aaa ttt agg act ctt gct     2667
Asp Glu Ser Cys Met Glu Thr Leu Asp Pro Lys Phe Arg Thr Leu Ala
    830                 835                 840

gag atc tgc tta aac aca gaa att gaa cca ttt cct tca cac cag gct     2715
Glu Ile Cys Leu Asn Thr Glu Ile Glu Pro Phe Pro Ser His Gln Ala
845                 850                 855                 860

tgt ata cca atc agt act gac ctc cct ttg ctc gga cct aat tac ttt     2763
Cys Ile Pro Ile Ser Thr Asp Leu Pro Leu Leu Gly Pro Asn Tyr Phe
                865                 870                 875

gtt aat gaa tct tca gga ttg act ccc tca gaa gtt gaa ttc caa gaa     2811
Val Asn Glu Ser Ser Gly Leu Thr Pro Ser Glu Val Glu Phe Gln Glu
            880                 885                 890

gaa atg gca gca tct gaa ccc gtg gtc cat ggg gat att att gtg act     2859
Glu Met Ala Ala Ser Glu Pro Val Val His Gly Asp Ile Ile Val Thr
        895                 900                 905

gag act tac ggt aat gct gat cca tgt gtg caa ccc act aca att att     2907
Glu Thr Tyr Gly Asn Ala Asp Pro Cys Val Gln Pro Thr Thr Ile Ile
    910                 915                 920

ttt gat cct cag ctt gca ccc aat gtt gta gta acc gaa gca gta atg     2955
Phe Asp Pro Gln Leu Ala Pro Asn Val Val Val Thr Glu Ala Val Met
925                 930                 935                 940

gca cct gtc tat gat att caa ggg aat att tgt gta cct gct gag tta     3003
Ala Pro Val Tyr Asp Ile Gln Gly Asn Ile Cys Val Pro Ala Glu Leu
                945                 950                 955

gca gat tac aac aat gta atc tat gct gag aga gta ctg gct agt cct     3051
Ala Asp Tyr Asn Asn Val Ile Tyr Ala Glu Arg Val Leu Ala Ser Pro
            960                 965                 970

ggt gtg cct gac atg agc aat agt agc acg act gag ggt tgt atg gga     3099
Gly Val Pro Asp Met Ser Asn Ser Ser Thr Thr Glu Gly Cys Met Gly
        975                 980                 985

cct gtg atg agc ggc aat att tta gta ggg cca gaa  att caa gtg atg    3147
Pro Val Met Ser Gly Asn Ile Leu Val Gly Pro Glu  Ile Gln Val Met
    990                 995                 1000

caa  atg atg agt cca gac  ctt ccc ata ggc caa  acc gtt ggc tcc      3192
Gln  Met Met Ser Pro Asp  Leu Pro Ile Gly Gln  Thr Val Gly Ser
1005                 1010                 1015

aca  tcc ccc atg aca tct  cga cac aga gta aca  cga tac agt aac      3237
Thr  Ser Pro Met Thr Ser  Arg His Arg Val Thr  Arg Tyr Ser Asn
1020                 1025                 1030

ata  cat tac acc caa cag  taa gtgctttatg gtcagtattc tatgtggaga      3288
Ile  His Tyr Thr Gln Gln
1035                 1040

ccttgcacct tgtaatcatc aatacatcca ccaaaaatat ataatgtacc atatatatta   3348

atagtcaaca aatactcaga tattctaagg tcaatgccat tatttgatta taccattttg   3408

agggtgaata tggctaggca ctttagataa gcctttttaa aattctttct gattttaaat   3468
```

-continued aatgcgtcaa aaaatgtgca gaaaatgtat tgcatccctt gatactgtct aacgaatagc 3528 acataactca tattgtgaat cctatgggtc ttgaggcctg tagaaccaat c 3579

<210> SEQ ID NO 76
<211> LENGTH: 1040
<212> TYPE: PRT
<213> ORGANISM: Homo sapiens

<400> SEQUENCE: 76

Met Asp Trp Leu Phe Phe Arg Asn Ile Cys Leu Leu Ile Ile Leu Met
1 5 10 15

Val Val Met Glu Val Asn Ser Glu Phe Ile Val Glu Val Lys Glu Phe
20 25 30

Asp Ile Glu Asn Gly Thr Thr Lys Trp Gln Thr Val Arg Arg Gln Lys
35 40 45

Arg Glu Trp Ile Lys Phe Ala Ala Ala Cys Arg Glu Gly Glu Asp Asn
50 55 60

Ser Lys Arg Asn Pro Ile Ala Lys Ile Arg Ser Asp Cys Glu Ser Asn
65 70 75 80

Gln Lys Ile Thr Tyr Arg Ile Ser Gly Val Gly Ile Asp Arg Pro Pro
85 90 95

Tyr Gly Val Phe Thr Ile Asn Pro Arg Thr Gly Glu Ile Asn Ile Thr
100 105 110

Ser Val Val Asp Arg Glu Ile Thr Pro Leu Phe Leu Ile Tyr Cys Arg
115 120 125

Ala Leu Asn Ser Arg Gly Glu Asp Leu Glu Arg Pro Leu Glu Leu Arg
130 135 140

Val Lys Val Met Asp Ile Asn Asp Asn Ala Pro Val Phe Ser Gln Ser
145 150 155 160

Val Tyr Thr Ala Ser Ile Glu Glu Asn Ser Asp Ala Asn Thr Leu Val
165 170 175

Val Lys Leu Cys Ala Thr Asp Ala Asp Glu Glu Asn His Leu Asn Ser
180 185 190

Lys Ile Ala Tyr Lys Ile Val Ser Gln Glu Pro Ser Gly Ala Pro Met
195 200 205

Phe Ile Leu Asn Arg Tyr Thr Gly Glu Val Cys Thr Met Ser Ser Phe
210 215 220

Leu Asp Arg Glu Gln His Ser Met Tyr Asn Leu Val Val Arg Gly Ser
225 230 235 240

Asp Arg Asp Gly Ala Ala Asp Gly Leu Ser Ser Glu Cys Asp Cys Arg
245 250 255

Ile Lys Val Leu Asp Val Asn Asp Asn Phe Pro Thr Leu Glu Lys Thr
260 265 270

Ser Tyr Ser Ala Ser Ile Glu Glu Asn Cys Leu Ser Ser Glu Leu Ile
275 280 285

Arg Leu Gln Ala Ile Asp Leu Asp Glu Glu Gly Thr Asp Asn Trp Leu
290 295 300

Ala Gln Tyr Leu Ile Leu Ser Gly Asn Asp Gly Asn Trp Phe Asp Ile
305 310 315 320

Gln Thr Asp Pro Gln Thr Asn Glu Gly Ile Leu Lys Val Val Lys Met
325 330 335

Leu Asp Tyr Glu Gln Ala Pro Asn Ile Gln Leu Ser Ile Gly Val Lys
340 345 350

Asn Gln Ala Asp Phe His Tyr Ser Val Ala Ser Gln Phe Gln Met His

-continued

```
        355                 360                 365

Pro Thr Pro Val Arg Ile Gln Val Val Asp Val Arg Glu Gly Pro Ala
    370                 375                 380

Phe His Pro Ser Thr Met Ala Phe Ser Val Arg Glu Gly Ile Lys Gly
385                 390                 395                 400

Ser Ser Leu Leu Asn Tyr Val Leu Gly Thr Tyr Thr Ala Ile Asp Leu
                405                 410                 415

Asp Thr Gly Asn Pro Ala Thr Asp Val Arg Tyr Ile Ile Gly His Asp
            420                 425                 430

Ala Gly Ser Trp Leu Lys Ile Asp Ser Arg Thr Gly Glu Ile Gln Phe
        435                 440                 445

Ser Arg Glu Phe Asp Lys Lys Ser Lys Tyr Ile Ile Asn Gly Ile Tyr
    450                 455                 460

Thr Ala Glu Ile Leu Ala Ile Asp Asp Gly Ser Gly Lys Thr Ala Thr
465                 470                 475                 480

Gly Thr Ile Cys Ile Glu Val Pro Asp Ile Asn Asp Tyr Cys Pro Asn
                485                 490                 495

Ile Phe Pro Glu Arg Arg Thr Ile Cys Ile Asp Ser Pro Ser Val Leu
            500                 505                 510

Ile Ser Val Asn Glu His Ser Tyr Gly Ser Pro Phe Thr Phe Cys Val
        515                 520                 525

Val Asp Glu Pro Pro Gly Ile Ala Asp Met Trp Asp Val Arg Ser Thr
    530                 535                 540

Asn Ala Thr Ser Ala Ile Leu Thr Ala Lys Gln Val Leu Ser Pro Gly
545                 550                 555                 560

Phe Tyr Glu Ile Pro Ile Leu Val Lys Asp Ser Tyr Asn Arg Ala Cys
                565                 570                 575

Glu Leu Ala Gln Met Val Gln Leu Tyr Ala Cys Asp Cys Asp Asp Asn
            580                 585                 590

His Met Cys Leu Asp Ser Gly Ala Ala Gly Ile Tyr Thr Glu Asp Ile
        595                 600                 605

Thr Gly Asp Thr Tyr Gly Pro Val Thr Glu Asp Gln Ala Gly Val Ser
    610                 615                 620

Asn Val Gly Leu Gly Pro Ala Gly Ile Gly Met Met Val Leu Gly Ile
625                 630                 635                 640

Leu Leu Leu Ile Leu Ala Pro Leu Leu Leu Leu Leu Cys Cys Cys Lys
                645                 650                 655

Gln Arg Gln Pro Glu Gly Leu Gly Thr Arg Phe Ala Pro Val Pro Glu
            660                 665                 670

Gly Gly Glu Gly Val Met Gln Ser Trp Arg Ile Glu Gly Ala His Pro
        675                 680                 685

Glu Asp Arg Asp Val Ser Asn Ile Cys Ala Pro Met Thr Ala Ser Asn
    690                 695                 700

Thr Gln Asp Arg Met Asp Ser Ser Glu Ile Tyr Thr Asn Thr Tyr Ala
705                 710                 715                 720

Ala Gly Gly Thr Val Glu Gly Gly Val Ser Gly Val Glu Leu Asn Thr
                725                 730                 735

Gly Met Gly Thr Ala Val Gly Leu Met Ala Ala Gly Ala Ala Gly Ala
            740                 745                 750

Ser Gly Ala Ala Arg Lys Arg Ser Ser Thr Met Gly Thr Leu Arg Asp
        755                 760                 765

Tyr Ala Asp Ala Asp Ile Asn Met Ala Phe Leu Asp Ser Tyr Phe Ser
    770                 775                 780
```

```
Glu Lys Ala Tyr Ala Tyr Ala Asp Glu Asp Glu Gly Arg Pro Ala Asn
785                 790                 795                 800

Asp Cys Leu Leu Ile Tyr Asp His Glu Gly Val Gly Ser Pro Val Gly
                805                 810                 815

Ser Ile Gly Cys Cys Ser Trp Ile Val Asp Asp Leu Asp Glu Ser Cys
            820                 825                 830

Met Glu Thr Leu Asp Pro Lys Phe Arg Thr Leu Ala Glu Ile Cys Leu
        835                 840                 845

Asn Thr Glu Ile Glu Pro Phe Pro Ser His Gln Ala Cys Ile Pro Ile
    850                 855                 860

Ser Thr Asp Leu Pro Leu Leu Gly Pro Asn Tyr Phe Val Asn Glu Ser
865                 870                 875                 880

Ser Gly Leu Thr Pro Ser Glu Val Glu Phe Gln Glu Glu Met Ala Ala
                885                 890                 895

Ser Glu Pro Val Val His Gly Asp Ile Ile Val Thr Glu Thr Tyr Gly
            900                 905                 910

Asn Ala Asp Pro Cys Val Gln Pro Thr Thr Ile Ile Phe Asp Pro Gln
        915                 920                 925

Leu Ala Pro Asn Val Val Val Thr Glu Ala Val Met Ala Pro Val Tyr
    930                 935                 940

Asp Ile Gln Gly Asn Ile Cys Val Pro Ala Glu Leu Ala Asp Tyr Asn
945                 950                 955                 960

Asn Val Ile Tyr Ala Glu Arg Val Leu Ala Ser Pro Gly Val Pro Asp
                965                 970                 975

Met Ser Asn Ser Ser Thr Thr Glu Gly Cys Met Gly Pro Val Met Ser
            980                 985                 990

Gly Asn Ile Leu Val Gly Pro Glu  Ile Gln Val Met Gln  Met Met Ser
        995                 1000                1005

Pro Asp  Leu Pro Ile Gly Gln  Thr Val Gly Ser Thr  Ser Pro Met
    1010                 1015                 1020

Thr Ser  Arg His Arg Val Thr  Arg Tyr Ser Asn Ile  His Tyr Thr
    1025                 1030                 1035

Gln Gln
    1040
```

```
<210> SEQ ID NO 77
<211> LENGTH: 26
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 77

gggatataca cagcagagat cctggc                                          26


<210> SEQ ID NO 78
<211> LENGTH: 25
<212> TYPE: DNA
<213> ORGANISM: Artificial Sequence
<220> FEATURE:
<223> OTHER INFORMATION: Description fo the artificial sequence:
      Oligonucleotide

<400> SEQUENCE: 78

ttagccgtaa ggattgccga ggtag                                           25
```

<210> SEQ ID NO 79
<211> LENGTH: 279
<212> TYPE: DNA
<213> ORGANISM: Homo sapiens

<400> SEQUENCE: 79
gggatataca cagcagagat cctggctata gatgatggct ctggaaaaac agctacagga 60
accatatgta ttgaggttcc tgatatcaat gattattgtc caaacatttt tcctgaaaga 120
agaaccatct gcattgactc tccatcagtc cttatctctg ttaatgaaca ttcttatggg 180
tctccgttta ctttctgtgt tgttgatgag ccaccaggaa tagctgacat gtgggatgtc 240
agatcaacaa atgctacctc ggcaatcctt acggctaag 279

<210> SEQ ID NO 80
<211> LENGTH: 659
<212> TYPE: DNA
<213> ORGANISM: Homo sapiens

<400> SEQUENCE: 80
cagatatatc atagggcatg atgcaggcag ctggttaaaa attgattcaa gaactggtga 60
gatacaattt tctagagaat ttgataagaa gtcaaaatat attatcaatg ggatatacac 120
agcagagatc ctggctatag atgatggctc tggaaaaaca gctacaggaa ccatatgtat 180
tgaggttcct gatatcaatg attattgtcc aaacattttt cctgaaagaa gaaccatctg 240
cattgactct ccatcagtcc ttatctctgt taatgaacat tcttatgggt ctccgtttac 300
tttctgtgtt gttgatgagc caccaggaat agctgacatg tgggatgtca gatcaacaaa 360
tgctacctcg gcaatcctta cggctaagca ggttttatct ccaggatttt atgaaatccc 420
aatcctggtg aaggacagct ataacagagc atgtgaattg gcacaaatgg tgcagttata 480
tgcctgtgat tgcgatgaca accacatgtg cctggactct ggtgccgcgg gcatctacac 540
agaggacata actggtgaca cgtatgggcc tgtcactgaa gaccaagctg gagtttcaaa 600
tgttggtctt ggaccagcag ggattggcat gatggttctg ggcatcctgc tactgattt 659

<210> SEQ ID NO 81
<211> LENGTH: 93
<212> TYPE: PRT
<213> ORGANISM: Homo sapiens

<400> SEQUENCE: 81

Gly Ile Tyr Thr Ala Glu Ile Leu Ala Ile Asp Asp Gly Ser Gly Lys
1 5 10 15

Thr Ala Thr Gly Thr Ile Cys Ile Glu Val Pro Asp Ile Asn Asp Tyr
20 25 30

Cys Pro Asn Ile Phe Pro Glu Arg Arg Thr Ile Cys Ile Asp Ser Pro
35 40 45

Ser Val Leu Ile Ser Val Asn Glu His Ser Tyr Gly Ser Pro Phe Thr
50 55 60

Phe Cys Val Val Asp Glu Pro Pro Gly Ile Ala Asp Met Trp Asp Val
65 70 75 80

Arg Ser Thr Asn Ala Thr Ser Ala Ile Leu Thr Ala Lys
85 90

<210> SEQ ID NO 82
<211> LENGTH: 224
<212> TYPE: PRT
<213> ORGANISM: Homo sapiens

<400> SEQUENCE: 82

Val Arg Tyr Ile Ile Gly His Asp Ala Gly Ser Trp Leu Lys Ile Asp
1               5                   10                  15

Ser Arg Thr Gly Glu Ile Gln Phe Ser Arg Glu Phe Asp Lys Lys Ser
            20                  25                  30

Lys Tyr Ile Ile Asn Gly Ile Tyr Thr Ala Glu Ile Leu Ala Ile Asp
        35                  40                  45

Asp Gly Ser Gly Lys Thr Ala Thr Gly Thr Ile Cys Ile Glu Val Pro
    50                  55                  60

Asp Ile Asn Asp Tyr Cys Pro Asn Ile Phe Pro Glu Arg Arg Thr Ile
65                  70                  75                  80

Cys Ile Asp Ser Pro Ser Val Leu Ile Ser Val Asn Glu His Ser Tyr
                85                  90                  95

Gly Ser Pro Phe Thr Phe Cys Val Val Asp Glu Pro Pro Gly Ile Ala
            100                 105                 110

Asp Met Trp Asp Val Arg Ser Thr Asn Ala Thr Ser Ala Ile Leu Thr
        115                 120                 125

Ala Lys Gln Val Leu Ser Pro Gly Phe Tyr Glu Ile Pro Ile Leu Val
    130                 135                 140

Lys Asp Ser Tyr Asn Arg Ala Cys Glu Leu Ala Gln Met Val Gln Leu
145                 150                 155                 160

Tyr Ala Cys Asp Cys Asp Asp Asn His Met Cys Leu Asp Ser Gly Ala
                165                 170                 175

Ala Gly Ile Tyr Thr Glu Asp Ile Thr Gly Asp Thr Tyr Gly Pro Val
            180                 185                 190

Thr Glu Asp Gln Ala Gly Val Ser Asn Val Gly Leu Gly Pro Ala Gly
        195                 200                 205

Ile Gly Met Met Val Leu Gly Ile Leu Leu Leu Ile Leu Ala Pro Leu
    210                 215                 220

<210> SEQ ID NO 83
<211> LENGTH: 27
<212> TYPE: DNA
<213> ORGANISM: Artificial Sequence
<220> FEATURE:
<223> OTHER INFORMATION: Description of the artificial sequence: Oligonucleotide

<400> SEQUENCE: 83
aagacgaggg ctcaaattga atctcac                                          27

<210> SEQ ID NO 84
<211> LENGTH: 24
<212> TYPE: DNA
<213> ORGANISM: Artificial Sequence
<220> FEATURE:
<223> OTHER INFORMATION: Description of the artificial sequence: Oligonucleotide

<400> SEQUENCE: 84
cgtgaattca gagcccggca atag                                             24

<210> SEQ ID NO 85
<211> LENGTH: 973
<212> TYPE: DNA
<213> ORGANISM: Homo sapiens

<400> SEQUENCE: 85
caccacagtt atcacccatg ccctcctaaa agggtgtctc aaagcatatc tttctgtaga     60

-continued

```
gcagaattcg gaactgagaa gacgagggct caaattgaat ctcacaggat ttgcgtgcaa    120

gagaaaccca aaggaatgga ttggctcttc ttcagaaaca tttgcctttt gatcattcta    180

atgcaacaca gtatgtacaa cctggttgtg agaggctcag atcgggatgg agctgcagat    240

ggactgtctt ctgagtgtga ctgtagaatc aaggttttag acgtcaacga taatttcccc    300

accttagaga aaacttcata tatcataggg catgatgcag gcagctggtt aaaaattgat    360

tcaagaactg gtgagataca attttctaga gaatttgata agaagtcaaa atatattatc    420

aatgggatat acacagcaga gatcctggct atagatgatg gctctggaaa aacagctaca    480

ggaaccatat gtattgaggt tcctgatatc aatgattatt gtccaaacat tttcctgaa    540

agaagaacca tctgcattga ctctccatca gtccttatct ctgttaatga acattcttat    600

gggtctccgt ttactttctg tgttgttgat gagccaccag gaatagctga catgtgggat    660

gtcagatcaa caaatgctac ctcggcaatc cttacggcta agcaggtttt atctccagga    720

ttttatgaaa tcccaatcct ggtgaaggac agctataaca gagcatgtga attggcacaa    780

atggtgcagt tatatgcctg tgattgcgat gacaaccaca tgtgcctgga ctctggtgcc    840

gcgggcatct acacagagga cataactggt gacacgtatg ggcctgtcac tgaagaccaa    900

gctggagttt caaatgttgg tcttggacca gcagggattg gcatgatggt tctgggcatc    960

ctgctactga ttt                                                       973
```

```
<210> SEQ ID NO 86
<211> LENGTH: 279
<212> TYPE: PRT
<213> ORGANISM: Homo sapiens

<400> SEQUENCE: 86

Met Asp Trp Leu Phe Phe Arg Asn Ile Cys Leu Leu Ile Ile Leu Met
1               5                   10                  15

Gln His Ser Met Tyr Asn Leu Val Val Arg Gly Ser Asp Arg Asp Gly
            20                  25                  30

Ala Ala Asp Gly Leu Ser Ser Glu Cys Asp Cys Arg Ile Lys Val Leu
        35                  40                  45

Asp Val Asn Asp Asn Phe Pro Thr Leu Glu Lys Thr Ser Tyr Ile Ile
    50                  55                  60

Gly His Asp Ala Gly Ser Trp Leu Lys Ile Asp Ser Arg Thr Gly Glu
65                  70                  75                  80

Ile Gln Phe Ser Arg Glu Phe Asp Lys Lys Ser Lys Tyr Ile Ile Asn
                85                  90                  95

Gly Ile Tyr Thr Ala Glu Ile Leu Ala Ile Asp Asp Gly Ser Gly Lys
            100                 105                 110

Thr Ala Thr Gly Thr Ile Cys Ile Glu Val Pro Asp Ile Asn Asp Tyr
        115                 120                 125

Cys Pro Asn Ile Phe Pro Glu Arg Arg Thr Ile Cys Ile Asp Ser Pro
    130                 135                 140

Ser Val Leu Ile Ser Val Asn Glu His Ser Tyr Gly Ser Pro Phe Thr
145                 150                 155                 160

Phe Cys Val Val Asp Glu Pro Pro Gly Ile Ala Asp Met Trp Asp Val
                165                 170                 175

Arg Ser Thr Asn Ala Thr Ser Ala Ile Leu Thr Ala Lys Gln Val Leu
            180                 185                 190

Ser Pro Gly Phe Tyr Glu Ile Pro Ile Leu Val Lys Asp Ser Tyr Asn
        195                 200                 205
```

```
Arg Ala Cys Glu Leu Ala Gln Met Val Gln Leu Tyr Ala Cys Asp Cys
    210                 215                 220

Asp Asp Asn His Met Cys Leu Asp Ser Gly Ala Ala Gly Ile Tyr Thr
225                 230                 235                 240

Glu Asp Ile Thr Gly Asp Thr Tyr Gly Pro Val Thr Glu Asp Gln Ala
                245                 250                 255

Gly Val Ser Asn Val Gly Leu Gly Pro Ala Gly Ile Gly Met Met Val
            260                 265                 270

Leu Gly Ile Leu Leu Leu Ile
        275


<210> SEQ ID NO 87
<211> LENGTH: 964
<212> TYPE: DNA
<213> ORGANISM: Homo sapiens

<400> SEQUENCE: 87

caccacagtt atcacccatg ccctcctaaa agggtgtctc aaagcatatc tttctgtaga      60

gcagaattcg gaactgagaa gacgagggct caaattgaat ctcacaggat ttgcgtgcaa     120

gagaaaccca aaggaatgga ttggctcttc ttcagaaaca tttgcctttt gatcattcta     180

atggaatttg acattgaaaa tggcactaca aaatggcaaa cagtcagaag acaaaagcgg     240

gagtggatca agtttgccgc agcctgtcga gaaggagagg acaactcgaa gaggaacccc     300

attgccaaaa ttcgaatagg gcatgatgca ggcagctggt taaaaattga ttcaagaact     360

ggtgagatac aattttctag agaatttgat aagaagtcaa aatatattat caatgggata     420

tacacagcag agatcctggc tatagatgat ggctctggaa aaacagctac aggaaccata     480

tgtattgagg ttcctgatat caatgattat tgtccaaaca tttttcctga aagaagaacc     540

atctgcattg actctccatc agtccttatc tctgttaatg aacattctta tgggtctccg     600

tttactttct gtgttgttga tgagccacca ggaatagctg acatgtggga tgtcagatca     660

acaaatgcta cctcggcaat ccttacggct aagcaggttt tatctccagg attttatgaa     720

atcccaatcc tggtgaagga cagctataac agagcatgtg aattggcaca aatggtgcag     780

ttatatgcct gtgattgcga tgacaaccac atgtgcctgg actctggtgc cgcgggcatc     840

tacacagagg acataactgg tgacacgtat gggcctgtca ctgaagacca agctggagtt     900

tcaaatgttg gtcttggacc agcagggatt ggcatgatgg ttctgggcat cctgctactg     960

attt                                                                  964


<210> SEQ ID NO 88
<211> LENGTH: 276
<212> TYPE: PRT
<213> ORGANISM: Homo sapiens

<400> SEQUENCE: 88

Met Asp Trp Leu Phe Phe Arg Asn Ile Cys Leu Leu Ile Ile Leu Met
1               5                   10                  15

Glu Phe Asp Ile Glu Asn Gly Thr Thr Lys Trp Gln Thr Val Arg Arg
            20                  25                  30

Gln Lys Arg Glu Trp Ile Lys Phe Ala Ala Ala Cys Arg Glu Gly Glu
        35                  40                  45

Asp Asn Ser Lys Arg Asn Pro Ile Ala Lys Ile Arg Ile Gly His Asp
    50                  55                  60

Ala Gly Ser Trp Leu Lys Ile Asp Ser Arg Thr Gly Glu Ile Gln Phe
```

```
65                  70                  75                  80

Ser Arg Glu Phe Asp Lys Lys Ser Lys Tyr Ile Ile Asn Gly Ile Tyr
                85                  90                  95

Thr Ala Glu Ile Leu Ala Ile Asp Asp Gly Ser Gly Lys Thr Ala Thr
            100                 105                 110

Gly Thr Ile Cys Ile Glu Val Pro Asp Ile Asn Asp Tyr Cys Pro Asn
        115                 120                 125

Ile Phe Pro Glu Arg Arg Thr Ile Cys Ile Asp Ser Pro Ser Val Leu
    130                 135                 140

Ile Ser Val Asn Glu His Ser Tyr Gly Ser Pro Phe Thr Phe Cys Val
145                 150                 155                 160

Val Asp Glu Pro Pro Gly Ile Ala Asp Met Trp Asp Val Arg Ser Thr
                165                 170                 175

Asn Ala Thr Ser Ala Ile Leu Thr Ala Lys Gln Val Leu Ser Pro Gly
            180                 185                 190

Phe Tyr Glu Ile Pro Ile Leu Val Lys Asp Ser Tyr Asn Arg Ala Cys
        195                 200                 205

Glu Leu Ala Gln Met Val Gln Leu Tyr Ala Cys Asp Cys Asp Asp Asn
    210                 215                 220

His Met Cys Leu Asp Ser Gly Ala Ala Gly Ile Tyr Thr Glu Asp Ile
225                 230                 235                 240

Thr Gly Asp Thr Tyr Gly Pro Val Thr Glu Asp Gln Ala Gly Val Ser
                245                 250                 255

Asn Val Gly Leu Gly Pro Ala Gly Ile Gly Met Met Val Leu Gly Ile
            260                 265                 270

Leu Leu Leu Ile
        275
```

<210> SEQ ID NO 89
<211> LENGTH: 26
<212> TYPE: DNA
<213> ORGANISM: Artificial Sequence
<220> FEATURE:
<223> OTHER INFORMATION: Description of the artificial sequence:
Oligonucleotide

<400> SEQUENCE: 89
aatgataacg ctccagtctt ttcgca 26

<210> SEQ ID NO 90
<211> LENGTH: 27
<212> TYPE: DNA
<213> ORGANISM: Artificial Sequence
<220> FEATURE:
<223> OTHER INFORMATION: Description of the artificial sequence:
Oligonucleotide

<400> SEQUENCE: 90
gccttcttca tcaagatcaa ttgcttg 27

<210> SEQ ID NO 91
<211> LENGTH: 26
<212> TYPE: DNA
<213> ORGANISM: Artificial Sequence
<220> FEATURE:
<223> OTHER INFORMATION: Description of the artificial sequence:
Oligonucleotide

<400> SEQUENCE: 91
caccatgaat tgtgatgctt tgctac 26

<210> SEQ ID NO 92
<211> LENGTH: 22
<212> TYPE: DNA
<213> ORGANISM: Artificial Sequence
<220> FEATURE:
<223> OTHER INFORMATION: Description of the artificial sequence:
Oligonucleotide

<400> SEQUENCE: 92
ctaggtagct ggtcttgggg aa 22

<210> SEQ ID NO 93
<211> LENGTH: 21
<212> TYPE: DNA
<213> ORGANISM: Artificial Sequence
<220> FEATURE:
<223> OTHER INFORMATION: Description of the artificial sequence:
Oligonucleotide

<400> SEQUENCE: 93
ttctcagcct ccagaatgaa g 21

<210> SEQ ID NO 94
<211> LENGTH: 21
<212> TYPE: DNA
<213> ORGANISM: Artificial Sequence
<220> FEATURE:
<223> OTHER INFORMATION: Description of the artificial sequence:
Oligonucleotide

<400> SEQUENCE: 94
gaaggtaagg acagacgtgt c 21

<210> SEQ ID NO 95
<211> LENGTH: 27
<212> TYPE: DNA
<213> ORGANISM: Artificial Sequence
<220> FEATURE:
<223> OTHER INFORMATION: Description of the artificial sequence:
Oligonucleotide

<400> SEQUENCE: 95
accaatgaag gcattttgaa agttgtc 27

<210> SEQ ID NO 96
<211> LENGTH: 12
<212> TYPE: PRT
<213> ORGANISM: Homo sapiens

<400> SEQUENCE: 96

Thr His Ser Phe Thr Ala Phe Lys Arg His Val Cys
1 5 10

<210> SEQ ID NO 97
<211> LENGTH: 13
<212> TYPE: PRT
<213> ORGANISM: Homo sapiens

<400> SEQUENCE: 97

Asn Leu Ser Leu Pro Pro Ser Leu Ser Leu Ser Ile Cys
1 5 10

<210> SEQ ID NO 98
<211> LENGTH: 16
<212> TYPE: PRT

<213> ORGANISM: Homo sapiens

<400> SEQUENCE: 98

Glu Arg Pro Ser Ser Val Leu Thr Ile Tyr Asp Ile Gly Ile Gln Cys
1 5 10 15

<210> SEQ ID NO 99
<211> LENGTH: 15
<212> TYPE: PRT
<213> ORGANISM: Homo sapiens

<400> SEQUENCE: 99

Cys Tyr Gln Gln Tyr Thr Asn Leu Gln Glu Arg Pro Ser Ser Val
1 5 10 15

<210> SEQ ID NO 100
<211> LENGTH: 15
<212> TYPE: PRT
<213> ORGANISM: Homo sapiens

<400> SEQUENCE: 100

Thr Val Glu Pro Glu Thr Gly Asp Pro Val Thr Leu Arg Leu Cys
1 5 10 15

<210> SEQ ID NO 101
<211> LENGTH: 17
<212> TYPE: PRT
<213> ORGANISM: Homo sapiens

<400> SEQUENCE: 101

Cys Ser Arg Lys Lys Arg Ala Asp Lys Lys Glu Asn Gly Thr Lys Leu
1 5 10 15

Leu

<210> SEQ ID NO 102
<211> LENGTH: 3439
<212> TYPE: DNA
<213> ORGANISM: Homo sapiens

<400> SEQUENCE: 102
caccacagtt atcacccatg ccctcctaaa agggtgtctc aaagcatatc tttctgtaga 60
gcagaattcg gaactgagaa gacgagggct caaattgaat ctcacaggat ttgcgtgcaa 120
gagaaaccca aaggaatgga ttggctcttc ttcagaaaca tttgcctttt gatcattcta 180
atggtggtga tggaagtaaa cagtgaattt attgttgagg tgaaggaatt tgacattgaa 240
aatggcacta caaaatggca aacagtcaga agacaaaagc gggagtggat caagtttgcc 300
gcagcctgtc gagaaggaga ggacaactcg aagaggaacc ccattgccaa aattcgatca 360
gactgcgaat cgaaccagaa gataacatac cggatttctg gagtagggat tgatcgacca 420
ccatatgggg tattcaccat taatcctcgc actggggaaa ttaacatcac ttcagtggta 480
gacagagaaa taactccact ttcttgatc tattgccggg ctctgaattc acggggtgaa 540
gatttagaaa ggcctcttga gcttagagtc aaagttatgg acataaatga taacgctcca 600
gtcttttcgc aaagtgtata cacagccagc attgaagaaa atagtgatgc caatacattg 660
gtagtaaagt tatgtgccac agatgcagat gaagaaaatc atctgaattc taaaattgcc 720
tacaagatcg tctctcagga gccatcaggt gcacccatgt tcattctgaa taggtacact 780
ggagaagtct gcaccatgtc cagtttcttg gacagagagc aacacagtat gtacaacctg 840
gttgtgagag gctcagatcg ggatggagct gcagatggac tgtcttctga gtgtgactgt 900

```
agaatcaagg ttttagacgt caacgataat ttccccacct tagagaaaac ttcatactca    960
gccagtattg aagagaattg tttaagttcg gaactgatac gattacaagc aattgatctt   1020
gatgaagaag gcactgataa ctggttggct caatatttaa ttctctctgg aaatgatggg   1080
aattggttcg atattcaaac agatccacaa accaatgaag gcattttgaa agttgtcaag   1140
atgctggatt atgaacaagc acctaacatt cagcttagta tcggagttaa aaaccaagct   1200
gattttcact actccgttgc ttctcaattc caaatgcacc caacccctgt gagaattcaa   1260
gttgttgatg tgagagaagg acctgcattt catccaagta ctatggcttt tagtgtgcgg   1320
gaaggaataa aaggaagttc cttattgaat tatgtgcttg gcacatatac agccatagat   1380
ttggacacag gaaaccctgc aacagatgtc agatggctct ggaaaaacag ctacaggaac   1440
catatgtatt gaggttcctg atatcaatga ttattgtcca aacatttttc ctgaaagaag   1500
aaccatctgc attgactctc catcagtcct tatctctgtt aatgaacatt cttatgggtc   1560
tccgtttact ttctgtgttg ttgatgagcc accaggaata gctgacatgt gggatgtcag   1620
atcaacaaat gctacctcgg caatccttac ggctaagcag gttttatctc caggatttta   1680
tgaaatccca atcctggtga aggacagcta taacagagca tgtgaattgg cacaaatggt   1740
gcagttatat gcctgtgatt gcgatgacaa ccacatgtgc ctggactctg gtgccgcggg   1800
catctacaca gaggacataa ctggtgacac gtatgggcct gtcactgaag accaagctgg   1860
agtttcaaat gttggtcttg gaccagcagg gattggcatg atggttctgg gcatcctgct   1920
actgattttg gctccactct tgctgctcct gtgttgctgc aaacagagac agccagaagg   1980
cctgggaaca agatttgctc ctgtgcctga gggcggagaa ggagtgatgc agtcttggag   2040
aattgaaggg gcccatcccg aggacaggga tgtgtcaaat atatgtgcac ccatgacagc   2100
ctcaaatacc caggatcgga tggattcctc tgaaatctac accaacacct atgcagccgg   2160
gggcacggtg gaaggaggtg tatcgggagt ggagctcaac acaggtatgg ggacagccgt   2220
tggcctcatg gccgcagggg ccgcaggagc ctcaggggcc gcaaggaaga ggagctctac   2280
catgggaacc ctgcgggact acgctgacgc agacatcaac atggctttct tggacagcta   2340
cttctcggag aaagcgtatg cttatgcaga tgaagatgaa ggtcgaccag ccaatgactg   2400
cttgctcatt tatgaccacg agggagtcgg gtctcccgta ggctctattg gttgttgcag   2460
ttggattgtg gatgacttag atgaaagctg catggaaact ttagatccaa aatttaggac   2520
tcttgctgag atctgcttaa acacagaaat tgaaccattt ccttcacacc aggcttgtat   2580
accaatcagt actgacctcc ctttgctcgg acctaattac tttgttaatg aatcttcagg   2640
attgactccc tcagaagttg aattccaaga agaaatggca gcatctgaac ccgtggtcca   2700
tggggatatt attgtgactg agacttacgg taatgctgat ccatgtgtgc aacccactac   2760
aattattttt gatcctcagc ttgcacccaa tgttgtagta accgaagcag taatggcacc   2820
tgtctatgat attcaaggga atatttgtgt acctgctgag ttagcagatt acaacaatgt   2880
aatctatgct gagagagtac tggctagtcc tggtgtgcct gacatgagca atagtagcac   2940
gactgagggt tgtatgggac ctgtgatgag cggcaatatt ttagtagggc cagaaattca   3000
agtgatgcaa atgatgagtc cagaccttcc cataggccaa accgttggct ccacatcccc   3060
catgacatct cgacacagag taacacgata cagtaacata cattacaccc aacagtaagt   3120
gctttatggt cagtattcta tgtggagacc ttgcaccttg taatcatcaa tacatccacc   3180
aaaaatatat aatgtaccat atatattaat agtcaacaaa tactcagata ttctaaggtc   3240
```

-continued

```
aatgccatta tttgattata ccattttgag ggtgaatatg gctaggcact ttagataagc   3300

ctttttaaaa ttctttctga ttttaaataa tgcgtcaaaa aatgtgcaga aaatgtattg   3360

catcccttga tactgtctaa cgaatagcac ataactcata ttgtgaatcc tatgggtctt   3420

gaggcctgta gaaccaatc                                                3439


<210> SEQ ID NO 103
<211> LENGTH: 438
<212> TYPE: PRT
<213> ORGANISM: Homo sapiens

<400> SEQUENCE: 103

Met Asp Trp Leu Phe Phe Arg Asn Ile Cys Leu Leu Ile Ile Leu Met
1               5                   10                  15

Val Val Met Glu Val Asn Ser Glu Phe Ile Val Glu Val Lys Glu Phe
            20                  25                  30

Asp Ile Glu Asn Gly Thr Thr Lys Trp Gln Thr Val Arg Arg Gln Lys
        35                  40                  45

Arg Glu Trp Ile Lys Phe Ala Ala Ala Cys Arg Glu Gly Glu Asp Asn
    50                  55                  60

Ser Lys Arg Asn Pro Ile Ala Lys Ile Arg Ser Asp Cys Glu Ser Asn
65                  70                  75                  80

Gln Lys Ile Thr Tyr Arg Ile Ser Gly Val Gly Ile Asp Arg Pro Pro
                85                  90                  95

Tyr Gly Val Phe Thr Ile Asn Pro Arg Thr Gly Glu Ile Asn Ile Thr
            100                 105                 110

Ser Val Val Asp Arg Glu Ile Thr Pro Leu Phe Leu Ile Tyr Cys Arg
        115                 120                 125

Ala Leu Asn Ser Arg Gly Glu Asp Leu Glu Arg Pro Leu Glu Leu Arg
    130                 135                 140

Val Lys Val Met Asp Ile Asn Asp Asn Ala Pro Val Phe Ser Gln Ser
145                 150                 155                 160

Val Tyr Thr Ala Ser Ile Glu Glu Asn Ser Asp Ala Asn Thr Leu Val
                165                 170                 175

Val Lys Leu Cys Ala Thr Asp Ala Asp Glu Glu Asn His Leu Asn Ser
            180                 185                 190

Lys Ile Ala Tyr Lys Ile Val Ser Gln Glu Pro Ser Gly Ala Pro Met
        195                 200                 205

Phe Ile Leu Asn Arg Tyr Thr Gly Glu Val Cys Thr Met Ser Ser Phe
    210                 215                 220

Leu Asp Arg Glu Gln His Ser Met Tyr Asn Leu Val Val Arg Gly Ser
225                 230                 235                 240

Asp Arg Asp Gly Ala Ala Asp Gly Leu Ser Ser Glu Cys Asp Cys Arg
                245                 250                 255

Ile Lys Val Leu Asp Val Asn Asp Asn Phe Pro Thr Leu Glu Lys Thr
            260                 265                 270

Ser Tyr Ser Ala Ser Ile Glu Glu Asn Cys Leu Ser Ser Glu Leu Ile
        275                 280                 285

Arg Leu Gln Ala Ile Asp Leu Asp Glu Glu Gly Thr Asp Asn Trp Leu
    290                 295                 300

Ala Gln Tyr Leu Ile Leu Ser Gly Asn Asp Gly Asn Trp Phe Asp Ile
305                 310                 315                 320

Gln Thr Asp Pro Gln Thr Asn Glu Gly Ile Leu Lys Val Val Lys Met
                325                 330                 335
```

```
Leu Asp Tyr Glu Gln Ala Pro Asn Ile Gln Leu Ser Ile Gly Val Lys
            340                 345                 350

Asn Gln Ala Asp Phe His Tyr Ser Val Ala Ser Gln Phe Gln Met His
        355                 360                 365

Pro Thr Pro Val Arg Ile Gln Val Val Asp Val Arg Glu Gly Pro Ala
    370                 375                 380

Phe His Pro Ser Thr Met Ala Phe Ser Val Arg Glu Gly Ile Lys Gly
385                 390                 395                 400

Ser Ser Leu Leu Asn Tyr Val Leu Gly Thr Tyr Thr Ala Ile Asp Leu
                405                 410                 415

Asp Thr Gly Asn Pro Ala Thr Asp Val Arg Trp Leu Trp Lys Asn Ser
            420                 425                 430

Tyr Arg Asn His Met Tyr
        435
```

<210> SEQ ID NO 104
<211> LENGTH: 3360
<212> TYPE: DNA
<213> ORGANISM: Homo sapiens

<400> SEQUENCE: 104

```
caccacagtt atcacccatg ccctcctaaa agggtgtctc aaagcatatc tttctgtaga     60

gcagaattcg gaactgagaa gacgagggct caaattgaat ctcacaggat ttgcgtgcaa    120

gagaaaccca aaggaatgga ttggctcttc ttcagaaaca tttgcctttt gatcattcta    180

atggtggtga tggaagtaaa cagtgaattt attgttgagg tgaaggaatt tgacattgaa    240

aatggcacta caaaatggca aacagtcaga agacaaaagc gggagtggat caagtttgcc    300

gcagcctgtc gagaaggaga ggacaactcg aagaggaacc ccattgccaa aattcgatca    360

gactgcgaat cgaaccagaa gataacatac cggatttctg gagtagggat tgatcgacca    420

ccatatgggg tattcaccat taatcctcgc actggggaaa ttaacatcac ttcagtggta    480

gacagagaaa taactccact tttcttgatc tattgccggg ctctgaattc acggggtgaa    540

gatttagaaa ggcctcttga gcttagagtc aaagttatgg acataaatga taacgctcca    600

gtcttttcgc aaagtgtata cacagccagc attgaagaaa atagtgatgc caatacattg    660

gtagtaaagt tatgtgccac agatgcagat gaagaaaatc atctgaattc taaaattgcc    720

tacaagatcg tctctcagga gccatcaggt gcacccatgt tcattctgaa taggtacact    780

ggagaagtct gcaccatgtc cagtttcttg gacagagagc aacacagtat gtacaacctg    840

gttgtgagag gctcagatcg ggatggagct gcagatggac tgtcttctga gtgtgactgt    900

agaatcaagg ttttagacgt caacgataat ttccccacct tagagaaaac ttcatactca    960

gccagtattg aagagaattg tttaagttcg gaactgatac gattacaagc aattgatctt   1020

gatgaagaag gcactgataa ctggttggct caatatttaa ttctctctgg aaatgatggg   1080

aattggttcg atattcaaac agatccacaa accaatgaag gcattttgaa agttgtcaag   1140

atgctggatt atgaacaagc acctaacatt cagcttagta tcggagttaa aaaccaagct   1200

gattttcact actccgttgc ttctcaattc caaatgcacc caacccctgt gagaattcaa   1260

gttgttgatg tgagagaagg acctgcattt catccaagta ctatggcttt tagtgtgcgg   1320

gaaggaataa aaggaagttc cttattgaat tatgtgcttg gcacatatac agccatagat   1380

ttggacacag gaaaccctgc aacagatgtc agatatatca tagggcatga tgcaggcagc   1440

tggttaaaaa ttgattcaag aactggtgag atacaatttt ctagagaatt tgataagaag   1500
```

-continued tcaaaatata ttatcaatgg gatatacaca gcagagatcc tggctataga tgctacctcg 1560
gcaatcctta cggctaagca ggttttatct ccaggatttt atgaaatccc aatcctggtg 1620
aaggacagct ataacagagc atgtgaattg gcacaaatgg tgcagttata tgcctgtgat 1680
tgcgatgaca accacatgtg cctggactct ggtgccgcgg gcatctacac agaggacata 1740
actggtgaca cgtatgggcc tgtcactgaa gaccaagctg gagtttcaaa tgttggtctt 1800
ggaccagcag ggattggcat gatggttctg ggcatcctgc tactgatttt ggctccactc 1860
ttgctgctcc tgtgttgctg caaacagaga cagccagaag gcctgggaac aagatttgct 1920
cctgtgcctg agggcggaga aggagtgatg cagtcttgga gaattgaagg ggcccatccc 1980
gaggacaggg atgtgtcaaa tatatgtgca cccatgacag cctcaaatac ccaggatcgg 2040
atggattcct ctgaaatcta caccaacacc tatgcagccg gggggcacggt ggaaggaggt 2100 gtatcgggag tggagctcaa cacaggtatg ggacagccg ttggcctcat ggccgcaggg 2160
gccgcaggag cctcaggggc cgcaaggaag aggagctcta ccatgggaac cctgcgggac 2220
tacgctgacg cagacatcaa catggctttc ttggacagct acttctcgga gaaagcgtat 2280
gcttatgcag atgaagatga aggtcgacca gccaatgact gcttgctcat ttatgaccac 2340
gagggagtcg ggtctcccgt aggctctatt ggttgttgca gttggattgt ggatgactta 2400
gatgaaagct gcatggaaac tttagatcca aaatttagga ctcttgctga gatctgctta 2460
aacacagaaa ttgaaccatt tccttcacac caggcttgta taccaatcag tactgacctc 2520
cctttgctcg gacctaatta ctttgttaat gaatcttcag gattgactcc ctcagaagtt 2580
gaattccaag aagaaatggc agcatctgaa cccgtggtcc atggggatat tattgtgact 2640
gagacttacg gtaatgctga tccatgtgtg caacccacta caattatttt tgatcctcag 2700
cttgcaccca atgttgtagt aaccgaagca gtaatggcac ctgtctatga tattcaaggg 2760
aatatttgtg tacctgctga gttagcagat tacaacaatg taatctatgc tgagagagta 2820
ctggctagtc ctggtgtgcc tgacatgagc aatagtagca cgactgaggg ttgtatggga 2880
cctgtgatga gcggcaatat tttagtaggg ccagaaattc aagtgatgca aatgatgagt 2940
ccagaccttc ccataggcca aaccgttggc tccacatccc ccatgacatc tcgacacaga 3000
gtaacacgat acagtaacat acattacacc caacagtaag tgctttatgg tcagtattct 3060
atgtggagac cttgcacctt gtaatcatca atacatccac caaaaatata taatgtacca 3120
tatatattaa tagtcaacaa atactcagat attctaaggt caatgccatt atttgattat 3180
accattttga gggtgaatat ggctaggcac tttagataag ccttttttaaa attctttctg 3240 attttaaata atgcgtcaaa aaatgtgcag aaaatgtatt gcatcccttg atactgtcta 3300
acgaatagca cataactcat attgtgaatc ctatgggtct tgaggcctgt agaaccaatc 3360

<210> SEQ ID NO 105
<211> LENGTH: 967
<212> TYPE: PRT
<213> ORGANISM: Homo sapiens

<400> SEQUENCE: 105

Met Asp Trp Leu Phe Phe Arg Asn Ile Cys Leu Leu Ile Ile Leu Met
1 5 10 15

Val Val Met Glu Val Asn Ser Glu Phe Ile Val Glu Val Lys Glu Phe
20 25 30

Asp Ile Glu Asn Gly Thr Thr Lys Trp Gln Thr Val Arg Arg Gln Lys
35 40 45

```
Arg Glu Trp Ile Lys Phe Ala Ala Ala Cys Arg Glu Gly Glu Asp Asn
    50                  55                  60

Ser Lys Arg Asn Pro Ile Ala Lys Ile Arg Ser Asp Cys Glu Ser Asn
65                  70                  75                  80

Gln Lys Ile Thr Tyr Arg Ile Ser Gly Val Gly Ile Asp Arg Pro Pro
                85                  90                  95

Tyr Gly Val Phe Thr Ile Asn Pro Arg Thr Gly Glu Ile Asn Ile Thr
            100                 105                 110

Ser Val Val Asp Arg Glu Ile Thr Pro Leu Phe Leu Ile Tyr Cys Arg
        115                 120                 125

Ala Leu Asn Ser Arg Gly Glu Asp Leu Glu Arg Pro Leu Glu Leu Arg
    130                 135                 140

Val Lys Val Met Asp Ile Asn Asp Asn Ala Pro Val Phe Ser Gln Ser
145                 150                 155                 160

Val Tyr Thr Ala Ser Ile Glu Glu Asn Ser Asp Ala Asn Thr Leu Val
                165                 170                 175

Val Lys Leu Cys Ala Thr Asp Ala Asp Glu Glu Asn His Leu Asn Ser
            180                 185                 190

Lys Ile Ala Tyr Lys Ile Val Ser Gln Glu Pro Ser Gly Ala Pro Met
        195                 200                 205

Phe Ile Leu Asn Arg Tyr Thr Gly Glu Val Cys Thr Met Ser Ser Phe
    210                 215                 220

Leu Asp Arg Glu Gln His Ser Met Tyr Asn Leu Val Val Arg Gly Ser
225                 230                 235                 240

Asp Arg Asp Gly Ala Ala Asp Gly Leu Ser Ser Glu Cys Asp Cys Arg
                245                 250                 255

Ile Lys Val Leu Asp Val Asn Asp Asn Phe Pro Thr Leu Glu Lys Thr
            260                 265                 270

Ser Tyr Ser Ala Ser Ile Glu Glu Asn Cys Leu Ser Ser Glu Leu Ile
        275                 280                 285

Arg Leu Gln Ala Ile Asp Leu Asp Glu Glu Gly Thr Asp Asn Trp Leu
    290                 295                 300

Ala Gln Tyr Leu Ile Leu Ser Gly Asn Asp Gly Asn Trp Phe Asp Ile
305                 310                 315                 320

Gln Thr Asp Pro Gln Thr Asn Glu Gly Ile Leu Lys Val Val Lys Met
                325                 330                 335

Leu Asp Tyr Glu Gln Ala Pro Asn Ile Gln Leu Ser Ile Gly Val Lys
            340                 345                 350

Asn Gln Ala Asp Phe His Tyr Ser Val Ala Ser Gln Phe Gln Met His
        355                 360                 365

Pro Thr Pro Val Arg Ile Gln Val Val Asp Val Arg Glu Gly Pro Ala
    370                 375                 380

Phe His Pro Ser Thr Met Ala Phe Ser Val Arg Glu Gly Ile Lys Gly
385                 390                 395                 400

Ser Ser Leu Leu Asn Tyr Val Leu Gly Thr Tyr Thr Ala Ile Asp Leu
                405                 410                 415

Asp Thr Gly Asn Pro Ala Thr Asp Val Arg Tyr Ile Ile Gly His Asp
            420                 425                 430

Ala Gly Ser Trp Leu Lys Ile Asp Ser Arg Thr Gly Glu Ile Gln Phe
        435                 440                 445

Ser Arg Glu Phe Asp Lys Lys Ser Lys Tyr Ile Ile Asn Gly Ile Tyr
    450                 455                 460

Thr Ala Glu Ile Leu Ala Ile Asp Ala Thr Ser Ala Ile Leu Thr Ala
```

```
465                 470                 475                 480

Lys Gln Val Leu Ser Pro Gly Phe Tyr Glu Ile Pro Ile Leu Val Lys
                485                 490                 495

Asp Ser Tyr Asn Arg Ala Cys Glu Leu Ala Gln Met Val Gln Leu Tyr
            500                 505                 510

Ala Cys Asp Cys Asp Asp Asn His Met Cys Leu Asp Ser Gly Ala Ala
        515                 520                 525

Gly Ile Tyr Thr Glu Asp Ile Thr Gly Asp Thr Tyr Gly Pro Val Thr
    530                 535                 540

Glu Asp Gln Ala Gly Val Ser Asn Val Gly Leu Gly Pro Ala Gly Ile
545                 550                 555                 560

Gly Met Met Val Leu Gly Ile Leu Leu Leu Ile Leu Ala Pro Leu Leu
                565                 570                 575

Leu Leu Leu Cys Cys Cys Lys Gln Arg Gln Pro Glu Gly Leu Gly Thr
            580                 585                 590

Arg Phe Ala Pro Val Pro Glu Gly Gly Glu Gly Val Met Gln Ser Trp
        595                 600                 605

Arg Ile Glu Gly Ala His Pro Glu Asp Arg Asp Val Ser Asn Ile Cys
    610                 615                 620

Ala Pro Met Thr Ala Ser Asn Thr Gln Asp Arg Met Asp Ser Ser Glu
625                 630                 635                 640

Ile Tyr Thr Asn Thr Tyr Ala Ala Gly Gly Thr Val Glu Gly Gly Val
                645                 650                 655

Ser Gly Val Glu Leu Asn Thr Gly Met Gly Thr Ala Val Gly Leu Met
            660                 665                 670

Ala Ala Gly Ala Ala Gly Ala Ser Gly Ala Ala Arg Lys Arg Ser Ser
        675                 680                 685

Thr Met Gly Thr Leu Arg Asp Tyr Ala Asp Ala Asp Ile Asn Met Ala
    690                 695                 700

Phe Leu Asp Ser Tyr Phe Ser Glu Lys Ala Tyr Ala Tyr Ala Asp Glu
705                 710                 715                 720

Asp Glu Gly Arg Pro Ala Asn Asp Cys Leu Leu Ile Tyr Asp His Glu
                725                 730                 735

Gly Val Gly Ser Pro Val Gly Ser Ile Gly Cys Cys Ser Trp Ile Val
            740                 745                 750

Asp Asp Leu Asp Glu Ser Cys Met Glu Thr Leu Asp Pro Lys Phe Arg
        755                 760                 765

Thr Leu Ala Glu Ile Cys Leu Asn Thr Glu Ile Glu Pro Phe Pro Ser
    770                 775                 780

His Gln Ala Cys Ile Pro Ile Ser Thr Asp Leu Pro Leu Leu Gly Pro
785                 790                 795                 800

Asn Tyr Phe Val Asn Glu Ser Ser Gly Leu Thr Pro Ser Glu Val Glu
                805                 810                 815

Phe Gln Glu Glu Met Ala Ala Ser Glu Pro Val Val His Gly Asp Ile
            820                 825                 830

Ile Val Thr Glu Thr Tyr Gly Asn Ala Asp Pro Cys Val Gln Pro Thr
        835                 840                 845

Thr Ile Ile Phe Asp Pro Gln Leu Ala Pro Asn Val Val Val Thr Glu
    850                 855                 860

Ala Val Met Ala Pro Val Tyr Asp Ile Gln Gly Asn Ile Cys Val Pro
865                 870                 875                 880

Ala Glu Leu Ala Asp Tyr Asn Asn Val Ile Tyr Ala Glu Arg Val Leu
                885                 890                 895
```

```
Ala Ser Pro Gly Val Pro Asp Met Ser Asn Ser Ser Thr Thr Glu Gly
            900                 905                 910

Cys Met Gly Pro Val Met Ser Gly Asn Ile Leu Val Gly Pro Glu Ile
        915                 920                 925

Gln Val Met Gln Met Met Ser Pro Asp Leu Pro Ile Gly Gln Thr Val
    930                 935                 940

Gly Ser Thr Ser Pro Met Thr Ser Arg His Arg Val Thr Arg Tyr Ser
945                 950                 955                 960

Asn Ile His Tyr Thr Gln Gln
                965


<210> SEQ ID NO 106
<211> LENGTH: 3636
<212> TYPE: DNA
<213> ORGANISM: Homo sapiens

<400> SEQUENCE: 106

caccacagtt atcacccatg ccctcctaaa agggtgtctc aaagcatatc tttctgtaga      60

gcagaattcg gaactgagaa gacgagggct caaattgaat ctcacaggat ttgcgtgcaa     120

gagaaaccca aaggaatgga ttggctcttc ttcagaaaca tttgcctttt gatcattcta     180

atggtggtga tggaagtaaa cagtgaattt attgttgagg tgaaggaatt tgacattgaa     240

aatggcacta caaaatggca aacagtcaga agacaaaagc gggagtggat caagtttgcc     300

gcagcctgtc gagaaggaga ggacaactcg aagaggaacc ccattgccaa aattcgatca     360

gactgcgaat cgaaccagaa gataacatac cggatttctg gagtagggat tgatcgacca     420

ccatatgggg tattcaccat taatcctcgc actggggaaa ttaacatcac ttcagtggta     480

gacagagaaa taactccact tttcttgatc tattgccggg ctctgaattc acggggtgaa     540

gatttagaaa ggcctcttga gcttagagtc aaagttatgg acataaatga taacgctcca     600

gtcttttcgc aaagtgtata cacagccagc attgaagaaa atagtgatgc caatacattg     660

gtagtaaagt tatgtgccac agatgcagat gaagaaaatc atctgaattc taaaattgcc     720

tacaagatcg tctctcagga gccatcaggt gcacccatgt tcattctgaa taggtacact     780

ggagaagtct gcaccatgtc cagtttcttg gacagagagc aacacagtat gtacaacctg     840

gttgtgagag gctcagatcg ggatggagct gcagatggac tgtcttctga gtgtgactgt     900

agaatcaagg ttttagacgt caacgataat ttccccacct tagagaaaac ttcatactca     960

gccagtattg aagagaattg tttaagttcg gaactgatac gattacaagc aattgatctt    1020

gatgaagaag gcactgataa ctggttggct caatatttaa ttctctctgg aaatgatggg    1080

aattggttcg atattcaaac agatccacaa accaatgaag gcattttgaa agttgtcaag    1140

atgctggatt atgaacaagc acctaacatt cagcttagta tcggagttaa aaaccaagct    1200

gattttcact actccgttgc ttctcaattc caaatgcacc caacccctgt gagaattcaa    1260

gttgttgatg tgagagaagg acctgcattt catccaagta ctatggcttt tagtgtgcgg    1320

gaaggaataa aaggaagttc cttattgaat tatgtgcttg gcacatatac agccatagat    1380

ttggacacag gaaaccctgc aacagatgtc agatatatca tagggcatga tgcaggcagc    1440

tggttaaaaa ttgattcaag aactggtgag atacaatttt ctagagaatt tgataagaag    1500

tcaaaatata ttatcaatgg gatatacaca gcagagatcc tggctataga tgatggctct    1560

ggaaaaacag ctacaggaac catatgtatt gaggttcctg atatcaatga ttattgtcca    1620

aacattttc ctgaaagaag aaccatctgc attgactctc catcagtcct tatctctgtt    1680
```

```
aatgaacatt cttatgggtc tccgtttact ttctgtgttg ttgatgagcc accaggaata   1740

gctgacatgt gggatgtcag atcaacaaat gctacctcgg caatccttac ggctaagcag   1800

gttttatctc caggatttta tgaaatccca atcctggtga aggacagcta taacagagca   1860

tgtgaattgg cacaaatggt gcagttatat gcctgtgatt gcgatgacaa ccacatgtgc   1920

ctggactctg gtgccgcggg catctacaca gaggacataa ctggtgacac gtatgggcct   1980

gtcactgaag accaagctgg agtttcaaat gttggtcttg gaccagcagg gattggcatg   2040

atggttctgg gcatcctgct actgattttg gctccactct tgctgctcct gtgttgctgc   2100

aaacagagac agccagaagg cctgggaaca agatttgctc ctgtgcctga gggcggagaa   2160

ggagtgatgc agtcttggag aattgaaggg gcccatcccg aggacaggct tttagcgcc   2220

tacgccttgc cgggtggtgg tggcaccgca gacggcggcg gcagcgtttt aggcagatgc   2280

gcgctgcagg caactccagc gctgttaaac caacatcctc ccttttcaga aatctacacc   2340

aacacctatg cagccggggg cacggtggaa ggaggtgtat cgggagtgga gctcaacaca   2400

ggtatgggga cagccgttgg cctcatggcc gcaggggccg caggagcctc aggggccgca   2460

aggaagagga gctctaccat gggaaccctg cgggactacg ctgacgcaga catcaacatg   2520

gctttcttgg acagctactt ctcggagaaa gcgtatgctt atgcagatga agatgaaggt   2580

cgaccagcca atgactgctt gctcatttat gaccacgagg gagtcgggtc tcccgtaggc   2640

tctattggtt gttgcagttg gattgtggat gacttagatg aaagctgcat ggaaacttta   2700

gatccaaaat ttaggactct tgctgagatc tgcttaaaca cagaaattga accatttcct   2760

tcacaccagg cttgtatacc aatcagtact gacctccctt tgctcggacc taattacttt   2820

gttaatgaat cttcaggatt gactccctca gaagttgaat tccaagaaga aatggcagca   2880

tctgaacccg tggtccatgg ggatattatt gtgactgaga cttacggtaa tgctgatcca   2940

tgtgtgcaac ccactacaat tatttttgat cctcagcttg cacccaatgt tgtagtaacc   3000

gaagcagtaa tggcacctgt ctatgatatt caagggaata tttgtgtacc tgctgagtta   3060

gcagattaca acaatgtaat ctatgctgag agagtactgg ctagtcctgg tgtgcctgac   3120

atgagcaata gtagcacgac tgagggttgt atgggacctg tgatgagcgg caatatttta   3180

gtagggccag aaattcaagt gatgcaaatg atgagtccag accttcccat aggccaaacc   3240

gttggctcca catcccccat gacatctcga cacagagtaa cacgatacag taacatacat   3300

tacacccaac agtaagtgct ttatggtcag tattctatgt ggagaccttg caccttgtaa   3360

tcatcaatac atccaccaaa aatatataat gtaccatata tattaatagt caacaaatac   3420

tcagatattc taaggtcaat gccattattt gattatacca ttttgagggt gaatatggct   3480

aggcacttta gataagcctt tttaaaattc tttctgattt taaataatgc gtcaaaaaat   3540

gtgcagaaaa tgtattgcat cccttgatac tgtctaacga atagcacata actcatattg   3600

tgaatcctat gggtcttgag gcctgtagaa ccaatc                              3636
```

<210> SEQ ID NO 107
<211> LENGTH: 1059
<212> TYPE: PRT
<213> ORGANISM: Homo sapiens

<400> SEQUENCE: 107

```
Met Asp Trp Leu Phe Phe Arg Asn Ile Cys Leu Leu Ile Ile Leu Met
1               5                   10                  15

Val Val Met Glu Val Asn Ser Glu Phe Ile Val Glu Val Lys Glu Phe
```

```
            20                  25                  30

Asp Ile Glu Asn Gly Thr Thr Lys Trp Gln Thr Val Arg Arg Gln Lys
        35                  40                  45

Arg Glu Trp Ile Lys Phe Ala Ala Ala Cys Arg Glu Gly Glu Asp Asn
    50                  55                  60

Ser Lys Arg Asn Pro Ile Ala Lys Ile Arg Ser Asp Cys Glu Ser Asn
65                  70                  75                  80

Gln Lys Ile Thr Tyr Arg Ile Ser Gly Val Gly Ile Asp Arg Pro Pro
                85                  90                  95

Tyr Gly Val Phe Thr Ile Asn Pro Arg Thr Gly Glu Ile Asn Ile Thr
            100                 105                 110

Ser Val Val Asp Arg Glu Ile Thr Pro Leu Phe Leu Ile Tyr Cys Arg
        115                 120                 125

Ala Leu Asn Ser Arg Gly Glu Asp Leu Glu Arg Pro Leu Glu Leu Arg
    130                 135                 140

Val Lys Val Met Asp Ile Asn Asp Asn Ala Pro Val Phe Ser Gln Ser
145                 150                 155                 160

Val Tyr Thr Ala Ser Ile Glu Glu Asn Ser Asp Ala Asn Thr Leu Val
                165                 170                 175

Val Lys Leu Cys Ala Thr Asp Ala Asp Glu Glu Asn His Leu Asn Ser
            180                 185                 190

Lys Ile Ala Tyr Lys Ile Val Ser Gln Glu Pro Ser Gly Ala Pro Met
        195                 200                 205

Phe Ile Leu Asn Arg Tyr Thr Gly Glu Val Cys Thr Met Ser Ser Phe
    210                 215                 220

Leu Asp Arg Glu Gln His Ser Met Tyr Asn Leu Val Val Arg Gly Ser
225                 230                 235                 240

Asp Arg Asp Gly Ala Ala Asp Gly Leu Ser Ser Glu Cys Asp Cys Arg
                245                 250                 255

Ile Lys Val Leu Asp Val Asn Asp Asn Phe Pro Thr Leu Glu Lys Thr
            260                 265                 270

Ser Tyr Ser Ala Ser Ile Glu Glu Asn Cys Leu Ser Ser Glu Leu Ile
        275                 280                 285

Arg Leu Gln Ala Ile Asp Leu Asp Glu Glu Gly Thr Asp Asn Trp Leu
    290                 295                 300

Ala Gln Tyr Leu Ile Leu Ser Gly Asn Asp Gly Asn Trp Phe Asp Ile
305                 310                 315                 320

Gln Thr Asp Pro Gln Thr Asn Glu Gly Ile Leu Lys Val Val Lys Met
                325                 330                 335

Leu Asp Tyr Glu Gln Ala Pro Asn Ile Gln Leu Ser Ile Gly Val Lys
            340                 345                 350

Asn Gln Ala Asp Phe His Tyr Ser Val Ala Ser Gln Phe Gln Met His
        355                 360                 365

Pro Thr Pro Val Arg Ile Gln Val Val Asp Val Arg Glu Gly Pro Ala
    370                 375                 380

Phe His Pro Ser Thr Met Ala Phe Ser Val Arg Glu Gly Ile Lys Gly
385                 390                 395                 400

Ser Ser Leu Leu Asn Tyr Val Leu Gly Thr Tyr Thr Ala Ile Asp Leu
                405                 410                 415

Asp Thr Gly Asn Pro Ala Thr Asp Val Arg Tyr Ile Ile Gly His Asp
            420                 425                 430

Ala Gly Ser Trp Leu Lys Ile Asp Ser Arg Thr Gly Glu Ile Gln Phe
        435                 440                 445
```

-continued

```
Ser Arg Glu Phe Asp Lys Lys Ser Lys Tyr Ile Ile Asn Gly Ile Tyr
    450                 455                 460

Thr Ala Glu Ile Leu Ala Ile Asp Asp Gly Ser Gly Lys Thr Ala Thr
465                 470                 475                 480

Gly Thr Ile Cys Ile Glu Val Pro Asp Ile Asn Asp Tyr Cys Pro Asn
                485                 490                 495

Ile Phe Pro Glu Arg Arg Thr Ile Cys Ile Asp Ser Pro Ser Val Leu
            500                 505                 510

Ile Ser Val Asn Glu His Ser Tyr Gly Ser Pro Phe Thr Phe Cys Val
        515                 520                 525

Val Asp Glu Pro Pro Gly Ile Ala Asp Met Trp Asp Val Arg Ser Thr
    530                 535                 540

Asn Ala Thr Ser Ala Ile Leu Thr Ala Lys Gln Val Leu Ser Pro Gly
545                 550                 555                 560

Phe Tyr Glu Ile Pro Ile Leu Val Lys Asp Ser Tyr Asn Arg Ala Cys
                565                 570                 575

Glu Leu Ala Gln Met Val Gln Leu Tyr Ala Cys Asp Cys Asp Asp Asn
            580                 585                 590

His Met Cys Leu Asp Ser Gly Ala Ala Gly Ile Tyr Thr Glu Asp Ile
        595                 600                 605

Thr Gly Asp Thr Tyr Gly Pro Val Thr Glu Asp Gln Ala Gly Val Ser
    610                 615                 620

Asn Val Gly Leu Gly Pro Ala Gly Ile Gly Met Met Val Leu Gly Ile
625                 630                 635                 640

Leu Leu Leu Ile Leu Ala Pro Leu Leu Leu Leu Leu Cys Cys Cys Lys
                645                 650                 655

Gln Arg Gln Pro Glu Gly Leu Gly Thr Arg Phe Ala Pro Val Pro Glu
            660                 665                 670

Gly Gly Glu Gly Val Met Gln Ser Trp Arg Ile Glu Gly Ala His Pro
        675                 680                 685

Glu Asp Arg Leu Phe Ser Ala Tyr Ala Leu Pro Gly Gly Gly Gly Thr
    690                 695                 700

Ala Asp Gly Gly Gly Ser Val Leu Gly Arg Cys Ala Leu Gln Ala Thr
705                 710                 715                 720

Pro Ala Leu Leu Asn Gln His Pro Pro Phe Ser Glu Ile Tyr Thr Asn
                725                 730                 735

Thr Tyr Ala Ala Gly Gly Thr Val Glu Gly Gly Val Ser Gly Val Glu
            740                 745                 750

Leu Asn Thr Gly Met Gly Thr Ala Val Gly Leu Met Ala Ala Gly Ala
        755                 760                 765

Ala Gly Ala Ser Gly Ala Ala Arg Lys Arg Ser Ser Thr Met Gly Thr
    770                 775                 780

Leu Arg Asp Tyr Ala Asp Ala Asp Ile Asn Met Ala Phe Leu Asp Ser
785                 790                 795                 800

Tyr Phe Ser Glu Lys Ala Tyr Ala Tyr Ala Asp Glu Asp Glu Gly Arg
                805                 810                 815

Pro Ala Asn Asp Cys Leu Leu Ile Tyr Asp His Glu Gly Val Gly Ser
            820                 825                 830

Pro Val Gly Ser Ile Gly Cys Cys Ser Trp Ile Val Asp Asp Leu Asp
        835                 840                 845

Glu Ser Cys Met Glu Thr Leu Asp Pro Lys Phe Arg Thr Leu Ala Glu
    850                 855                 860
```

```
Ile Cys Leu Asn Thr Glu Ile Glu Pro Phe Pro Ser His Gln Ala Cys
865                 870                 875                 880

Ile Pro Ile Ser Thr Asp Leu Pro Leu Leu Gly Pro Asn Tyr Phe Val
                885                 890                 895

Asn Glu Ser Ser Gly Leu Thr Pro Ser Glu Val Glu Phe Gln Glu Glu
            900                 905                 910

Met Ala Ala Ser Glu Pro Val Val His Gly Asp Ile Ile Val Thr Glu
        915                 920                 925

Thr Tyr Gly Asn Ala Asp Pro Cys Val Gln Pro Thr Thr Ile Ile Phe
    930                 935                 940

Asp Pro Gln Leu Ala Pro Asn Val Val Val Thr Glu Ala Val Met Ala
945                 950                 955                 960

Pro Val Tyr Asp Ile Gln Gly Asn Ile Cys Val Pro Ala Glu Leu Ala
                965                 970                 975

Asp Tyr Asn Asn Val Ile Tyr Ala Glu Arg Val Leu Ala Ser Pro Gly
            980                 985                 990

Val Pro Asp Met Ser Asn Ser Ser  Thr Thr Glu Gly Cys  Met Gly Pro
        995                 1000                1005

Val Met  Ser Gly Asn Ile Leu  Val Gly Pro Glu Ile  Gln Val Met
    1010                1015                1020

Gln Met  Met Ser Pro Asp Leu  Pro Ile Gly Gln Thr  Val Gly Ser
    1025                1030                1035

Thr Ser  Pro Met Thr Ser Arg  His Arg Val Thr Arg  Tyr Ser Asn
    1040                1045                1050

Ile His  Tyr Thr Gln Gln
    1055
```

<210> SEQ ID NO 108
<211> LENGTH: 2074
<212> TYPE: DNA
<213> ORGANISM: Homo sapiens

<400> SEQUENCE: 108

```
tatacagcca tagatttgga cacaggaaac cctgcaacag atgtcagatg gctctggaaa      60

aacagctaca ggaaccatat gtattgaggt tcctgatatc aatgattatt gtccaaacat     120

ttttcctgaa agaagaacca tctgcattga ctctccatca gtccttatct ctgttaatga     180

acattcttat gggtctccgt ttactttctg tgttgttgat gagccaccag gaatagctga     240

catgtgggat gtcagatcaa caaatgctac ctcggcaatc cttacggcta agcaggtttt     300

atctccagga ttttatgaaa tcccaatcct ggtgaaggac agctataaca gagcatgtga     360

attggcacaa atggtgcagt tatatgcctg tgattgcgat gacaaccaca tgtgcctgga     420

ctctggtgcc gcgggcatct acacagagga cataactggt gacacgtatg ggcctgtcac     480

tgaagaccaa gctggagttt caaatgttgg tcttggacca gcagggattg gcatgatggt     540

tctgggcatc ctgctactga ttttggctcc actcttgctg ctcctgtgtt gctgcaaaca     600

gagacagcca gaaggcctgg gaacaagatt tgctcctgtg cctgagggcg gagaaggagt     660

gatgcagtct tggagaattg aaggggccca tcccgaggac agggatgtgt caaatatatg     720

tgcacccatg acagcctcaa atacccagga tcggatggat tcctctgaaa tctacaccaa     780

cacctatgca gccgggggca cggtggaagg aggtgtatcg ggagtggagc tcaacacagg     840

tatggggaca gccgttggcc tcatggccgc aggggccgca ggagcctcag ggccgcaagg     900

gaagaggagc tctaccatgg gaaccctgcg ggactacgct gacgcagaca tcaacatggc     960
```

-continued

```
tttcttggac agctacttct cggagaaagc gtatgcttat gcagatgaag atgaaggtcg   1020
accagccaat gactgcttgc tcatttatga ccacgaggga gtcgggtctc ccgtaggctc   1080
tattggttgt tgcagttgga ttgtggatga cttagatgaa agctgcatgg aaactttaga   1140
tccaaaattt aggactcttg ctgagatctg cttaaacaca gaaattgaac catttccttc   1200
acaccaggct tgtataccaa tcagtactga cctccctttg ctcggaccta attactttgt   1260
taatgaatct tcaggattga ctccctcaga agttgaattc caagaagaaa tggcagcatc   1320
tgaacccgtg gtccatgggg atattattgt gactgagact tacggtaatg ctgatccatg   1380
tgtgcaaccc actacaatta tttttgatcc tcagcttgca cccaatgttg tagtaaccga   1440
agcagtaatg gcacctgtct atgatattca agggaatatt tgtgtacctg ctgagttagc   1500
agattacaac aatgtaatct atgctgagag agtactggct agtcctggtg tgcctgacat   1560
gagcaatagt agcacgactg agggttgtat gggacctgtg atgagcggca atattttagt   1620
agggccagaa attcaagtga tgcaaatgat gagtccagac cttcccatag gccaaaccgt   1680
tggctccaca tcccccatga catctcgaca cagagtaaca cgatacagta acatacatta   1740
cacccaacag taagtgcttt atggtcagta ttctatgtgg agaccttgca ccttgtaatc   1800
atcaatacat ccaccaaaaa tatataatgt accatatata ttaatagtca acaaatactc   1860
agatattcta aggtcaatgc cattatttga ttataccatt ttgagggtga atatggctag   1920
gcactttaga taagcctttt taaaattctt tctgatttta aataatgcgt caaaaaatgt   1980
gcagaaaatg tattgcatcc cttgatactg tctaacgaat agcacataac tcatattgtg   2040
aatcctatgg gtcttgaggc ctgtagaacc aatc                                2074
```

```
<210> SEQ ID NO 109
<211> LENGTH: 570
<212> TYPE: PRT
<213> ORGANISM: Homo sapiens

<400> SEQUENCE: 109

Met Ser Asp Gly Ser Gly Lys Thr Ala Thr Gly Thr Ile Cys Ile Glu
1               5                   10                  15

Val Pro Asp Ile Asn Asp Tyr Cys Pro Asn Ile Phe Pro Glu Arg Arg
            20                  25                  30

Thr Ile Cys Ile Asp Ser Pro Ser Val Leu Ile Ser Val Asn Glu His
        35                  40                  45

Ser Tyr Gly Ser Pro Phe Thr Phe Cys Val Val Asp Glu Pro Pro Gly
    50                  55                  60

Ile Ala Asp Met Trp Asp Val Arg Ser Thr Asn Ala Thr Ser Ala Ile
65                  70                  75                  80

Leu Thr Ala Lys Gln Val Leu Ser Pro Gly Phe Tyr Glu Ile Pro Ile
                85                  90                  95

Leu Val Lys Asp Ser Tyr Asn Arg Ala Cys Glu Leu Ala Gln Met Val
            100                 105                 110

Gln Leu Tyr Ala Cys Asp Cys Asp Asp Asn His Met Cys Leu Asp Ser
        115                 120                 125

Gly Ala Ala Gly Ile Tyr Thr Glu Asp Ile Thr Gly Asp Thr Tyr Gly
    130                 135                 140

Pro Val Thr Glu Asp Gln Ala Gly Val Ser Asn Val Gly Leu Gly Pro
145                 150                 155                 160

Ala Gly Ile Gly Met Met Val Leu Gly Ile Leu Leu Leu Ile Leu Ala
                165                 170                 175
```

-continued

```
Pro Leu Leu Leu Leu Leu Cys Cys Cys Lys Gln Arg Gln Pro Glu Gly
            180                 185                 190

Leu Gly Thr Arg Phe Ala Pro Val Pro Glu Gly Gly Glu Gly Val Met
        195                 200                 205

Gln Ser Trp Arg Ile Glu Gly Ala His Pro Glu Asp Arg Asp Val Ser
    210                 215                 220

Asn Ile Cys Ala Pro Met Thr Ala Ser Asn Thr Gln Asp Arg Met Asp
225                 230                 235                 240

Ser Ser Glu Ile Tyr Thr Asn Thr Tyr Ala Ala Gly Gly Thr Val Glu
                245                 250                 255

Gly Gly Val Ser Gly Val Glu Leu Asn Thr Gly Met Gly Thr Ala Val
            260                 265                 270

Gly Leu Met Ala Ala Gly Ala Ala Gly Ala Ser Gly Ala Ala Arg Lys
        275                 280                 285

Arg Ser Ser Thr Met Gly Thr Leu Arg Asp Tyr Ala Asp Ala Asp Ile
    290                 295                 300

Asn Met Ala Phe Leu Asp Ser Tyr Phe Ser Glu Lys Ala Tyr Ala Tyr
305                 310                 315                 320

Ala Asp Glu Asp Glu Gly Arg Pro Ala Asn Asp Cys Leu Leu Ile Tyr
                325                 330                 335

Asp His Glu Gly Val Gly Ser Pro Val Gly Ser Ile Gly Cys Cys Ser
            340                 345                 350

Trp Ile Val Asp Asp Leu Asp Glu Ser Cys Met Glu Thr Leu Asp Pro
        355                 360                 365

Lys Phe Arg Thr Leu Ala Glu Ile Cys Leu Asn Thr Glu Ile Glu Pro
    370                 375                 380

Phe Pro Ser His Gln Ala Cys Ile Pro Ile Ser Thr Asp Leu Pro Leu
385                 390                 395                 400

Leu Gly Pro Asn Tyr Phe Val Asn Glu Ser Ser Gly Leu Thr Pro Ser
                405                 410                 415

Glu Val Glu Phe Gln Glu Glu Met Ala Ala Ser Glu Pro Val Val His
            420                 425                 430

Gly Asp Ile Ile Val Thr Glu Thr Tyr Gly Asn Ala Asp Pro Cys Val
        435                 440                 445

Gln Pro Thr Thr Ile Ile Phe Asp Pro Gln Leu Ala Pro Asn Val Val
    450                 455                 460

Val Thr Glu Ala Val Met Ala Pro Val Tyr Asp Ile Gln Gly Asn Ile
465                 470                 475                 480

Cys Val Pro Ala Glu Leu Ala Asp Tyr Asn Asn Val Ile Tyr Ala Glu
                485                 490                 495

Arg Val Leu Ala Ser Pro Gly Val Pro Asp Met Ser Asn Ser Ser Thr
            500                 505                 510

Thr Glu Gly Cys Met Gly Pro Val Met Ser Gly Asn Ile Leu Val Gly
        515                 520                 525

Pro Glu Ile Gln Val Met Gln Met Met Ser Pro Asp Leu Pro Ile Gly
    530                 535                 540

Gln Thr Val Gly Ser Thr Ser Pro Met Thr Ser Arg His Arg Val Thr
545                 550                 555                 560

Arg Tyr Ser Asn Ile His Tyr Thr Gln Gln
                565                 570
```

<210> SEQ ID NO 110
<211> LENGTH: 1995
<212> TYPE: DNA

<213> ORGANISM: Homo sapiens

<400> SEQUENCE: 110
tatacagcca tagatttgga cacaggaaac cctgcaacag atgtcagata tatcataggg 60
catgatgcag gcagctggtt aaaaattgat tcaagaactg gtgagataca attttctaga 120
gaatttgata agaagtcaaa atatattatc aatgggatat acacagcaga gatcctggct 180
atagatgcta cctcggcaat ccttacggct aagcaggttt tatctccagg attttatgaa 240
atcccaatcc tggtgaagga cagctataac agagcatgtg aattggcaca aatggtgcag 300
ttatatgcct gtgattgcga tgacaaccac atgtgcctgg actctggtgc cgcgggcatc 360
tacacagagg acataactgg tgacacgtat gggcctgtca ctgaagacca agctggagtt 420
tcaaatgttg gtcttggacc agcagggatt ggcatgatgg ttctgggcat cctgctactg 480
attttggctc cactcttgct gctcctgtgt tgctgcaaac agagacagcc agaaggcctg 540
ggaacaagat ttgctcctgt gcctgagggc ggagaaggag tgatgcagtc ttggagaatt 600
gaaggggccc atcccgagga cagggatgtg tcaaatatat gtgcacccat gacagcctca 660
aatacccagg atcggatgga ttcctctgaa atctacacca acacctatgc agccgggggc 720
acggtggaag gaggtgtatc gggagtggag ctcaacacag gtatggggac agccgttggc 780
ctcatggccg caggggccgc aggagcctca ggggccgcaa ggaagaggag ctctaccatg 840
ggaaccctgc gggactacgc tgacgcagac atcaacatgg ctttcttgga cagctacttc 900
tcggagaaag cgtatgctta tgcagatgaa gatgaaggtc gaccagccaa tgactgcttg 960
ctcatttatg accacgaggg agtcgggtct cccgtaggct ctattggttg ttgcagttgg 1020
attgtggatg acttagatga aagctgcatg gaaactttag atccaaaatt taggactctt 1080
gctgagatct gcttaaacac agaaattgaa ccatttcctt cacaccaggc ttgtatacca 1140
atcagtactg acctcccttt gctcggacct aattactttg ttaatgaatc ttcaggattg 1200
actccctcag aagttgaatt ccaagaagaa atggcagcat ctgaacccgt ggtccatggg 1260
gatattattg tgactgagac ttacggtaat gctgatccat gtgtgcaacc cactacaatt 1320
atttttgatc ctcagcttgc acccaatgtt gtagtaaccg aagcagtaat ggcacctgtc 1380
tatgatattc aagggaatat ttgtgtacct gctgagttag cagattacaa caatgtaatc 1440
tatgctgaga gagtactggc tagtcctggt gtgcctgaca tgagcaatag tagcacgact 1500
gagggttgta tgggacctgt gatgagcggc aatattttag tagggccaga aattcaagtg 1560
atgcaaatga tgagtccaga ccttcccata ggccaaaccg ttggctccac atcccccatg 1620
acatctcgac acagagtaac acgatacagt aacatacatt acacccaaca gtaagtgctt 1680
tatggtcagt attctatgtg gagaccttgc accttgtaat catcaataca tccaccaaaa 1740
atatataatg taccatatat attaatagtc aacaaatact cagatattct aaggtcaatg 1800
ccattatttg attataccat tttgagggtg aatatggcta ggcactttag ataagccttt 1860
ttaaaattct ttctgatttt aaataatgcg tcaaaaaatg tgcagaaaat gtattgcatc 1920
ccttgatact gtctaacgaa tagcacataa ctcatattgt gaatcctatg ggtcttgagg 1980
cctgtagaac caatc 1995

<210> SEQ ID NO 111
<211> LENGTH: 460
<212> TYPE: PRT
<213> ORGANISM: Homo sapiens

<400> SEQUENCE: 111

-continued

```
Met Val Gln Leu Tyr Ala Cys Asp Cys Asp Asp Asn His Met Cys Leu
1               5                   10                  15

Asp Ser Gly Ala Ala Gly Ile Tyr Thr Glu Asp Ile Thr Gly Asp Thr
            20                  25                  30

Tyr Gly Pro Val Thr Glu Asp Gln Ala Gly Val Ser Asn Val Gly Leu
        35                  40                  45

Gly Pro Ala Gly Ile Gly Met Met Val Leu Gly Ile Leu Leu Leu Ile
    50                  55                  60

Leu Ala Pro Leu Leu Leu Leu Leu Cys Cys Cys Lys Gln Arg Gln Pro
65                  70                  75                  80

Glu Gly Leu Gly Thr Arg Phe Ala Pro Val Pro Glu Gly Gly Glu Gly
                85                  90                  95

Val Met Gln Ser Trp Arg Ile Glu Gly Ala His Pro Glu Asp Arg Asp
            100                 105                 110

Val Ser Asn Ile Cys Ala Pro Met Thr Ala Ser Asn Thr Gln Asp Arg
        115                 120                 125

Met Asp Ser Ser Glu Ile Tyr Thr Asn Thr Tyr Ala Ala Gly Gly Thr
    130                 135                 140

Val Glu Gly Gly Val Ser Gly Val Glu Leu Asn Thr Gly Met Gly Thr
145                 150                 155                 160

Ala Val Gly Leu Met Ala Ala Gly Ala Ala Gly Ala Ser Gly Ala Ala
                165                 170                 175

Arg Lys Arg Ser Ser Thr Met Gly Thr Leu Arg Asp Tyr Ala Asp Ala
            180                 185                 190

Asp Ile Asn Met Ala Phe Leu Asp Ser Tyr Phe Ser Glu Lys Ala Tyr
        195                 200                 205

Ala Tyr Ala Asp Glu Asp Glu Gly Arg Pro Ala Asn Asp Cys Leu Leu
    210                 215                 220

Ile Tyr Asp His Glu Gly Val Gly Ser Pro Val Gly Ser Ile Gly Cys
225                 230                 235                 240

Cys Ser Trp Ile Val Asp Asp Leu Asp Glu Ser Cys Met Glu Thr Leu
                245                 250                 255

Asp Pro Lys Phe Arg Thr Leu Ala Glu Ile Cys Leu Asn Thr Glu Ile
            260                 265                 270

Glu Pro Phe Pro Ser His Gln Ala Cys Ile Pro Ile Ser Thr Asp Leu
        275                 280                 285

Pro Leu Leu Gly Pro Asn Tyr Phe Val Asn Glu Ser Ser Gly Leu Thr
    290                 295                 300

Pro Ser Glu Val Glu Phe Gln Glu Glu Met Ala Ala Ser Glu Pro Val
305                 310                 315                 320

Val His Gly Asp Ile Ile Val Thr Glu Thr Tyr Gly Asn Ala Asp Pro
                325                 330                 335

Cys Val Gln Pro Thr Thr Ile Ile Phe Asp Pro Gln Leu Ala Pro Asn
            340                 345                 350

Val Val Val Thr Glu Ala Val Met Ala Pro Val Tyr Asp Ile Gln Gly
        355                 360                 365

Asn Ile Cys Val Pro Ala Glu Leu Ala Asp Tyr Asn Asn Val Ile Tyr
    370                 375                 380

Ala Glu Arg Val Leu Ala Ser Pro Gly Val Pro Asp Met Ser Asn Ser
385                 390                 395                 400

Ser Thr Thr Glu Gly Cys Met Gly Pro Val Met Ser Gly Asn Ile Leu
                405                 410                 415
```

-continued

Val Gly Pro Glu Ile Gln Val Met Gln Met Met Ser Pro Asp Leu Pro
420 425 430

Ile Gly Gln Thr Val Gly Ser Thr Ser Pro Met Thr Ser Arg His Arg
435 440 445

Val Thr Arg Tyr Ser Asn Ile His Tyr Thr Gln Gln
450 455 460

<210> SEQ ID NO 112
<211> LENGTH: 2367
<212> TYPE: DNA
<213> ORGANISM: Homo sapiens

<400> SEQUENCE: 112
tccgttgctt ctcaattcca aatgcaccca acccctgtga gaattcaagt tgttgatgtg 60
agagaaggac ctgcatttca tccaagtact atggctttta gtgtgcggga aggaataaaa 120
ggaagttcct tattgaatta tgtgcttggc acatatacag ccatagattt ggacacagga 180
aaccctgcaa cagatgtcag atatatcata gggcatgatg caggcagctg gttaaaaatt 240
gattcaagaa ctggtgagat acaattttct agagaatttg ataagaagtc aaaatatatt 300
atcaatggga tatacacagc agagatcctg gctatagatg atggctctgg aaaaacagct 360
acaggaacca tatgtattga ggttcctgat atcaatgatt attgtccaaa catttttcct 420
gaaagaagaa ccatctgcat tgactctcca tcagtcctta tctctgttaa tgaacattct 480
tatgggtctc cgtttacttt ctgtgttgtt gatgagccac caggaatagc tgacatgtgg 540
gatgtcagat caacaaatgc tacctcggca atccttacgg ctaagcaggt tttatctcca 600
ggattttatg aaatcccaat cctggtgaag gacagctata acagagcatg tgaattggca 660
caaatggtgc agttatatgc ctgtgattgc gatgacaacc acatgtgcct ggactctggt 720
gccgcgggca tctacacaga ggacataact ggtgacacgt atgggcctgt cactgaagac 780
caagctggag tttcaaatgt tggtcttgga ccagcaggga ttggcatgat ggttctgggc 840
atcctgctac tgattttggc tccactcttg ctgctcctgt gttgctgcaa acagagacag 900
ccagaaggcc tgggaacaag atttgctcct gtgcctgagg gcggagaagg agtgatgcag 960
tcttggagaa ttgaaggggc ccatcccgag gacagggatg tgtcaaatat atgtgcaccc 1020
atgacagcct caaataccca ggatcggatg gattcctctg aaatctacac caacacctat 1080
gcagccgggg gcacggtgga aggaggtgta tcgggagtgg agctcaacac aggtatgggg 1140
acagccgttg gcctcatggc cgcaggggcc gcaggagcct caggggccgc aaggaagagg 1200
agctctacca tgggaaccct gcgggactac gctgacgcag acatcaacat ggctttcttg 1260
gacagctact tctcggagaa agcgtatgct tatgcagatg aagatgaagg tcgaccagcc 1320
aatgactgct tgctcattta tgaccacgag ggagtcgggt ctcccgtagg ctctattggt 1380
tgttgcagtt ggattgtgga tgacttagat gaaagctgca tggaaacttt agatccaaaa 1440
tttaggactc ttgctgagat ctgcttaaac acagaaattg aaccatttcc ttcacaccag 1500
gcttgtatac caatcagtac tgacctccct ttgctcggac ctaattactt tgttaatgaa 1560
tcttcaggat tgactccctc agaagttgaa ttccaagaag aaatggcagc atctgaaccc 1620
gtggtccatg gggatattat tgtgactgag acttacggta atgctgatcc atgtgtgcaa 1680
cccactacaa ttatttttga tcctcagctt gcacccaatg ttgtagtaac cgaagcagta 1740
atggcacctg tctatgatat tcaagggaat atttgtgtac ctgctgagtt agcagattac 1800
aacaatgtaa tctatgctga gagagtactg gctagtcctg gtgtgcctga catgagcaat 1860
agtagcacga ctgagggttg tatgggacct gtgatgagcg gcaatatttt agtagggcca 1920
gaaattcaag tgatgcaaat gatgagtcca gaccttccca taggccaaac cgttggctcc 1980
acatccccca tgacatctcg acacagagta acacgataca gtaacataca ttacacccaa 2040
cagtaagtgc tttatggtca gtattctatg tggagacctt gcaccttgta atcatcaata 2100
catccaccaa aaatatataa tgtaccatat atattaatag tcaacaaata ctcagatatt 2160
ctaaggtcaa tgccattatt tgattatacc attttgaggg tgaatatggc taggcacttt 2220
agataagcct ttttaaaatt ctttctgatt ttaaataatg cgtcaaaaaa tgtgcagaaa 2280
atgtattgca tcccttgata ctgtctaacg aatagcacat aactcatatt gtgaatccta 2340
tgggtcttga ggcctgtaga accaatc 2367

<210> SEQ ID NO 113
<211> LENGTH: 674
<212> TYPE: PRT
<213> ORGANISM: Homo sapiens

<400> SEQUENCE: 113

Met His Pro Thr Pro Val Arg Ile Gln Val Val Asp Val Arg Glu Gly
1 5 10 15

Pro Ala Phe His Pro Ser Thr Met Ala Phe Ser Val Arg Glu Gly Ile
20 25 30

Lys Gly Ser Ser Leu Leu Asn Tyr Val Leu Gly Thr Tyr Thr Ala Ile
35 40 45

Asp Leu Asp Thr Gly Asn Pro Ala Thr Asp Val Arg Tyr Ile Ile Gly
50 55 60

His Asp Ala Gly Ser Trp Leu Lys Ile Asp Ser Arg Thr Gly Glu Ile
65 70 75 80

Gln Phe Ser Arg Glu Phe Asp Lys Lys Ser Lys Tyr Ile Ile Asn Gly
85 90 95

Ile Tyr Thr Ala Glu Ile Leu Ala Ile Asp Asp Gly Ser Gly Lys Thr
100 105 110

Ala Thr Gly Thr Ile Cys Ile Glu Val Pro Asp Ile Asn Asp Tyr Cys
115 120 125

Pro Asn Ile Phe Pro Glu Arg Arg Thr Ile Cys Ile Asp Ser Pro Ser
130 135 140

Val Leu Ile Ser Val Asn Glu His Ser Tyr Gly Ser Pro Phe Thr Phe
145 150 155 160

Cys Val Val Asp Glu Pro Pro Gly Ile Ala Asp Met Trp Asp Val Arg
165 170 175

Ser Thr Asn Ala Thr Ser Ala Ile Leu Thr Ala Lys Gln Val Leu Ser
180 185 190

Pro Gly Phe Tyr Glu Ile Pro Ile Leu Val Lys Asp Ser Tyr Asn Arg
195 200 205

Ala Cys Glu Leu Ala Gln Met Val Gln Leu Tyr Ala Cys Asp Cys Asp
210 215 220

Asp Asn His Met Cys Leu Asp Ser Gly Ala Ala Gly Ile Tyr Thr Glu
225 230 235 240

Asp Ile Thr Gly Asp Thr Tyr Gly Pro Val Thr Glu Asp Gln Ala Gly
245 250 255

Val Ser Asn Val Gly Leu Gly Pro Ala Gly Ile Gly Met Met Val Leu
260 265 270

Gly Ile Leu Leu Leu Ile Leu Ala Pro Leu Leu Leu Leu Leu Cys Cys
275 280 285

```
Cys Lys Gln Arg Gln Pro Glu Gly Leu Gly Thr Arg Phe Ala Pro Val
    290                 295                 300

Pro Glu Gly Gly Glu Gly Val Met Gln Ser Trp Arg Ile Glu Gly Ala
305                 310                 315                 320

His Pro Glu Asp Arg Asp Val Ser Asn Ile Cys Ala Pro Met Thr Ala
                325                 330                 335

Ser Asn Thr Gln Asp Arg Met Asp Ser Ser Glu Ile Tyr Thr Asn Thr
            340                 345                 350

Tyr Ala Ala Gly Gly Thr Val Glu Gly Gly Val Ser Gly Val Glu Leu
        355                 360                 365

Asn Thr Gly Met Gly Thr Ala Val Gly Leu Met Ala Ala Gly Ala Ala
    370                 375                 380

Gly Ala Ser Gly Ala Ala Arg Lys Arg Ser Ser Thr Met Gly Thr Leu
385                 390                 395                 400

Arg Asp Tyr Ala Asp Ala Asp Ile Asn Met Ala Phe Leu Asp Ser Tyr
                405                 410                 415

Phe Ser Glu Lys Ala Tyr Ala Tyr Ala Asp Glu Asp Glu Gly Arg Pro
            420                 425                 430

Ala Asn Asp Cys Leu Leu Ile Tyr Asp His Glu Gly Val Gly Ser Pro
        435                 440                 445

Val Gly Ser Ile Gly Cys Cys Ser Trp Ile Val Asp Asp Leu Asp Glu
    450                 455                 460

Ser Cys Met Glu Thr Leu Asp Pro Lys Phe Arg Thr Leu Ala Glu Ile
465                 470                 475                 480

Cys Leu Asn Thr Glu Ile Glu Pro Phe Pro Ser His Gln Ala Cys Ile
                485                 490                 495

Pro Ile Ser Thr Asp Leu Pro Leu Leu Gly Pro Asn Tyr Phe Val Asn
            500                 505                 510

Glu Ser Ser Gly Leu Thr Pro Ser Glu Val Glu Phe Gln Glu Glu Met
        515                 520                 525

Ala Ala Ser Glu Pro Val Val His Gly Asp Ile Ile Val Thr Glu Thr
    530                 535                 540

Tyr Gly Asn Ala Asp Pro Cys Val Gln Pro Thr Thr Ile Ile Phe Asp
545                 550                 555                 560

Pro Gln Leu Ala Pro Asn Val Val Val Thr Glu Ala Val Met Ala Pro
                565                 570                 575

Val Tyr Asp Ile Gln Gly Asn Ile Cys Val Pro Ala Glu Leu Ala Asp
            580                 585                 590

Tyr Asn Asn Val Ile Tyr Ala Glu Arg Val Leu Ala Ser Pro Gly Val
        595                 600                 605

Pro Asp Met Ser Asn Ser Ser Thr Thr Glu Gly Cys Met Gly Pro Val
    610                 615                 620

Met Ser Gly Asn Ile Leu Val Gly Pro Glu Ile Gln Val Met Gln Met
625                 630                 635                 640

Met Ser Pro Asp Leu Pro Ile Gly Gln Thr Val Gly Ser Thr Ser Pro
                645                 650                 655

Met Thr Ser Arg His Arg Val Thr Arg Tyr Ser Asn Ile His Tyr Thr
            660                 665                 670

Gln Gln
```

<210> SEQ ID NO 114
<211> LENGTH: 6
<212> TYPE: PRT

-continued

```
<213> ORGANISM: artificial
<220> FEATURE:
<223> OTHER INFORMATION: binding to specific fluorescent substances
<220> FEATURE:
<221> NAME/KEY: misc_feature
<222> LOCATION: (3)..(4)
<223> OTHER INFORMATION: Xaa can be any naturally occurring amino acid

<400> SEQUENCE: 114

Cys Cys Xaa Xaa Cys Cys
1               5
```